United States Patent
Baldino et al.

(10) Patent No.: US 10,428,098 B2
(45) Date of Patent: Oct. 1, 2019

(54) PROCESSES FOR PREPARING AND USING RUTHENIUM AND OSMIUM COMPLEXES

(71) Applicants: JOHNSON MATTHEY PUBLIC LIMITED COMPANY, London (GB); UNIVERSITA DEGLI STUDI DI UDINE, Udine (IT)

(72) Inventors: Salvatore Baldino, Udine (IT); Walter Baratta, Udine (IT); Steven Giboulot, Cambridgeshire (GB); Hans Guenter Nedden, Cambridgeshire (GB); Antonio Zanotti-Gerosa, Cambridgeshire (GB)

(73) Assignees: Johnson Matthey Public Limited Company, London, England (GB); Universita Degli Studi Di Udine, Udine (IT)

( * ) Notice: Subject to any disclaimer, the term of this patent is extended or adjusted under 35 U.S.C. 154(b) by 0 days.

(21) Appl. No.: 15/577,848

(22) PCT Filed: Jun. 3, 2016

(86) PCT No.: PCT/GB2016/051658
§ 371 (c)(1),
(2) Date: Nov. 29, 2017

(87) PCT Pub. No.: WO2016/193762
PCT Pub. Date: Dec. 8, 2016

(65) Prior Publication Data
US 2018/0148465 A1    May 31, 2018

(30) Foreign Application Priority Data
Jun. 3, 2015 (GB) .................. 1509664.7

(51) Int. Cl.
| C07F 15/00 | (2006.01) |
| C07C 29/14 | (2006.01) |
| C07C 29/143 | (2006.01) |
| B01J 31/22 | (2006.01) |

(52) U.S. Cl.
CPC .......... *C07F 15/0053* (2013.01); *B01J 31/22* (2013.01); *C07C 29/14* (2013.01); *C07C 29/143* (2013.01); *C07F 15/0046* (2013.01); *C07C 2601/14* (2017.05)

(58) Field of Classification Search
CPC ... C07F 15/0053; C07F 15/0046; B01J 31/22; C07C 29/143; C07C 29/14; C07C 2601/14
See application file for complete search history.

(56) References Cited

U.S. PATENT DOCUMENTS

| 9,090,534 B2 * | 7/2015 | Dupau .................. B01J 31/1805 |
| 2009/0216019 A1 | 8/2009 | Noyori et al. |
| 2015/0031920 A1 | 1/2015 | Katayama et al. |

FOREIGN PATENT DOCUMENTS

| WO | WO2001074829 | 10/2001 |
| WO | WO2002022526 | 3/2002 |
| WO | WO2013050297 A1 | 4/2013 |

OTHER PUBLICATIONS

Bonomo et al., "Ruthenium-Catalyzed Highly Chemoselective Hydrogenation of Aldehydes," ChemCatChem, vol. 7 (6), 2015 (published online Feb. 5, 2015), 907-910.
Dupau et al., "Unexpected Role of Anionic Ligands in the Ruthenium-Catalyzed Base-Free Selective Hydrogenation of Aldehydes," Angewandte Chemie, International Edition, 52(43), 2013, 11347-11350.
Ramakrishnan et al., "Experimental and Theoretical Study of CO2 Insertion into Ruthenium Hydride Complexes," Inorganic Chemistry, 55(4), 2016 (published online Feb. 2, 2016), 1623-1632.
Baratta et al., "Pincer CNN Ruthenium(II) Complexes with Oxygen-Containing Ligands (O2CR, OAr, OR, OSiR3, O3SCF3): Synthesis, Structure, and Catalytic Activity in Fast Transfer Hydrogenation," Organometallics, 28(15), 2009, 4421-4430.
Karabuga et al., "Efficient Transfer Hydrogenation Reactions With Quinazoline-Based Ruthenium Complexes," Tetrahedron Letters, 56(1), Nov. 13, 2014, 101-104.
GB1609785.9, Combined Search and Examination Report under Sections 17 and 18(3) dated Mar. 14, 2017.
PCT/GB2016,051658, International Search Report dated Sep. 12, 2016.
PCT/GB2016,051658, Written Opinion dated Sep. 12, 2016.
Baratta et al., 2-(Aminomethyl)pyridine-Phosphine Ruthenium(II) Complexes: Novel Highly Active Transfer Hydrogenation Catalysts, Organometallics, Feb. 26, 2005, 24, pp. 1660-1669.
Rodriguez et al., Amine-Tunable Ruthenium Catalysts for Asymmetric Reduction of Ketones, Advanced Synthesis and Catalysis, Feb. 2, 2014, vol. 356, pp. 301-307.
Song et al., Synthesis, structure and catalytic properties of CNN pincer palladium(II) and ruthenium(II) complexes with N-substituted-2-aminomethyl-6-phenylpyridines, Dalton Transactions, 2011, 40, pp. 8964-8976.
GB1509664.7, Search Report Under Section 17(5) dated Mar. 16, 2016.

* cited by examiner

*Primary Examiner* — John M Mauro
(74) *Attorney, Agent, or Firm* — BakerHostetler

(57) ABSTRACT

The present invention relates to improved processes for the preparation of ruthenium or osmium complexes comprising acetate ligands, in particular, ruthenium complexes.

20 Claims, No Drawings

PROCESSES FOR PREPARING AND USING RUTHENIUM AND OSMIUM COMPLEXES

CROSS-REFERENCE TO RELATED APPLICATIONS

This application is the National Stage of International Patent Application No. PCT/GB2016/051658 filed Jun. 3, 2016, which claims priority from Great Britain Patent Application No. 1509664.7 filed Jun. 3, 2015, the disclosures of each of which are incorporated herein by reference in their entirety.

Process

The present invention relates to improved processes for the preparation of ruthenium or osmium complexes comprising P and N donor ligands, in particular, ruthenium complexes.

Baratta et al (Organometallics, 2005, 24, 1660-1669) describes the synthesis of 2-(aminomethyl)pyridine-phosphine ruthenium(II) complexes. The complexes represent an active class of catalysts in transfer hydrogenations and in hydrogenation reactions. The procedure described in Baratta et al for the synthesis of trans-RuCl$_2$(dppb)(AMPY) is summarised below:

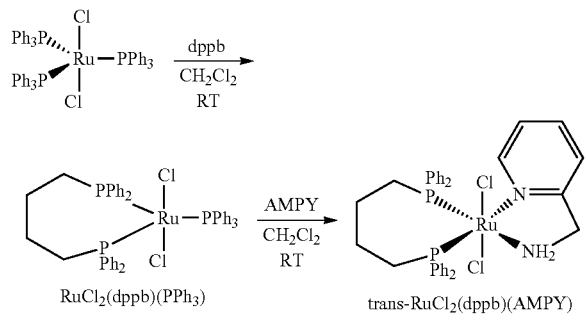

Synthesis of Trans-RuCl2(dppb)(AMPY)

dppb=1,4-bis(diphenylphosphino)butane; CH$_2$Cl$_2$=dichloromethane; RT=room temperature; AMPY=2-(aminomethyl)pyridine Baratta et al (2005) does not describe the processes or complexes of the present invention.

Baratta et al (Organometallics, 2009, 28, 4421-4430) describes the synthesis of the pincer formate complex [Ru(O$_2$CH)(CNN)(dppb)] and acetate complex [Ru(O$_2$CCH$_3$)(CNN)(dppb)](H—CNN=1-[6-(4'-methylphenyl)pyridine-2-yl]methanamine; dppb=Ph$_2$P(CH$_2$)$_4$PPh$_2$). The formate complex was prepared utilising a thallium reagent, HCOOTl. The acetate complex was prepared by treating [Ru(OiPr)(CNN)(dppb)]n(iPrOH) with acetic acid in excess. The preparation of the acetate complex in this way is not industrially viable.

Rodriguez et al (Advanced Synthesis and Catalysis, 2014, 356, 301-307) describes RuCl$_2$(BIBOP)(diamine) complexes (BIBOP=bisdihydrobenzooxaphosphole ligands). Song et al (Dalton Transactions, 2011, 40, 8964-8976) describes N-substituted-2-aminomethyl-6-phenylpyridines. US2009/0216019 and US2015/0031920 (both to Kanto Kagaku Kabushiki Kaisha) describes the use of ruthenium complexes comprising Skewphos and diamine ligands in the synthesis of 3-quinuclidinols. Karabuga et al (Tetrahedron Letters, 2015, 56, 101-104) describes the ligand (4-phenylquinazolin-2-yl)methanamine. Prim et al (Tetrahedron Letters, 2015, 56, 1378-1382) describe the preparation of pyridylmethylamines. None of these documents describes the processes or complexes of the present invention.

The present inventors have developed processes for the preparation of ruthenium complexes comprising P and N donor ligands which overcome problems associated with the prior art. The processes are more suited to large-scale manufacture of ruthenium and osmium complexes.

SUMMARY OF THE INVENTION

In one aspect, the invention provides a process for the preparation of an [M (Y)$_2$(L$^1$)$_{m'}$(L$^2$)] complex, the process comprising the step of:
(a) reacting an [M (Y)$_2$(L)$_2$] complex with a phosphorus ligand L$^1$ and a bidentate N,N ligand L$^2$ in a polar aprotic solvent to form the [M (Y)$_2$(L$^1$)$_{m'}$(L$^2$)] complex; or
(b) reacting an [M (X)$_2$(L)$_3$] complex, an alkali metal carboxylate salt, a phosphorus ligand L$^1$ and a bidentate N,N ligand L$^2$ in a polar aprotic solvent, an alcohol solvent or a mixture thereof to form the [M (Y)$_2$(L$^1$)$_{m'}$(L$^2$)] complex; or
(c) reacting an [M (Y)$_2$(L)$_2$(L$^2$)] complex with a phosphorus ligand L$^1$ in a polar aprotic solvent to form the [M (Y)$_2$(L$^1$)$_{m'}$(L$^2$)] complex;
wherein,
M is ruthenium or osmium;
X is a halide ligand;
Y is a carboxylate ligand;
L is a monodentate phosphorus ligand;
L$^1$ is a monodentate phosphorus ligand which is different to L, or a bidentate phosphorus ligand;
m' is 1 or 2, wherein,
when m' is 1, L$^1$ is a bidentate phosphorus ligand;
when m' is 2, each L$^1$ is a monodentate phosphorus ligand; and
L$^2$ is a bidentate N,N ligand comprising two nitrogen-containing groups.

In another aspect, the invention a process for the preparation of an [M (Y)$_2$(L)$_2$(L$^2$)] complex, the process comprising the step of:
reacting an [M (Y)$_2$(L)$_2$] complex with a bidentate N,N ligand L$^2$ in a polar aprotic solvent to form the [M (Y)$_2$(L)$_2$(L$^2$)] complex;
wherein,
M is ruthenium or osmium;
Y is an carboxylate ligand;
L is a monodentate phosphorus ligand; and
L$^2$ is a bidentate N,N ligand comprising two nitrogen-containing groups.

In another aspect, the invention provides a process for preparing a cis-[M (Y)$_2$(L$^1$)$_{m'}$(L$^2$)] complex, the process comprising the steps of:
a) treating a trans-[M (Y)$_2$(L$^1$)$_{m'}$(L$^2$)] complex in an alcohol solvent; and
b) heating the reaction mixture to form the cis-[M (Y)$_2$(L$^1$)$_{m'}$(L$^2$)] complex;
or:
(c) reacting an [M (Y)$_2$(L)$_2$(L$^2$)] complex with a phosphorus ligand L$^1$ in an alcohol solvent to form the cis-[M (Y)$_2$(L$^1$)$_{m'}$(L$^2$)] complex;

or:

(d) reacting an [M (X)$_2$(L$^1$)$_m$(L$^2$)] complex, a phosphorus ligand L$^1$ and an alkali metal carboxylate in an alcohol solvent to form the cis-[M (Y)$_2$(L$^1$)$_m$(L$^2$)] complex;

wherein,

M is ruthenium or osmium;

X is a halide ligand;

Y is an carboxylate ligand;

L is a monodentate phosphorus ligand;

L$^1$ is a monodentate phosphorus ligand which is different to L, or a bidentate phosphorus ligand;

m is 1 or 2, wherein, when m is 1, L$^1$ is a bidentate phosphorus ligand;

when m is 2, each L$^1$ is a monodentate phosphorus ligand; and

L$^2$ is a bidentate N,N ligand comprising two nitrogen-containing groups.

In another aspect, the invention provides a process for preparing an [M Y(L$^1$)$_{m'}$(L$^3$)] complex, the process comprising the step of:

(a) reacting an [M (Y)$_2$(L)$_2$] complex, a phosphorus ligand L$^1$, a HCNN ligand L$^3$ and a base in an alcohol solvent to form the [M Y(L$^1$)$_{m'}$(L$^3$)] complex; or (b) reacting an [M (Y)$_2$(L$^1$)$_{m'}$] complex, a HCNN ligand L$^3$ and a base in an alcohol solvent to form the [M Y(L$^1$)$_{m'}$(L$^3$)] complex; or (c) reacting an [M (X)$_2$(L)$_3$] complex, a phosphorus ligand L$^1$, a HCNN ligand L$^3$, an alkali metal carboxylate in a polar aprotic solvent, an alcohol solvent or a mixture thereof to form the [M Y(L$^1$)$_{m'}$(L$^3$)] complex;

wherein,

M is ruthenium or osmium;

X is a halide ligand;

Y is a carboxylate ligand;

L is a monodentate phosphorus ligand;

for (a), L$^1$ is a monodentate phosphorus ligand which is different to L, or a bidentate phosphorus ligand;

for (b), L$^1$ is a monodentate phosphorus ligand, or a bidentate phosphorus ligand;

m' is 1 or 2, wherein, when m' is 1, L$^1$ is a bidentate phosphorus ligand;

when m' is 2, each L$^1$ is a monodentate phosphorus ligand; and

L$^3$ is a HCNN ligand of formula (3'), (4'), (6') or (7'):

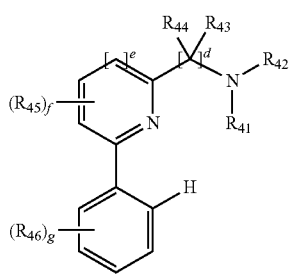

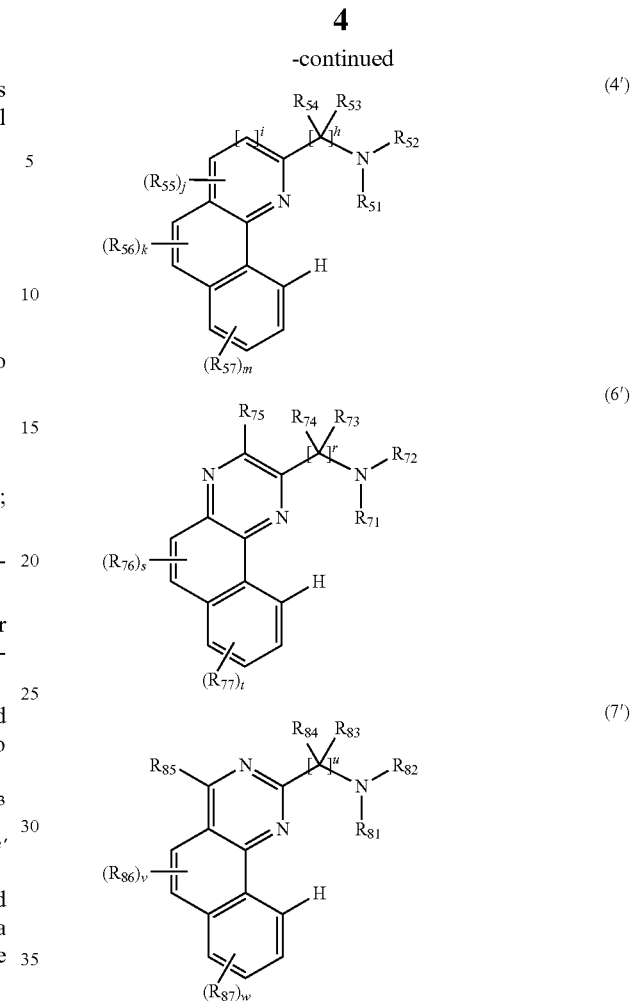

wherein:

$R_{41}$, $R_{42}$, $R_{51}$, $R_{52}$, $R_{71}$, $R_{72}$, $R_{51}$ and $R_{52}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

$R_{43}$, $R_{44}$, $R_{53}$, $R_{54}$, $R_{73}$, $R_{74}$, $R_{83}$ and $R_{54}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

$R_{45}$, $R_{46}$, $R_{55}$, $R_{56}$, $R_{57}$, $R_{76}$, $R_{77}$, $R_{86}$ and $R_{87}$ are independently selected from the groups consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

$R_{75}$ and $R_{85}$ are independently selected from the groups consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

the integers d, h, r and u are independently selected from 1 or 2;

the integers e and i are independently selected from 0 or 1;

when e is 0, f is 0, 1 or 2;

when e is 1, f is 0, 1, 2 or 3;

when i is 0, j is 0 or 1;

when i is 1, j is 0, 1 or 2;

the integer g is 0, 1, 2, 3 or 4;

the integers k, s, v are independently selected from 0, 1 or 2; and the integers m, t, w are independently selected from 0, 1, 2 or 3.

In another aspect, the invention provides a process for the preparation of an [M Y L L³] complex, the process comprising the step of:

reacting an [M (Y)₂(L)₂] complex, a HCNN ligand L³ and a base in an alcohol solvent to form the [M Y L L³] complex;

wherein,

M is ruthenium or osmium;

Y is a carboxylate ligand;

L is a monodentate phosphorus ligand; and

L³ is a HCNN ligand of formula (3'), (4'), (6') or (7'):

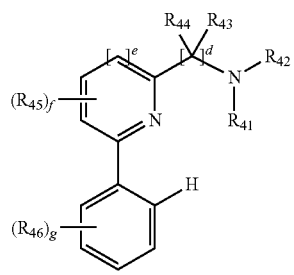

(3')

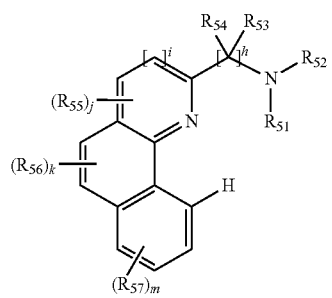

(4')

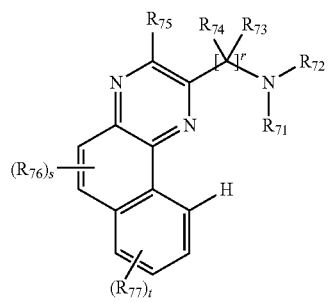

(6')

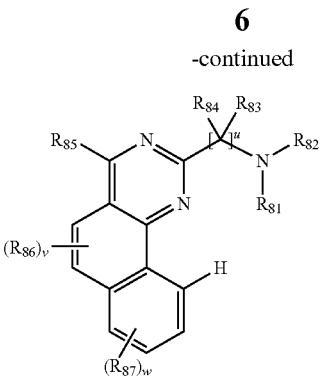

(7')

wherein:

$R_{41}$, $R_{42}$, $R_{51}$, $R_{52}$, $R_{71}$, $R_{72}$, $R_{51}$ and $R_{52}$ are as defined herein;

$R_{43}$, $R_{44}$, $R_{53}$, $R_{54}$, $R_{73}$, $R_{74}$, $R_{53}$ and $R_{54}$ are as defined herein;

$R_{45}$, $R_{46}$, $R_{55}$, $R_{56}$, $R_{57}$, $R_{76}$, $R_{77}$, $R_{56}$ and $R_{57}$ are as defined herein;

$R_{75}$ and $R_{55}$ are as defined herein;

the integers d, h, r and u are independently selected from 1 or 2;

the integers e and i are independently selected from 0 or 1;

when e is 0, f is 0, 1 or 2;

when e is 1, f is 0, 1, 2 or 3;

when i is 0, j is 0 or 1;

when i is 1, j is 0, 1 or 2;

the integer g is 0, 1, 2, 3 or 4;

the integers k, s, v are independently selected from 0, 1 or 2; and the integers m, t, w are independently selected from 0, 1, 2 or 3.

In another aspect, the invention provides a complex which is an [M (Y)₂(L¹)ₘ(L²)] or [M (Y)₂(L)₂(L²)] complex as defined herein provided that:

(a) L² is not a bidentate N,N-ligand of formula (8); or (b) the carboxylate ligand Y is not RCOO— wherein R is a $C_2$-$C_{12}$ hydrocarbon group branched or cyclic in the α and or β position.

In another aspect, the invention provides a complex which is an [M Y(L¹)ₘ(L³)] or [M Y L L³] complex as defined herein provided that the [M Y(L¹)ₘ(L³)] complex is not:

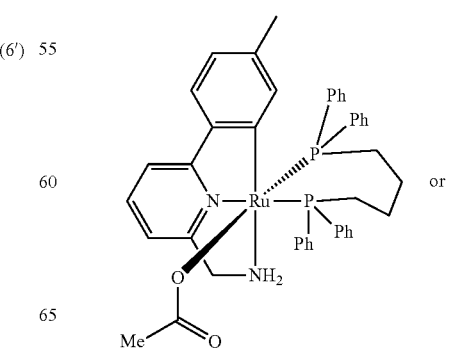

or

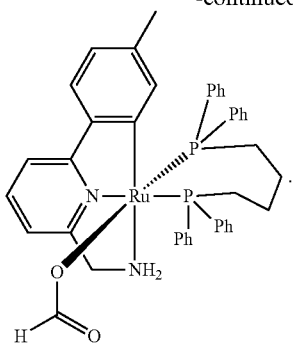

In another aspect, the invention provides a method of catalysing a reaction, the method comprising the step of reacting a substrate comprising a carbon-oxygen double bond in the presence of a complex, wherein the complex is selected from the group consisting of [M (Y)$_2$(L$^1$)$_m$(L$^2$)], [M (Y)$_2$(L)$_2$ (L$^2$)], [M Y(L$^1$)$_m$(L$^3$)] and [M Y L L$^3$] as defined herein.

In another aspect, the invention provides a method of catalysing a reaction, the method comprising the step of performing the reaction in the presence of metal complex selected from the group consisting of [M (Y)$_2$(L$^1$)$_m$(L$^2$)], [M (Y)$_2$(L)$_2$(L$^2$)], [M Y(L$^1$)$_m$(L$^3$)] and [M Y L L$^3$] as defined herein, wherein the reaction is selected from the group consisting of the racemization of alcohols, dehydrogenation of alcohols and carbon-carbon coupling reactions.

Definitions

The point of attachment of a moiety or substituent is represented by "-". For example, —OH is attached through the oxygen atom.

"Alkyl" refers to a straight-chain or branched saturated hydrocarbon group. In certain embodiments, the alkyl group may have from 1-20 carbon atoms, in certain embodiments from 1-15 carbon atoms, in certain embodiments, 1-8 carbon atoms. The alkyl group may be unsubstituted. Alternatively, the alkyl group may be substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, n-butyl, iso-butyl, sec-butyl, tert-butyl, n-pentyl, n-hexyl and the like.

The term "cycloalkyl" is used to denote a saturated carbocyclic hydrocarbon radical. In certain embodiments, the cycloalkyl group may have from 3-15 carbon atoms, in certain embodiments, from 3-10 carbon atoms, in certain embodiments, from 3-8 carbon atoms. The cycloalkyl group may unsubstituted. Alternatively, the cycloalkyl group may be substituted. Unless other specified, the cycloalkyl group may be attached at any suitable carbon atom and, if substituted, may be substituted at any suitable atom. Typical cycloalkyl groups include but are not limited to cyclopropyl, cyclobutyl, cyclopentyl, cyclohexyl and the like.

"Alkoxy" refers to an optionally substituted group of the formula alkyl-O— or cycloalkyl-O—, wherein alkyl and cycloalkyl are as defined above.

"Aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-12 carbon atoms. The aryl group may be unsubstituted. Alternatively, the aryl group may be substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Arylalkyl" refers to an optionally substituted group of the formula aryl-alkyl-, where aryl and alkyl are as defined above.

"Aryloxy" refers to an optionally substituted group of the formula aryl-O—, where aryl is as defined above.

"Halo", "hal" or "halide" refers to —F, —Cl, —Br and —I.

"Heteroalkyl" refers to a straight-chain or branched saturated hydrocarbon group wherein one or more carbon atoms are independently replaced with one or more heteroatoms (e.g. nitrogen, oxygen, phosphorus and/or sulfur atoms). In certain embodiments, the heteroalkyl group may have from 1-20 carbon atoms, in certain embodiments from 1-15 carbon atoms, in certain embodiments, 1-8 carbon atoms. The heteroalkyl group may be unsubstituted. Alternatively, the heteroalkyl group may substituted. Unless otherwise specified, the heteroalkyl group may be attached at any suitable atom and, if substituted, may be substituted at any suitable atom. Examples of heteralkyl groups include but are not limited to ethers, thioethers, primary amines, secondary amines, tertiary amines and the like.

"Heterocycloalkyl" refers to a saturated cyclic hydrocarbon group wherein one or more carbon atoms are independently replaced with one or more heteroatoms (e.g. nitrogen, oxygen, phosphorus and/or sulfur atoms). In certain embodiments, the heterocycloalkyl group may have from 2-20 carbon atoms, in certain embodiments from 2-10 carbon atoms, in certain embodiments, 2-8 carbon atoms. The heterocycloalkyl group may be unsubstituted. Alternatively, the heterocycloalkyl group may be substituted. Unless otherwise specified, the heterocycloalkyl group may be attached at any suitable atom and, if substituted, may be substituted at any suitable atom. Examples of heterocycloalkyl groups include but are not limited to epoxide, morpholinyl, piperadinyl, piperazinyl, thirranyl, pyrrolidinyl, pyrazolidinyl, imidazolidinyl, thiazolidinyl, thiomorpholinyl and the like.

"Heteroaryl" refers to an aromatic carbocyclic group wherein one or more carbon atoms are independently replaced with one or more heteroatoms (e.g. nitrogen, oxygen, phosphorus and/or sulfur atoms). In certain embodiments, the heteroaryl group may have from 3-20 carbon atoms, in certain embodiments from 3-15 carbon atoms, in certain embodiments, 3-8 carbon atoms. The heteroaryl group may be unsubstituted. Alternatively, the heteroaryl group may substituted. Unless otherwise specified, the heteroaryl group may be attached at any suitable atom and, if substituted, may be substituted at any suitable atom. Examples of heteroaryl groups include but are not limited to thienyl, furanyl, pyrrolyl, imidazolyl, pyrazolyl, thiazolyl, isothiazolyl, oxazolyl, isoxazolyl, triazolyl, thiadiazolyl, thiophenyl, oxadiazolyl, pyridinyl, pyrimidyl, benzoxazolyl, benzthiazolyl, benzimidazolyl, indolyl, quinolinyl and the like.

"Substituted" refers to a group in which one or more hydrogen atoms are each independently replaced with substituents (e.g. 1, 2, 3, 4, 5 or more) which may be the same or different. Examples of substituents include but are not limited to -halo, —CF$_3$, —R$^a$, —O—R$^a$, —S—R$^a$, —NR$^a$R$^b$, —CN, —C(O)—R$^a$, —COOR$^a$, —C(S)—R$^a$, —C(S)OR$^a$, —S(O)$_2$OH, —S(O)$_2$—R$^a$, —S(O)$_2$NR$^a$R$^b$ and —CONR$^a$R$^b$, preferably -halo, —CF$_3$, —R$^a$, —O—R$^a$, —NR$^a$R$^b$, —COOR$^a$, —S(O)$_2$OH, —S(O)$_2$—R$^a$, —S(O)$_2$NR$^a$R$^b$ and —CONR$^a$R$^b$. R$^a$ and R$^b$ are independently selected from the groups consisting of H, alkyl, aryl, arylalkyl, heteroalkyl, heteroaryl, or R$^a$ and R$^b$ together with the atom to which they are attached form a heterocycloalkyl group, and wherein R$^a$ and R$^b$ may be unsubstituted or further substituted as defined herein.

DETAILED DESCRIPTION

In one aspect, the invention provides a process for the preparation of an [M (Y)$_2$(L$^1$)$_{m'}$(L$^2$)] complex, the process comprising the step of:
reacting an [M (Y)$_2$(L)$_2$] complex with a phosphorus ligand L$^1$ and a bidentate N,N ligand L$^2$ in a polar aprotic solvent to form the [M (Y)$_2$(L$^1$)$_{m'}$(L$^2$)] complex;
wherein,
M is ruthenium or osmium;
Y is a carboxylate ligand;
L is a monodentate phosphorus ligand;
L$^1$ is a monodentate phosphorus ligand which is different to L, or a bidentate phosphorus ligand;
m' is 1 or 2, wherein,
when m' is 1, L$^1$ is a bidentate phosphorus ligand;
when m' is 2, each L$^1$ is a monodentate phosphorus ligand; and
L$^2$ is a bidentate N,N ligand comprising two nitrogen-containing groups.

The inventors believe that complexes comprising carboxylate ligands may have a greater solubility than an [M (X)$_2$(L$^1$)$_{m'}$(L$^2$)] complex where X is a halide.

The metal M is a platinum group metal selected from ruthenium or osmium.

In one embodiment, M is ruthenium. When M is ruthenium, M may be Ru(II). In another embodiment, M is osmium. When M is osmium, M may be Os(II).

Y is a carboxylate ligand which may have the formula —OC(O)R$_A$. R$_A$ may be selected from the group consisting of —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl. R$_A$ may be substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In one embodiment, the alkyl groups may be optionally substituted with one or more substituents such as halide (F, Cl, Br or I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_1$-C$_{10}$-(dialkyl)amino, C$_{3-10}$ heterocycloalkyl groups (such as morpholinyl and piperadinyl) or tri(halo)methyl (e.g. F$_3$C—). Substituted or unsubstituted heteroaryl groups such as pyridyl may also be used. In one embodiment, the carboxylate ligand is an acetate ligand (i.e. —OC(O)Me). In one embodiment, the carboxylate ligand is a pivalate ligand (i.e. —OC(O)$^t$Bu). In another embodiment, the carboxylate ligand is a benzoate, 2,4,6-trimethylbenzoate or an adamantane-1-carboxylate ligand.

L is a monodentate phosphorus ligand and each L may be the same or different. Preferably, L is a tertiary phosphine ligand PR$_{11}$R$_{12}$R$_{13}$. R$_{11}$, R$_{12}$ and R$_{13}$ may be independently selected from the group consisting of unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl. R$_{11}$, R$_{12}$ and R$_{13}$ may be independently substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_1$-C$_{10}$-(dialkyl)amino, C$_{3-10}$ heterocycloalkyl groups (such as morpholinyl and piperadinyl) or tri(halo)methyl (e.g. F$_3$C—). Substituted or unsubstituted heteroaryl groups such as pyridyl may also be used. In an alternative embodiment, any two of R$_{11}$, R$_{12}$ and R$_{13}$ may be linked to form a ring structure with the phosphorus atom, preferably 4- to 7-membered rings. In one embodiment, R$_{11}$, R$_{12}$ and R$_{13}$ are the same and are phenyl i.e. PR$_{11}$R$_{12}$R$_{13}$ is triphenylphosphine. Alternatively, R$_{11}$, R$_{12}$ and R$_{13}$ are the same and are tolyl i.e. PR$_{11}$R$_{12}$R$_{13}$ is tritolylphosphine (e.g. ortho-, meta- or para-tritolylphosphine).

In one embodiment, the [M (Y)$_2$(L)$_2$] complex may be a [ruthenium (OC(O)R$_1$)$_2$(PR$_{11}$R$_{12}$R$_{13}$)$_2$] complex, wherein R$_{11}$, R$_{12}$ and R$_{13}$ are independently selected from unsubstituted C$_{5-20}$-aryl and substituted C$_{5-20}$-aryl. In one preferred embodiment, the [M (Y)$_2$(L)$_2$] complex may be [Ru(OC(O)Me)$_2$ (PPh$_3$)$_2$]. In another preferred embodiment, the [M (Y)$_2$(L)$_2$] complex may be [Ru(OC(O)Me)$_2$ (P(tolyl)$_3$)$_2$].

In one embodiment, the [M (Y)$_2$(L)$_2$] complex may be an [osmium (OCOR$_1$)$_2$(PR$_{11}$R$_{12}$R$_{13}$)$_2$] complex, wherein R$_{11}$, R$_{12}$ and R$_{13}$ are independently selected from unsubstituted C$_{5-20}$-aryl and substituted C$_{5-20}$-aryl. In one preferred embodiment, the [M (Y)$_2$(L)$_2$] complex may be [Os(OCOMe)$_2$(PPh$_3$)$_2$]. In another preferred embodiment, the [M (Y)$_2$(L)$_2$] complex may be [Os(OCOMe)$_2$(P(tolyl)$_3$)$_2$].

L$^1$ is a monodentate phosphorus ligand which is different to L. In this instance, m' is 2. Alternatively, L$^1$ is a bidentate phosphorus ligand and, in this instance, m' is 1.

Any suitable phosphorus compound capable of forming a ligand-metal interaction with the M atom may be used. In the ligand, each phosphorus atom is covalently bonded to either 3 carbon atoms (tertiary phosphines) or to n heteroatoms and 3-n carbon atoms, where n=1, 2 or 3. Preferably, the heteroatom is selected from the group consisting of N and O.

The phosphorus ligand may be monodentate, e.g. PPh$_3$, or bidentate. The ligand may be chiral or achiral, although in many instances it is preferred that the phosphorus ligand is chiral. A variety of chiral phosphorus ligands has been described and reviews are available, for example see W. Tang and X. Zhang, Chem Rev. 2003, 103, 3029 3070 and J. C. Carretero, Angew. Chem. Int. Ed., 2006, 45, 7674-7715. Phosphorus ligands that may be used in the present invention include but are not restricted to the following structural types:

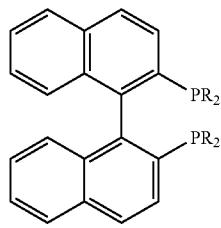

BINAP, R = aryl and alkyl

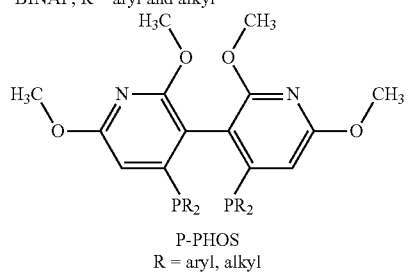

P-PHOS
R = aryl, alkyl

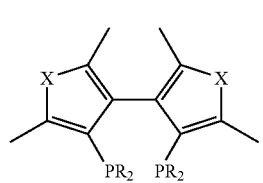

TMBITIOP
R = aryl, alkyl
X = O, S, N

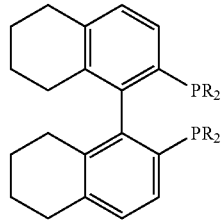

H⁸-BINAP, R = aryl and alkyl

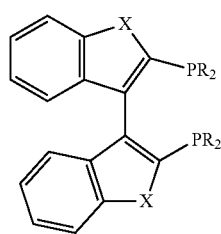

BITIANAP
R = aryl, alkyl
X = O, S, N

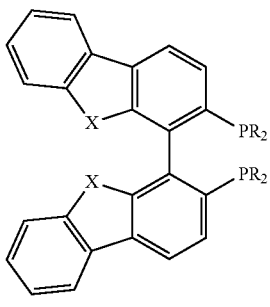

R = aryl, alkyl
X = O BIBFUP
X = NH or S

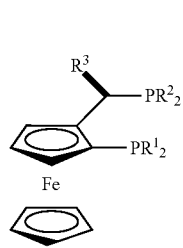

JOSIPHOS
$R^1$ = alkyl, aryl
$R^2$ = alkyl, aryl
$R^3$ = alkyl, aryl

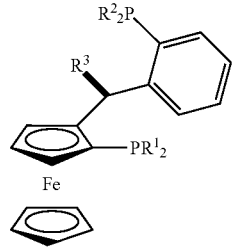

TANIAPHOS
$R^1$ = alkyl, aryl
$R^2$ = alkyl, aryl
$R^3$ = alkyl

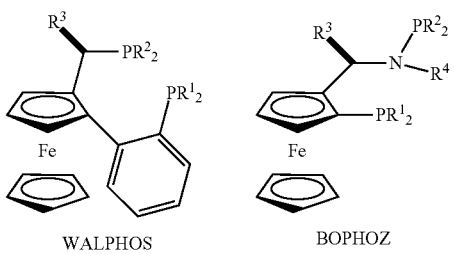

WALPHOS
$R^1$ = alkyl, aryl
$R^2$ = alkyl, aryl

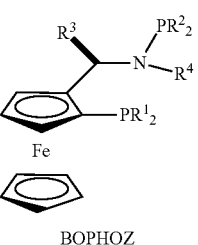

BOPHOZ
$R^1$ = alkyl, aryl
$R^2$ = alkyl, aryl, Oalkyl, Oaryl
$R^3$ = alkyl, aryl
$R^4$ = alkyl, aryl

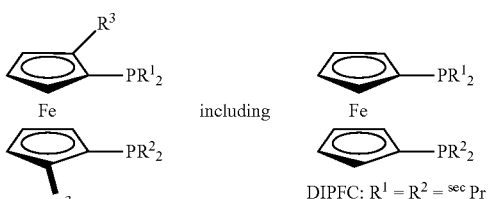

including

DIPFC: $R^1 = R^2 = {}^{sec}Pr$
DCyPFC: $R^1 = R^2 = Cy$

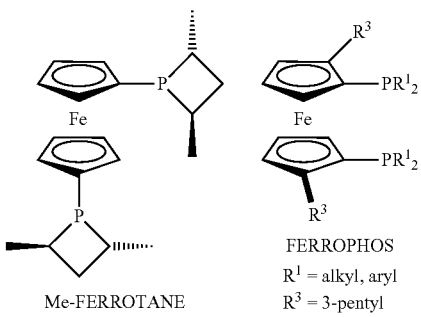

Me-FERROTANE

FERROPHOS
$R^1$ = alkyl, aryl
$R^3$ = 3-pentyl

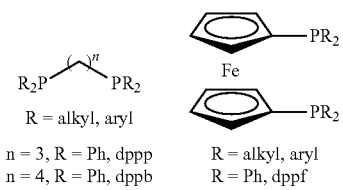

n = 3, R = Ph, dppp
n = 4, R = Ph, dppb

R = alkyl, aryl
R = Ph, dppf

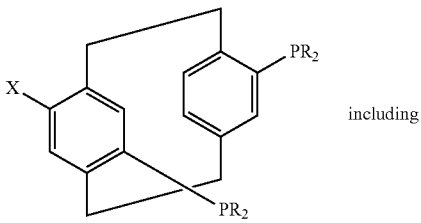

PARAPHOS
X = functional group
R = aryl, alkyl including

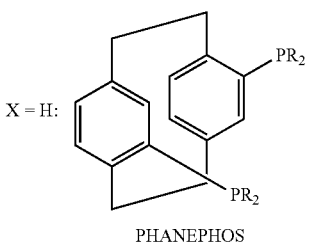

X = H:

PHANEPHOS

13
-continued

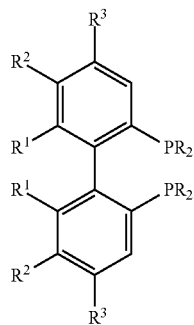

Substituted Biphenyl:
R = aryl and alkyl
$R^1$ = alkyl, alkoxy
$R^2$ = H, alkyl, alkoxy, halide
$R^3$ = H, alkyl

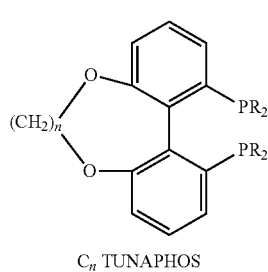

$C_n$ TUNAPHOS $R^1$ = OMe: BIPHEP
$R^1$ = OMe, $R^2$ = Cl: Cl, MeO BIPHEP
$R^1$ and $R^3$ = Me, $R^2$ = OMe, BIMOP
$R^1$ = Me: BIPHEMP
$R^1$ and $R^3$ = Me: TETRAPHEMP
$R^1$, $R^2$ and $R^3$ = Me: HEXAPHEMP

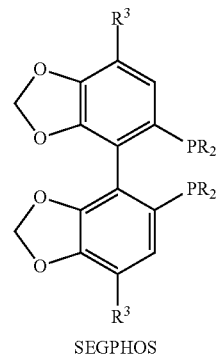

SEGPHOS

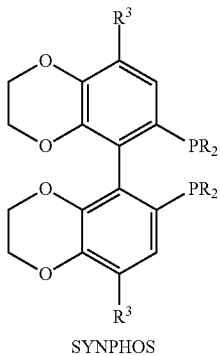

SYNPHOS

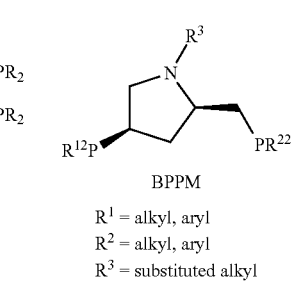

BPPM
$R^1$ = alkyl, aryl
$R^2$ = alkyl, aryl
$R^3$ = substituted alkyl

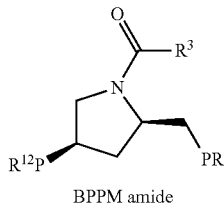

BPPM amide
$R^1$ = alkyl, aryl
$R^2$ = alkyl, aryl
$R^3$ = alkyl, aryl, $OR^4$, $NR^4_2$
$R^4$ = alkyl, aryl

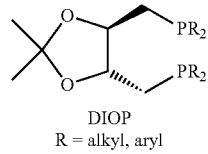

DIOP
R = alkyl, aryl

14
-continued

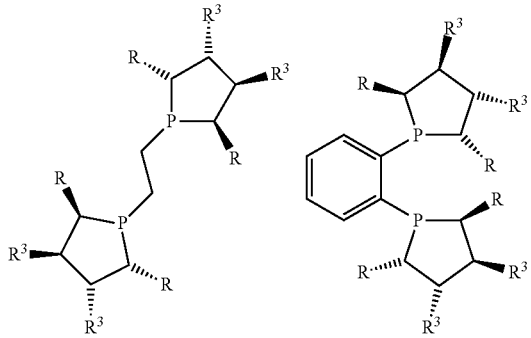

BPE-type
R = alkyl, aryl, $CH_2OR^2$
$R^3$ = H or $OR^2$
$R^2$ = alkyl

DUPHOS-type
R = alkyl, $CH_2OR^2$
$R^3$ = H or $OR^2$
$R^2$ = alkyl

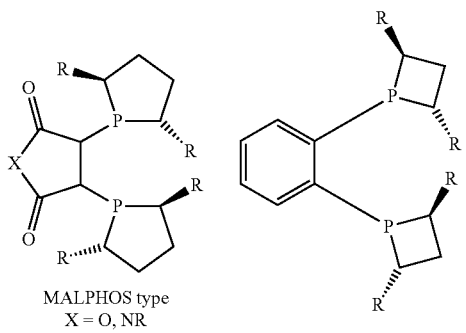

MALPHOS type
X = O, NR

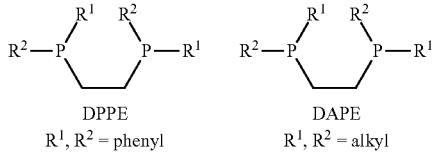

DPPE
$R^1$, $R^2$ = phenyl

DAPE
$R^1$, $R^2$ = alkyl

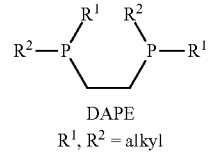

DIPAMP
$R^1$ = phenyl
$R^2$ = 4-MeO-phenyl

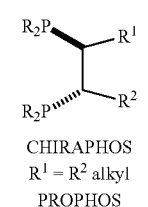

CHIRAPHOS
$R^1$ = $R^2$ alkyl
PROPHOS
$R^2$ = alkyl $R^1$ = H

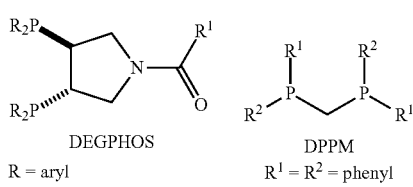

DEGPHOS
R = aryl
$R^1$ = alkyl, aryl, $OR^2$, $NR^2_2$
$R^2$ = alkyl, aryl

DPPM
$R^1$ = $R^2$ = phenyl

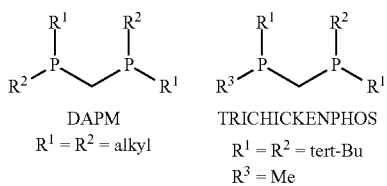

DAPM
$R^1$ = $R^2$ = alkyl

TRICHICKENPHOS
$R^1$ = $R^2$ = tert-Bu
$R^3$ = Me

-continued

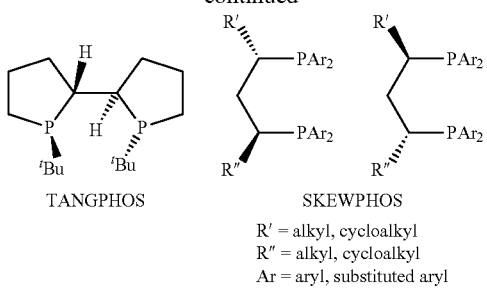

TANGPHOS    SKEWPHOS

R' = alkyl, cycloalkyl
R" = alkyl, cycloalkyl
Ar = aryl, substituted aryl

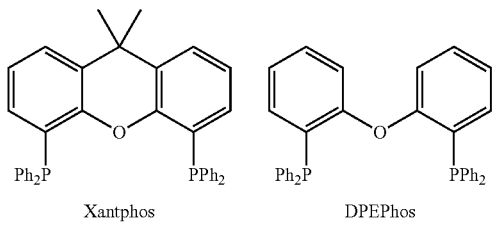

Xantphos    DPEPhos

In the above structures —PR$_2$ may be —P(alkyl)$_2$ in which alkyl is preferably C$_1$-C$_{10}$ alkyl, —P(aryl)$_2$ where aryl includes phenyl and naphthyl which may be substituted or unsubstituted or —P(O-alkyl)$_2$ and —P(O-aryl)$_2$ with alkyl and aryl as defined above. —PR$_2$ may also be substituted or unsubstituted —P(heteroaryl)$_2$, where heteroaryl includes furanyl (e.g. 2-furanyl or 3-furanyl). —PR$_2$ is preferably either —P(aryl)$_2$ where aryl includes phenyl, tolyl, xylyl or anisyl or —P(O-aryl)$_2$. If —PR$_2$ is —P(O-aryl)$_2$, the most preferred O-aryl groups are those based on chiral or achiral substituted 1,1'-biphenol and 1,1'-binaphtol. Alternatively, the R groups on the P-atom may be linked as part of a cyclic structure.

Substituting groups may be present on the alkyl or aryl substituents in the phosphorus ligands. Such substituting groups are typically branched or linear C$_{1-6}$ alkyl groups such as methyl, ethyl, propyl, isopropyl, tert butyl and cyclohexyl.

The phosphorus ligands are preferably used in their single enantiomer form. These phosphorus ligands are generally available commercially and their preparation is known. For example, the preparation of PARAPHOS ligands is given in WO 04/111065, the preparation of Bophoz ligands in WO02/26750 and U.S. Pat. No. 6,906,212 and the preparation of Josiphos ligands in EP564406B and EP612758B.

The phosphorus ligand L$^1$ preferably includes Binap ligands, PPhos ligands, PhanePhos ligands, QPhos ligands, Josiphos ligands, Bophoz ligands and Skewphos ligands.

When L$^1$ is a Binap ligand, the ligand may be of formula (Ia) or (Ia):

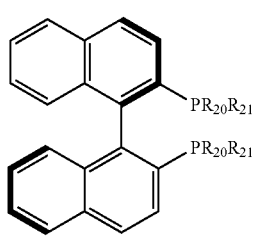

(Ia)

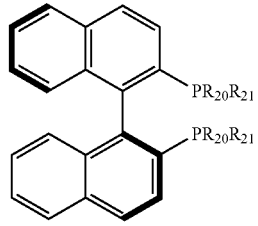

(Ib)

wherein,
R$_{20}$ and R$_{21}$ are each independently selected from the group consisting of unsubstituted C$_{3-20}$-cycloalkyl, substituted C$_{3-20}$-cycloalkyl, unsubstituted C$_{6-20}$-aryl and substituted C$_{6-20}$-aryl. In one embodiment, R$_{20}$ and R$_{21}$ are each independently selected from the group consisting of cycloalkyl groups such as cyclopropyl, cyclobutyl, cyclopentyl, cyclohexyl or adamantly, or aryl groups such as phenyl, naphthyl or anthracyl. In one embodiment, the cycloalkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain C$_1$-C$_{10}$-alkyl (e.g. methyl), C$_1$-C$_{10}$ alkoxy, straight- or branched-chain C$_1$-C$_{10}$-(dialkyl)amino, C$_{3-10}$ heterocycloalkyl groups (such as morpholinyl and piperadinyl) or tri(halo)methyl (e.g. F$_3$C—). Preferably, R$_{20}$ and R$_{21}$ are the same and are selected from the group consisting of phenyl, tolyl (o-, m- or p-, preferably p-tolyl) and xylyl (e.g. 3,5-xylyl).

When L$^1$ is a Josiphos ligand, the ligand may be of formula (IIa) or (IIb):

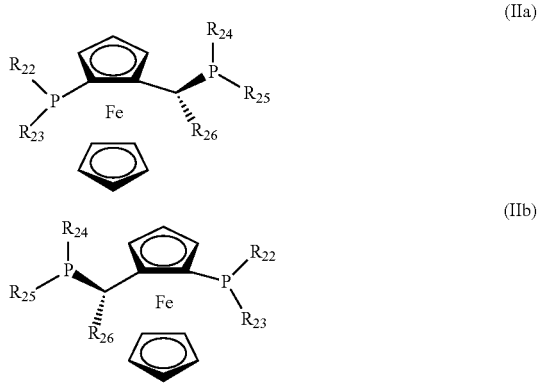

wherein,
R$_{22}$ and R$_{23}$ are independently selected from the group consisting of unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl and substituted C$_{4-20}$-heteroaryl;
R$_{24}$ and R$_{25}$ are independently selected from the group consisting of unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$- alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl; and $R_{26}$ is selected from the group consisting of unsubstituted $C_{1-20}$-alkyl and substituted $C_{1-20}$-alkyl.

In one embodiment, $R_{22}$ and $R_{23}$ are independently selected from the group consisting of substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, aryl groups such as phenyl, naphthyl or anthracyl and heteroaryl groups such as furyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl (e.g. methyl), $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). The heteroaryl group may be optionally substituted with one or more (e.g. 1, 2, 3, 4, or 5) substituents such as halide (—F, —Cl, —Br or —I), straight- or branched-chain $C_1$-$C_{10}$-alkyl (e.g. methyl), $C_1$-$C_{10}$ alkoxy, straight- or branched-chain $C_1$-$C_{10}$-(dialkyl)amino or tri(halo)methyl (e.g. $F_3C$—). Preferably, $R_{22}$ and $R_{23}$ are the same and are selected from the group consisting of tert-butyl, cyclohexyl, phenyl, 3,5-bis(trifluoromethyl)phenyl, 4-methoxy-3,5-dimethylphenyl, 4-trifluoromethylphenyl, 1-naphthyl, 3,5-xylyl, 2-methylphenyl and 2-furyl, most preferably tert-butyl, cyclohexyl, phenyl, 3,5-bis(trifluoromethyl)phenyl, 4-methoxy-3,5-dimethylphenyl, 4-trifluoromethylphenyl, 1-naphthyl and 2-furyl.

In one embodiment, $R_{24}$ and $R_{25}$ are independently selected from the group consisting of substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, aryl groups such as phenyl, naphthyl or anthracyl and heteroaryl groups such as furyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl (e.g. methyl), $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). The heteroaryl group may be optionally substituted with one or more (e.g. 1, 2, 3, 4, or 5) substituents such as halide (—F, —Cl, —Br or —I), straight- or branched-chain $C_1$-$C_{10}$-alkyl (e.g. methyl), $C_1$-$C_{10}$ alkoxy, straight- or branched-chain $C_1$-$C_{10}$-(dialkyl)amino or tri(halo)methyl (e.g. $F_3C$—). Preferably, $R_{24}$ and $R_{25}$ are the same and are selected from the group consisting of tert-butyl, cyclohexyl, phenyl, 3,5-bis(trifluoromethyl)phenyl, 4-methoxy-3,5-dimethylphenyl, 4-trifluoromethylphenyl, 1-naphthyl, 3,5-xylyl, 2-methylphenyl and 2-furyl, most preferably tert-butyl, cyclohexyl, phenyl, 3,5-xylyl and 2-methylphenyl.

In one embodiment, $R_{26}$ is an unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl. Preferable, $R_{26}$ is methyl.

In one embodiment, the ligand of formula (IIa) is selected from the group consisting of:
(R)-1-[(S)-2-(diphenylphosphino)ferrocenyl]ethyldicyclohexylphosphine,
(R)-1-[(S)-2-(diphenylphosphino)ferrocenyl]ethyldi-tert-butylphosphine,
(R)-1-[(S)-2-(dicyclohexylphosphino)ferrocenyl]ethyldicyclohexylphosphine,
(R)-1-[(S)-2-(dicyclohexylphosphino)ferrocenyl]ethyldiphenylphosphine,
(R)-1-[(S)-2-(diphenylphosphino)ferrocenyl]ethyldi-3,5-xylylphosphine,
(R)-1-[(S)-2-(di-3,5-bis(trifluoromethyl)phenylphosphino)ferrocenyl]ethyldicyclohexylphosphine,
(R)-1-[(S)-2-(di-4-methoxy-3,5-dimethylphenylphosphino)ferrocenyl]ethyldicyclohexylphosphine,
(R)-1-[(S)-2-(di-3,5-bis(trifluoromethyl)phenylphosphino)ferrocenyl]ethyldi-3,5-xylylphosphine,
(R)-1-[(S)-2-(dicyclohexylphosphino)ferrocenyl]ethyldi-tert-butylphosphine,
(R)-1-[(S)-2-(di-(4-trifluoromethyl)phenylphosphino)ferrocenyl]ethyldi-tert-butylphosphine,
(R)-1-[(S)-2-(di-4-methoxy-3,5-dimethylphenylphosphino)ferrocenyl]ethyldi-tert-butylphosphine,
(R)-1-[(S)-2-(di-2-furylphosphino)ferrocenyl]ethyldi-3,5-xylylphosphine,
(R)-1-[(S)-2-(di-2-furylphosphino)ferrocenyl]ethyldi-tert-butylphosphine,
(R)-1-[(S)-2-(di-1-naphthylphosphino)ferrocenyl]ethyldi-tert-butylphosphine,
(R)-1-[(S)-2-(di-1-naphthylphosphino)ferrocenyl]ethyldi-3,5-xylylphosphine,
(R)-1-[(S)-2-(di-4-methoxy-3,5-dimethylphenylphosphino)ferrocenyl]ethyldi-3,5-xylylphosphine,
(R)-1-[(S)-2-(di-4-methoxy-3,5-dimethylphenylphosphino)ferrocenyl]ethyldi-(2-methylphenyl)phosphine,
(R)-1-[(S)-2-(di-2-furylphosphino)ferrocenyl]ethyldi-(2-methylphenyl)phosphine,
(R)-1-[(S)-2-(di-tert-butylphosphino)ferrocenyl]ethyldiphenylphosphine,
(R)-1-[(S)-2-(di-tert-butylphosphino)ferrocenyl]ethyldi-(2-methylphenyl)phosphine,
(R)-1-[(S)-2-(diphenylphosphino)ferrocenyl]ethyldiphenylphosphine,
(R)-1-[(S)-2-(diphenylphosphino)ferrocenyl]ethyldi(adamantyl)phosphine, and
(R)-1-[(S)-2-(di(adamantyl)phosphino)ferrocenyl]ethyldiphenylphosphine.

In one embodiment, the ligand of formula (IIb) is selected from the group consisting of:
(S)-1-[(R)-2-di(phenylphosphino)ferrocenyl]ethyldicyclohexylphosphine,
(S)-1-[(R)-2-di(phenylphosphino)ferrocenyl]ethyldi-tert-butylphosphine,
(S)-1-[(R)-2-di(cyclohexylphosphino)ferrocenyl]ethyldicyclohexylphosphine,
(S)-1-[(R)-2-di(cyclohexylphosphino)ferrocenyl]ethyldiphenylphosphine,
(S)-1-[(R)-2-di(phenylphosphino)ferrocenyl]ethyldi-3,5-xylylphosphine,
(S)-1-[(R)-2-di-(3,5-bis(trifluoromethyl)phenylphosphino)ferrocenyl]ethyldicyclohexylphosphine, (S)-1-[(R)-2-di-(4-methoxy-3,5-dimethyl)phenylphosphino)ferrocenyl]ethyldicyclohexylphosphine,
(S)-1-[(R)-2-di-(3,5-bis(trifluoromethyl)phenylphosphino)ferrocenyl]ethyldi-3,5-xylylphosphine,
(S)-1-[(R)-2-di(cyclohexylphosphino)ferrocenyl]ethyldi-tert-butylphosphine,
(S)-1-[(R)-2-di-((4-trifluoromethyl)phenylphosphino)ferrocenyl]ethyldi-tert-butylphosphine,
(S)-1-[(R)-2-di-(4-methoxy-3,5-dimethyl)phenylphosphino)ferrocenyl]ethyldi-tert-butylphosphine,
(S)-1-[(R)-2-di-(2-furyl)phosphino)ferrocenyl]ethyldi-3,5-xylylphosphine,
(S)-1-[(R)-2-di-(2-furyl)phosphino)ferrocenyl]ethyldi-tert-butylphosphine,
(S)-1-[(R)-2-di(1-naphthyl)phosphino)ferrocenyl]ethyldi-tert-butylphosphine,
(S)-1-[(R)-2-di(1-naphthyl)phosphino)ferrocenyl]ethyldi-3,5-xylylphosphine,
(S)-1-[(R)-2-di-(4-methoxy-3,5-dimethyl)phenylphosphino)ferrocenyl]ethyldi-3,5-xylylphosphine,
(S)-1-[(R)-2-di-(4-methoxy-3,5-dimethyl)phenylphosphino)ferrocenyl]ethyldi-(2-methylphenyl)phosphine,
(S)-1-[(R)-2-di-(2-furyl)phosphinoferrocenyl]ethyldi-(2-methylphenyl)phosphine,
(S)-1-[(R)-2-di(tert-butylphosphino)ferrocenyl]ethyldiphenylphosphine,
(S)-1-[(R)-2-di(tert-butylphosphino)ferrocenyl]ethyldi-(2-methylphenyl)phosphine,
(S)-1-[(R)-2-diphenylphosphinoferrocenyl]ethyldiphenylphosphine,
(S)-1-[(R)-2-(diphenylphosphino)ferrocenyl]ethyldi(adamantyl)phosphine, and
(S)-1-[(R)-2-(di(adamantyl)phosphino)ferrocenyl]ethyldiphenylphosphine.

In one embodiment, the ligand of formula (IIa) is (R)-1-[(S)-2-diphenylphosphinoferrocenyl]ethyldiphenylphosphine. In another preferred embodiment, the ligand of formula (IIb) is (S)-1-[(R)-2-diphenylphosphinoferrocenyl]ethyldiphenylphosphine.

The phosphorus ligand $L^1$ may also be selected from the group consisting of $PPh_3$, $PCy_3$ (tricyclohexylphosphine), dppf (1,1'-bis(diphenylphosphino)ferrocene), dppp (1,3-bis(diphenylphosphino)propane), dppb (1,4-bis(diphenylphosphino)butane), Dipfc (1,1'-bis(di-isopropylphosphino)ferrocene), dCyPfc (1,1'-bis(di-cyclohexylphosphino)ferrocene, DB'PF (1,1'-bis(di-tert-butylphosphino)ferrocene), dppm (bis(diphenylphosphino)methane), dppe (1,2-bis(diphenylphosphino)ethane), Xantphos (4,5-bis(diphenylphosphino)-9,9-dimethylxanthene) and DPEPhos (bis[(2-diphenylphosphino)phenyl] ether). In one embodiment, the phosphorus ligand $L^1$ is unsubstituted. In another embodiment, the ligand $L^1$ is substituted.

Particularly preferred phosphorus ligands $L^1$ may be selected from the group consisting of $PPh_3$, dppf, dppp, dppb, dCyPfc, BINAP, dppm, dppe, Xantphos and DPEPhos.

$L^2$ is a bidentate N,N ligand comprising two nitrogen-containing groups. In one embodiment, the bidentate N,N-ligand comprises a nitrogen-containing heteroaryl group and an amino group.

The nitrogen-containing heteroaryl group may include a pyridinyl, pyrrolyl, imidazolyl, pyrazolyl, pyrimidyl, indolyl or quinolinyl groups. In one embodiment, the nitrogen-containing heteroaryl group is pyridinyl. In another embodiment, the nitrogen-containing heteroaryl group is a pyrrolyl group. In another embodiment, the nitrogen-containing heteraryl group is a pyrazinyl group. In another embodiment, the nitrogen-containing heteraryl group is a pyrimidinyl group.

The amino group may comprise primary, secondary or tertiary amino groups. In one embodiment, the amino group is $—NH_2$.

In another embodiment, the bidentate N,N-ligand comprises two amino groups. Each amino group may independently comprise primary, secondary or tertiary amino groups. In one embodiment, both amino group are $—NH_2$.

The bidentate N,N-ligand may selected from the group consisting of ligands of formulae (2), (3), (4), (5), (6), (7), (8), (9) and (10):

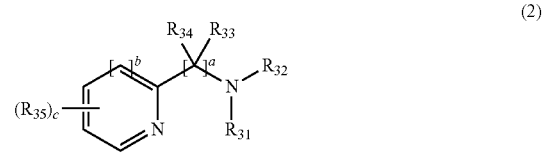

(2)

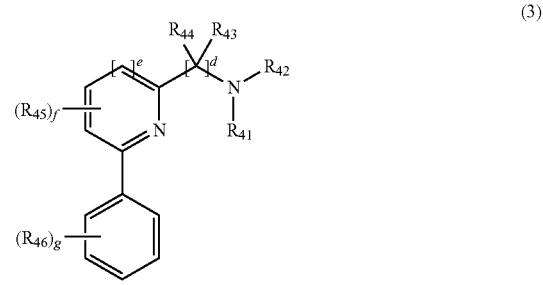

(3)

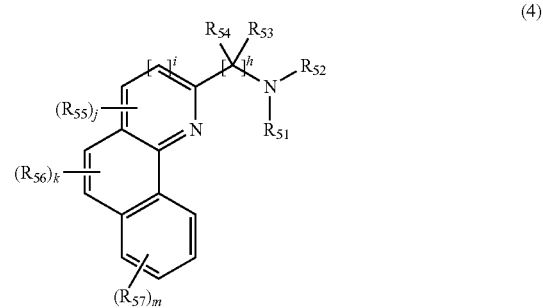

(4)

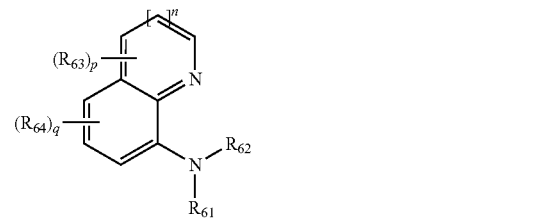

(5)

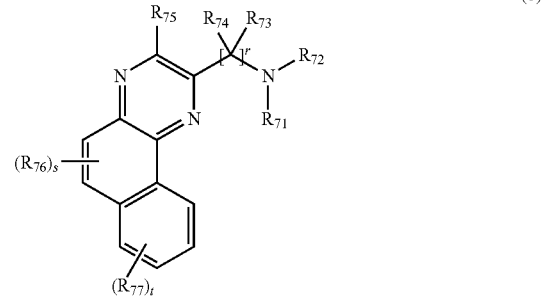

(6)

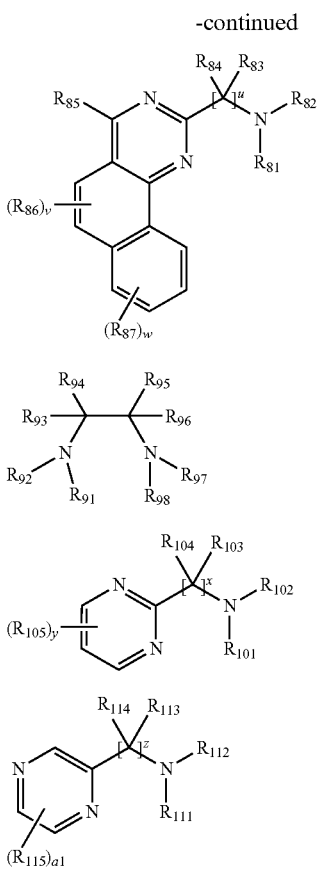

(7)

(8)

(9)

(10)

The ligands (2), (3), (4), (5), (6), (7), (8), (9) and (10) are bidentate ligands as each ligand coordinates to the M atom through the nitrogen-containing groups. For ligands (2), (3), (4), (5), (6), (7), (9) and (10), each ligand coordinates to the M atom through (a) the amino and (b) the or one of the nitrogen-containing heteroaryl functional groups. For ligand (8), the ligand coordinates to the M atom through the two amino groups.

The ligands (3), (4), (6) and (7) are bidentate ligands when the process for the preparation of the [M (Y)$_2$(L$^1$)$_m$(L$^2$)] complex is carried out in the absence of a base and/or the ligands do not comprise hydrogen atoms as depicted below for the HCNN ligands of formulae (3'), (4'), (6') and (7').

In one embodiment, the bidentate N,N-ligand is ligand (2). In another embodiment, the bidentate N,N-ligand is ligand (3). In yet another embodiment, the bidentate N,N-ligand is ligand (4). In another embodiment, the bidentate N,N-ligand is ligand (5). In yet another embodiment, the bidentate N,N-ligand is ligand (6). In another embodiment, the bidentate N,N-ligand is ligand (7). In another embodiment, the bidentate N,N-ligand is ligand (8). In another embodiment, the bidentate N,N-ligand is ligand (9). In another embodiment, the bidentate N,N-ligand is ligand (10).

The bidentate N,N ligands of formulae (2), (3), (4), (5), (6), (7), (8), (9) or (10) may be added to the reaction mixture as the free base. If salts of the ligands are utilised (e.g. the hydrochloride salt), the salt may be treated with a base (such as triethylamine) in order to liberate the free base of the ligand before the free base is added to the reaction mixture.

$R_{31}$ and $R_{32}$ may be independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one embodiment, $R_{31}$ and $R_{32}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In one embodiment, the alkyl groups may be optionally functionalised with one or more substituents such as halide (—F, —Cl, —Br or —I) or alkoxy groups, e.g. methoxy, ethoxy or propoxy. The aryl group may be optionally functionalised with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3$C—).

In one embodiment, one of $R_{31}$ and $R_{32}$ is —H and the other is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one preferred embodiment, one of $R_{31}$ and $R_{32}$ is —H and the other is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as —H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally functionalised with one or more substituents such as halide (—F, —Cl, —Br or —I) or alkoxy groups, e.g. methoxy, ethoxy or propoxy. The aryl group may be optionally functionalised with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3$C—).

In one preferred embodiment, $R_{31}$ and $R_{32}$ are both —H.

The integer "a" may be 1 or 2. In one embodiment, the integer "a" is 1. In this instance, the side chain of the ligand of formula (2) is

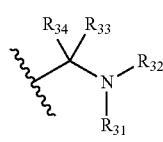

In another embodiment, the integer "a" is 2, in which case, the side chain of the ligand (2) is

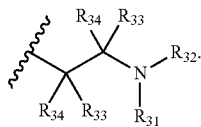

When the integer "a" is 2, each $R_{33}$ may be the same or different and each $R_{34}$ may be the same or different.

$R_{33}$ and $R_{34}$ may be the same or different. When $R_{33}$ and $R_{34}$ are different, the ligand (2) will contain 1 or 2 chiral centres. The ligand (2) can be used as a racemic mixture, as either single enantiomer, as any single diastereomer, as a mixture of enantiomers, or as a mixture of diastereomers, preferably as a single enantiomer. The enantiomers or diastereomers of ligand (2) may be obtained in enantiomerically pure form by resolution of e.g. a racemic mixture of ligand (2).

$R_{33}$ and $R_{34}$ may be independently selected from the group consisting of —H, unsubstituted substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one embodiment, $R_{33}$ and $R_{34}$ are independently selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). More preferably, $R_{33}$ and $R_{34}$ are independently selected from —H, methyl, ethyl, n-propyl, iso-propyl, n-butyl, iso-butyl, sec-butyl, tert-butyl and phenyl.

In one embodiment, one of $R_{33}$ and $R_{34}$ is —H and the other is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one preferred embodiment, one of $R_{33}$ and $R_{34}$ is —H and the other is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as H, methyl, ethyl, n-propyl, iso-propyl, n-butyl, iso-butyl, sec-butyl, tea-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). In one embodiment, $R_{33}$ and $R_{34}$ are independently selected from —H, methyl, ethyl, n-propyl, iso-propyl, n-butyl, iso-butyl, sec-butyl, tert-butyl and phenyl. In another embodiment, one of $R_{33}$ and $R_{34}$ is —H and the other of $R_{33}$ and $R_{34}$ is selected from the group of consisting of —H, methyl, ethyl, n-propyl, iso-propyl, n-butyl, iso-butyl, sec-butyl, tert-butyl and phenyl.

The integer b may be 0 or 1. In one embodiment, b is 0, in which case the nitrogen-containing aromatic ring is a pyrrolyl ring. In another embodiment, b is 1. In this instance, the nitrogen-containing aromatic ring is a pyridinyl ring.

$R_{35}$ may be present or absent. When absent, c is 0 i.e. the pyrrolyl or pyridinyl ring is not substituted. When b is 0, c may be 1, 2 or 3 (i.e. the pyrrolyl ring may have one, two or three $R_{35}$ groups). When b is 1, c may be 1, 2, 3 or 4 (i.e. the pyridinyl ring may have one, two, three or four $R_{35}$ groups). When c is 2, 3 or where appropriate 4, each $R_{35}$ may be the same or different to each other. The or each $R_{35}$ may be independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. Preferably, $R_{35}$ is independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In one embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). Preferably, c is 0 i.e. $R_{35}$ is absent and the pyridine ring is unsubstituted.

In one preferred embodiment, the bidentate N,N-ligand (2) is selected from the group consisting of:

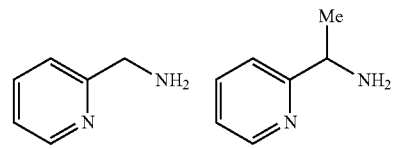

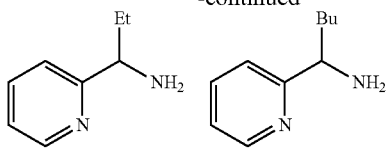

In one particular preferred embodiment, the bidentate N,N-ligand is 2-aminomethylpyridine (AMPY).

For the ligand of formula (3), $R_{41}$ and $R_{42}$ may be independently selected from the groups described above for $R_{31}$ and $R_{32}$.

The integer d may be 1 or 2. In one embodiment, the integer d is 1. In this instance, the side chain of the ligand of formula (3) is

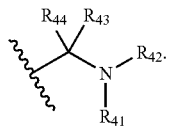

In another embodiment, the integer d is 2, in which case, the side chain of the ligand (3) is

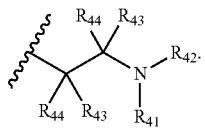

When the integer d is 2, each $R_{43}$ may be the same or different and each $R_{44}$ may be the same or different.

$R_{43}$ and $R_{44}$ may be the same or different. When $R_{43}$ and $R_{44}$ are different, the ligand (3) will contain one or two chiral centres. The ligand (3) can be used as a racemic mixture, as either single enantiomer, as any single diastereomer, as a mixture of enantiomers, or as a mixture of diastereomers, preferably as a single enantiomer. The enantiomers or diastereomers of ligand (3) may be obtained in enantiomerically pure form by resolution of e.g. a racemic mixture of ligand (3). The or each $R_{43}$ and $R_{44}$ may be independently selected from the groups as described above for $R_{33}$ and $R_{34}$.

The integer e may be 0 or 1. In one embodiment, e is 0, in which case the nitrogen-containing aromatic ring is a pyrrolyl ring. In another embodiment, e is 1. In this instance, the nitrogen-containing aromatic ring is a pyridinyl ring.

$R_{45}$ may be present or absent. When absent, f is 0 i.e. the pyrrolyl or pyridinyl ring is not substituted. When e is 0, f may be 1 or 2 (i.e. the pyrrolyl ring may have one or two $R_{45}$ groups). When e is 1, f may be 1, 2 or 3 (i.e. the pyridinyl ring may have one, two or three $R_{45}$ groups). When f is 2 or where appropriate 3, each $R_{45}$ may be the same or different to each other. The or each $R_{45}$ may be selected from the groups described above for $R_{35}$. Preferably, d is 0 i.e. $R_{45}$ is absent.

$R_{46}$ may be present or absent. When absent, g is 0 i.e. the phenyl ring is unsubstituted. When $R_{46}$ is present, g may be 1, 2, 3, 4 or 5. When g is 2, 3, 4 or 5, each $R_{46}$ may be the same or different to each other. The or each $R_{46}$ may be selected from the groups described above for $R_{35}$. In one preferred embodiment, g is 0 i.e. $R_{46}$ is absent. In another preferred embodiment, $R_{46}$ is 1 and is selected from the group consisting of methyl, ethyl, n-propyl, iso-propyl, n-butyl, iso-butyl, sec-butyl and tert-butyl, preferably, 4-Me.

In one preferred embodiment, the bidentate N,N-ligand (3) is selected from the group consisting of:

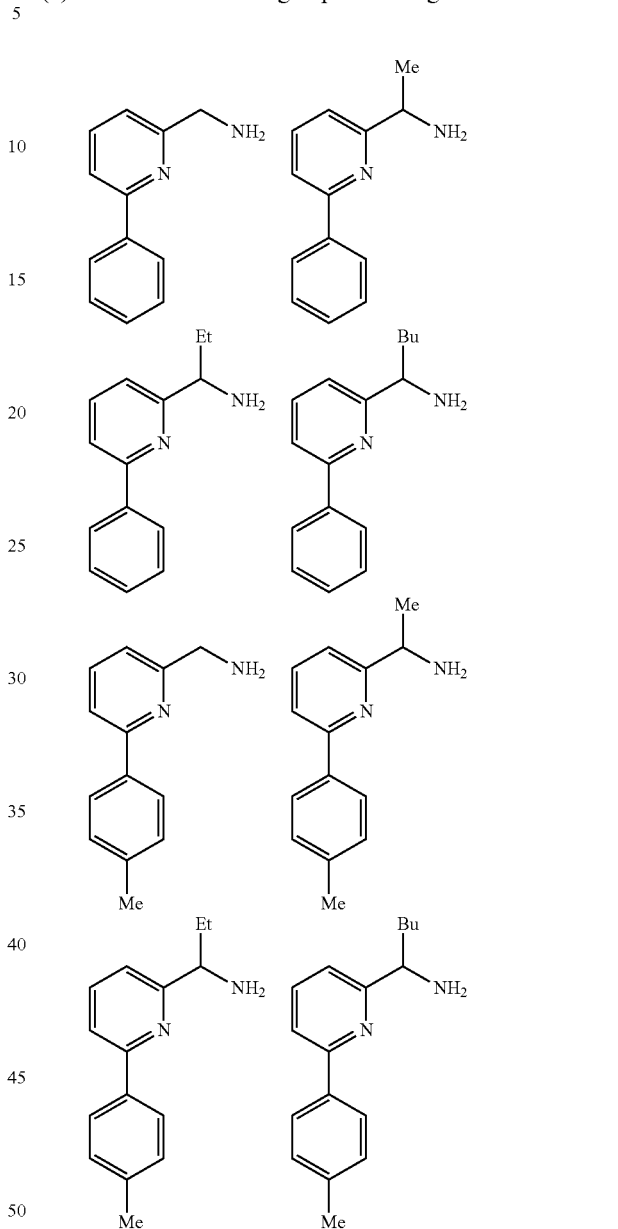

For the ligand of formula (4), $R_{51}$ and $R_{52}$ may be independently selected from the groups described above for $R_{31}$ and $R_{32}$.

The integer h may be 1 or 2. In one embodiment, the integer h is 1. In this instance, the side chain of the ligand of formula (4) is

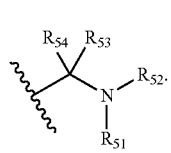

In another embodiment, the integer h is 2, in which case, the side chain of the ligand (4) is

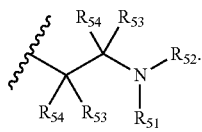

When the integer h is 2, each $R_{53}$ may be the same or different and each $R_{54}$ may be the same or different.

$R_{53}$ and $R_{54}$ may be the same or different. When $R_{53}$ and $R_{54}$ are different, the ligand (4) will contain one or two chiral centres. The ligand (4) can be used as a racemic mixture, as either single enantiomer, as any single diastereomer, as a mixture of enantiomers, or as a mixture of diastereomers, preferably as a single enantiomer. The enantiomers or diastereomers of ligand (4) may be obtained in enantiomerically pure form by resolution of e.g. a racemic mixture of ligand (4). The or each $R_{53}$ and $R_{54}$ may be independently selected from the groups as described above for $R_{33}$ and $R_{34}$.

The integer i may be 0 or 1. In one embodiment, i is 0, in which case the nitrogen-containing aromatic ring is a pyrrolyl ring. In another embodiment, i is 1. In this instance, the nitrogen-containing aromatic ring is a pyridinyl ring.

$R_{55}$ may be present or absent. When absent, i is 0 i.e. the pyrrolyl or pyridinyl ring is not substituted. When i is 0, j may be 1 (i.e. the pyrrolyl ring may have one $R_{55}$ group). When i is 1, j may be 1 or 2 (i.e. the pyridinyl ring may have one or two $R_{55}$ groups). When j is 1 or where appropriate 2, each $R_{55}$ may be the same or different to each other. The or each $R_{55}$ may be selected from the groups described above for $R_{35}$. Preferably, j is 0 i.e. $R_{55}$ is absent.

$R_{56}$ may be present or absent. When absent, k is 0. When $R_{56}$ is present, k may be 1 or 2. When k is 2, each $R_{56}$ may be the same or different to each other. The or each $R_{56}$ may be selected from the groups described above for $R_{35}$. In one preferred embodiment, k is 0 i.e. $R_{56}$ is absent.

$R_{57}$ may be present or absent. When absent, m is 0. When $R_{57}$ is present, m may be 1, 2, 3 or 4. When m is 2, 3 or 4, each $R_{57}$ may be the same or different to each other. The or each $R_{57}$ may be selected from the groups described above for $R_{35}$. In one preferred embodiment, m is 0 i.e. $R_{57}$ is absent.

In one embodiment, the ligand (4) is selected from the substituted AMBQ ligands described in the section below.

In one preferred embodiment, the bidentate N,N-ligand (4) is selected from the group consisting of:

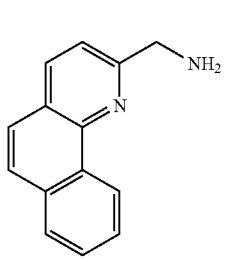 [SMILES: NCc1cnc2ccc3ccccc3c2n1]
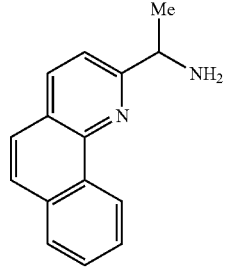

-continued

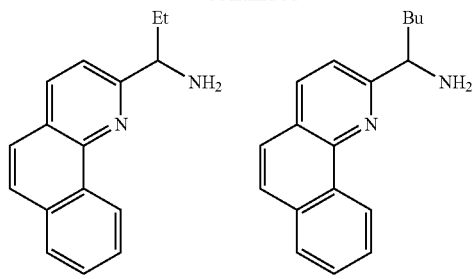

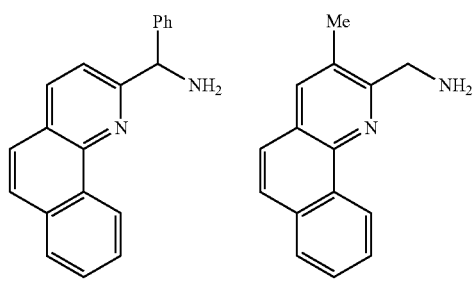

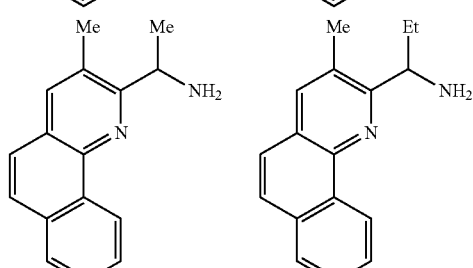

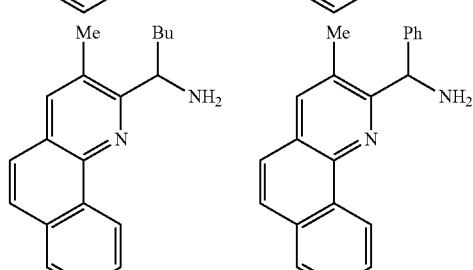

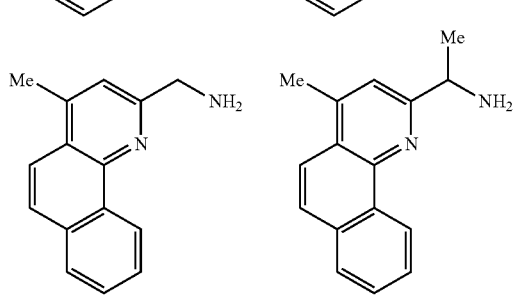

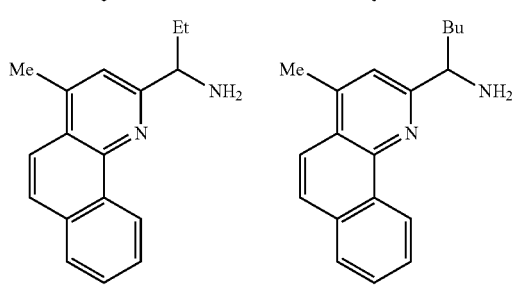

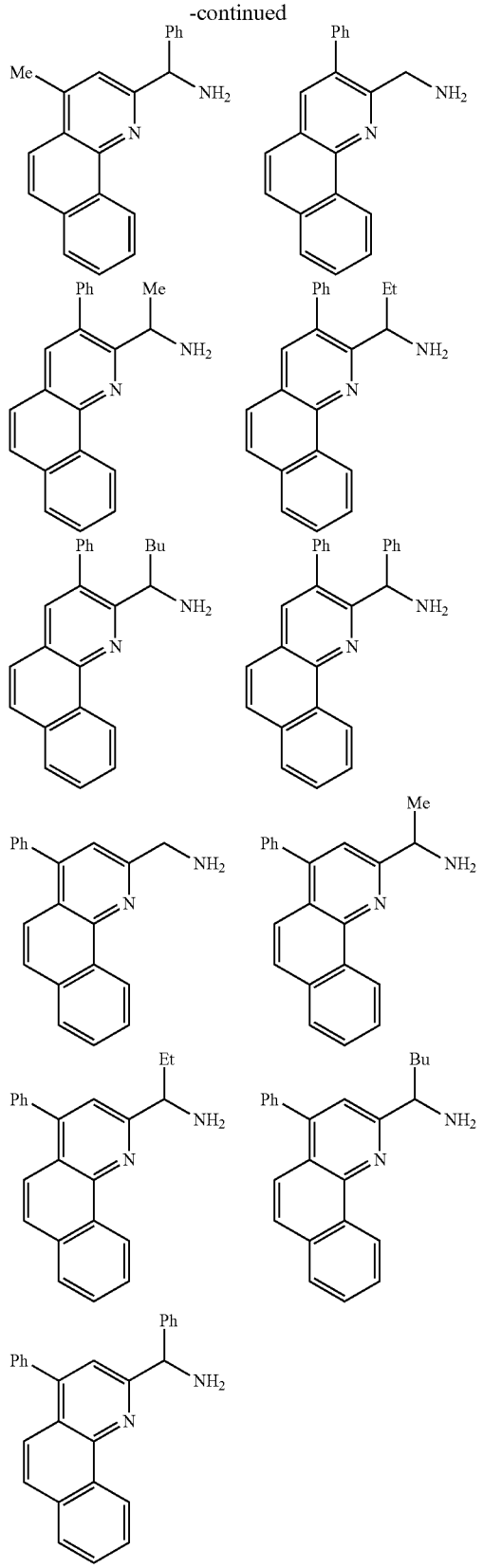

In one particularly preferred embodiment, the bidentate N,N-ligand (4) may be selected from the group consisting of:

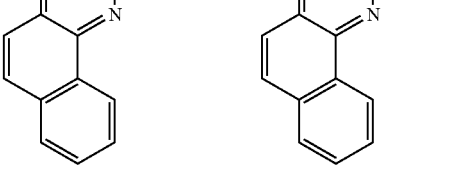
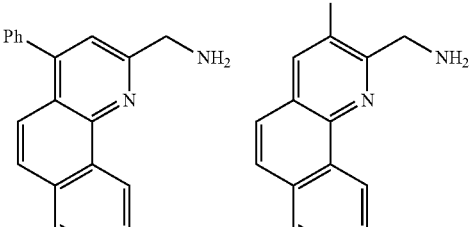
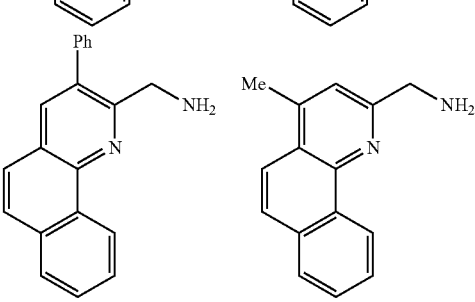
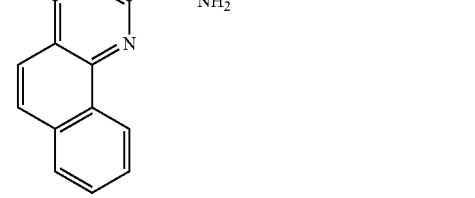

In one particularly preferred embodiment, the bidentate N,N-ligand is 1-(benzo[h]quinoline-2-yl-methanamine (AMBQ).

For the ligand of formula (5), $R_{61}$ and $R_{62}$ may be independently selected from the groups described above for $R_{31}$ and $R_{32}$.

The integer n may be 0 or 1. In one embodiment, n is 0, in which case the nitrogen-containing aromatic ring is a pyrrolyl ring. In another embodiment, n is 1. In this instance, the nitrogen-containing aromatic ring is a pyridinyl ring.

$R_{63}$ may be present or absent. When absent, p is 0 i.e. the pyrrolyl or pyridinyl ring is not substituted. When n is 0, p may be 1 or 2 (i.e. the pyrrolyl ring may have one or two $R_{63}$ groups). When n is 1, p may be 1, 2 or 3 (i.e. the pyridinyl ring may have one, two or three $R_{63}$ groups). When p is 2 or where appropriate 3, each $R_{63}$ may be the same or different to each other. The or each $R_{63}$ may be selected from the groups described above for $R_{35}$. In one embodiment, p is 0 i.e. $R_{63}$ is absent.

$R_{64}$ may be present or absent. When absent, q is 0. When $R_{64}$ is present, q may be 1, 2 or 3. When q is 2 or 3, each $R_{64}$ may be the same or different to each other. The or each $R_{64}$ may be selected from the groups described above for $R_{35}$. In one embodiment, q is 0 i.e. $R_{64}$ is absent.

In one preferred embodiment, the ligand (5) may be:

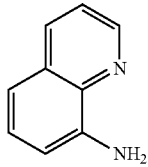

For the ligand of formula (6), $R_{71}$ and $R_{72}$ may be independently selected from the groups described above for $R_{31}$ and $R_{32}$.

The integer r may be 1 or 2. In one embodiment, the integer r is 1. In this instance, the side chain of the ligand of formula (6) is

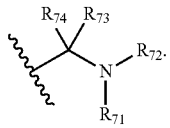

In another embodiment, the integer r is 2, in which case, the side chain of the ligand (6) is

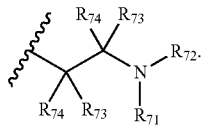

When the integer r is 2, each $R_{73}$ may be the same or different and each $R_{74}$ may be the same or different.

$R_{73}$ and $R_{74}$ may be the same or different. When $R_{73}$ and $R_{74}$ are different, the ligand (6) will contain one or two chiral centres. The ligand (6) can be used as a racemic mixture, as either single enantiomer, as any single diastereomer, as a mixture of enantiomers, or as a mixture of diastereomers, preferably as a single enantiomer. The enantiomers or diastereomers of ligand (6) may be obtained in enantiomerically pure form by resolution of e.g. a racemic mixture of ligand (6). The or each $R_{73}$ and $R_{74}$ may be independently selected from the groups as described above for $R_{33}$ and $R_{34}$.

$R_{75}$ may be selected from —H or the groups as described above for $R_{35}$.

$R_{76}$ may be present or absent. When absent, s is 0. When $R_{76}$ is present, s may be 1 or 2. When s is 2, each $R_{76}$ may be the same or different to each other. The or each $R_{76}$ may be selected from the groups described above for $R_{35}$. In one preferred embodiment, s is 0 i.e. $R_{76}$ is absent.

$R_{77}$ may be present or absent. When absent, t is 0. When $R_{77}$ is present, t may be 1, 2, 3 or 4. When t is 2, 3 or 4, each $R_{77}$ may be the same or different to each other. The or each $R_{77}$ may be selected from the groups described above for $R_{35}$. In one preferred embodiment, t is 0 i.e. $R_{77}$ is absent.

In one preferred embodiment, the ligand (6) may be:

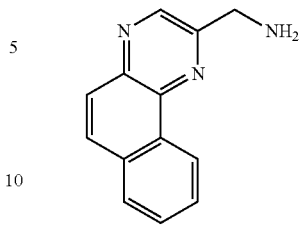

For the ligand of formula (7), $R_{81}$ and $R_{82}$ may be independently selected from the groups described above for $R_{31}$ and $R_{32}$.

The integer u may be 1 or 2. In one embodiment, the integer u is 1. In this instance, the side chain of the ligand of formula (7) is

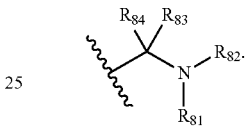

In another embodiment, the integer u is 2, in which case, the side chain of the ligand (7) is

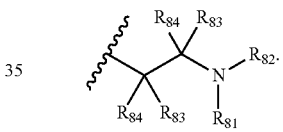

When the integer u is 2, each $R_{83}$ may be the same or different and each $R_{84}$ may be the same or different.

$R_{83}$ and $R_{84}$ may be the same or different. When $R_{83}$ and $R_{84}$ are different, the ligand (7) will contain one or two chiral centres. The ligand (7) can be used as a racemic mixture, as either single enantiomer, as any single diastereomer, as a mixture of enantiomers, or as a mixture of diastereomers, preferably as a single enantiomer. The enantiomers or diastereomers of ligand (7) may be obtained in enantiomerically pure form by resolution of e.g. a racemic mixture of ligand (7).

The or each $R_{53}$ and $R_{54}$ may be independently selected from the groups as described above for $R_{33}$ and $R_{34}$.

$R_{55}$ may be selected from —H or the groups as described above for $R_{35}$.

$R_{56}$ may be present or absent. When absent, v is 0. When $R_{56}$ is present, v may be 1 or 2. When v is 2, each $R_{56}$ may be the same or different to each other. The or each $R_{56}$ may be selected from the groups described above for $R_{35}$. In one preferred embodiment, v is 0 i.e. $R_{56}$ is absent.

$R_{57}$ may be present or absent. When absent, w is 0. When $R_{57}$ is present, w may be 1, 2, 3 or 4.

When w is 2, 3 or 4, each $R_{57}$ may be the same or different to each other. The or each $R_{57}$ may be selected from the groups described above for $R_{35}$. In one preferred embodiment, w is 0 i.e. $R_{57}$ is absent.

In one preferred embodiment, the ligand (7) may be:

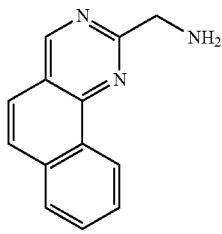 [SMILES: NCc1ncc2ccc3ccccc3c2n1]

For ligand (8), $R_{91}$ and $R_{92}$ may be independently selected from the groups defined above for $R_{31}$ and $R_{32}$. $R_{95}$ and $R_{97}$ may independently be selected from the groups defined above for $R_{31}$ and $R_{32}$.

$R_{93}$, $R_{94}$, $R_{95}$ and $R_{96}$ may each independently be selected from the group consisting of hydrogen, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted-$C_{6-20}$-aryl, substituted-$C_{6-20}$-aryl, unsubstituted-$C_{6-20}$-aryloxy and substituted-$C_{6-20}$-aryloxy. The substituents may be selected from the group consisting of one or more unsubstituted $C_{1-20}$-alkyl, unsubstituted $C_{3-20}$-cycloalkyl, unsubstituted $C_{1-20}$-alkoxy, unsubstituted $C_{2-20}$-cycloalkoxy, unsubstituted-$C_{6-20}$-aryl, unsubstituted-$C_{6-20}$-aryloxy, —OH, —CN, —NR$^a$R$^b$, —COOR$^a$, —CONR$^a$R$^b$ and CF$_3$.

In one embodiment, $R_{93}$, $R_{94}$, $R_{95}$ and $R_{96}$ are each independently selected from the group consisting of hydrogen, unsubstituted $C_{1-20}$-alkyl, substituted $C_{1-20}$-alkyl, unsubstituted-$C_{6-20}$-aryl, substituted-$C_{6-20}$-aryl, unsubstituted-$C_{6-20}$-aryloxy and substituted-$C_{6-20}$-aryloxy. The substituents may be selected from the group consisting of one or more unsubstituted $C_{1-20}$-alkyl, unsubstituted $C_{1-20}$-alkoxy, unsubstituted-$C_{6-20}$-aryl, unsubstituted-$C_{6-20}$-aryloxy and OH. In another embodiment, the groups $R_{93}$, $R_{94}$, $R_{95}$ and $R_{96}$ may each independently be selected from the group consisting of hydrogen, unsubstituted-$C_{6-20}$-aryl and substituted-$C_{6-20}$-aryl. In another embodiment, $R_{93}$, $R_{94}$, $R_{95}$ and $R_{96}$ are each independently selected from the group consisting of hydrogen or phenyl. In yet another embodiment, one of $R_{93}$ and $R_{94}$ is phenyl and the other of $R_{95}$ and $R_{96}$ is hydrogen. In another embodiment, one of $R_{95}$ and $R_{96}$ is phenyl and the other of $R_{95}$ and $R_{96}$ is hydrogen.

In one embodiment, $R_{93}$, $R_{94}$, $R_{95}$ and $R_{96}$ are each hydrogen.

$R_{93}$ and $R_{94}$ together with the carbon atom to which they are bound and/or $R_{95}$ and $R_{96}$ together with the carbon atom to which they are bound may form an unsubstituted $C_{3-20}$-cycloalkyl or substituted $C_{3-20}$-cycloalkyl. The substituents may be selected from the group consisting of one or more unsubstituted $C_{1-20}$-alkyl, unsubstituted $C_{3-20}$-cycloalkyl, unsubstituted $C_{1-20}$-alkoxy, unsubstituted $C_{2-20}$-cycloalkoxy, unsubstituted-$C_{6-20}$-aryl, unsubstituted-$C_{6-20}$-aryloxy, —OH, —CN, —NR$^a$R$^b$, —COOR$^a$, —CONR$^a$R$^b$ and CF$_3$.

In another embodiment, one of $R_{93}$ and $R_{94}$ and one of $R_{95}$ and $R_{96}$ together with the carbon atoms to which they are bound form an unsubstituted $C_{3-20}$-cycloalkyl or substituted $C_{3-20}$-cycloalkyl. The substituents may be selected from the group consisting of one or more unsubstituted $C_{1-20}$-alkyl, unsubstituted $C_{3-20}$-cycloalkyl, unsubstituted $C_{1-20}$-alkoxy, unsubstituted $C_{2-20}$-cycloalkoxy, unsubstituted-$C_{6-20}$-aryl, unsubstituted-$C_{6-20}$-aryloxy, —OH, —CN, —NR$^a$R$^b$, —COOR$^a$, —CONR$^a$R$^b$ and CF$_3$.

In yet another embodiment, one of $R_{93}$ and $R_{94}$ and one of $R_{95}$ and $R_{96}$ together with the carbon atoms to which they are bound form an unsubstituted $C_{5-10}$-cycloalkyl or substituted $C_{5-10}$-cycloalkyl. The substituents may be selected from the group consisting of one or more unsubstituted $C_{1-20}$-alkyl, unsubstituted $C_{3-20}$-cycloalkyl, unsubstituted $C_{1-20}$-alkoxy, unsubstituted $C_{2-20}$-cycloalkoxy, unsubstituted-$C_{6-20}$-aryl, unsubstituted-$C_{6-20}$-aryloxy and —OH.

In another embodiment, $R_{93}$ and $R_{94}$ together with the carbon atom to which they are bound and/or $R_{95}$ and $R_{96}$ together with the carbon atom to which they are bound form an unsubstituted $C_{5-10}$-cycloalkyl or substituted $C_{5-10}$-cycloalkyl. The substituents may be selected from the group consisting of one or more unsubstituted $C_{1-20}$-alkyl, unsubstituted $C_{3-20}$-cycloalkyl, unsubstituted $C_{1-20}$-alkoxy, unsubstituted $C_{2-20}$-cycloalkoxy, unsubstituted-$C_{6-20}$-aryl, unsubstituted-$C_{6-20}$-aryloxy and —OH.

For the ligand of formula (9), $R_{101}$ and $R_{102}$ may be independently selected from the groups described above for $R_{31}$ and $R_{32}$.

The integer x may be 1 or 2. In one embodiment, the integer x is 1. In this instance, the side chain of the ligand of formula (9) is

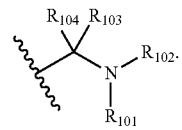

In another embodiment, the integer x is 2, in which case, the side chain of the ligand (9) is

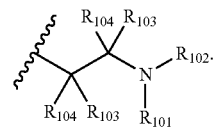

When the integer x is 2, each $R_{103}$ may be the same or different and each $R_{104}$ may be the same or different.

$R_{103}$ and $R_{104}$ may be the same or different. When $R_{103}$ and $R_{104}$ are different, the ligand (9) will contain one or two chiral centres. The ligand (9) can be used as a racemic mixture, as either single enantiomer, as any single diastereomer, as a mixture of enantiomers, or as a mixture of diastereomers, preferably as a single enantiomer. The enantiomers or diastereomers of ligand (9) may be obtained in enantiomerically pure form by resolution of e.g. a racemic mixture of ligand (9). The or each $R_{103}$ and $R_{104}$ may be independently selected from the groups as described above for $R_{33}$ and $R_{34}$.

$R_{105}$ may be present or absent. When absent, y is 0. When $R_{105}$ is present, y may be 1, 2 or 3. When y is 2 or 3, each $R_{105}$ may be the same or different to each other. The or each $R_{105}$ may be selected from the groups described above for $R_{35}$. In one preferred embodiment, y is 0 i.e. $R_{105}$ is absent.

In one preferred embodiment, the ligand (9) may be:

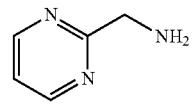

For the ligand of formula (10), $R_{111}$ and $R_{112}$ may be independently selected from the groups described above for $R_{31}$ and $R_{32}$.

The integer z may be 1 or 2. In one embodiment, the integer z is 1. In this instance, the side chain of the ligand of formula (10) is

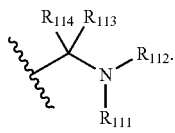

In another embodiment, the integer is 2, in which case, the side chain of the ligand (10) is

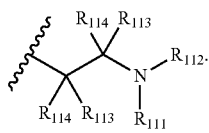

When the integer z is 2, each $R_{113}$ may be the same or different and each $R_{114}$ may be the same or different.

$R_{113}$ and $R_{114}$ may be the same or different. When $R_{113}$ and $R_{114}$ are different, the ligand (10) will contain one or two chiral centres. The ligand (10) can be used as a racemic mixture, as either single enantiomer, as any single diastereomer, as a mixture of enantiomers, or as a mixture of diastereomers, preferably as a single enantiomer. The enantiomers or diastereomers of ligand (10) may be obtained in enantiomerically pure form by resolution of e.g. a racemic mixture of ligand (10). The or each $R_{113}$ and $R_{114}$ may be independently selected from the groups as described above for $R_{33}$ and $R_{34}$.

$R_{115}$ may be present or absent. When absent, the integer "a1" is 0. When $R_{115}$ is present, "a1" may be 1, 2 or 3. When "a1" is 2 or 3, each $R_{115}$ may be the same or different to each other. The or each $R_{115}$ may be selected from the groups described above for $R_{35}$. In one preferred embodiment, "a1" is 0 i.e. $R_{115}$ is absent.

In one preferred embodiment, the ligand (10) may be:

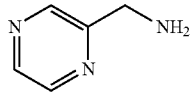

In one embodiment, the $[M(Y)_2(L^1)_m(L^2)]$ complex may be selected from the group consisting of:

[Ru(OAc)$_2$(dppp) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(dppb) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(dppf) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinolineor or 2-(aminomethyl)pyrimidine (AMPYRIM);

[Ru(OAc)$_2$(DCyPFc) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(DiPFc) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(DB$^t$PFc) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(Josiphos*) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(BINAP) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(TolBINAP) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(Xantphos) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(DPEPhos) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(dppm) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(dppe) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(dppp) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(dppb) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(dppf) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(DCyPFc) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(DiPFc) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(DB'PFc) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(Josiphos*) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(BINAP) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(TolBINAP) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(Xantphos) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(DPEPhos) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(dppm) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM); and

[Os(OAc)$_2$(dppe) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM).

In another embodiment, the [M (Y)$_2$(L$^1$)$_m$(L$^2$)] complex may be selected from the group consisting of:
[Ru(OAc)$_2$(dppp) AMPY];
[Ru(OAc)$_2$(dppb) AMPY];
[Ru(OAc)$_2$(dppf) AMPY];
[Ru(OAc)$_2$(dppf) EN];
[Ru(OAc)$_2$(BINAP) AMPY];
[Ru(OAc)$_2$(dppb) (quinoline-8-NH$_2$)];
[Ru(OAc)$_2$(PPh$_3$)$_2$(2-(aminomethyl)-6-(4-methylphenyl) pyridine)];
[Ru(OAc)$_2$(dppb) (2-(aminomethyl)-6-(4-methylphenyl) pyridine)];
[Ru(OAc)$_2$(BINAP) EN];
[Ru(OAc)$_2$(Xantphos) AMPY];
[Ru(OAc)$_2$(DPEPhos) AMPY];
[Ru(OAc)$_2$(dppb) AMPYRIM];
[Ru(OAc)$_2$(dppp) AMPYRIM];
[Ru(OAc)$_2$(dppf) AMPYRIM];
[Ru(OAc)$_2$(dppm) AMPY];
[Ru(OAc)$_2$(dppm) EN];
[Ru(OAc)$_2$(dppm) AMPYRIM].

The [M (Y)$_2$(L)$_2$] complex is reacted with the phosphorus ligand L$^1$ and the bidentate N,N ligand L$^2$ in a polar aprotic solvent to form the [M (Y)$_2$(L$^1$)$_m$(L$^2$)] complex. The polar aprotic solvent may be selected from the group consisting of aromatic solvents (such as benzene or toluene) and chlorinated solvents (such as chloroform or dichloromethane).

When chlorinated solvents (e.g. dichloromethane) or aromatic solvents (e.g. toluene) are used, the reaction mixture is typically in solution as the components of the reaction have been dissolved. The product complex, therefore, typically requires precipitation from the reaction mixture (e.g. through the addition of an alkane solvent, such as pentane or hexane).

In another embodiment, the polar aprotic solvent may be a ketone solvent. By "ketone solvent" we mean a liquid ketone which has a boiling point at atmospheric pressure (i.e. $1.0135 \times 10^5$ Pa) below 180° C. and more preferably below 165° C. Preferred examples are acetone, methyl-ethyl ketone (MEK) also known as 2-butanone, methyl-isobutyl ketone (MIBK) also known as 4-methyl-2-pentanone, diethylketone also known as 3-pentanone and cyclic ketones such as cyclopentanone and cyclohexanone. A particularly preferred ketone solvent is MEK. Another particularly preferred ketone solvent is acetone.

There are several advantages associated with using a ketone solvent. One advantage is that ketone solvents such as acetone are non-chlorinated and have a low toxicological potential.

Another advantage is that reaction solvent volumes may be reduced in comparison to the use of e.g dichloromethane.

Furthermore, the ketone solvents are generally easier to remove by evaporation.

When the polar aprotic solvent is a ketone solvent, the complexes may be slurried in the ketone solvent. "Slurry" means a heterogeneous mixture of at least a portion of the complex (or complexes) in the ketone solvent. "Slurry" therefore includes a mixture of a complex or complexes which are partially present as a solid, as well as being partially dissolved in the ketone solvent. The complexes which can be slurried include the [M $(Y)_2(L)_2$] starting material, intermediate metal complexes and/or the [M $(Y)_2(L^1)_m(L^2)$] product.

It is envisaged that another advantage is that the ketone solvent may be capable of removing large quantities of the monodentate phosphorus ligand L which is released from the [M $(Y)_2(L)_2$] starting material during the reaction. For example, when [Ru(OAc)$_2$(PPh$_3$)$_2$] is utilised as the starting material and acetone as the ketone solvent, it is envisaged that substantially complete removal of PPh$_3$ can be obtained. In this respect, the metal complexes are generally in solid form in reaction mixture (because they form a slurry in the ketone solvent), while the ligand L is substantially dissolved in the ketone solvent, together with unreacted ligand $L^1$.

In another embodiment, the [M $(Y)_2(L)_2$] starting material may form a slurry with the ketone solvent but on reaction with the phosphorus ligand $L^1$ or bidentate N,N ligand $L^2$ may form intermediate metal complexes and/or the [M $(Y)_2(L^1)_m(L^2)$] product which are soluble in the ketone solvent. In this instance, the ketone solvent may still be capable of removing large quantities of the monodentate phosphorus ligand L which is released from the [M $(Y)_2(L)_2$] starting material during the reaction. If any solid [M $(Y)_2(L)_2$] starting material remains on termination of the reaction, the [M $(Y)_2(L)_2$] starting material may be separated from the soluble [M $(Y)_2(L^1)_m(L^2)$] product by filtering, decanting or centrifuging.

Any suitable volume of polar aprotic solvent may be used. For example, the ratio of [M $(Y)_2(L)_2$] complex to solvent may be about 25 to about 250 g/L, such as about 50 to about 150 g/L. In certain embodiments, the ratio may be about 60 to about 125 g/L.

The reactants may be added in any suitable order, but in one preferred process of the invention, the phosphorus ligand $L^1$ may be added (e.g. portion wise) to a mixture of the [M $(Y)_2(L)_2$] complex in the polar aprotic solvent and, after stirring for a suitable period of time and at a suitable temperature, the bidentate N,N ligand $L^2$ may be added (e.g. portion wise). If desired, the bidentate N,N ligand $L^2$ may be added to the reaction mixture as a solution in polar aprotic solvent. The reaction may then be stirred for a further suitable period of time and at a suitable temperature. If desired, the polar aprotic solvent may be saturated with an inert gas (e.g. nitrogen) before it is added to the reaction mixture.

In another embodiment, the bidentate N,N ligand $L^2$ may be added (e.g. portion wise) to a mixture of the [M $(Y)_2(L)_2$] complex in the polar aprotic solvent and, after stirring for a suitable period of time and at a suitable temperature, the phosphorus ligand $L^1$ may be added (e.g. portion wise). If desired, the bidentate N,N ligand $L^2$ may be added to the reaction mixture as a solution in polar aprotic solvent. The reaction may then be stirred for a further suitable period of time and at a suitable temperature. If desired, the polar aprotic solvent may be saturated with an inert gas (e.g. nitrogen) before it is added to the reaction mixture.

The phosphorus ligand $L^1$ may be present in stoichiometric or slight excess to the [M $(Y)_2(L)_2$] complex. When stoichiometric quantities are utilised, the methodology does not require the use of excess ligand and thereby makes the whole process highly efficient and atom-economical for commercial production. When a slight excess is utilised, the molar ratio of the phosphorus ligand $L^1$:the [M $(Y)_2(L)_2$] complex may be about 1.001 to about 1.2:about 1, such as about 1.002:about 1, about 1.01:about 1, about 1.1:about 1, about 1.15:about 1, or about 1.15:about 1.

The bidentate N,N ligand $L^2$ may be present in stoichiometric or slight excess to the [M $(Y)_2(L)_2$] complex. When stoichiometric quantities are utilised, the methodology does not require the use of excess ligand and thereby makes the whole process highly efficient and atom-economical for commercial production. When a slight excess is utilised, the molar ratio of the bidentate N,N ligand $L^2$:the [M $(Y)_2(L)_2$] complex may be about 1.05 to about 1.75:about 1, such as about 1.1 to about 1.5:about 1, such as about 1.4 to about 1.5:about 1.

The reaction may be carried out under an inert atmosphere, such as under nitrogen or argon, preferably nitrogen.

The process of the invention may be preferably carried out at one or more temperatures in the range of about −10° C. to the reflex temperature of the polar aprotic solvent e.g. about 150° C. More preferably, the process of the invention may be carried out from about −5° C. to about 120° C. When the polar aprotic solvent is a chlorinated or ketone solvent, the process may be carried out at one or more temperatures in the range of about 0° C. to about 50° C., for example 15° C. to about 30° C., for instance, room temperature. When the polar aprotic solvent is an aromatic solvent, the process may be carried out at one or more temperature in the range of about 50° C. to about 120° C., such as about 75° C. to about 115° C. In one embodiment, the temperature of the process may be the boiling point of the aromatic solvent (e.g. about 111° C. for toluene). It is preferred that the temperature is maintained below the decomposition temperature, and so, when the [M $(Y)_2(L)_2$] starting material and/or the [M $(Y)_2(L^1)_m(L^2)$] product are known to decompose within the temperature ranges given above, the temperature should be maintained below the decomposition temperature.

The reaction may be carried out for a period of from about several minutes to about 72 hours but is usually complete within about 24 hours. On completion, the [M $(Y)_2(L^1)_m(L^2)$] product is separated from the reaction mixture by any appropriate method which is dependent upon the physical form of the product. When the [M $(Y)_2(L^1)_m(L^2)$] complex is in solution, an anti-solvent (e.g. an alkane solvent such as pentane or hexane) may be added to precipitate the complex from solution. Generally, when the [M (Y)$_2$(L$^1$)$_m$(L$^2$)] complex is a solid, it may be recovered from the reaction mixture by filtering, decanting or centrifuging.

When a ketone solvent is used, if desired, the reaction mixture may be allowed to cool to a temperature which is above room temperature and below the reaction temperature of the ketone solvent (for example, about 45-50° C. when the ketone solvent is methyl ethyl ketone) before recovering the [M (Y)$_2$(L$^1$)$_w$ (L$^2$)] complex. Recovering the [M (Y)$_2$(L$^1$)$_{m'}$ (L$^2$)] complex while the reaction mixture remains warm has the advantage that the free phosphorus ligand L$^1$ and/or its oxide (if present) is more soluble in warm ketone solvent, thus facilitating the separation of the [M (Y)$_2$(L$^1$)$_m$(L$^2$)] complex from the reaction mixture. If free phosphorus ligand L$^1$ and/or its oxide is present, the presence of these compounds may colour the [M (Y)$_2$(L$^1$)$_m$(L$^2$)] product. In this case, the [M (Y)$_2$ (L$^1$)$_m$(L$^2$)] complex may be stirred one or more times (e.g. 1, 2 or 3 times) in ketone solvent (e.g. acetone) until the free phosphorus ligand L$^1$ and/or its oxide is substantially removed. Alternatively or in addition, the [M (Y)$_2$(L$^1$)$_m$(L$^2$)] complex may be washed one or more times (e.g. 1, 2 or 3 times) with ketone solvent. The ketone solvent aliquots may be warmed (e.g. to 45-50° C.) before the [M (Y)$_2$ (L$^1$)$_m$(L$^2$)] complex is washed.

When the [M (Y)$_2$(L$^1$)$_m$(L$^2$)] complex is in solution, an anti-solvent (e.g. an alkane solvent such as pentane or hexane) may be added to precipitate the complex from solution. Alternatively, the polar aprotic solvent may be removed (for example, by distillation or stripping methods) from the solution of the [M (Y)$_2$(L$^1$)$_m$(L$^2$)] product until a more concentrated solution of the [M (Y)$_2$(L$^1$)$_m$(L$^2$)] product in a remaining portion of the polar aprotic solvent is obtained. Then, an anti-solvent such as an alkane may be added to cause precipitation of the complex. Suitable alkanes have boiling points at atmospheric pressure between 0 to 150° C. Alkanes that may be used are low boiling alkanes such as pentane isomers, hexane isomers, heptane isomers or octane isomers. Preferably, the alkane is n-pentane, n-hexane cyclohexane or n-heptane and more preferably cyclohexane.

Howsoever the [M (Y)$_2$(L$^1$)$_m$(L$^2$)] complex is recovered, the [M (Y)$_2$(L$^1$)$_m$(L$^2$)] complex may then be dried using known methods, for example at temperatures in the range 10-60° C. and preferably 20-40° C. under 1-30 mbar vacuum for 1 hour to 5 days. If desired the complex may be recrystallized, although this may not be necessary.

The [M (Y)$_2$(L$^1$)$_m$(L$^2$)] complex obtained may contain residual polar aprotic solvent. Hence, the complexes thus obtained may be suitable as catalysts for applications using polar aprotic solvents.

In certain embodiments, the [M (Y)$_2$(L$^1$)$_m$(L$^2$)] complex prepared according to the process of the present invention is substantially trans-[M (Y)$_2$(L$^1$)$_m$(L$^2$)] i.e. the [M (Y)$_2$ (L$^1$)$_m$(L$^2$)] complex comprises the structure:

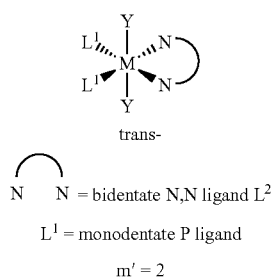

-continued

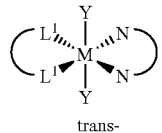

The trans-terminology is determined with reference to orientation of the Y ligands. In this respect, the octahedral complex is described as trans- when the Y ligands are 180° C. to each other. Conversely, the octahedral complex is described as cis- when the Y ligands are mutually adjacent to each other.

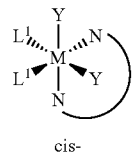

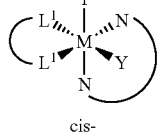

In certain embodiments, the [M (Y)$_2$(L$^1$)$_m$(L$^2$)] complex prepared according to the process of the present invention is substantially cis-[M (Y)$_2$(L$^1$)$_m$(L$^2$)].

In one embodiment, the [M (X)$_2$(L$^1$)$_m$(L$^2$)] complex may be selected from the group consisting of: trans-[Ru(OAc)$_2$ (PPh$_3$)$_2$ AMPY];
trans-[Ru(OAc)$_2$(dppp) AMPY];
trans-[Ru(OAc)$_2$(dppb) AMPY];
trans-[Ru(OAc)$_2$(dppf) AMPY];
trans-[Ru(OAc)$_2$(dppf) EN];
trans-[Ru(OAc)$_2$(BINAP) AMPY];
trans-[Ru(OAc)$_2$(dppb) (quinoline-8-NH$_2$)];
trans-[Ru(OAc)$_2$(PPh$_3$)$_2$(2-(aminomethyl)-6-(4-methylphenyl)pyridine)];
trans-[Ru(OAc)$_2$(dppb) (2-(aminomethyl)-6-(4-methylphenyl)pyridine)];
trans-[Ru(OAc)$_2$(BINAP) EN];
trans-[Ru(OAc)$_2$(Xantphos) AMPY];
trans-[Ru(OAc)$_2$(DPEPhos) AMPY];
trans-[Ru(OAc)$_2$(dppb) AMPYRIM];
trans-[Ru(OAc)$_2$(dppp) AMPYRIM];
trans-[Ru(OAc)$_2$(dppf) AMPYRIM];

trans-[Ru(OAc)$_2$(dppm) AMPY];
trans-[Ru(OAc)$_2$(dppe) AMPY];

In another aspect, the invention provides a process for the preparation of an [M (Y)$_2$(L$^1$)$_{m'}$(L$^2$)] complex, the process comprising the step of:

reacting an [M (X)$_2$(L)$_3$] complex, an alkali metal carboxylate salt, a phosphorus ligand L$^1$ and a bidentate N,N ligand L$^2$ in a polar aprotic solvent, an alcohol solvent or a mixture thereof to form the [M (Y)$_2$(L$^1$)$_{m'}$(L$^2$)] complex;

wherein,

M is ruthenium or osmium;

X is a halide ligand;

Y is a carboxylate ligand;

L is a monodentate phosphorus ligand;

L$^1$ is a monodentate phosphorus ligand which is different to L, or a bidentate phosphorus ligand;

m' is 1 or 2, wherein, when m' is 1, L$^1$ is a bidentate phosphorus ligand;

when m' is 2, each L$^1$ is a monodentate phosphorus ligand; and

L$^2$ is a bidentate N,N ligand comprising two nitrogen-containing groups.

M, Y, L, L$^1$, L$^2$, m', the [M (Y)$_2$(L$^1$)$_{m'}$(L$^2$)] complex, the polar aprotic solvent, the reaction conditions and the recovery of the [M (Y)$_2$(L$^1$)$_{m'}$(L$^2$)] complex are as generally described above.

X is a halide ligand, such as —Cl, —Br, and —I. Preferably, X is —Cl.

In one embodiment, the [M (X)$_2$(L)$_3$] complex may be a [ruthenium (Hal)$_2$(PR$_{11}$R$_{12}$R$_{13}$)$_3$] complex, wherein R$_{11}$, R$_{12}$ and R$_{13}$ are as described above and may be, for example, independently selected from unsubstituted C$_{5-20}$-aryl and substituted C$_{5-20}$-aryl. In one preferred embodiment, the [M (X)$_2$(L)$_3$] complex may be [Ru Cl$_2$ (PPh$_3$)$_3$]. In another preferred embodiment, the [M (X)$_2$(L)$_3$] complex may be [Ru Cl$_2$ (P(tolyl)$_3$)$_3$], such as [Ru Cl$_2$ (P(p-tolyl)$_3$)$_3$].

In another embodiment, the [M (X)$_2$(L)$_3$] complex may be an [osmium (Hal)$_2$(PR$_{11}$R$_{12}$R$_{13}$)$_3$] complex, wherein R$_{11}$, R$_{12}$ and R$_{13}$ are as described above and may be, for example, independently selected from unsubstituted C$_{5-20}$-aryl and substituted C$_{5-20}$-aryl. In one preferred embodiment, the [M (X)$_2$(L)$_3$] complex may be [Os Cl$_2$ (PPh$_3$)$_3$]. In another preferred embodiment, the [M (X)$_2$(L)$_3$] complex may be [Os Cl$_2$ (P(tolyl)$_3$)$_3$], such as [Os Cl$_2$ (P(p-tolyl)$_3$)$_3$].

The alkali metal carboxylate may be selected from the group consisting of sodium carboxylates and potassium carboxylates, such as sodium acetate and potassium acetate. The alkali metal carboxylate may be anhydrous.

The [M (X)$_2$(L)$_3$] complex, an alkali metal carboxylate salt, a phosphorus ligand L$^1$ and a bidentate N,N ligand L$^2$ is reacted in a polar aprotic solvent, an alcohol solvent or a mixture thereof to form the [M (Y)$_2$(O$_{m'}$(L$^2$)] complex. In one embodiment, the solvent is a polar aprotic solvent. In another embodiment, the solvent is an alcohol solvent. In yet another embodiment, the solvent is a mixture of polar aprotic and alcohol solvents. By "alcohol solvent" we mean a liquid alcohol that has a boiling point at atmospheric pressure (i.e. 1.0135×10$^5$ Pa) below 160° C. and more preferably below 120° C. Examples of alcohol solvents included but are not limited to methanol, ethanol, propanol isomers (e.g. n-propanol or iso-propanol), butanol isomers (e.g. n-butanol, isobutanol or tert-butanol), pentanol isomers (e.g. 1-propanol, 2-pentanol, 3-pentanol, neopentyl alcohol, tert-pentyl alcohol, iso-pentyl alcohol or cyclopropanol) and hexanol isomers (e.g. 1-hexanol, 2-hexanol, 3-hexanol or cyclohexanol). Preferred examples are methanol, ethanol, n-propanol, isopropanol, n-butanol, isobutanol or tert-butanol. A particularly preferred alcohol solvent is isopropanol. While a mixture of alcohol solvents may be used, typically a single alcohol is suitable. Preferably, the alcohol solvent is dry.

Any suitable volume of solvent may be used. For example, the ratio of [M (X)$_2$(L)$_3$] complex to solvent may be about 50 to about 150 g/L. In certain embodiments, the ratio may be about 60 to about 125 g/L.

The reactants may be added in any suitable order, but in one preferred process of the invention, the phosphorus ligand L$^1$ may be added (e.g. portion wise) to a mixture of the [M (X)$_2$(L)$_3$] complex and alkali metal carboxylate in the solvent and, after stirring for a suitable period of time and at a suitable temperature, the bidentate N,N ligand L$^2$ may be added (e.g. portion wise). If desired, the bidentate N,N ligand L$^2$ may be added to the reaction mixture as a solution in solvent. The reaction may then be stirred for a further suitable period of time and at a suitable temperature. If desired, the solvent may be saturated with an inert gas (e.g. nitrogen) before it is added to the reaction mixture.

In another embodiment, the bidentate N,N ligand L$^2$ may be added (e.g. portion wise) to a mixture of the [M (X)$_2$(L)$_3$] complex and alkali metal carboxylate in the solvent and, after stirring for a suitable period of time and at a suitable temperature, the phosphorus ligand L$^1$ may be added (e.g. portion wise). If desired, the bidentate N,N ligand L$^2$ may be added to the reaction mixture as a solution in solvent. The reaction may then be stirred for a further suitable period of time and at a suitable temperature. If desired, the solvent may be saturated with an inert gas (e.g. nitrogen) before it is added to the reaction mixture.

The phosphorus ligand L$^1$ may be present in stoichiometric or slight excess to the [M (X)$_2$(L)$_3$] complex. When stoichiometric quantities are utilised, the methodology does not require the use of excess ligand and thereby makes the whole process highly efficient and atom-economical for commercial production. When a slight excess is utilised, the molar ratio of the phosphorus ligand L$^1$:the [M (X)$_2$(L)$_3$] complex may be about 1.001 to about 1.2:about 1, such as about 1.002:about 1, about 1.01:about 1, about 1.1:about 1, about 1.15:about 1, or about 1.15:about 1.

The bidentate N,N ligand L$^2$ may be present in stoichiometric or slight excess to the [M (X)$_2$(L)$_3$] complex. When stoichiometric quantities are utilised, the methodology does not require the use of excess ligand and thereby makes the whole process highly efficient and atom-economical for commercial production. When a slight excess is utilised, the molar ratio of the bidentate N,N ligand L$^2$:the [M (X)$_2$(L)$_3$] complex may be about 1.05 to about 1.75:about 1, such as about 1.1 to about 1.5:about 1, such as about 1.4 to about 1.5:about 1.

The reaction may be carried out under an inert atmosphere, such as under nitrogen or argon, preferably nitrogen.

The process of the invention may be preferably carried out at one or more temperatures in the range of about −10° C. to the reflux temperature of the polar aprotic solvent e.g. about 150° C. More preferably, the process of the invention may be carried out from about −5° C. to about 120° C. When the polar aprotic solvent is a chlorinated or ketone solvent, the process may be carried out at one or more temperatures in the range of about 0° C. to about 50° C., for example 15° C. to about 30° C., for instance, room temperature. When the polar aprotic solvent is an aromatic solvent, the process may be carried out at one or more temperature in the range of about 50° C. to about 120° C., such as about 75° C. to about 115° C. In one embodiment, the temperature of the process may be the boiling point of the aromatic solvent (e.g. about 111° C. for toluene). It is preferred that the temperature is maintained below the decomposition temperature, and so, when the [M (X)$_2$(L)$_3$] starting material and/or the [M (Y)$_2$(L$^1$)$_{m'}$(L$^2$)] product are known to decompose within the temperature ranges given above, the temperature should be maintained below the decomposition temperature.

The reaction may be carried out for a period of from about several minutes to about 72 hours but is usually complete within about 24 hours. On completion, the [M (Y)$_2$(L$^1$)$_{m'}$(L$^2$)] product is separated from the reaction mixture by any appropriate method which is dependent upon the physical form of the product. When the [M (Y)$_2$(L$^1$)$_m$(L$^2$)] complex is in solution, an anti-solvent (e.g. an alkane solvent such as pentane or hexane) may be added to precipitate the complex from solution. Generally, when the [M (Y)$_2$(L$^1$)$_w$ (L$^2$)] complex is a solid, it may be recovered from the reaction mixture by filtering, decanting or centrifuging.

In another aspect, the invention provides a process for the preparation of an [M (Y)$_2$(L$^1$)$_m$(L$^2$)] complex, the process comprising the step of:

reacting an [M (Y)$_2$(L)$_2$(L$^2$)] complex with a phosphorus ligand L$^1$ in a polar aprotic solvent to form the [M (Y)$_2$(L$^1$)$_m$(L$^2$)] complex;

wherein,
M is ruthenium or osmium;
Y is a carboxylate ligand;
L is a monodentate phosphorus ligand;
L$^1$ is a monodentate phosphorus ligand which is different to L, or a bidentate phosphorus ligand;
m' is 1 or 2, wherein,
when m' is 1, L$^1$ is a bidentate phosphorus ligand;
when m' is 2, each L$^1$ is a monodentate phosphorus ligand; and
L$^2$ is a bidentate N,N ligand comprising two nitrogen-containing groups.

M, Y, L, L$^1$, L$^2$, m', the [M (Y)$_2$(L$^1$)$_m$(L$^2$)] complex, the polar aprotic solvent, the reaction conditions and the recovery of the [M (Y)$_2$(L$^1$)$_m$(L$^2$)] complex are as generally described above.

The [M (Y)$_2$(L)$_2$(L$^2$)] complex may be a [ruthenium (Y)$_2$(PR$_{11}$R$_{12}$R$_{13}$)$_3$ (L$^2$)] complex, wherein R$_{11}$, R$_{12}$ and R$_{13}$ are as described above and may be, for example, independently selected from unsubstituted C$_{5-20}$-aryl and substituted C$_{5-20}$-aryl. In one embodiment, the [M (Y)$_2$(L)$_2$(L$^2$)] complex may be selected from the group consisting of [Ru (OAc)$_2$ (PPh$_3$)$_2$ AMPY], [Ru(OAc)$_2$(P(tolyl)$_3$)$_2$ AMPY] (such as [Ru(OAc)$_2$(P(p-tolyl)$_3$)$_2$ AMPY]) and [Ru(OAc)$_2$ (PPh$_3$)$_2$ AMPYRIM].

The [M (Y)$_2$(L)$_2$(L$^2$)] complex may be a [osmium (Y)$_2$ (PR$_{11}$R$_{12}$R$_{13}$)$_3$ (L$^2$)] complex, wherein R$_{11}$, R$_{12}$ and R$_{13}$ are as described above and may be, for example, independently selected from unsubstituted C$_{5-20}$-aryl and substituted C$_{5-20}$-aryl. In one embodiment, the [M (Y)$_2$(L)$_2$(L$^2$)] complex may be selected from the group consisting of [Os(OAc)$_2$(PPh$_3$)$_2$ AMPY], [Os(OAc)$_2$(P(tolyl)$_3$)$_2$ AMPY] (such as [Os(OAc)$_2$ (P(p-tolyl)$_3$)$_2$ AMPY]) and [Os(OAc)$_2$(PPh$_3$)$_2$ AMPYRIM].

In one embodiment, the [M (Y)$_2$(L)$_2$(L$^2$)] complex may be selected from the group consisting of: [Ru(OAc)$_2$(PPh$_3$)$_2$ L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl) pyrimidine (AMPYRIM); and

[Os(OAc)$_2$(PPh$_3$)$_2$ L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or or 2-(aminomethyl) pyrimidine (AMPYRIM).

In one embodiment, the [M (Y)$_2$(L)$_2$(L$^2$)] complex is [Ru(OAc)$_2$(PPh$_3$)$_2$ AMPY] or [Os(OAc)$_2$(PPh$_3$)$_2$ AMPY]. In one embodiment, the [M (Y)$_2$(L)$_2$(L$^2$)] complex is [Ru (OAc)$_2$(PPh$_3$)$_2$ EN] or [Os(OAc)$_2$ (PPh$_3$)$_2$ EN]. In one embodiment, the [M (Y)$_2$(L)$_2$(L$^2$)] complex is [Ru(OAc)$_2$ (PPh$_3$)$_2$ AMPYRIM] or [Os(OAc)$_2$(PPh$_3$)$_2$ AMPYRIM].

Any suitable volume of solvent may be used. For example, the ratio of [M (Y)$_2$(L)$_2$(L$^2$)] complex to solvent may be about 50 to about 150 g/L. In certain embodiments, the ratio may be about 60 to about 125 g/L.

The phosphorus ligand L$^1$ may be present in stoichiometric or slight excess to the [M (Y)$_2$(L)$_2$(L$^2$)] complex. When stoichiometric quantities are utilised, the methodology does not require the use of excess ligand and thereby makes the whole process highly efficient and atom-economical for commercial production. When a slight excess is utilised, the molar ratio of the phosphorus ligand L$^1$:the [M (Y)$_2$(L)$_2$] complex may be about 1.001 to about 1.2:about 1, such as about 1.002:about 1, about 1.01:about 1, about 1.1:about 1, about 1.15:about 1, or about 1.15:about 1.

In one embodiment, the [M (Y)$_2$(L$^1$)$_m$(L$^2$)] complex may be selected from the group consisting of: [Ru(OAc)$_2$(dppp) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl) pyrimidine (AMPYRIM);

[Ru(OAc)$_2$(dppb) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl) pyrimidine (AMPYRIM);

[Ru(OAc)$_2$(dppf) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2(aminomethyl) pyrimidine (AMPYRIM);

[Ru(OAc)$_2$(BINAP) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl) pyrimidine (AMPYRIM);

[Ru(OAc)$_2$(dppm) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OAc)$_2$(dppe) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(dppp) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl) pyrimidine (AMPYRIM);

[Os(OAc)$_2$(dppb) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl) pyrimidine (AMPYRIM);

[Os(OAc)$_2$(dppf) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl) pyrimidine (AMPYRIM);

[Os(OAc)$_2$(BINAP) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl) pyrimidine (AMPYRIM);

[Os(OAc)$_2$(dppm) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM); and

[Os(OAc)$_2$(dppe) L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM).

In one embodiment, the [M (Y)$_2$(L)$_2$(L$^2$)] complex is selected from the group consisting of [Ru(OAc)$_2$ (dppp) AMPY], [Ru(OAc)$_2$(dppf) AMPY], [Ru(OAc)$_2$(BINAP) AMPY] and [Ru(OAc)$_2$(BINAP) EN].

In another embodiment, the [M (Y)$_2$(L)$_2$(L$^2$)] complex is selected from the group consisting of [Ru(OAc)$_2$(dppp) AMPY], [Ru(OAc)$_2$(dppf) AMPY], [Ru(OAc)$_2$(BINAP) AMPY] and [Ru(OAc)$_2$(BINAP) EN].

In another aspect, the present invention provides a process for the preparation of an [M (Y)$_2$(L)$_2$(L$^2$)] complex, the process comprising the step of:
reacting an [M (Y)$_2$(L)$_2$] complex with a bidentate N,N ligand L$^2$ in a polar aprotic solvent to form the [M (Y)$_2$(L)$_2$ (L$^2$)] complex;
wherein,
M is ruthenium or osmium;
Y is a carboxylate ligand;
L is a monodentate phosphorus ligand; and
L$^2$ is a bidentate N,N ligand comprising two nitrogen-containing groups.

M, Y, L, L$^2$, the [M (Y)$_2$(L)$_2$] complex, the polar aprotic solvent, the reaction conditions and the recovery of the [M (Y)$_2$(L)$_2$(L$^2$)] complex may be as generally described above.

Any suitable volume of solvent may be used. For example, the ratio of [M (Y)$_2$(L)$_2$] complex to solvent may be about 50 to about 150 g/L. In certain embodiments, the ratio may be about 60 to about 125 g/L.

The bidentate N,N ligand L$^2$ may be present in stoichiometric or slight excess to the [M (Y)$_2$(L)$_2$] complex. When stoichiometric quantities are utilised, the methodology does not require the use of excess ligand and thereby makes the whole process highly efficient and atom-economical for commercial production. When a slight excess is utilised, the molar ratio of the bidentate N,N ligand L$^2$:the [M (Y)$_2$(L)$_2$] complex may be about 1.05 to about 1.75:about 1, such as about 1.1 to about 1.5:about 1, such as about 1.4 to about 1.5:about 1.

In one embodiment, the [M (Y)$_2$(L)$_2$(L$^2$)] complex may be selected from the group consisting of:

[Ru(OAc)$_2$(PPh$_3$)$_2$ L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Ru(OPiv)$_2$(PPh$_3$)$_2$ L$^2$], where OPiv is —OC(O)($^t$Bu) and L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

[Os(OAc)$_2$(PPh$_3$)$_2$ L$^2$], where L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM); and

[Os(OPiv)$_2$(PPh$_3$)$_2$ L$^2$], where OPiv is —OC(O)($^t$Bu) and L$^2$ is EN, AMPY, 2-(aminomethyl)-6-(4-methylphenyl)pyridine, quinoline-8-NH$_2$, 1-(benzo[h]quinoline-2-yl-methanamine (AMBQ), 4-phenyl-2-aminomethyl-benzo[h]quinoline, 4-methyl-2-aminomethyl-benzo[h]quinoline, 3-methyl-2-aminomethyl-benzo[h]quinoline or 2-(aminomethyl)pyrimidine (AMPYRIM);

In one embodiment, the [M (Y)$_2$(L)$_2$(L$^2$)] complex is [Ru(OAc)$_2$(PPh$_3$)$_2$ AMPY] or [Os(OAc)$_2$(PPh$_3$)$_2$ AMPY].

In another embodiment, the [M (Y)$_2$(L)$_2$(L$^2$)] complex is [Ru(OAc)$_2$(PPh$_3$)$_2$ EN] or [Os(OAc)$_2$(PPh$_3$)$_2$ EN], where EN is ethylenediamine.

In one embodiment, the [M (Y)$_2$(L)$_2$(L$^2$)] complex is [Ru(OAc)$_2$(PPh$_3$)$_2$ AMPYRIM] or [Os(OAc)$_2$ (PPh$_3$)$_2$ AMPYRIM], where AMPYRIM is 2-(aminomethyl)pyrimidine.

In one embodiment, the [M (Y)$_2$(L)$_2$(L$^2$)] complex is [Ru(OPiv)$_2$(PPh$_3$)$_2$ AMPY] or [Os(OPiv)$_2$ (PPh$_3$)$_2$ AMPY], where OPiv is OC(O)($^t$Bu). In another embodiment, the [M (Y)$_2$(L)$_2$(L$^2$)] complex is [Ru(OPiv)$_2$(PPh$_3$)$_2$ EN] or [Os (OPiv)$_2$(PPh$_3$)$_2$ EN]. In one embodiment, the [M (Y)$_2$(L)$_2$ (L$^2$)] complex is [Ru(OPiv)$_2$(PPh$_3$)$_2$ AMPYRIM] or [Os (OPiv)$_2$(PPh$_3$)$_2$ AMPYRIM.

In another aspect, the present invention provides a process for preparing a cis-[M (Y)$_2$(L$^1$)$_m$(L$^2$)] complex, the process comprising the steps of:

a) treating a trans-[M $(Y)_2(L^1)_{m'}(L^2)$] complex in an alcohol solvent; and
b) heating the reaction mixture to form the cis-[M $(Y)_2 (L^1)_{m'}(L^2)$] complex;
wherein,
M is ruthenium or osmium;
Y is a carboxylate ligand;
$L^1$ is a monodentate phosphorus ligand or a bidentate phosphorus ligand;
m' is 1 or 2, wherein,
when m' is 1, $L^1$ is a bidentate phosphorus ligand;
when m' is 2, each $L^1$ is a monodentate phosphorus ligand; and
$L^2$ is a bidentate N,N ligand comprising two nitrogen-containing groups.

The advantage in preparing the cis-[M $(Y)_2(L^1)_{m'}(L^2)$] complex is that in some embodiments it may be more catalytically active in catalytic applications. The inventors have noted that little isomerisation appears to occur when the trans-[M $(Y)_2(L^1)_{m'}(L^2)$] complex is heated in an aromatic solvent, such as toluene. In certain embodiments, it has been found that the trans-[M $(Y)_2(L^1)_{m'}(L^2)$] complex undergoes decomposition rather than isomerising as desired.

M, Y, $L^1$, $L^2$, m' and the [M $(Y)_2(L^1)_{m'}(L^2)$] complex are as generally described above.

The trans-[M $(Y)_2(L^1)_{m'}(L^2)$] complex is treated in an alcohol solvent. The trans-[M $(Y)_2(L^1)_{m1}$ $(L^2)$] complex may form a solution with the alcohol solvent or may form a slurry. "Slurry" means a heterogeneous mixture of at least a portion of the complex (or complexes) in the alcohol solvent. "Slurry" therefore includes a mixture of a complex or complexes which are partially present as a solid, as well as being partially dissolved in the alcohol solvent. The complexes which can be slurried include the trans-[M $(Y)_2 (L^1)_{m'}(L^2)$] starting material, and/or the cis-[M $(Y)_2(L^1)_{m'} (L^2)$] product.

By "alcohol solvent" we mean a liquid alcohol that has a boiling point at atmospheric pressure (i.e. $1.0135 \times 10^5$ Pa) below 160° C. and more preferably below 120° C. Examples of alcohol solvents included but are not limited to methanol, ethanol, propanol isomers (e.g. n-propanol or iso-propanol), butanol isomers (e.g. n-butanol, isobutanol or tert-butanol), pentanol isomers (e.g. 1-propanol, 2-pentanol, 3-pentanol, neopentyl alcohol, tert-pentyl alcohol, iso-pentyl alcohol or cyclopropanol) and hexanol isomers (e.g. 1-hexanol, 2-hexanol, 3-hexanol or cyclohexanol). Preferred examples are methanol, ethanol, n-propanol, isopropanol, n-butanol, isobutanol or tert-butanol. A particularly preferred alcohol solvent is isopropanol or methanol. While a mixture of alcohol solvents may be used, typically a single alcohol is suitable. Preferably, the alcohol solvent is dry.

Any suitable volume of alcohol solvent may be used. For example, the ratio of [M $(Y)_2(L)_2$] complex to solvent may be about 5 to about 200 g/L. In certain embodiments, the ratio may be about 7 to about 100 g/L or about 100 to about 190 g/L.

The trans-[M $(Y)_2(L^1)_{m'}(L^2)$] complex may contain residual solvent. In this case it may be desirable to first partially strip (e.g. by distillation) a portion of the solvent in order to remove remaining solvent. If desired, an additional portion of alcohol solvent may be added to the reaction mixture in order to make up the volume removed by stripping.

The reaction mixture is heated to form the cis-[M $(Y)_2 (L^1)_{m'}(L^2)$] complex. In one embodiment, the reaction mixture may be heated to reflux. The conversion of the trans-complex to the cis-complex may be monitored by NMR.

Step (a) may further comprise a phosphorus ligand $L^1$. In this respect, therefore, step (a) involves treating a trans-[M $(Y)_2(L^1)_{m'}(L^2)$] complex and a phosphorus ligand $L^1$ in an alcohol solvent. The trans-[M $(Y)_2(L^1)_{m'}(L^2)$] complex may comprise an [M $(Y)_2(L)_2(L^2)$] complex as a by-product. The advantages therefore of heating the trans-[M $(Y)_2(L^1)_{m'}(L^2)$] complex with the phosphorus ligand $L^1$ in an alcohol solvent may be twofold. In this respect, without wishing to be bound by theory, the inventors believe that the phosphorus ligand $L^1$ may convert the [M $(Y)_2(L)_2(L^2)$] by-product (if present) to the [M $(Y)_2(L^1)_{m'}(L^2)$] complex and, secondly, the phosphorus ligand $L^1$ may assist in the isomerisation of the trans-[M $(Y)_2(L^1)_{m'}(L^2)$] complex to the cis-[M $(Y)_2(L^1)_{m'} (L^2)$] complex.

The amount of the phosphorus ligand $L^1$ may be in the range of about 0.001 to about 0.7 mol eq of the molar quantity of the trans-[M $(Y)_2(L^1)_{m'}(L^2)$] complex, for example, about 0.002 to about 0.5 mol eq.

The reaction may be carried out for a period of from about several minutes to about 90 hours but in certain embodiments it may be completed within about 24 hours. On completion, the cis-[M $(Y)_2(L^1)_{m'}(L^2)$] product is separated from the reaction mixture by any appropriate method which is dependent upon the physical form of the product. Generally, when the cis-[M $(Y)_2(L^1)_{m'}(L^2)$] complex is a solid, it may be recovered from the reaction mixture by filtering, decanting or centrifuging and optionally washed (e.g. with water) one or more times.

If desired, the reaction mixture may be allowed to cool to a temperature which is above room temperature and below the refluxing temperature of the alcohol solvent (for example, about 50° C. when the alcohol solvent is isopropanol) before recovering the cis-[M $(Y)_2(L^1)_{m'}(L^2)$] complex. Recovering the cis-[M $(Y)_2(L^1)_{m'}(L^2)$] complex while the reaction mixture remains warm has the advantage that the free phosphorus ligand $L^1$ and/or its oxide (if present) is more soluble in warm alcohol solvent, thus facilitating the separation of the cis-[M $(Y)_2(L^1)_{m'}(L^2)$] complex from the reaction mixture. If free phosphorus ligand $L^1$ and/or its oxide is present, the presence of these compounds may colour the cis-[M $(Y)_2(L^1)_{m'}(L^2)$] product. In this case, the cis-[M $(Y)_2(L^1)_{m'}(L^2)$] complex may be stirred one or more times (e.g. 1, 2 or 3 times) with one of the above described ketone solvents (such as acetone) until the free phosphorus ligand $L^1$ and/or its oxide is substantially removed.

Alternatively or in addition, the cis-[M $(Y)_2(L^1)_{m'}(L^2)$] complex may be washed one or more times (e.g. 1, 2 or 3 times) with alcohol solvent (such as isopropanol). The alcohol solvent aliquots may be warmed (e.g. to 50° C.) before the cis-[M $(Y)_2(L^1)_{m'}(L^2)$] complex is washed.

Alternatively, the alcohol solvent may be removed (for example, by distillation or stripping methods) from the solution of the cis-[M $(Y)_2(L^1)_{m'}(L^2)$] product until a more concentrated solution of the cis-[M $(Y)_2(L^1)_{m'}(L^2)$] product in a remaining portion of the alcohol solvent is obtained. Then, an anti-solvent selected from low boiling alkanes may be added to cause precipitation of the complex. Suitable alkanes have boiling points at atmospheric pressure between 0 to 150° C. Alkanes that may be used are low boiling alkanes such as pentane isomers, hexane isomers, heptane isomers or octane isomers. Preferably, the alkane is n-pentane, n-hexane cyclohexane or n-heptane and more preferably cyclohexane.

Howsoever the cis-[M $(Y)_2(L^1)_{m'}(L^2)$] complex is recovered, the complex may then be dried using known methods, for example at temperatures in the range 10-60° C. and preferably 20-40° C. under 1-30 mbar vacuum for 1 hour to 5 days. If desired the complex may be recrystallized, although this may not be necessary.

In another aspect, the present invention provides a process for the preparation of a cis-[M (Y)$_2$(L$^1$)$_{m'}$(L$^2$)] complex, the process comprising the step of:

reacting an [M (Y)$_2$(L)$_2$(L$^2$)] complex with a phosphorus ligand L$^1$ in an alcohol solvent to form the cis-[M (Y)$_2$(L$^1$)$_{m'}$(L$^2$)] complex;

wherein,

M is ruthenium or osmium;

Y is an carboxylate ligand;

L is a monodentate phosphorus ligand;

L$^1$ is a monodentate phosphorus ligand which is different to L, or a bidentate phosphorus ligand;

m' is 1 or 2, wherein, when m' is 1, L$^1$ is a bidentate phosphorus ligand;

when m' is 2, each L$^1$ is a monodentate phosphorus ligand; and

L$^2$ is a bidentate N,N ligand comprising two nitrogen-containing groups.

M, Y, L, L$^1$, L$^2$, m', the [M (Y)$_2$(L)$_2$(L$^2$)] complex, the cis-[M (Y)$_2$(L$^1$)$_{m'}$(L$^2$)] complex, the alcohol solvent, the reaction conditions and the recovery of the cis-[M (Y)$_2$(L$^1$)$_{m'}$(L$^2$)] complex are as generally described above.

In another aspect, the present invention provides a process for the preparation of a cis-[M (Y)$_2$(L$^1$)$_{m'}$(L$^2$)] complex, the process comprising the step of:

reacting an [M (X)$_2$(L$^1$)$_{m'}$(L$^2$)] complex, a phosphorus ligand L$^1$ and an alkali metal carboxylate in an alcohol solvent to form the cis-[M (Y)$_2$(L$^1$)$_{m'}$(L$^2$)] complex;

wherein,

M is ruthenium or osmium;

X is a halide ligand;

Y is an carboxylate ligand;

L$^1$ is a monodentate phosphorus ligand, or a bidentate phosphorus ligand;

m' is 1 or 2, wherein, when m' is 1, L$^1$ is a bidentate phosphorus ligand;

when m' is 2, each L$^1$ is a monodentate phosphorus ligand; and

L$^2$ is a bidentate N,N ligand comprising two nitrogen-containing groups.

M, Y, L$^1$, L$^2$, m', the alkali metal carboxylate, the alcohol solvent, the cis-[M (Y)$_2$(L$^1$)$_{m'}$(L$^2$)] complex, the reaction conditions and the recovery of the cis-[M (Y)$_2$(L$^1$)$_{m'}$(L$^2$)] complex are as generally described above.

The cis-[M (Y)$_2$(L$^1$)$_{m'}$(L$^2$)] complex may be prepared in a combined process i.e. by firstly preparing the trans-[M (Y)$_2$(L$^1$)$_{m'}$(L$^2$)] or [M (Y)$_2$(L)$_2$(L$^2$)] complexes using a ketone solvent and secondly by preparing the cis-[M (Y)$_2$(L$^1$)$_{m'}$(L$^2$)] complex using an alcohol solvent. The advantage in doing so is that pure cis-[M (Y)$_2$(L$^1$)$_{m'}$(L$^2$)] complex may be obtained. This is because the process utilising the ketone solvent may facilitate the removal of free phosphorus ligand thus producing a better quality trans-[M (Y)$_2$(L$^1$)$_{m'}$(L$^2$)] or [M (Y)$_2$(L)$_2$(L$^2$)] product and the process utilising the alcohol solvent facilitates the exchange of one phosphorus ligand for another (if desired) and facilitates the isomerisation of a trans-complex to the cis-complex. These advantages may be lost in methods using e.g. toluene where the trans-complex and its subsequent isomerisation may occur in a one-pot process.

The complexes obtained by the methods of the present invention are pure and, if desired, may be used in catalytic applications as obtained. The complexes may contain small amounts of a residual alcohol. The catalysts can be used in catalytic applications as obtained or further dried. In this respect, alcohols are typically easier to remove than aromatic solvents such as toluene upon drying under vacuum. Furthermore the complexes obtained using the present methods may be easy to filter and therefore may be suited to large-scale manufacture.

In another aspect, the invention provides a process for preparing an [M Y(L$^1$)$_m$(L$^3$) complex, the process comprising the step of:

reacting an [M (Y)$_2$(L)$_2$] complex, a phosphorus ligand L$^1$, a HCNN ligand L$^3$ and a base in a polar aprotic solvent, an alcohol solvent or a mixture thereof to form the [M Y(L$^1$)$_m$(L$^3$)] complex;

wherein,

M is ruthenium or osmium;

Y is a carboxylate ligand;

L is a monodentate phosphorus ligand;

L$^1$ is a monodentate phosphorus ligand which is different to L, or a bidentate phosphorus ligand;

m is 1 or 2, wherein, when m' is 1, L$^1$ is a bidentate phosphorus ligand;

when m' is 2, each L$^1$ is a monodentate phosphorus ligand; and

L$^3$ is a HCNN ligand of formula (3'), (4'), (6') or (7'):

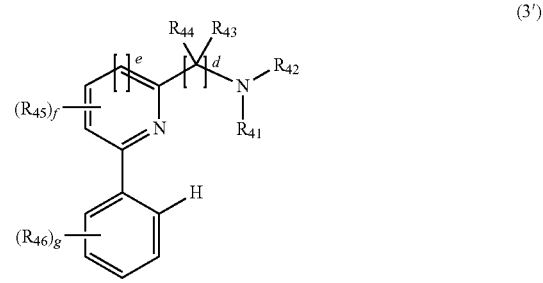

(3')

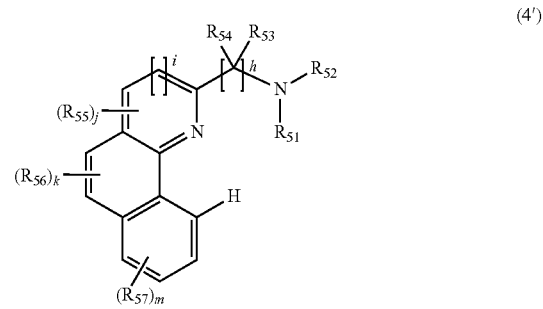

(4')

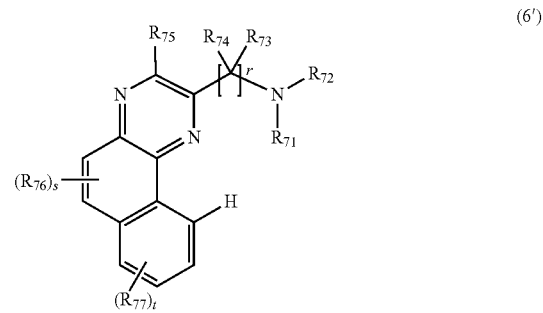

(6')

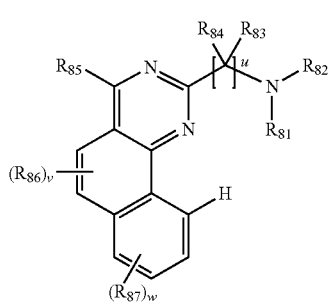

(7')

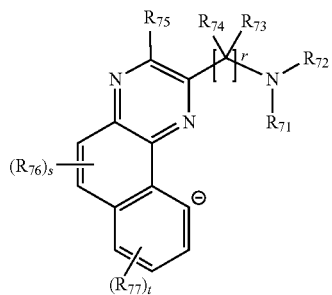

(6")

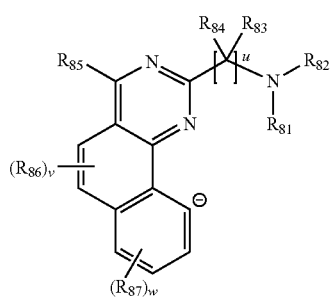

(7")

M, Y, L, L¹, m', the [M (Y)₂(L)₂] complex, the polar aprotic solvent and the alcohol solvent are as generally described above.

The HCNN ligands of formulae (3'), (4'), (6') and (7') are as generally described above for the ligands (3), (4), (6) and (7) except that ligands (3'), (4'), (6') and (7') each comprise a —H atom on the aryl ring as depicted above. For ligand (3'), therefore, g may be 0, 1, 2, 3 or 4 (but not 5). For ligand (4'), m may be 0, 1, 2 or 3 (but not 4). For ligand (6'), t may be 0, 1, 2 or 3 (but not 4). For ligand (7'), w may be 0, 1, 2 or 3 (but not 4).

In one embodiment, L³ is a tridentate ligand of formula (3'). In another embodiment, L³ is a tridentate ligand of formula (4'). In another embodiment, L³ is a tridentate ligand of formula (6'). In another embodiment, L³ is a tridentate ligand of formula (7').

In the presence of a suitable base and when the depicted hydrogen atoms are present, the ligands (3'), (4'), (6') and (7') orthometallate in the presence of a suitable transition metal atom M (e.g. Ru or Os) to form a transition metal complexes comprising CNN-tridentate ligands (3"), (4"), (6") and (7"). The ligands are tridentate as they coordinate through the amino and nitrogen-containing heteroaryl functional groups, as well as through the carbon-metal bond created by ortho-metallation.

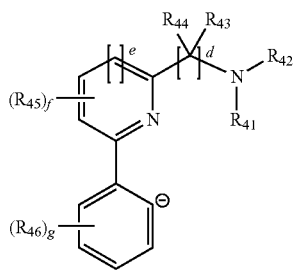

(3")

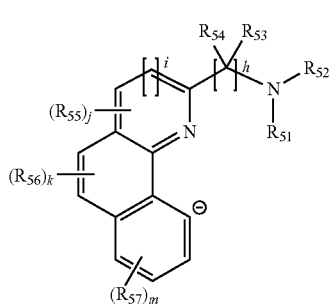

(4")

The base may be any suitable base which is capable of removing the depicted hydrogen atoms in the ligands (3'), (4'), (6') and (7'). Examples of suitable bases include but are not limited to trialkylamines (such as triethylamine), pyridine, dimethylpyridine (e.g. 2,6-, 2,3-, 3,5-, 2,5- or 3,4-dimethylpyridine), alkali metal hydroxides (such as sodium hydroxide or potassium hydroxide) or alkali metal alkoxides (such as sodium methoxide or potassium methoxide).

The base may be present in stoichiometric or greater quantities to the ligand (3'), (4'), (6') or (7'). Stoichiometric or excess of base may be suitable, for example, about 1:1.1 to about 1:20 molar ratio of ligand (3'), (4'), (6') or (7') to base, such as about 1:1.1 to about 1:15.

Any suitable volume of solvent may be used. For example, the ratio of [M (Y)₂(L)₂] complex to solvent may be about 50 to about 150 g/L. In certain embodiments, the ratio may be about 60 to about 125 g/L.

The phosphorus ligand L¹ may be present in stoichiometric or slight excess to the [M (Y)₂(L)₂] complex. When stoichiometric quantities are utilised, the methodology does not require the use of excess ligand and thereby makes the whole process highly efficient and atom-economical for commercial production. When a slight excess is utilised, the ratio of the phosphorus ligand L¹:the [M (Y)₂(L)₂] complex may be about 1.001 to about 1.2:about 1, such as about 1.002:about 1, about 1.01:about 1, about 1.1:about 1, about 1.15:about 1, or about 1.15:about 1.

The HCNN ligand L³ may be present in stoichiometric or slight excess to the [M (Y)₂(L)₂] complex. When stoichiometric quantities are utilised, the methodology does not require the use of excess ligand and thereby makes the whole process highly efficient and atom-economical for commercial production. When a slight excess is utilised, the molar ratio of the HCNN ligand L³:the [M (Y)₂(L)₂] complex may be about 1.01 to about 1.75:about 1, such as about 1.1 to about 1.5:about 1, such as about 1.4 to about 1.5:about 1.

In combining the [M (Y)₂(L)₂] complex, the ligand L¹, the ligand L³ and base in the solvent, the components may be mixed in any order, although, in one embodiment, the [M (Y)₂(L)₂] complex and ligand L¹ are slurried or suspended in the solvent. After the [M (Y)₂(L)₂] complex and the ligand L¹ is combined with the solvent, the reaction mixture may be stirred and heated (e.g. at reflux) for a period of time (e.g. for up to 2-3 hours). The mixture may be stirred for a period e.g. preferably 1 minute to 3 hours, more preferably 2 minutes to 2 hours and most preferably 2.5 minutes to 1.5 hours. The HCNN ligand L³ and the base may then be added to the reaction mixture and the reaction mixture stirred and heated (e.g. at reflux) for a further period of time (e.g. for up to 5-6 hours).

The reaction may be conducted under an inert atmosphere, such as nitrogen or argon.

The reaction mixture may be treated with an alkane (such as pentane, hexane or heptane) which causes the the [M Y(L¹)$_m$(L³)] complex to precipitate or crystallise. The solid the [M Y(L¹)$_m$(L³)] complex may be recovered directly by filtering, decanting or centrifuging. If desired a proportion of the alcohol/alkane solvent mixture may be evaporated prior to the recovery of the complex.

Alternatively, the solid the [M Y(L¹)$_m$(L³)] complex may be recovered simply by evaporating the alcohol/alkane solvent mixture.

Howsoever the complex is recovered, the separated complex is preferably dried. Drying may be performed using known methods, for example, at temperatures in the range of about 10-60° C. and such as bout 20-40° C. under 0.1-30 mbar for 1 hour to 5 days.

The [M Y(L¹)$_m$(L³)] complex may be selected from the group consisting of:

[Ru(OAc) (dppp) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (dppb) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (dppf) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (DCyPFc) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (DiPFc) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (DB'PFc) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (Josiphos*) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (BINAP) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (ToIBINAP) L³], where L³ is 2-(aminoethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (dppp) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (dppb) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (dppf) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (DCyPFc) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (DiPFc) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (DB'PFc) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (Josiphos*) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (BINAP) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline; and

[Os(OAc) (ToIBINAP) L³], where L³ is 2-(aminomethyl)-6-(4-methylphenyl)pyridine, 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline.

In one embodiment, the [M Y(L¹)$_m$(L³)] complex may be selected from the group consisting of:

[Ru(OAc) (dppp) L³], where L³ is 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Ru(OAc) (dppb) L³], where L³ is 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (dppp) L³], where L³ is 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline;

[Os(OAc) (dppb) L³], where L³ is 1-(benzo[h]quinoline-2-yl-methanamine (AMBQ), 4-phenyl-2-aminomethyl-benzo[h]quinoline, 4-methyl-2-aminomethyl-benzo[h]quinoline or 3-methyl-2-aminomethyl-benzo[h]quinoline.

In another aspect, the invention provides a process for preparing an [M Y(L¹)$_{m'}$(L³)] complex, the process comprising the step of:

reacting an [M (Y)₂(L¹)$_{m'}$] complex, a HCNN ligand L³ and a base in an alcohol solvent to form the [M Y(L¹)$_{m'}$(L³)] complex;

wherein,

M is ruthenium or osmium;

Y is a carboxylate ligand;

L¹ is a monodentate phosphorus ligand, or a bidentate phosphorus ligand;

m' is 1 or 2, wherein, when m' is 1, L¹ is a bidentate phosphorus ligand;

when m' is 2, each L¹ is a monodentate phosphorus ligand; and

L³ is a HCNN ligand of formula (3'), (4'), (6') or (7'):

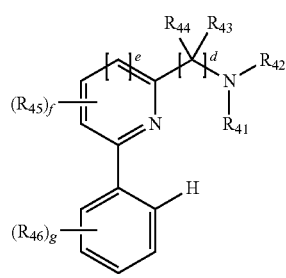

(3')

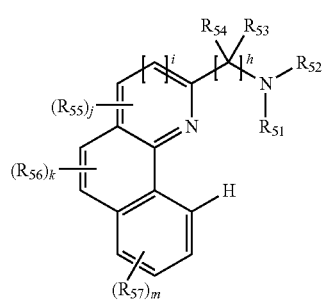

(4')

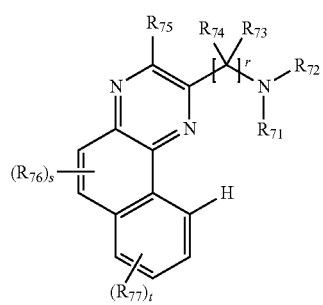

(6')

-continued

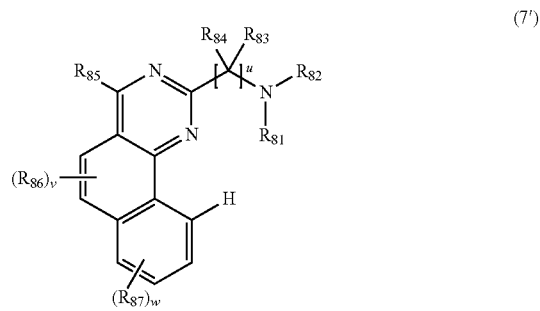

(7')

M, Y, L¹, L³, m', the base, the alcohol solvent, the [M Y(L¹)$_{m'}$ (L³)] complex, the reaction conditions and the recovery of the [M Y(L¹)$_{m'}$(L³)] complex are as generally described above.

Examples of [M (Y)₂(L¹)$_{m'}$] complexes include but are not limited to [M (Y)₂(L¹)] where L¹ is a bidentate ligand, such as [Ru(OAc)₂(dppp)], [Ru(OAc)₂(dppb)], [Os(OAc)₂(dppp)] and [Os(OAc)₂ (dppb)].

The phosphorus ligand L¹ may be present in stoichiometric or slight excess to the [M (Y)₂(L¹)$_{m'}$] complex. When stoichiometric quantities are utilised, the methodology does not require the use of excess ligand and thereby makes the whole process highly efficient and atom-economical for commercial production. When a slight excess is utilised, the molar ratio of the phosphorus ligand L¹:the [M (Y)₂(L¹)$_{m'}$] complex may be about 1.001 to about 1.2:about 1, such as about 1.002:about 1, about 1.01:about 1, about 1.1:about 1, about 1.15:about 1, or about 1.15:about 1.

The HCNN ligand L³ may be present in stoichiometric or slight excess to the [M (Y)₂(L¹)$_{m'}$] complex. When stoichiometric quantities are utilised, the methodology does not require the use of excess ligand and thereby makes the whole process highly efficient and atom-economical for commercial production. When a slight excess is utilised, the molar ratio of the HCNN ligand L³:the [M (Y)₂(L¹)$_{m'}$] complex may be about 1.01 to about 1.75:about 1, such as about 1.1 to about 1.5:about 1, such as about 1.4 to about 1.5:about 1.

In another aspect, the invention provides a process for preparing an [M Y(L¹)$_{m'}$(L³) complex, the process comprising the step of:

reacting an [M (X)₂(L)₃] complex, a phosphorus ligand L¹, a HCNN ligand L³, an alkali metal carboxylate in a polar aprotic solvent, an alcohol solvent or a mixture thereof to form the [M Y(L¹)$_{m'(L}$³)] complex;

wherein,

M is ruthenium or osmium;

X is a halide ligand

Y is a carboxylate ligand;

L is a monodentate phosphorus ligand;

L¹ is a monodentate phosphorus ligand which is different to L, or a bidentate phosphorus ligand;

m' is 1 or 2, wherein, when m' is 1, L¹ is a bidentate phosphorus ligand;

when m' is 2, each L¹ is a monodentate phosphorus ligand; and $L^3$ is a HCNN ligand of formula (3'), (4'), (6') or (7'):

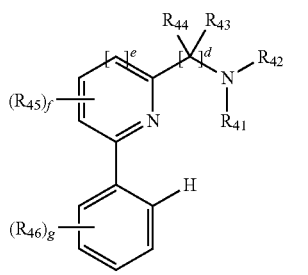
(3')

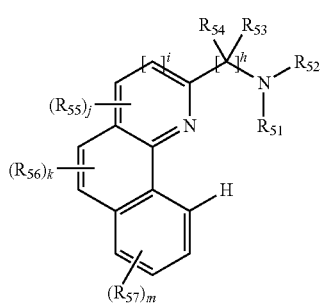
(4')

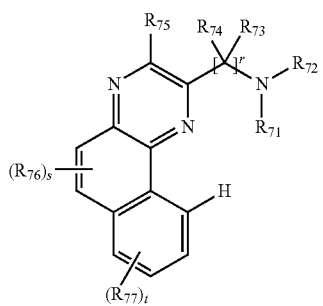
(6')

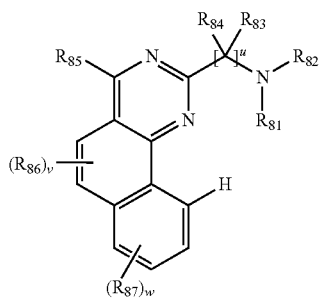
(7')

M, Y, L, $L^1$, $L^3$, m', the alkali metal carboxylate, the polar aprotic solvent, the alcohol solvent, and the [M $(X)_2(L)_3$] complex, the reaction conditions and the recovery of the [M $Y(L^1)_{m'}(L^3)$] complex are as generally described above.

The alkali metal carboxylate provides the carboxylate ligand in the [M $Y(L^1)_{m'}(L^3)$] complex. Without wishing to be bound by theory, it is believed the alkali metal carboxylate may also act as a base to remove the hydrogen atom from the HCNN ligand of formula (3'), (4'), (6') or (7') thus permitting the formation of the tridentate CNN ligand. If the alkali metal carboxylate, however, does not act as a base or is not a strong enough base to remove the necessary hydrogen atom from the HCNN ligands, the process may further comprise a suitable base which is capable of removing the depicted hydrogen atoms. Examples of suitable bases include but are not limited to trialkylamines (such as triethylamine), pyridine, dimethylpyridine (e.g. 2,6-, 2,3-, 3,5-, 2,5- or 3,4-dimethylpyridine), alkali metal hydroxides (such as sodium hydroxide or potassium hydroxide) or alkali metal alkoxides (such as sodium methoxide or potassium methoxide).

In another aspect, the present invention provides a process for the preparation of an [M Y L $L^3$] complex, the process comprising the step of:

reacting an [M $(Y)_2(L)_2$] complex, a HCNN ligand $L^3$ and a base in an alcohol aprotic solvent to form the [M Y L $L^3$] complex;

wherein,

M is ruthenium or osmium;

Y is a carboxylate ligand;

L is a monodentate phosphorus ligand; and $L^3$ is a HCNN ligand of formula (3'), (4'), (6') or (7'):

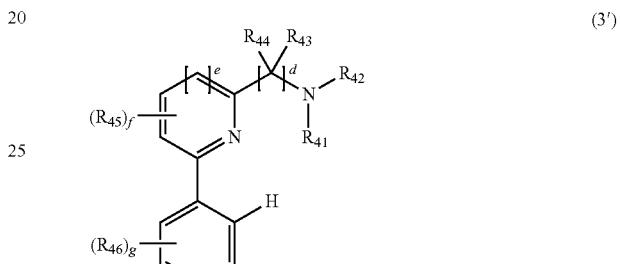
(3')

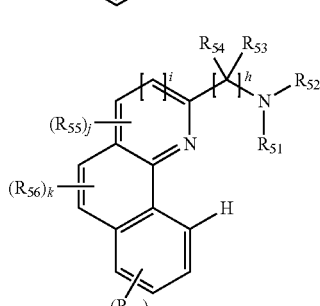
(4')

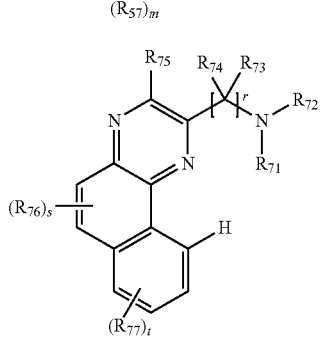
(6')

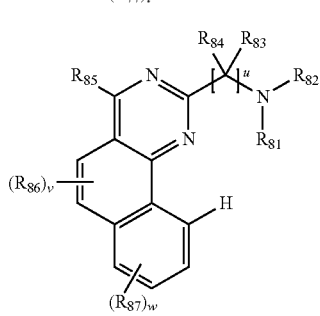
(7')

M, Y, L, L³, the [M (Y)₂(L)₂] complex, the base, the alcohol solvent, the reaction conditions and the recovery of the [M Y L L³] complex are as generally described above.

In another aspect, the present invention provides an [M (Y)₂(L¹)ₘ(L²)] complex as described above provided:
(a) L² is not a bidentate N,N-ligand of formula (8); or
(b) the carboxylate ligand Y is not RCOO— wherein R is a C₂-C₁₂ hydrocarbon group branched or cyclic in the α and or β position, such as pivalate, benzoate, 2,4,6-trimethylbenzoate or adamantane-1-carboxylate.

In one embodiment, when M is ruthenium, L¹ is a Skewphos ligand, m' is 1, L² is an N,N-bidentate ligand of formula (2), the integers a and b are both 1, Y is not a carboxylate ligand, such as an acetoxy, benzoyloxy, (2,6-dihydroxpenzoyl)oxy, (2,5-dihydroxybenzoyl)oxy, (3-aminobenzoyl) oxy, (2,6-methoxybenzoyl)oxy, (2,4,6-triisopropylbenzoyl) oxy, 1-naphthalenecarboxylic acid, 2-napthalenecarboxylic acid or trifluoroacetoxy anion.

In another aspect, the present invention provides an [M (Y)₂(L)₂(L²)] complex as described above provided L² is not a bidentate N,N-ligand of formula (8).

In another aspect, the present invention provides an [M Y(L¹)ₘ(L³)] complex as described above provided that the [M Y(L¹)ₘ(L³)] complex is not [Ru(O₂CCH₃)(CNN)(dppb)] (HCNN=1-[6-(4'-methylphenyl)pyridine-2-yl]methanamine; dppb=Ph₂P(CH₂)₄PPh₂) or [Ru(OC(O)H)(CNN)(dppb)] (HCNN=1-[6-(4'-methylphenyl)pyridine-2-yl]methanamine; dppb=Ph₂P(CH₂)₄PPh₂) i.e.

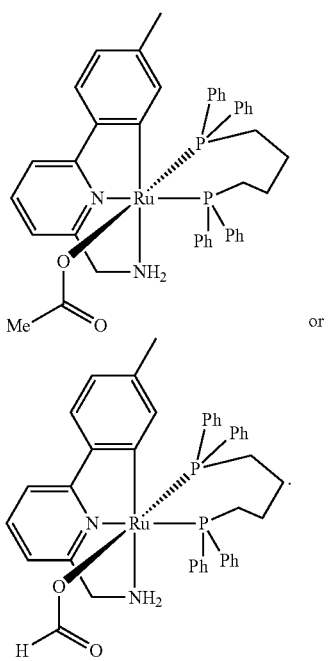

In another aspect, the present invention provides an [M Y L L³] complex as described above.

In another aspect, the present invention provides a cis-[M (Y)₂(L¹)ₘ(L²)] complex as described above.

Methods of Catalysis

In one aspect of the invention there is provided the use of a complex selected from the group consisting of [M (Y)₂ (L¹)ₘ(L²)], [M (Y)₂(L)₂(L²)], [M Y(L¹)ₘ(L³)] and [M Y L L³] as a catalyst, for example in a hydrogenation reaction or a transfer hydrogenation reaction. Such reactions may be broadly referred to as hydrogen reduction reactions. It is envisaged that the complexes may also be used in deuteration reactions, tritiation reactions, the racemization of alcohols (e.g. the racemization of an enantiomerically enriched alcohol), the dehydrogenation of alcohols (e.g. the reaction of an alcohol and an amine to form an amine) and in the formation of C—C bonds (e.g. the reaction of a ketone and an alcohol to form a C—C bond). The [M (Y)₂(L¹)ₘ(L²)], [M (Y)₂(L)₂(L²)], [M Y(L¹)ₘ(L³)] and [M Y L L³] complexes are as described above.

In one embodiment, the method comprises the step of reacting a substrate comprising a carbon-oxygen double bond in the presence of a complex selected from the group consisting of [M (Y)₂(L¹)ₘ(L²)], [M (Y)₂(L)₂(L²)], [M Y(L¹)ₘ'(L³)] and [M Y L L³].

In certain embodiments, L² is not a bidentate N,N-ligand of formula (8) in an [M (Y)₂(L¹)ₘ(L²)] or [M (Y)₂(L)₂(L²) complex.

In certain embodiments, the complex [M Y(L¹)ₘ(L³)] is not:

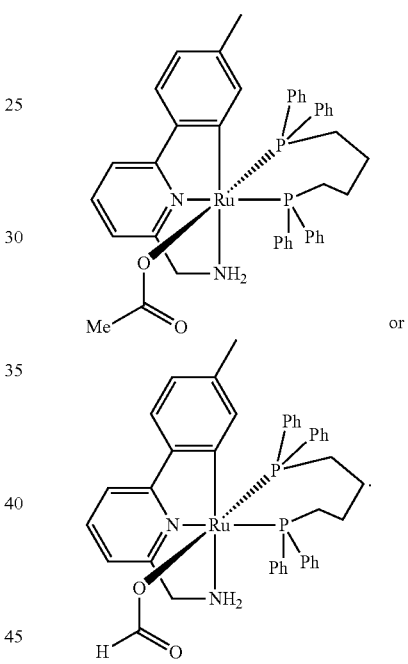

In one embodiment, the reaction is a hydrogenation reaction, and the method includes reacting the substrate with hydrogen gas in the presence of a complex selected from the group consisting of [M (Y)₂(L¹)ₘ(L²), [M (Y)₂(L)₂(L²)], [M Y(L¹)ₘ(L³)] and [M Y L L³]. The reaction may further comprise an alkali metal alkoxide (such as i-PrONa).

In another embodiment, the reaction is a deuteration reaction, and the method includes reacting the substrate with deuterium gas in the presence of a complex selected from the group consisting of [M (Y)₂(L¹)ₘ(L²)], [M (Y)₂(L)₂(L²)], [M Y(L¹)ₘ(L³)] and [M Y L L³]. The reaction may further comprise an alkali metal alkoxide (such as i-PrONa).

In another embodiment, the reaction is a tritiation reaction, and the method includes reacting the substrate with tritium gas in the presence of a complex selected from the group consisting of [M (Y)₂ (L¹)ₘ(L²)], [M (Y)₂(L)₂(L²)], [M Y(L¹)ₘ(L³)] and [M Y L L³]. The reaction may further comprise an alkali metal alkoxide (such as i-PrONa).

In one embodiment, the reaction is a transfer hydrogenation, and the method includes reacting the substrate with a hydrogen donor in the in the presence of a complex selected from the group consisting of [M (Y)$_2$(L$^1$)$_m$(L$^2$)], [M (Y)$_2$(L)$_2$(L$^2$)], [M Y(L$^1$)$_m$(L$^3$)] and [M Y L L$^3$]. The hydrogen donor may be selected from formic acid, a formic acid alkali metal salt, and an alcohol, such as an alcohol having a hydrogen atom at a carbon atom that is α to the carbon atom to which the alcohol group is attached, such as iso-propanol. The reaction may further comprise an alkali metal alkoxide (such as i-PrONa). In certain embodiments, the transfer hydrogenation may be base-free. As used herein, a hydrogen donor is not gaseous hydrogen.

Examples of compounds containing a carbon-oxygen double bond include ketones, aldehydes, esters and lactones, amongst others.

The method may include the step of reducing a substrate, for example the hydrogenation of a carbonyl-containing substrate to yield the corresponding alcohol.

A suitable substrate to be hydrogenated includes, but is not limited to, a carbonyl of formula (I):

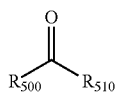

(I)

wherein, $R_{500}$ and $R_{510}$ are each independently selected from the group consisting of hydrogen, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{3-20}$-cycloalkoxy, substituted $C_{3-20}$-cycloalkoxy, unsubstituted $C_{2-20}$-alkenyl, substituted $C_{2-20}$-alkenyl, unsubstituted $C_{4-20}$-cycloalkenyl, substituted $C_{4-20}$-cycloalkenyl, unsubstituted $C_{2-20}$-alkynyl, substituted $C_{2-20}$-alkynyl, unsubstituted $C_{6-20}$-aryl, substituted $C_{6-20}$-aryl, unsubstituted $C_{1-20}$-heteroalkyl, substituted $C_{1-20}$-heteroalkyl, unsubstituted $C_{2-20}$-cycloheteroalkyl, substituted $C_{2-20}$-cycloheteroalkyl, unsubstituted $C_{3-20}$-heteroaryl, substituted $C_{3-20}$-heteroaryl, —NR$_{600}$R$_{610}$, —COR$_{600}$, —COOR$_{600}$, —CONR$_{600}$R$_{610}$, unsubstituted —C$_{1-20}$-alkyl-COOR$_{600}$, substituted —C$_{1-20}$-alkyl-COOR$_{600}$, unsubstituted —C$_{1-20}$-alkyl-COR$_{600}$, substituted —C$_{1-20}$-alkyl-COR$_{600}$, unsubstituted —C$_{1-20}$-alkyl-CONR$_{600}$R$_{610}$, substituted —C$_{1-20}$-alkyl-CONR$_{600}$R$_{610}$, unsubstituted —C$_{2-20}$-alkynyl-C$_{6-20}$-aryl, substituted —C$_{2-20}$-alkynyl-C$_{6-20}$-aryl, unsubstituted —C$_{2-20}$-alkynyl-C$_{1-20}$-alkyl, substituted —C$_{2-20}$-alkynyl-C$_{1-20}$-alkyl; or $R_{500}$ and $R_{510}$ are bound by an unsubstituted $C_{1-20}$ alkyl, substituted $C_{1-20}$ alkyl, unsubstituted $C_{1-20}$ alkoxy, substituted $C_{1-20}$ alkoxy, unsubstituted $C_{2-20}$ alkenyl or substituted $C_{2-20}$ alkenyl; or $R_{500}$ and $R_{510}$ are bound to form a 5, 6 or 7 membered ring by an unsubstituted —(CH$_2$)$_t$-(ortho-C$_{5-6}$-aryl)-(CH$_2$)$_u$— chain, substituted —(CH$_2$)$_t$-(ortho-C$_{5-6}$-aryl)-(CH$_2$)$_u$— chain, unsubstituted —(CH$_2$)$_t$-(ortho-C$_{5-6}$-aryl)-L$^Q$-(CH$_2$)$_u$— chain, substituted —(CH$_2$)$_t$-(ortho-C$_{5-6}$-aryl)-L$^4$-(CH$_2$)$_u$— chain, unsubstituted —(CH$_2$)$_t$-(ortho-C$_{5-6}$-heteroaryl)-(CH$_2$)$_u$— chain or substituted —(CH$_2$)$_t$-(ortho-C$_{5-6}$-heteroaryl)-(CH$_2$)$_u$— chain;

wherein t is an integer selected from 0 or 1, u is an integer selected from 2, 3 or 4, -L$^Q$- is selected from the group consisting of —O—, —N— and —SO$_2$—, wherein the substituents are selected from the group consisting of unsubstituted $C_{1-20}$-alkyl, unsubstituted $C_{3-20}$-cycloalkyl, unsubstituted $C_{1-20}$-alkoxy, unsubstituted $C_{3-20}$-cycloalkoxy, unsubstituted $C_{6-20}$-aryl, unsubstituted $C_{6-20}$ aryloxy, unsubstituted $C_{1-20}$-heteroalkyl, unsubstituted $C_{2-20}$-cycloheteroalkyl, unsubstituted $C_{3-20}$-heteroaryl, straight or branched tri-$C_{1-20}$-alkylsilyl-, -Hal, —OH, —CN, —NR$_{600}$R$_{610}$, —COR$_{600}$, —COOR$_{600}$, —CONR$_{600}$R$_{610}$ and —CF$_3$, wherein $R_{600}$ and $R_{610}$ are independently selected from the group consisting of hydrogen, unsubstituted $C_{1-20}$-alkyl, unsubstituted $C_{3-20}$-cycloalkyl, unsubstituted $C_{1-20}$-alkoxy, unsubstituted $C_{3-20}$-cycloalkoxy, unsubstituted $C_{6-20}$-aryl, unsubstituted $C_{6-20}$ aryloxy and —OH.

In one embodiment, $R_{500}$ and $R_{510}$ are not both hydrogen.

The reaction may be a non-asymmetric or asymmetric reduction reaction.

When $R_{500}$ and/or $R_{510}$ are different, the compounds of formula (I) are prochiral. In this instance, the hydrogenation catalysed by the [M (Y)$_2$(L$^1$)$_m$(L$^2$)], [M (Y)$_2$(L)$_2$(L$^2$)], [M Y(L$^1$)$_m$(L$^3$)] or [M Y L may be enantioselective when the phosphorus ligands L and L$^1$ are chiral.

The enantiomeric excess may be greater than 80% ee. In certain embodiments, the enantiomeric excess may be greater than 85% ee, in certain embodiments greater than 90% ee, in certain embodiments greater than 93% ee.

The reaction conditions for the reduction reactions are not particularly limited, and may be performed at the temperatures, pressures, concentrations that are appropriate to maximise the yield and stereoselectivity of the reaction, whilst minimising reaction time and reaction impurities.

Example reaction conditions for transfer hydrogenation reactions are described in WO2009/007443, the contents of which are hereby incorporated by reference.

After the reduction reaction is deemed complete, the reaction mixture may be at least partially separated, for example to isolate the product, and/or to isolate the complex. In a stereoselective reaction the product may be isolated from undesired stereoisomers.

The complexes of the invention may be separated from the reaction mixture by precipitation, for example following the addition of an anti-solvent to the reaction mixture or following the concentration of the reaction mixture.

The methods described above may be performed under an inert atmosphere, such as an argon or nitrogen atmosphere.

Preparation of Ligands of Formula (4)

In the following section, certain ligands of formula (4) will be designated as compounds of formula (1a) and (1b).

The present invention provides a benzo[h]quinoline compound of formula (1a) or (1b), or salts thereof:

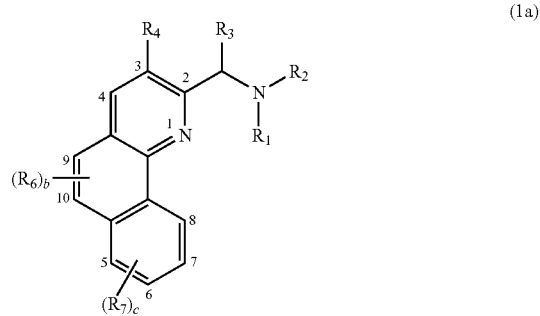

(1a)

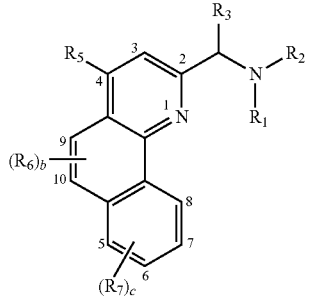

(1b)

wherein:

$R_1$ and $R_2$ are independently selected from the group consisting of —H, —OH, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

$R_3$ is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

$R_4$ is selected from the group consisting of unsubstituted $C_{1-20}$-alkyl, substituted $C_{1-20}$-alkyl, unsubstituted $C_{1-20}$-alkoxy, substituted $C_{1-20}$-alkoxy, unsubstituted $C_{5-20}$-aryl, substituted $C_{5-20}$-aryl;

$R_5$ is selected from the group consisting of unsubstituted $C_{1-20}$-alkyl, substituted $C_{1-20}$-alkyl, unsubstituted $C_{1-20}$-alkoxy, substituted $C_{1-20}$-alkoxy, unsubstituted $C_{5-20}$-aryl, substituted $C_{5-20}$-aryl;

$R_6$ is selected from the group consisting of —$CF_3$, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, substituted $C_{4-20}$-heteroaryl, —NR'R"—COOR', —S(O)$_2$OH, —S(O)$_2$—R', —S(O)$_2$NR'R" and —CONR'R", wherein R' and R" are independently selected from the group consisting of H, unsubstituted $C_{1-20}$-alkyl, substituted $C_{1-20}$-alkyl, unsubstituted $C_{5-20}$-aryl, substituted $C_{5-20}$-aryl, unsubstituted $C_{7-20}$-arylalkyl, substituted $C_{7-20}$-arylalkyl, or R' and R" together with the atom to which they are attached form a substituted or unsubstituted $C_{2-20}$-heterocycloalkyl group;

$R_7$ is selected from the group consisting of —$CF_3$, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, substituted $C_{4-20}$-heteroaryl, —NR'R"—COOR', —S(O)$_2$OH, —S(O)$_2$—R', —S(O)$_2$NR'R" and —CONR'R", wherein R' and R" are independently selected from the group consisting of H, unsubstituted $C_{1-20}$-alkyl, substituted $C_{1-20}$-alkyl, unsubstituted $C_{5-20}$-aryl, substituted $C_{5-20}$-aryl, unsubstituted $C_{7-20}$-arylalkyl, substituted $C_{7-20}$-arylalkyl, or R' and R" together with the atom to which they are attached form a substituted or unsubstituted $C_{2-20}$-heterocycloalkyl group;

b is an integer selected from 0, 1 or 2; and c is an integer selected from 0, 1, 2, 3 or 4.

The numbering of the atoms around the benzo[h]quinoline skeleton is illustrated in the formulae above.

The benzo-fused pyridine ring of the compounds of formulae (1) are disubstituted as a group is present at both C-2 and either at C-3 or C-4. The pyridine ring, therefore, may be substituted by a —CH($R_3$)—$NR_1R_2$ amino group at C-2 and group $R_4$ at C-3 for the compound (1a). In this instance, $R_5$ is —H. Alternatively, the pyridine ring may be substituted by the CH($R_3$)—$NR_1R_2$ amino group at C-2 and group $R_5$ at C-4 for the compound (1 b). For this compound, $R_4$ is —H.

$R_1$ and $R_2$ may be independently selected from the group consisting of —H, —OH, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one embodiment, $R_1$ and $R_2$ are independently selected from the group consisting of —H, —OH, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In another embodiment, the alkyl groups may be optionally functionalised with one or more substituents such as halide (—F, —Cl, —Br or —I) or alkoxy groups, e.g. methoxy, ethoxy or propoxy. The aryl group may be optionally functionalised with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—).

In one embodiment, one of $R_1$ and $R_2$ is —H and the other is selected from the group consisting of —H, —OH, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one preferred embodiment, one of $R_1$ and $R_2$ is —H and the other is selected from the group consisting of —H, —OH, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as H, —OH, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In one embodiment, the alkyl groups may be optionally functionalised with one or more substituents such as halide (—F, —Cl, —Br or —I) or alkoxy groups, e.g. methoxy, ethoxy or propoxy. The aryl group may be optionally functionalised with one or more (e.g. 1, 2, 3, 4, or 5)

substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—).

In one preferred embodiment, $R_1$ and $R_2$ are both —H.

$R_3$ is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one embodiment, $R_3$ is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as H, methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In another embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). More preferably, $R_3$ is selected from —H, methyl, ethyl, n-propyl, iso-propyl, n-butyl, iso-butyl, sec-butyl, tert-butyl and phenyl. In one embodiment, $R_3$ is —H.

When $R_3$ is —H, the carbon atom to which $R_3$ is attached is not chiral. However, when $R_3$ is not H, the compounds (1) will contain a chiral centre in the —$CH(R_3)$—$NR_1R_2$ group. The compounds (1) can be used as a racemic mixture, as either single enantiomer or as a mixture of enantiomers, preferably as a single enantiomer. The enantiomers of compounds (1) may be obtained in enantiomerically pure form by the resolution of e.g. a racemic mixture of compound (1a) or (1 b).

For the compound (1a), $R_4$ is selected from the group consisting of unsubstituted $C_{1-20}$-alkyl, substituted $C_{1-20}$-alkyl, unsubstituted $C_{1-20}$-alkoxy, substituted $C_{1-20}$-alkoxy, unsubstituted $C_{5-20}$-aryl, substituted $C_{5-20}$-aryl. In one embodiment, $R_4$ is selected from the group consisting of unsubstituted $C_{1-20}$-alkyl, substituted $C_{1-20}$-alkyl, unsubstituted $C_{5-20}$-aryl, substituted $C_{5-20}$-aryl. In another embodiment, $R_4$ may be selected from the group consisting of methyl, ethyl, n-propyl, iso-propyl, n-butyl, iso-butyl, sec-butyl, tert-butyl, pentyl, hexyl, heptyl, octyl, nonyl, decyl, dodecyl, stearyl, phenyl, -phenyl-$CF_3$ (e.g. 2-, 3- or 4-$CF_3$-phenyl, such as 4-$CF_3$-phenyl), -pentahalophenyl (e.g. pentafluorophenyl), naphthyl and anthracyl, such as methyl, ethyl, n-propyl, iso-propyl, n-butyl, iso-butyl, sec-butyl, tert-butyl, phenyl, -phenyl-$CF_3$ (e.g. 2-, 3- or 4-$CF_3$-phenyl, such as 4-$CF_3$-phenyl) or -pentahalophenyl (e.g. pentafluorophenyl). In another embodiment, $R_4$ is selected from the group consisting of unsubstituted $C_{1-20}$-alkyl and unsubstituted $C_{5-20}$-aryl. In another embodiment, $R_4$ may be selected from the group consisting of methyl, ethyl, n-propyl, iso-propyl, n-butyl, iso-butyl, sec-butyl, tert-butyl, pentyl, hexyl, heptyl, octyl, nonyl, decyl, dodecyl, stearyl, phenyl, naphthyl and anthracyl, such as methyl, ethyl, n-propyl, iso-propyl, n-butyl, iso-butyl, sec-butyl, tert-butyl, phenyl, naphthyl and anthracyl. In one embodiment, $R_4$ is methyl. In another embodiment, $R_4$ is phenyl. In another embodiment, $R_4$ is -phenyl-$CF_3$. In another embodiment, $R_4$ is pentafluorophenyl.

For the compound (1b), $R_5$ is selected from the group consisting of unsubstituted $C_{1-20}$-alkyl, substituted $C_{1-20}$-alkyl, unsubstituted $C_{1-20}$-alkoxy, substituted $C_{1-20}$-alkoxy, unsubstituted $C_{5-20}$-aryl, substituted $C_{5-20}$-aryl. In one embodiment, $R_5$ is selected from the group consisting of unsubstituted $C_{1-20}$-alkyl, substituted $C_{1-20}$-alkyl, unsubstituted $C_{5-20}$-aryl, substituted $C_{5-20}$-aryl. In another embodiment, $R_5$ may be selected from the group consisting of methyl, ethyl, n-propyl, iso-propyl, n-butyl, iso-butyl, sec-butyl, tert-butyl, pentyl, hexyl, heptyl, octyl, nonyl, decyl, dodecyl, stearyl, phenyl, -phenyl-$CF_3$ (e.g. 2-, 3- or 4-$CF_3$-phenyl, such as 4-$CF_3$-phenyl), -pentahalophenyl (e.g. pentafluorophenyl), naphthyl and anthracyl, such as methyl, ethyl, n-propyl, iso-propyl, n-butyl, iso-butyl, sec-butyl, tert-butyl, phenyl, -phenyl-$CF_3$ (e.g. 2-, 3- or 4-$CF_3$-phenyl, such as 4-$CF_3$-phenyl) or -pentahalophenyl (e.g. pentafluorophenyl). In another embodiment, $R_5$ is selected from the group consisting of unsubstituted $C_{1-20}$-alkyl and unsubstituted $C_{5-20}$-aryl. In another embodiment, $R_5$ may be selected from the group consisting of methyl, ethyl, n-propyl, iso-propyl, n-butyl, iso-butyl, sec-butyl, tert-butyl, pentyl, hexyl, heptyl, octyl, nonyl, decyl, dodecyl, stearyl, phenyl, naphthyl and anthracyl, such as methyl, ethyl, n-propyl, iso-propyl, n-butyl, iso-butyl, sec-butyl, tert-butyl, phenyl, naphthyl and anthracyl. In one preferred embodiment, $R_5$ is methyl. In another embodiment, $R_5$ is phenyl. In another embodiment, $R_5$ is -phenyl-$CF_3$. In another embodiment, $R_5$ is pentafluorophenyl.

$R_6$ may be present or absent. When absent, b is 0 i.e. the aryl ring is unsubstituted. When $R_6$ is present, b may be 1 or 2. When b is 2, each $R_6$ may be the same or different to each other. The or each $R_6$ may be selected from the group consisting of $CF_3$, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, substituted $C_{4-20}$-heteroaryl, —NR'R"—COOR', —S(O)$_2$OH, —S(O)$_2$—R', —S(O)$_2$NR'R" and —CONR'R", wherein R' and R" are independently selected from the group consisting of H, unsubstituted $C_{1-20}$-alkyl, substituted $C_{1-20}$-alkyl, unsubstituted $C_{5-20}$-aryl, substituted $C_{5-20}$-aryl, unsubstituted $C_{7-20}$-arylalkyl, substituted $C_{7-20}$-arylalkyl, or R' and R" together with the atom to which they are attached form a substituted or unsubstituted $C_{2-20}$-heterocycloalkyl group. In one embodiment, $R_6$ is selected from the group consisting of $CF_3$, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one embodiment, $R_6$ is independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{6-20}$-aryl, such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In another embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). In one preferred embodiment, b is 0 i.e. $R_6$ is absent.

$R_7$ may be present or absent. When absent, c is 0 i.e. the aryl ring is unsubstituted. When $R_7$ is present, c may be 1, 2, 3 or 4, such as 1, 2 or 3. When c is 2, 3 or 4, each $R_7$ may be the same or different to each other. The or each $R_7$ may be selected from the group consisting of —$CF_3$, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{6-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, substituted $C_{4-20}$-heteroaryl, —NR'R"— COOR', —S(O)$_2$OH, —S(O)$_2$—R', —S(O)$_2$NR'R" and —CONR'R", wherein R' and R" are independently selected from the group consisting of H, unsubstituted $C_{1-20}$-alkyl, substituted $C_{1-20}$-alkyl, unsubstituted $C_{5-20}$-aryl, substituted $C_{5-20}$-aryl, unsubstituted $C_{7-20}$-arylalkyl, substituted $C_{7-20}$-arylalkyl, or R' and R" together with the atom to which they are attached form a substituted or unsubstituted $C_{2-20}$-heterocycloalkyl group. In one embodiment, $R_7$ is selected from the group consisting of —$CF_3$, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{6-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl. In one embodiment, $R_7$ is independently selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl and substituted $C_{5-20}$-aryl, such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl, or aryl groups such as phenyl, naphthyl or anthracyl. In another embodiment, the alkyl groups may be optionally substituted with one or more substituents such as halide (—F, —Cl, —Br or —I) or alkoxy groups, e.g. methoxy, ethoxy or propoxy. The aryl group may be optionally substituted with one or more (e.g. 1, 2, 3, 4, or 5) substituents such as halide (—F, —Cl, —Br or —I), straight- or branched-chain $C_1$-$C_{10}$-alkyl, $C_1$-$C_{10}$ alkoxy, straight- or branched-chain $C_1$-$C_{10}$-(dialkyl)amino, $C_{3-10}$ heterocycloalkyl groups (such as morpholinyl and piperadinyl) or tri(halo)methyl (e.g. $F_3C$—). In one preferred embodiment, the aromatic ring is unsubstituted at C-8 i.e. $R_7$ is absent at C-8.

In one preferred embodiment, c is 0 i.e. $R_7$ is absent.

In another preferred embodiment, c is 1 and is present at C-5. $R_6$ may be present or absent as described above, preferably, absent i.e. b is 0. The compounds of formula (1a) and (1b) therefore have the following structures:

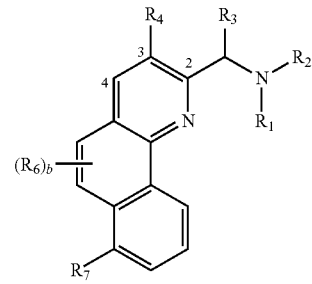

(1a)

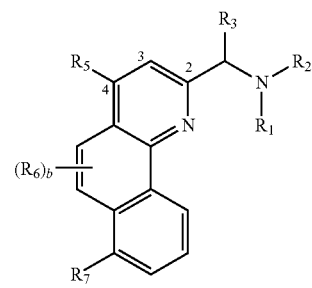

(1b)

In one preferred embodiment, the compound of formula (1a) may be selected from the group consisting of:

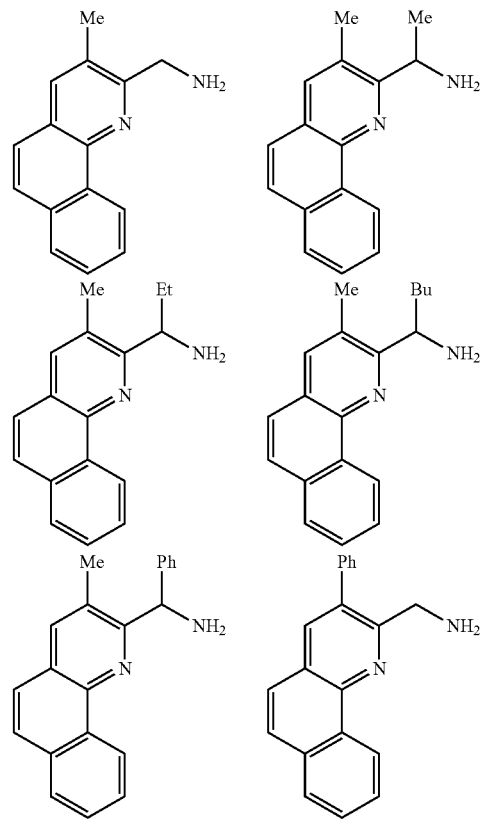

-continued

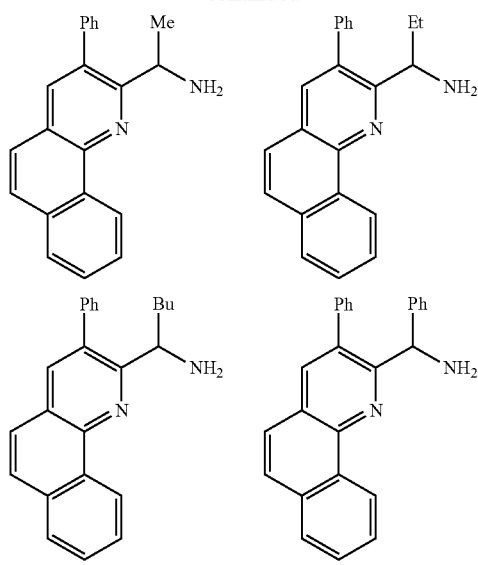

In one particularly preferred embodiment, the compound of formula (1a) may be selected from the group consisting of:

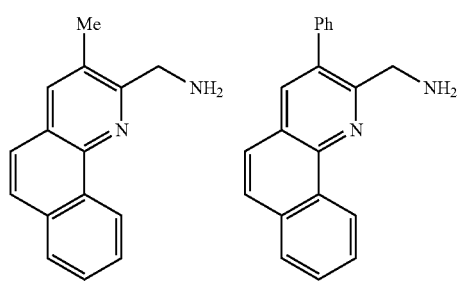 [SMILES: Cc1cc2ccc3ccccc3c2nc1CN ; NCc1nc2c(ccc3ccccc32)cc1-c1ccccc1]

In one preferred embodiment, the compound of formula (1b) may be selected from the group consisting of:

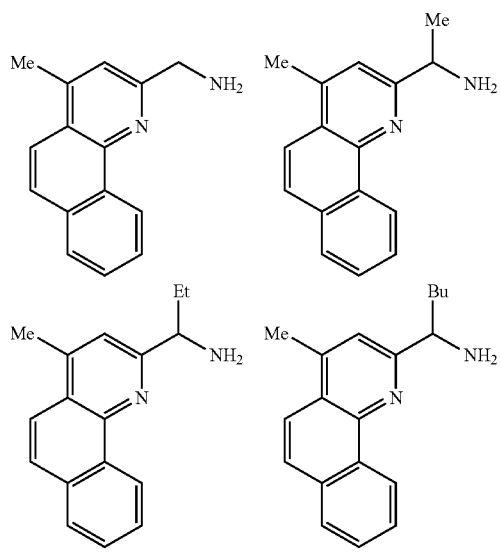

-continued

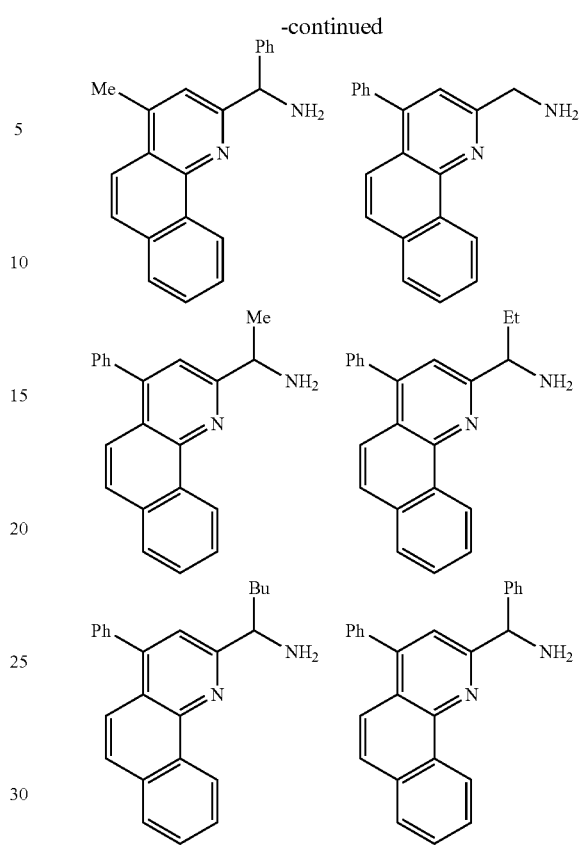

In one particularly preferred embodiment, the compound of formula (1b) may be selected from the group consisting of:

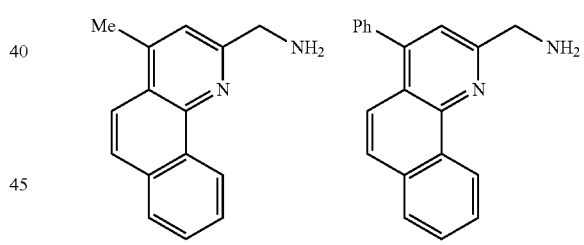

The compounds of formula (1a) and (1b) may form a salt with a suitable acid e.g. a suitable organic or inorganic acid. The compound (1a) or (1b) may be reacted as the free base with a suitable acid to form the salt. Alternatively, the acid may be present in situ during the preparation of the compounds (1a) and (1b). In this instance, the salts of (1a) and (1b) may be isolated directly from the reaction mixture. In one embodiment, the acid may be a hydrohalide acid, such as hydrochloric acid, hydrobromic acid or hydroiodic acid. The salts of compounds (1a) or (1b) may accordingly be hydrochloride salts, hydrobromide salts or hydroiodide salts. In one embodiment, the salt is a hydrochloride salt. In another embodiment, the acid may be selected from the group consisting of acetic acid, trifluoroacetic acid, methylsulfonic acid, trifluoromethylsulfonic acid, p-toluenesulfonic acid phosphoric acid, benzoic acid, salicylic acid, and citric acid. The salts of compounds (1a) or (1b) may accordingly be acetate salts, trifluoroacetate salts, methylsulfonate salts, trifluoromethylsulfonate salts, p-toluenesulfonate salts, phosphate salts, benzoate salts, salicylate salts, or citrate salts.

When $R_3$ of the compound (1a) or (1b) is not H, optical resolution of the enantiomers of compounds (1a) and (1b) may be performed by methods known in the art. For example, a racemic mixture of compound (1a) may be optically resolved using an acid chiral resolving agent. A racemic mixture of compound (1b) may be optically resolved likewise. Chiral resolving agents include but are not limited to L-(+)-tartaric acid, D-(−)-tartaric acid, L-(+)-mandelic acid or D-(−)-mandelic acid. It is envisaged that a racemic chiral acid may be used to form a diastereomeric mixture of salts of compounds (1a) and (1b). If desired, resolution of the diastereomers may occur by fractional crystallisation. It is also envisaged that enzymatic resolution of the enantiomers of compounds (1a) and (1b) may be possible with an enzyme such as a lipase.

The isolation of the compounds (1a) and (1 b) as salts (in particular, hydrochloride salts) provide stable ligand precursors, which can be stored in air at room temperature in the absence of moisture for a long time without degradation (for example, for more than two years) and can be used directly in the preparation of transition metal complexes.

Preparation of the Compounds of Formula (1a) and (1b)

The compounds of formula (1a) and (1 b), and salts thereof, may be prepared from a compound of formula (4a) or (4b), and salts thereof, by methods known in the art. In this respect, a compound (4a) reacts to form a compound (1a) and a compound (4b) reacts to form a compound (1b). For example, the compound (4a) or (4b) may be reacted with a base and a compound of formula (5):

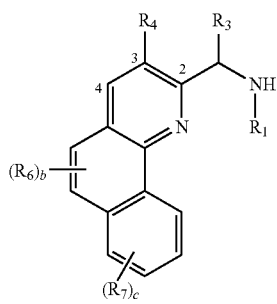

(4a)

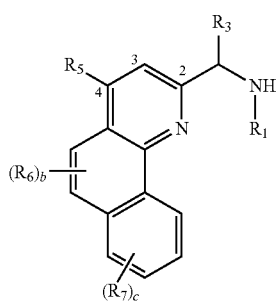

(4b)

$R_2$—Y (5)

wherein:
Y is a leaving group.

$R_1$, $R_3$, $R_4$, $R_5$, $R_6$, $R_7$, b and c are as generally described above.

In this instance, $R_2$ may be selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-heteroalkyl, substituted $C_{1-20}$-heteroalkyl, unsubstituted $C_{2-20}$-heterocycloalkyl and substituted $C_{2-20}$-heterocycloalkyl. In one embodiment, $R_2$ may be selected from the group consisting of unsubstituted $C_{1-20}$-alkyl, substituted $C_{1-20}$-alkyl, unsubstituted $C_{3-20}$-cycloalkyl and substituted $C_{3-20}$-cycloalkyl.

The base may be any suitable base which is capable of deprotonating the $NHR_1$ group of the compound (4a) or (4b). Suitable bases include but are not limited to organic or inorganic bases. Inorganic bases may be selected from the group consisting of hydroxides, alkoxides, carbonates, acetates. Suitable hydroxides include alkali metal hydroxides (e.g. lithium hydroxide, sodium hydroxide or potassium hydroxide) or tetraalkylammonium hydroxides (e.g. tetrabutylammonium hydroxide). Suitable alkoxides include alkali metal alkoxides (e.g. lithium alkoxide, sodium alkoxide (such as sodium methoxide) or potassium alkoxide) or tetraalkylammonium alkoxides (e.g tetrabutylammonium hydroxide). Suitable carbonates include but are not limited to potassium carbonate or sodium carbonate. Suitable acetates include but are not limited to potassium acetate or sodium acetate. Organic bases include but are not limited to organolithium reagents, such as butyllithium (e.g. n-, sec- or tert-butyllithium) or lithium diisopropylamide (LDA).

The reaction may be carried out under an inert atmosphere (such as nitrogen or argon). Suitably, a solvent may be used, for example, any suitable protic or aprotic polar solvent or combinations thereof). Suitable protic solvent include but are not limited to alcohols (such as methanol, ethanol, 1-propanol, 2-propanol, 1-butanol, 2-butanol, t-butanol or benzylic alcohol). Suitable aprotic solvents include but are not limited to ethers (e.g. tetrahydrofuran (THF), 2-methyltetrahydrofuran (2-Me-THF), dioxane, methyltertbutylether (MTBE) or diethylether), amides (e.g. dimethylformamide (DMF), N-methylpyrrolidine (NMP) or dimethylacetamide (DMAc)) or chlorinated alkanes (such as chloromethane or dichloromethane (DCM)). The solvent may be anhydrous.

The compound (4a) or (4b), the base, the solvent and the compound (5) may be added in any suitable order. In one embodiment of the invention, however, the compound (4a) or (4b) and the base is placed in a reaction vessel, together with the solvent, and then the compound (5) is added.

Y is a leaving group and may be a halide. In one embodiment, the halide may be selected from the group consisting of chloride, bromide or iodide.

The reaction may be continued for a suitable period of time until it is determined (e.g. by GC) that the reaction substantially complete. The period of time may vary from about 30 minutes to about 72 hours, preferably 30 minutes to about 24 hours. During this time, the reaction temperature may be varied one or more times between about 10° C. and about 25° C. If desired, on completion of the reaction, the compound of formula (1a) or (1b) may be separated from the reaction mixture by any appropriate method.

As described above, the compounds of formula (1a) and (1b) may form a salt with a suitable acid. The compounds (1a) and (1b) may be reacted as the free base with a suitable acid to form the salt. Alternatively, the acid may be present in situ during the preparation of compounds (1a) and (1b). For example, the compounds (4a) and (4b) may be reacted as acid addition salts of compounds (4a) and (4b) forming the acid addition salts of compounds (1a) and (1b). The extra addition of acid to the reaction mixture comprising compounds (4a) and (4b), therefore, may not be necessary in order to prepare salts of compounds (1a) and (1b). The acid used is as generally described above.

Preparation of the Compounds of Formulae (4a) and (4b)

The compound of formula (4a) or (4b) may be prepared by reducing a compound (6a) or (6b). In this respect, a compound (6a) is reduced to a compound (4a) and a compound (6b) is reduced to a compound (4b).

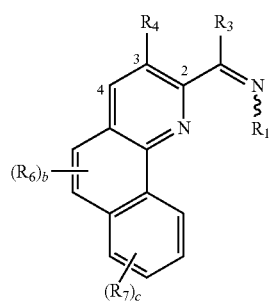

(6a)

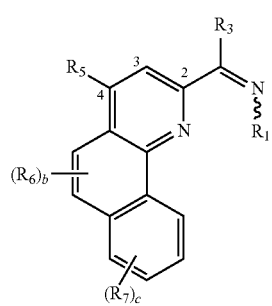

(6b)

$R_1$, $R_3$, $R_4$, $R_5$, $R_6$, $R_7$, b and c are as generally described above.

It will be understood that, in the depictions herein, where $R_1$ is connected by a wavy line ( ∿ ), both or either enantiomer may be present.

In one embodiment, the reduction may be a hydrogenation reaction. The hydrogenation reaction may comprise reacting the compound (6a) or (6b) with gaseous hydrogen in the presence of a hydrogenation catalyst and an acid in a suitable solvent. The hydrogenation catalyst may be a heterogeneous or homogeneous catalyst, preferably a heterogeneous catalyst. The catalyst (whether heterogeneous or homogeneous) should be selected such that the catalyst preferentially reduces the —($R_3$)C=N($R_1$)— double bond rather than reducing another group present in the compound (6a) or (6b). In one embodiment, the heterogeneous catalyst is a heterogeneous platinum group metal (PGM) catalyst, for example, a heterogeneous palladium or platinum catalyst. In one embodiment, the heterogeneous catalyst is a heterogeneous palladium catalyst. Examples of palladium catalysts include but are not limited to colloidal palladium, palladium sponge, palladium plate or palladium wire. Examples of platinum catalysts include but are not limited to colloidal platinum, platinum sponge, platinum plate or platinum wire.

The heterogeneous PGM metal catalyst may be a PGM on a solid support. The support may be selected from the group consisting of carbon, alumina, calcium carbonate, barium carbonate, barium sulfate, titania, silica, zirconia, ceria and a combination thereof. When the support is alumina, the alumina may be in the form of alpha-$Al_2O_3$, beta-$Al_2O_3$, gamma-$Al_2O_3$, delta-$Al_2O_3$, theta-$Al_2O_3$ or a combination thereof. When the support is carbon, the carbon may be in the form of activated carbon (e.g. neutral, basic or acidic activated carbon), carbon black or graphite (e.g. natural or synthetic graphite). An example of a heterogeneous PGM catalyst is palladium on carbon. An example of another heterogeneous PGM catalyst is platinum on carbon.

The catalyst loading may be up to about 20 mole %. A greater catalyst loading may perform the desired reduction, however, increasing the quantity of the PGM may make the process uneconomical. In one embodiment, the catalyst loading may be up to 10 mole % and, in another embodiment, may be in the range of about 0.1-10.0 mole %.

The acid may be any suitable acid, such as a hydrohalide acid e.g. hydrochloric acid, hydrobromic acid or hydroiodic acid. The acid may be added as a reagent to the hydrogenation reaction or the compounds (6a) and (6b) may be reacted as acid addition salts. The salts are as generally described above. Without wishing to be bound by theory, it is believed that the benzo-fused pyridinyl N atom needs to be protonated in order for the hydrogenation to proceed.

Any suitable solvent may be utilised e.g. polar solvents, such as an alcohol. The alcohol may be selected from the group consisting of methanol, ethanol, isopropanol and mixtures thereof. In one embodiment, the solvent is methanol.

The compound (6a) or (6b) may be placed in a pressure vessel together with the hydrogenation catalyst. The pressure vessel may then be assembled and purged with one or more nitrogen/vacuum cycles (e.g. one, two, three or four cycles). The alcohol solvent may then added via the injection port to form a solution of the compound (6a) or (6b), which may have concentration in the range of about 0.01 to about 1 molar, such as about 0.3 molar. If the hydrogenation catalyst is heterogeneous, the catalyst will not dissolve in the alcohol solvent. However, if the hydrogenation catalyst is homogeneous, it may dissolve in the alcohol solvent and form a solution with the compound (5a) or (5b).

Once the alcohol solvent has been added, the pressure vessel may be purged once again with one or more nitrogen/vacuum cycles (e.g. one, two, three, four or five cycles), followed by one or more hydrogen/vacuum cycles (e.g. one, two, three, four or five cycles). During purging the reaction mixture may be agitated (by either stirring or shaking) to encourage removal of dissolved oxygen. The pressure vessel may then be pressurised with hydrogen (e.g. to about 5 bar), stirred and heated to temperature (e.g. about 30° C.). Hydrogen gas uptake may begin after a period of time has elapsed (e.g. after about 45 minutes on a 6 g scale reaction). Once hydrogen uptake begins, the pressure vessel may optionally be depressurised with hydrogen While it is typically sufficient for a single charge of hydrogenation catalyst to be added to the reaction mixture, a second or further charge may be added and the hydrogenation continued if it has been determined (e.g. via in-process analysis) that the reaction has not gone substantially to completion and starting material remains.

There is no particular limitation on the pressure at which the hydrogenation is carried out. In this regard, the hydrogenation may conveniently be carried out with an initial hydrogen pressure in the range of up to about 7 bar (about 100 psi) e.g. about 5±1 bar.

The reaction temperature may be suitably in the range from about 15 to about 75° C., such as in the range from about 20 to about 60° C., for example, about 25 to about 50° C. In one embodiment, the reaction temperature may be about 30° C.

The reaction mixture may then be stirred in the presence of hydrogen gas until hydrogen uptake is no longer apparent. The hydrogenation reaction is carried out for a period of time until it is determined that the reaction is substantially complete. Completion of the reaction may be determined by in-process analysis or by identifying that there is no longer an uptake of hydrogen gas. Typically the hydrogenation is complete within about 24 hours, and in some embodiments, within about 90 minutes.

On completion of the reaction, the reaction vessel may be cooled to ambient temperature and purged with one or more nitrogen/vacuum cycles (e.g. one, two, three, four or five cycles) to remove excess hydrogen gas. The hydrogenation catalyst may be removed by any appropriate method, such as filtration (e.g. using a pad of Celite), washed one or more times with alcohol solvent (e.g. one, two, three or more times) and the filtrate further treated as desired. A proportion of the solvent may be evaporated if desired prior to recovery of the compound of formula (4a) or (4b).

Howsoever the compound (4a) or (4b) is recovered, the separated compounds may be washed and then dried. Drying may be performed using known methods, for example at temperatures in the range 10-60° C. and preferably 20-40° C. under 1-30 mbar vacuum for 1 hour to 5 days. If desired the compound (4a) or (4b) may be recrystallised, although in certain embodiments this is generally not required and the compounds (4a) and (4b), or salts thereof, may be used to form compounds (1a) and (1b), or salts thereof, without further purification.

In this embodiment, in the compounds (6a) and (6b), $R_1$ may be as generally described above or may be —OH. In one embodiment, $R_1$ is —OH i.e. the —$(R_3)C$=$N(OH)$ group is an oxime. In this instance, the compounds (6a) and (6b) have the following structure:

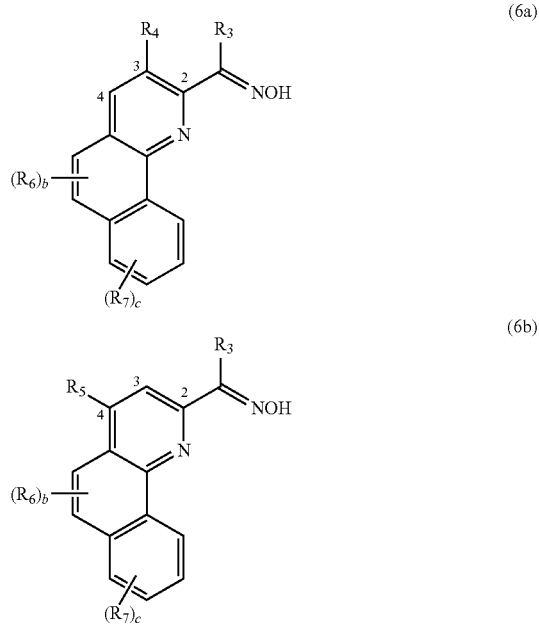

(6a)

(6b)

In this embodiment, when the —$(R_3)C$=$N(OH)$— group is hydrogenated, the OH is replaced by a H during the reaction. The compound (1a) or (1b), therefore, may be prepared directly from a compound (6a) or (6b) as the compound (1a) or (1b) comprises a primary amine i.e. an $NH_2$ group.

Alternatively, when $R_1$ is OH for the compounds (6a) and (6b), the oxime group —$(R_3)C$=$N(OH)$ may be reduced to the primary amine using a reducing agent selected from the group consisting of lithium aluminium hydride ($LiAlH_4$), $LiAlH(OMe)_3$, $LiAlH(OEt)_3$, $AlH_3$, $BH_3$.THF (borane tetrahydrofuran complex) solution, $BH_3$.DMS (borane dimethyl sulfide complex) solution, sodium borohydride ($NaBH_4$) and $B_2H_6$. In one embodiment, the reducing agent may be $LiAlH_4$. In another embodiment, the reducing agent may be $NaBH_4$.

In another embodiment, when $R_1$ is OH for the compounds (6a) and (6b), the oxime group —$(R_3)C$=$N(OH)$ may be reduced to the primary amine using a reducing agent which is zinc and acetic acid.

In another embodiment, the reduction may be a transfer hydrogenation reaction. The transfer hydrogenation reaction may comprise reacting a compound (6a) or (6b) with a hydrogen donor in the presence of a transfer hydrogenation catalyst. The hydrogen donor may be selected from formic acid, a formic acid alkali salt (for example, sodium formate) and an alcohol, such as an alcohol having a hydrogen atom at a carbon that is a to the carbon atom to which the alcohol group is attached. An example of a suitable alcohol includes but is not limited to iso-propanol. In this embodiment, hydrogen is formally added across the —$(R_3)C$=$N(R_1)$— double bond, however, gaseous hydrogen ($H_2$) is not the source.

The transfer hydrogenation catalyst may be catalysts of the type [(sulphonylated diamine) RuCl (arene)] or heterogeneous PGM catalysts as described above.

In this embodiment, $R_1$ is not OH and is as generally described above.

When $R_1$ is not —H or —OH, the compound (6a) or (6b) may be reduced with an achiral catalyst to form a racemate. Compounds (4a) and (4b) can then be obtained in enantiomerically pure form by resolution of the racemic mixture as generally described above. Suitable acid resolving agents are also as generally described above.

Alternatively, when $R_1$ is not H or OH, the compound (6a) or (6b) may be asymmetrically reduced with a chiral catalyst to produce an enantiomerically enriched compound (4a) or (4b). Each enantiomer is within the scope of the present invention.

The compounds of formula (6a) or (6b) may form a salt with a suitable acid. The compounds (6a) and (6b) may be reacted as the free base with a suitable acid to form the salt. Alternatively, the acid may be present in situ during the preparation of compounds (6a) and (6b). For example, the compounds (7a) and (7b), described below, may be reacted as acid addition salts of compounds (7a) and (7b) forming the acid addition salts of compounds (6a) and (6b). The extra addition of acid to the reaction mixture comprising compounds (7a) and (7b), therefore, may not be necessary in order to prepare salts of compounds (6a) and (6b). Suitable acids are as generally described above.

In one embodiment, the acid may be a hydrohalide acid, such as hydrochloric acid, hydrobromic acid or hydroiodic acid. The salts of compounds (6a) and (6b) may accordingly be hydrochloride salts, hydrobromide salts or hydroiodide salts. In one embodiment, the salt is a hydrochloride salt.

Preparation of Compounds of Formulae (6a) and (6b)

The compound (6a) or (6b), or salts thereof, may be prepared by the reaction of a compound of formula (7a) or (7b). In this respect, a compound (7a) reacts to form a compound (6a), or salt thereof, and a compound (7b) reacts to form a compound (6b), or salt thereof.

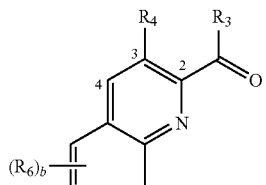
(7a)

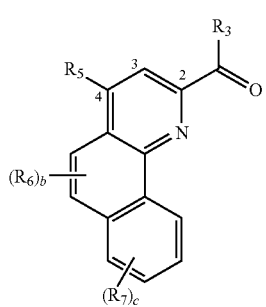
(7b)

R$_3$, R$_4$, R$_5$, R$_6$, R$_7$, b and c are as generally described above.

Compounds (7a) and (7b) may be reacted with a compound of formula (8), or salt thereof, in an alcohol solvent to form compound (6a) or (6b).

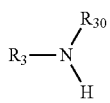
(8)

wherein,
R$_3$ is as defined above; and
R$_{30}$ is selected from the group consisting of H and OH.

The compound (8) reacts with the carbonyl group of compounds (7a) and (7b) to form the iminyl group of compounds (6a) and (6b). In one embodiment, R$_{30}$ is —H i.e. the compound (8) is a primary amine. In another embodiment, R$_{30}$ is —OH i.e. the compound (8) is a hydroxylamine.

Salts of compounds (8) may be used in this reaction. The salts of compounds (1a) or (1b) may be hydrochloride salts, hydrobromide salts or hydroiodide salts. In one embodiment, the salt is a hydrochloride salt. Salts of compounds (6a) and (6b) may be precipitated from the reaction mixture when salts of compounds (8) are utilised as a reactant, thus facilitating the isolation of the compounds (6a) and (6b) and, if desired, subsequent purification.

When compound (8) is a hydroxylamine (i.e. when R$_{30}$ is OH) and the hydroxylamine is reacted as the hydrochloride salt, the inventors have noted that the oxime hydrochlorides (6a) and (6b) may precipitate from the reaction mixture as stable solids.

The compound (8), or salt thereof, may be present in stoichiometric or greater quantities to the compound (7a) or (7b). The molar ratio of the compound (7a) or (7b) to compound (8), or salt thereof, may be in the range of about 1 to about 5, such as about 1 to about 3, for example, about 1 to about 2. In one embodiment, the molar ratio of the compound (7a) or (7b) to compound (8), or salt thereof, is about 1 to about 1. In another embodiment, the molar ratio of the compound (7a) or (7b) to compound (8), or salt thereof, is about 1 to about 1.8.

When the free base of compound (7a) or (7b) is reacted, stoichiometric or slight excess of base may be suitable, for example, about 1:about 1.1 to about 1:about 1.5 molar ratio of compound (1a) or (1b) to base.

The reaction comprises an alcohol solvent. The alcohol may be selected from the group consisting of methanol, ethanol, isopropanol and mixtures thereof. In one embodiment, the solvent is ethanol. The concentration of compound (7a) or (7b) in the alcohol solvent may be about 0.001 mol/L to about 1.0 mol/L, such as about 0.01 to about 0.75 mol/L, for example, about 0.1 mol/L to about 0.5 mol/L. In one embodiment, the concentration of compound (7a) or (7b) in the alcohol solvent is about 0.2 to about 0.4 mol/L, for example, about 0.28 mol/L or about 0.37 mol/L.

The compound (7a) or (7b), the solvent and the compound (8) may be added in any suitable order. In one embodiment, however, the compound (7a) or (7b) is suspended in the alcohol solvent in a reaction vessel, optionally heated to temperature, and then the compound (8) is added. The compound (8) may be added in one portion or portionwise. In one embodiment, the compound (8) is added in one portion. When compound (8) is a hydroxylamine hydrochloride (i.e. when R$_{30}$ is OH), the reaction mixture may form a solution on addition of the hydroxylamine.

The reaction temperature may be suitably in the range from about 15 to about 75° C., such as in the range from about 20 to about 60° C., for example, about 25 to about 50° C. In one embodiment, the reaction temperature may be about 40° C.

The reaction is carried out for a period of time until it is determined that the reaction is substantially complete. Completion of the reaction may be determined by in-process analysis. Typically the reaction is complete within about 24 hours, and in some embodiments, within about 90 minutes.

On completion of the reaction, the reaction mixture may be cooled (e.g. to 0° C. using an ice-bath). When a free base of compound (8) has been used, the free base of the compounds (6a) and (6b) may be isolated as the product by evaporating a proportion of the solvent. Alternatively, salts of compounds (6a) and (6b) may be isolated by treating the reaction mixture comprising the free bases of the compounds (6a) and (6b) with a suitable acid. Suitable acids are as generally described above. In one embodiment, the acid may be a hydrohalide acid, such as hydrochloric acid, hydrobromic acid or hydroiodic acid. The salts of compounds (6a) and (6b) may accordingly be hydrochloride salts, hydrobromide salts or hydroiodide salts. In one embodiment, the salt is a hydrochloride salt. In yet another embodiment, salts of compounds (6a) and (6b) may be obtained on utilising a salt of compound (8). In this instance, on completion of the reaction and on cooling the reaction vessel additional product may precipitate from the reaction mixture. The solid may be filtered and washed one or more times with alcohol solvent (e.g. one, two, three or more times).

Howsoever the compound (6a) or (6b), or salt thereof, is recovered, the compounds may be dried. Drying may be performed using known methods, for example at temperatures in the range 10-60° C. and preferably 20-40° C. under 1-30 mbar vacuum for 1 hour to 5 days. Typically, the compounds (6a) and (6b), or salts thereof, may be used to form the compounds (4a) and (4b) without further purification.

Preparation of the Compounds of Formulae (7a) and (7b)

The compounds of formula (7a) or (7b) may be prepared in a process comprising the steps of:

(a) reacting a compound of formula (9a) or (9b) with a lithiating agent in an ethereal solvent to form the lithiated compound (10a) or (10b); and

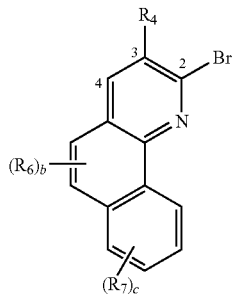
(9a)

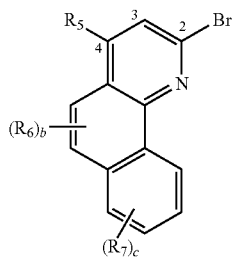
(9b)

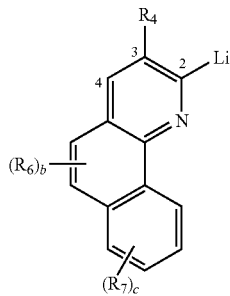
(10a)

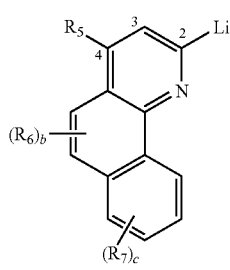
(10b)

(b) reacting the lithiated compound (10a) or (10b) with a compound of formula (11) to form the compound of formula (7a) or (7b).

(11)

wherein:
$R_3$, $R_4$, $R_5$, $R_6$, $R_7$, b and c are as generally described above; and
Z is —N(alkyl)$_2$ or -Hal.

A compound (9a) reacts via compound (10a) to form a compound (7a) and a compound (9b) reacts via a compound (10b) to form a compound (7b).

The lithiating agent may be an alkyl lithium reagent, such as n-BuLi or sec-BuLi. The alkyl lithium reagent may be conveniently purchased as a solution in a solvent, such as hexane. Stoichiometric or slight excess of lithiating agent may be used. For example, the molar ratio of compound (9a) or (9b) to lithiating agent may be about 1 to about 1 or about 1.1 to about 1 to about 1.5, such as about 1 to about 1.25.

The ethereal solvent may be an alkyl ether. Preferably, the alkyl ether is anhydrous. In one embodiment, the alkyl ether is a cyclic alkyl ether and more preferably tetrahydrofuran (THF). In another embodiment, the alkyl ether is diethyl ether or methyl tert-butyl ether (MTBE). With regard to THF and MTBE, the use of alkyl ethers such as these have higher flashpoint temperatures and, as such, may provide improved safety in handling. The concentration of compound (9a) or (9b) in the ethereal solvent may be about 0.001 mol/L to about 1.0 mol/L, such as about 0.01 to about 0.9 mol/L, for example, about 0.1 mol/L to about 0.85 mol/L. In one embodiment, the concentration of compound (9a) or (9b) in the ethereal solvent is about 0.25 to about 0.8 mol/L, for example, about 0.72 mol/L or about 0.33 mol/L.

The solution of the compound (9a) or (9b) may be cooled to e.g. about −78° C. before the lithiating agent is added. In this respect, the reaction temperature at which the lithiating reaction may occur can be suitably in the range from about −78 to about −20° C., such as in the range from about −78 to about −50° C. In one embodiment, the reaction temperature may be about −78° C. An isopropanol/dry ice bath may be used to cool the reaction mixture to about −78° C.

The compound (9a) or (9b), the ethereal solvent and the lithiating agent may be added in any suitable order. In one embodiment, the compound (9a) or (9b) is dissolved in the ethereal solvent in a reaction vessel, cooled, before adding the lithiating agent. The lithiating agent may be added in one portion or portionwise (e.g. dropwise) over a period of time. In one embodiment, the lithiating agent is added portionwise. The lithiating agent may be added using a syringe or a dropping funnel. If desired, the syringe or dropping funnel may be washed with a portion of ethereal solvent and the wash added to the reaction mixture.

The reaction mixture of step (a) is stirred for a period of time of up to about 3 hours when reacting compounds (9a) and (9b) with the lithiating agent on a scale of about 22 g or less. For larger reactions, however, the lithiating step may require a longer reaction time.

The compound of formula (11) is added to the reaction mixture comprising the compound (10a) or (10b) to form the compound (7a) or (7b). Stoichiometric or excess of compound (11) may be used. For example, the molar ratio of compound (9a) or (9b) to compound (11) may be about 1 to about 1 or about 1 to about 1.1 to about 1 to about 1.5, such as about 1 to about 1.25.

The compound (11) may be selected from the group consisting of N,N-dimethylformamide (DMF), N,N-dimethylacetamide (DMA), N,N-dimethylpropionamide, N,N-dimethylbutionamide and N,N-dimethylbenzamide. DMF provides a compound (7a) or (7b) where $R_3$ is —H, DMA provides a compound (7a) or (7b) where $R_3$ is -Me, N,N-dimethylpropionamide provides a compound (7a) or (7b) where $R_3$ is -Et, N,N-dimethylbutionamide provides a compound (7a) or (7b) where $R_3$ is —Bu and N,N-dimethylbenzamide provides a compound (7a) or (7b) where $R_3$ is -Ph.

Step (b) may be carried out at one or more temperatures in the range of about −78 to about 30° C. In one embodiment, the compound (11) is reacted with the compound (10a) or (10b) at a temperature lower than −65° C. and the reaction mixture allowed to warm slowly to room temperature.

Step (b) is carried out for a period of time until it is determined that the reaction is substantially complete. Completion of the reaction may be determined by in-process analysis. Typically the reaction is complete within about 24 hours, and in some embodiments, within about 16 hours.

Steps (a) and (b) are typically conducted under an inert atmosphere, such as nitrogen or argon.

On completion of the reaction, an alcohol (e.g. methanol) and an organic acid (e.g. acetic acid) may be added to quench the reaction mixture, followed by the addition of water and an aprotic solvent (such as dichloromethane). The organic phase may be separated from the aqueous phase and the organic phase washed one or more times with water (e.g. one, two, three or more times), one or more times with brine (e.g. one, two, three or more times), dried (e.g. using magnesium sulfate) and concentrated in vacuo to give the compound (7a) or (7b) as an oil or solid. Typically, the compounds (7a) and (7b) may be used to form the compounds (6a) and (6b) without further purification.

Preparation of the Compounds of Formulae (9a) and (9b)

The compound of formula (9a) or (9b) may be prepared in a process comprising the reaction of a compound of formula (12a) or (12b) with a halogenating agent in a solvent.

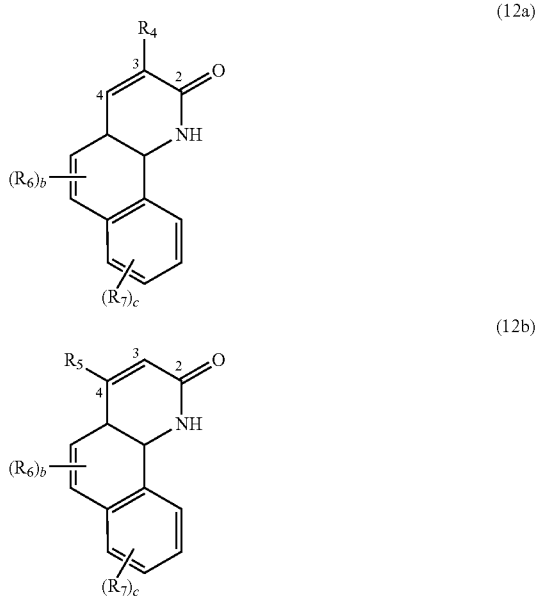

wherein:
$R_4$, $R_5$, $R_6$, $R_7$, b and c are as generally described above.

The compound (12a) reacts to form the compound (9a) and the compound (12b) reacts to form the compound (9b).

The halogenating agent may be a brominating agent or a chlorinating agent. The halogenating agent may be selected from the group consisting of phosphoryl bromide ($POBr_3$) and phosphoryl chloride ($POCl_3$). In one embodiment, the halogenating agent is $POBr_3$. In another embodiment, the halogenating agent is $POCl_3$.

Any suitable solvent may be used, for example, an aromatic hydrocarbon, such as benzene, toluene or xylene or amide solvent, such as dimethylformamide or dimethacetamide. In one embodiment, the aromatic solvent is toluene. In another embodiment, the amide solvent is dimethylformamide. In one embodiment, the solvent is anhydrous. The concentration of compound (12a) or (12b) in the solvent may be about 0.001 mol/L to about 2.0 mol/L, such as about 0.01 to about 1.75 mol/L, for example, about 0.05 mol/L to about 1.5 mol/L. In one embodiment, the concentration of compound (12a) or (12b) in the solvent is about 0.5 to about 2.0 mol/L, for example, about 0.7 to about 1.0, such as about 0.74 mol/L or about 0.75 mol/L or about 0.969 mol/L. In one embodiment, the concentration of compound (12a) or (12b) in the solvent is about 0.01 to about 0.5 mol/L, for example, about 0.05 to about 0.1 mol/L, such as about 0.06 mol/L.

If desired, the compound (12a) or (12b) may be azeotropically dried before it is reacted with the halogenating agent.

The compound (12a) or (12b), the solvent and the halogenating agent may be added in any suitable order. In one embodiment, however, the compound (12a) or (12b) and halogenating agent are combined with the solvent in a reaction vessel. In another embodiment, the compound (12) or (12b) is charged to a reaction vessel with the solvent, followed by the addition of the halogenating agent.

The reaction mixture may be heated to a temperature in the range from about 50 to about 200° C., such as in the range from about 60 to about 175° C., for example, about 75 to about 160° C. In one embodiment, the reaction may be heated to the reflux temperature of the solvent. Accordingly, when the solvent is benzene, the reaction temperature may be the boiling point of benzene i.e about 80° C. When the solvent is toluene, the reaction temperature may be the boiling point of toluene i.e. about 111° C. When the solvent is xylene, the reaction temperature may be in the boiling point of xylene i.e. in the range of about 138 to about 144° C. When the solvent is dimethylformamide, the reaction temperature may be the boiling point of DMF i.e. about 153° C.

The reaction may be conducted under an inert atmosphere, such as argon or nitrogen.

The reaction is carried out for a period of time until it is determined that the reaction is substantially complete. Completion of the reaction may be determined by in-process analysis. Typically the reaction is complete within about 24 hours, and in some embodiments, within about 16 hours. Hydrogen halide (e.g. HBr or HCl) may be formed during the course of the reaction which may be released through the use of a bubbler.

On completion of the reaction, the reaction mixture may be suspended in ice/water, stirred for a period of time (e.g. about 2 hours), filtered and dried in vacuum. Drying may be performed using known methods, for example at temperatures in the range 10-60° C. and preferably 20-40° C. under 1-30 mbar vacuum for 1 hour to 5 days.

Alternatively, the reaction mixture may be cooled (e.g. to room temperature). Water may be added to the reaction mixture and optionally an inorganic base. Examples of suitable inorganic bases include but are not limited to hydroxides and alkoxides. Suitable hydroxides include alkali metal hydroxides (e.g. lithium hydroxide, sodium hydroxide or potassium hydroxide) or tetraalkylammonium hydroxides (e.g. tetrabutylammonium hydroxide). In one embodiment, the inorganic base is a hydroxide which is sodium hydroxide. Sodium hydroxide may be added to the reaction mixture until the pH is about 10-14. Suitable alkoxides include alkali metal alkoxides (e.g. lithium alkoxide, sodium alkoxide or potassium alkoxide, such as lithium methoxide, sodium methoxide or potassium methoixde) or tetraalkylammonium alkoxides (e.g. tetrabutylammonium hydroxide).

The aqueous and organic phases may be separated and the aqueous phase washed one or more times with solvent (for example, one, two or three times with an aromatic solvent as described above). The organic phases may be combined and washed one or more times with brine (e.g. one, two, three or more times), dried (e.g. using magnesium sulfate) and concentrated in vacuo to give the compound (9a) or (9b). The compound (9a) or (9b) may be dissolved in a polar aprotic solvent (such as dichloromethane), optionally passed through a pad of silica gel, and the solvent removed in vacuo to provide a pure product.

Alternatively, the combined organic phases may be dried and concentrated in vacuo. The product may be taken up in a ketone solvent (e.g. acetone) and the solution heated to reflux, before being filtered hot. The ketone solvent may then be partially evaporated to produce a slurry, which may be filtered and dried.

Typically, the compounds (9a) and (9b) may be used to form the compounds (7a) and (7b) without further purification.

Preparation of the Compounds of Formula (12a) and (12b)

The compound of formula (12a) or (12b) may be prepared in a process comprising the step of reacting a compound of formula (13a) or (13b) with an acid.

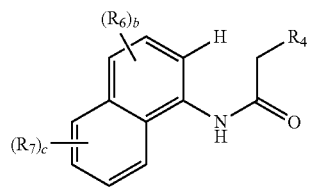
(13a)

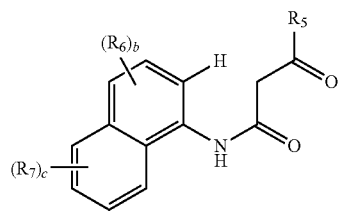
(13b)

wherein:
$R_4$, $R_5$, $R_6$, $R_7$, b and c are as generally described above.

The compound (13a) reacts to form the compound (12a) and the compound (13b) reacts to form the compound (12b).

Any suitable acid may be used which is capable of cyclising the compound (13a) or (13b) to form the compound (12a) or (12b). The acid may be mineral acid, such as sulphuric acid or hydrochloric acid. In one embodiment, the acid may be concentrated acid (e.g. 98% sulphuric acid). In another embodiment, the acid may be an aqueous solution of acid. Any suitable w/w ratio of water:acid may be used. For example, the w/w ratio of water:acid may be from about 10:about 0.01 to about 0.01:about 10, such as about 5:about 1 to about 1:about 5, e.g. about 1:about 3. The quantities of water and/or acid are not particularly limiting provided there is enough water and/or acid to cyclise the compound (13a) or (13b) into the compound (12a) or (12b).

The w/w ratio of compound of formula (13a) or (13b): acid may be in the range from about 10:about 0.01 to about 0.01:about 10, such as about 5:about 1 to about 1:about 5, e.g. about 1:about 3.

The acid may be heated to a temperature in the range of about 50 to about 95° C., such as about 50 to about 85° C., for example about 60 to about 80° C. e.g. about 75° C. before it is reacted with the compound (13a) or (13b). The compound (13a) or (13b) and the acid may be added in any suitable order. In one embodiment, however, the acid is charged to a reaction vessel and the compound (13a) or (13b) is added to the acid. The compound (13a) or (13b) may be added in one portion or portionwise over a period of time (e.g. 30 minutes). In another embodiment, the compound (13a) or (13b) is charged to a reaction vessel and the acid is added to the compound (13a) or (13b). The acid may be added in one portion or portionwise over a period of time.

The reaction mixture may be heated to a temperature in the range from about 50 to about 100° C., such as in the range from about 60 to about 100° C., for example, about 75 to about 100° C. The reaction mixture is typically stirred during the course of the reaction and if any lumps of solid are produced, these may be broken up as appropriate (e.g. using a Teflon rod).

The reaction is carried out for a period of time until it is determined that the reaction is substantially complete. Completion of the reaction may be determined by in-process analysis. Typically the reaction is complete within about 24 hours, and in some embodiments, within about 5 hours.

On completion of the reaction, the reaction mixture may be cooled (e.g. to room temperature). The reaction mixture may be diluted with water e.g. by adding the reaction mixture to water or adding water to the reaction mixture to afford a precipitate. The precipitate may be filtered and optionally washed one or more times with water (e.g. one, two, three or more times) and dried. In one embodiment, the precipitate may then crystallised from ethanol and the solid obtained stripped with an aromatic hydrocarbon solvent, such as toluene, one or more times (e.g. one, two, three or more times) to remove residual water. In another embodiment, the precipitate may be washed with a ketone solvent, such as acetone, one or more times (e.g. one, two, three or more times) and the solid dried.

Howsoever the compound (12a) or (12b) is recovered, the compounds may be dried. Drying may be performed using known methods, for example at temperatures in the range 10-60° C. and preferably 20-40° C. under 1-30 mbar vacuum for 1 hour to 5 days. Typically, the compounds (12a) and (12b) may be used to form the compounds (9a) and (9b) without further purification.

Preparation of the Compound of Formula (13a)

The compound of formula (13a) may be prepared in a process comprising the step of reacting a naphthylamine of formula (14), or salt thereof, with a compound of formula (15):

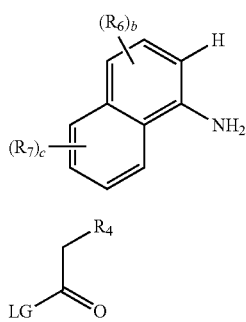

(14)

(15)

wherein:
$R_4$, $R_6$, $R_7$, b and c are as generally described above; and LG is a leaving group.

The naphthylamine of formula (14) may be a free base or salt thereof. In one embodiment, the salt of compounds (14) may be a hydrochloride salt, hydrobromide salt or hydroiodide salt.

LG is a leaving group which may be selected from the group consisting of a halide, —O-alkyl and a sulfonate ester. In one embodiment, the leaving group is a halide, such as —Cl, —Br or —I. In another embodiment, the leaving group is an —O-alkyl, such as —O-Et or —O-Me.

In one embodiment, the compound of formula (15) is propionyl chloride.

The reaction may further comprise a base. Any suitable base may be used which is capable of deprotonating the —$NH_2$ group of the compound (14) but does not otherwise adversely affect the reaction. Suitable bases include but are not limited to inorganic bases, such as sodium acetate, and organic bases, such as lutidine or triethylamine.

The compound (15) may be present in stoichiometric or greater quantities to the compound (14), or salt thereof. When the free base of compound (15) is reacted, stoichiometric or slight excess of base may be suitable, for example, about 1:1.1 to 1:1.5 molar ratio of compound (15) to base. When salts of compound (15) are utilised, however, excess base is generally required in order to form the free base of the compound (15) from the salt of compound (15), and deprotonate the amino group. In this respect, the molar ratio of the salts of compound (15) to base may be about 1:5 to about 1:20, such as about 1:7.5 to about 1:15, such as about 1:10.

The reaction may further comprise a solvent. Any suitable solvent may be used, for example, chlorinated solvents, such as dichloromethane (DCM), aromatic hydrocarbons, such as benzene, toluene or xylene, or ethereal solvents, for example alkyl ethers, such as THF or MTBE. In one embodiment, the solvent is xylene. The concentration of compound (14) in the solvent may be about 0.001 mol/L to about 10.0 mol/L, such as about 0.01 to about 7.5 mol/L, for example, about 0.05 mol/L to about 5.0 mol/L. In one embodiment, the concentration of compound (14) in the solvent is about 0.78 mol/L.

The reaction may be conducted under an inert atmosphere, such as argon or nitrogen.

The compound (14), the compound (15), the base (if any) and the solvent (if any) may be added in any suitable order. In one embodiment of the invention, however, the compound (14) and the solvent (if any) are charged to a reaction vessel, the base (if any) and compound (15) are added.

While the compound (15) is added to the reaction mixture, the temperature range of the reaction may generally be maintained at one or more temperatures between about −10° C. to about 35° C. In one embodiment, the reaction mixture is maintained at a temperature of less than about 5° C., such as about 0° C. In order to keep the temperature of the reaction mixture within these ranges, the compound of formula (15) may be added slowly over a period of time.

The reaction may be continued for a period of from about 30 minutes to about 72 hours, such as about 30 minutes to about 24 hours. During this time, the reaction temperature may be varied one or more times between about −10° C. and about 25° C. On completion of the reaction, the precipitate may be filtered off and the filtrate extracted with one or more times (e.g. one, two, three or more times) with e.g. DCM/10% HCl. The organic layer may be separated from the aqueous layer and the organic layers combined, dried (e.g. using magnesium sulfate) and concentrated in vacuo. Drying may be performed using known methods, for example at temperatures in the range 10-60° C. and preferably 20-40° C. under 1-30 mbar vacuum for 1 hour to 5 days. Typically, the compound (13a) may be used to form the compound (12a) without further purification.

Preparation of the Compound of Formula (13b)

The compound of formula (13b) may be prepared by reacting a compound of formula (14) with a compound of formula (16) or a compound of formula (17).

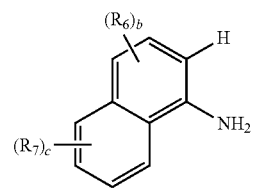

(14)

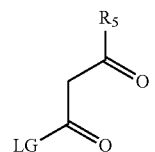

(16)

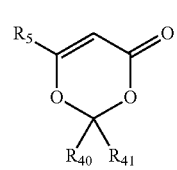

(17)

wherein:
$R_5$, $R_6$, $R_7$, b and c are as generally defined above;
$R_{40}$ and $R_{41}$ are independently selected from the group consisting of unsubstituted alkyl and substituted alkyl, or $R_{40}$ and $R_{41}$ are interconnected to form a ring with the carbon to which they are attached; and
LG is a leaving group.

In one embodiment, $R_{40}$ and $R_{41}$ are methyl groups.
When $R_{40}$ and $R_{41}$ are interconnected to form a ring with the carbon atom to which they are attached, the groups may form substituted or unsubstituted chiral or achiral bridges which are derived, for example, from the skeletons —$(CH_2)_n$— (n=2, 3 or 4), —$CH(CH_3)CH(CH_3)$—, —$CH(CH_3)CH_2CH(CH_3)$—, —$CMe_2$-, —CHMe-, no limitation being implied by this listing.

LG is a leaving group which may be selected from the group consisting of a halide, —O-alkyl and a sulfonate ester.

In one embodiment, the leaving group is a halide, such as —Cl, —Br or —I. In another embodiment, the leaving group is an —O-alkyl, such as —O-Et or —O-Me.

The reaction may further comprise a base. Any suitable base may be used which is capable of deprotonating the —$NH_2$ group of the compound (14) but does not otherwise adversely affect the reaction. Suitable bases include but are not limited to inorganic bases, such as sodium acetate, and organic bases, such as lutidine or triethylamine.

The compound (14) may be present in stoichiometric or greater quantities to the compound (14), or salt thereof. When the free base of compound (14) is reacted, stoichiometric or slight excess of base may be suitable, for example, about 1:1.1 to 1:1.5 molar ratio of compound (14) to base. When salts of compound (14) are utilised, however, excess base is generally required in order to form the free base of the compound (14) from the salt of compound (14), and deprotonate the amino group. In this respect, the molar ratio of the salts of compound (14) to base may be about 1:5 to about 1:20, such as about 1:7.5 to about 1:15, such as about 1:10.

The reaction may further comprise a solvent. Any suitable solvent may be used, for example, chlorinated solvents, such as dichloromethane (DCM), aromatic hydrocarbons, such as benzene, toluene or xylene, or ethereal solvents, for example alkyl ethers, such as THF or MTBE. In one embodiment, the solvent is xylene. The concentration of compound (14) in the solvent may be about 0.001 mol/L to about 10.0 mol/L, such as about 0.01 to about 7.5 mol/L, for example, about 0.05 mol/L to about 5.0 mol/L. In one embodiment, the concentration of compound (14) in the solvent is about 0.78 mol/L. In another embodiment, the concentration of compound (14) in the solvent is about 4.11 mol/L.

The napthylamine of formula (14), LG, the base (if any), the solvent (if any) are as generally described above.

The compound (16) or (17) may be present in stoichiometric or greater quantities to the compound (14), or salt thereof. When the free base of compound (14) is reacted, stoichiometric or slight excess of compound (16) or (17) may be suitable, for example, about 1:1.1 to 1:1.5 molar ratio of compound (14) to compound (16) or (17). When salts of compound (14) are utilised, however, excess base is generally required in order to form the free base of the compound (14) from the salt of compound (14), and deprotonate the amino group. In this respect, the molar ratio of the salts of compound (14) to base may be about 1:5 to about 1:20, such as about 1:7.5 to about 1:15, such as about 1:10.

The reaction may be conducted under an inert atmosphere, such as argon or nitrogen.

The compound (14), the compound (16) or (17), the base (if any) and the solvent (if any) may be added in any suitable order. In one embodiment of the invention, however, the compound (14) and the solvent (if any) are charged to a reaction vessel, the base (if any) and compound (16) or (17) are added.

While the compound (16) or (17) is added to the reaction mixture, the temperature range of the reaction may generally be maintained at one or more temperatures between about 50° C. to about 200° C. The temperature selected is such that the desired amide is formed instead of an imine. Without wishing to be bound by theory, it is believed that higher temperatures (e.g. by refluxing the reaction mixture in xylene) favour the formation of the desired amide, whereas lower temperatures favour the formation of an imine. In one embodiment, the reaction mixture is maintained at a temperature of less than about 175° C., such as about 160-165° C. In another embodiment, the reaction is maintained at the reflux temperature of THF i.e. at about 66° C.

The reaction may be continued for a period of from about 30 minutes to about 72 hours, such as about 30 minutes to about 24 hours. On completion of the reaction, the reaction mixture may be concentrated in vacuo until the product solidifies in the reaction flask. The precipitate may be collected using an alkane solvent (such as hexane or heptane) to do so and optionally washed one or more times with further alkane solvent (such as hexane or heptane). Alternatively, aqueous acid (e.g. aqueous HCl acid) may be added to the reaction mixture with vigorous stirring for a period of time before filtering the precipitate. The precipitate may then be washed one or more times with water and dried in a desiccator.

The precipitate may be dried using known methods, for example at temperatures in the range 10-60° C. and preferably 20-40° C. under 1-30 mbar vacuum for 1 hour to 5 days.

Alternatively, on completion of the reaction, the reaction mixture may be diluted with an ester solvent (such as ethyl acetate), washed one or more times (e.g. one, two, three or more times) with water, washed one or more times (e.g. one, two, three or more times) with brine and dried (e.g. over sodium sulfate). The product may be obtained by removal of the organic solvents, such as by increasing the temperature or reducing the pressure using distillation or stripping methods well known in the art.

The compound of formula (13b) may be used to form the compound (12b) without further purification.

Preparation of Compounds of Formulae (1a) and (1b)

In addition to the process described above, the compounds of formulae (1a) and (1b), or salts thereof, (illustrated below) may be prepared by reducing a compound of formula (20a) or (20b), or salts thereof. A compound (20a) is reduced to the compound (1a) and the compound (20b) is reduced to the compound (1b).

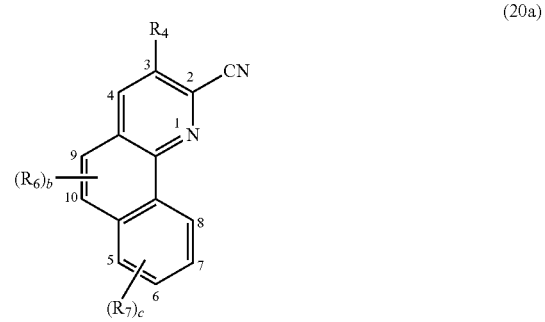

(20a)

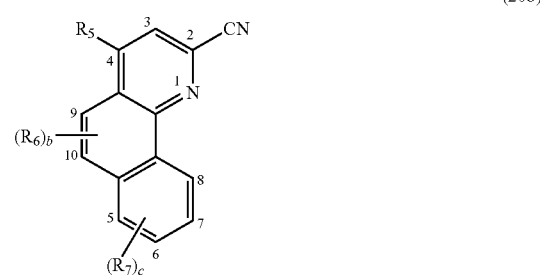

(20b)

-continued

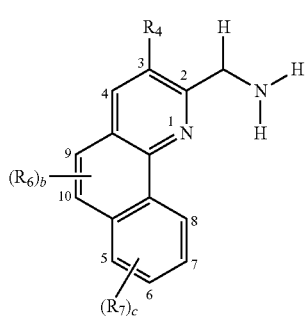
(1a)

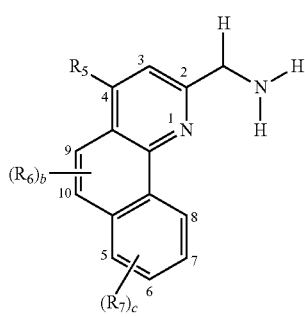
(1b)

As the process comprises the reduction of a cyano (—CN) group, $R_1$, $R_2$ and $R_3$ in the compounds of formulae (1a) and (1b) are all —H.

$R_4$, $R_5$, $R_6$, $R_7$, b and c are as generally described above.

In one embodiment, the reduction may be a hydrogenation reaction. The hydrogenation reaction may comprise reacting the compound (20a) or (20b) with gaseous hydrogen in the presence of a hydrogenation catalyst in a suitable solvent. The hydrogenation catalyst may be a heterogeneous or homogeneous catalyst, preferably a heterogeneous catalyst. The catalyst (whether heterogeneous or homogeneous) should be selected such that the catalyst preferentially reduces the cyano (—CN) group rather than reducing another group present in the compound (20a) or (20b). In one embodiment, the heterogeneous catalyst is a heterogeneous platinum group metal (PGM) catalyst, for example, a heterogeneous palladium or platinum catalyst. In one embodiment, the heterogeneous catalyst is a heterogeneous palladium catalyst. Examples of palladium catalysts include but are not limited to colloidal palladium, palladium sponge, palladium plate or palladium wire. Examples of platinum catalysts include but are not limited to colloidal platinum, platinum sponge, platinum plate or platinum wire.

The heterogeneous PGM metal catalyst may be a PGM on a solid support. The support may be selected from the group consisting of carbon, alumina, calcium carbonate, barium carbonate, barium sulfate, titania, silica, zirconia, ceria and a combination thereof. When the support is alumina, the alumina may be in the form of alpha-$Al_2O_3$, beta-$Al_2O_3$, gamma-$Al_2O_3$, delta-$Al_2O_3$, theta-$Al_2O_3$ or a combination thereof. When the support is carbon, the carbon may be in the form of activated carbon (e.g. neutral, basic or acidic activated carbon), carbon black or graphite (e.g. natural or synthetic graphite). An example of a heterogeneous PGM catalyst is palladium on carbon. An example of another heterogeneous PGM catalyst is platinum on carbon.

The catalyst loading may be up to about 20 mole %. A greater catalyst loading may perform the desired reduction, however, increasing the quantity of the PGM may make the process uneconomical. In one embodiment, the catalyst loading may be up to 10 mole % and, in another embodiment, may be in the range of about 0.1-10.0 mole %.

The reaction mixture may further comprise an acid. Without wishing to be bound by theory, it is believed the acid helps the formation of the amine by avoiding dimerization side reactions. The acid may be any suitable acid, such as a hydrohalide acid e.g. hydrochloric acid, hydrobromic acid or hydroiodic acid. The acid may be added as a reagent to the hydrogenation reaction or the compounds (20a) and (20b) may be reacted as acid addition salts. The salts are as generally described above. Without wishing to be bound by theory, it is believed that the benzo-fused pyridinyl N atom needs to be protonated in order for the hydrogenation to proceed.

Any suitable solvent may be utilised e.g. polar solvents, such as an alcohol. The alcohol may be selected from the group consisting of methanol, ethanol, isopropanol and mixtures thereof. In one embodiment, the solvent is methanol.

The compound (20a) or (20b) may be placed in a pressure vessel together with the hydrogenation catalyst. The pressure vessel may then be assembled and purged with one or more nitrogen/vacuum cycles (e.g. one, two, three or four cycles). The alcohol solvent may then added via the injection port to form a solution of the compound (20a) or (20b), which may have concentration in the range of about 0.01 to about 1 molar, such as about 0.3 molar. If the hydrogenation catalyst is heterogeneous, the catalyst will not dissolve in the alcohol solvent. However, if the hydrogenation catalyst is homogeneous, it may dissolve in the alcohol solvent and form a solution with the compound (20a) or (20b).

Once the alcohol solvent has been added, the pressure vessel may be purged once again with one or more nitrogen/vacuum cycles (e.g. one, two, three, four or five cycles), followed by one or more hydrogen/vacuum cycles (e.g. one, two, three, four or five cycles). During purging the reaction mixture may be agitated (by either stirring or shaking) to encourage removal of dissolved oxygen. The pressure vessel may then be pressurised with hydrogen (e.g. to about 5 bar), stirred and heated to temperature (e.g. about 30° C.). Hydrogen gas uptake may begin after a period of time has elapsed. Once hydrogen uptake begins, the pressure vessel may optionally be depressurised with hydrogen While it is typically sufficient for a single charge of hydrogenation catalyst to be added to the reaction mixture, a second or further charge may be added and the hydrogenation continued if it has been determined (e.g. via in-process analysis) that the reaction has not gone substantially to completion and starting material remains.

There is no particular limitation on the pressure at which the hydrogenation is carried out. In this regard, the hydrogenation may conveniently be carried out with an initial hydrogen pressure in the range of up to about 7 bar (about 100 psi) e.g. about 5±1 bar.

The reaction temperature may be suitably in the range from about 15 to about 75° C., such as in the range from about 20 to about 60° C., for example, about 25 to about 50° C. In one embodiment, the reaction temperature may be about 30° C.

The reaction mixture may then be stirred in the presence of hydrogen gas until hydrogen uptake is no longer apparent. The hydrogenation reaction is carried out for a period of time until it is determined that the reaction is substantially complete. Completion of the reaction may be determined by in-process analysis or by identifying that there is no longer an uptake of hydrogen gas. Typically the hydrogenation is complete within about 24 hours, and in some embodiments, within about 90 minutes.

On completion of the reaction, the reaction vessel may be cooled to ambient temperature and purged with one or more nitrogen/vacuum cycles (e.g. one, two, three, four or five cycles) to remove excess hydrogen gas. The hydrogenation catalyst may be removed by any appropriate method, such as filtration (e.g. using a pad of Celite), washed one or more times with alcohol solvent (e.g. one, two, three or more times) and the filtrate further treated as desired. A proportion of the solvent may be evaporated if desired prior to recovery of the compound of formula (1a) or (1b).

Howsoever the compound (1a) or (1b) is recovered, the separated compounds may be washed and then dried. Drying may be performed using known methods, for example at temperatures in the range 10-60° C. and preferably 20-40° C. under 1-30 mbar vacuum for 1 hour to 5 days. If desired the compound (1a) or (1b) may be recrystallised, although in certain embodiments this is generally not required.

Preparation of Compounds of Formulae (20a) and (20b)

The compounds of formulae (20a) and (20b) may be prepared by cyanating the compounds of formulae (9a) and (9b) (discussed above).

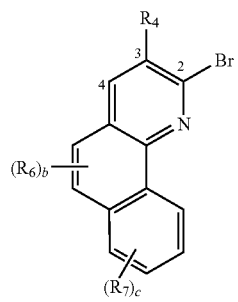

(9a)

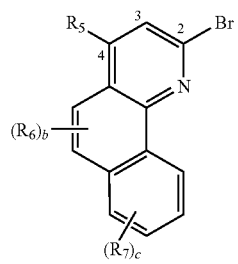

(9b)

In this respect, the compound (9a) is cyanated to the compound (20a) and the compound (9b) is cyanated to the compound (20b).

$R_4$, $R_5$, $R_6$, $R_7$, b and c are as generally described above.

The process may comprise treating the compound of formula (20a) or (20b) with a cyanating reagent in solvent.

The cyanation reagent may be any suitable cyanation reagent, such as copper(I) cyanide, $Zn(CN)_2$ or $K_4Fe(CN)_6$ (potassium ferrocyanide).

The solvent may be any suitable solvent, such as polar aprotic solvents. Polar aprotic solvents may be selected from the group consisting of amides (such as N,N-dimethylformamide (DMF) or N,N-dimethylacetamide (DMA)) and N-(alkyl)-pyrrolidinones (such as N-methyl-2-pyrrolidinone). In one embodiment, the solvent is N-methyl-2-pyrrolidinone (NMP). In one embodiment, the solvent is anhydrous. The concentration of compound (9a) or (9b) in the solvent may be about 0.001 mol/L to about 2.0 mol/L, such as about 0.01 to about 1.75 mol/L, for example, about 0.05 mol/L to about 1.5 mol/L. In one embodiment, the concentration of compound (9a) or (9b) in the solvent is about 0.1 to about 1.0 mol/L, for example, about 0.1 to about 0.9, such as about 0.2 mol/L or about 0.6 mol/L or about 0.7 mol/L. In one embodiment, the concentration of compound (9a) or (9b) in the solvent is about 0.01 to about 0.9 mol/L, for example, about 0.3 to about 0.7 mol/L, such as about 0.47 or 0.6 mol/L.

The compound (9a) or (9b), the cyanation reagent and the solvent may be added in any suitable order. In one embodiment, however, the compound (9a) or (9b) and cyanation reagent are combined with the solvent in a reaction vessel. In another embodiment, the compound (9a) or (9b) is charged to a reaction vessel with the solvent, followed by the addition of the cyanation reagent.

The reaction mixture may be heated to a temperature in the range from about 50 to about 200° C., such as in the range from about 60 to about 175° C., for example, about 100 to about 160° C. e.g. 150° C.

The reaction may be conducted under an inert atmosphere, such as argon or nitrogen.

The reaction is carried out for a period of time until it is determined that the reaction is substantially complete. Completion of the reaction may be determined by in-process analysis. Typically the reaction is complete within about 24 hours, and in some embodiments, within about 4 hours.

On completion of the reaction, the reaction mixture may be quenched (e.g. by adding it to a mixture of iron(III) chloride hexahydrate, water and hydrochloric acid), stirred for a period of time (e.g. about 2 hours) and extracted with a chlorinated solvent such as dichloromethane. The crude product may be recovered simply by evaporating the chlorinated solvent, whereupon it may be slurried in water and filtered. The compound of formula (20a) or (20b) may obtained in pure form by fractionally crystallising the crude material from toluene.

Howsoever the complex is recovered, the separated compound is preferably dried. Drying may be performed using known methods, for example, at temperatures in the range of about 10-60° C. and such as about 20-40° C. under 0.1-30 mbar for 1 hour to 5 days.

Transition Metal Complexes of Formula (3)

In another aspect, the invention provides transition metal complexes of formula (3):

$$[M X(L^1)_m(L^2)] \tag{3}$$

wherein:

M is ruthenium, osmium or iron;

X is an anionic ligand;

$L^1$ is a monodentate phosphorus ligand, or a bidentate phosphorus ligand;

m is 1 or 2, wherein, when m is 1, $L^1$ is a bidentate phosphorus ligand;

when m is 2, each $L^1$ is a monodentate phosphorus ligand; and $L^2$ is a tridentate ligand of formula (2a) or (2b):

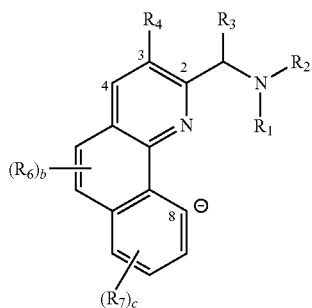

(2a)

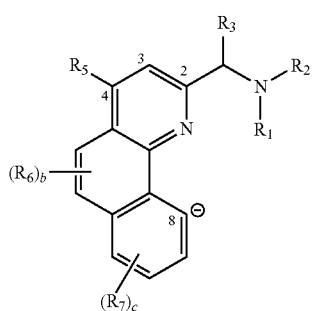

(2b)

wherein:
$R_1$ and $R_2$ are independently selected from the group consisting of —H, —OH, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

$R_3$ is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl and substituted $C_{4-20}$-heteroaryl;

$R_4$ is selected from the group consisting of unsubstituted $C_{1-20}$-alkyl, substituted $C_{1-20}$-alkyl, unsubstituted $C_{1-20}$-alkoxy, substituted $C_{1-20}$-alkoxy, unsubstituted $C_{5-20}$-aryl, substituted $C_{5-20}$-aryl;

$R_5$ is selected from the group consisting of unsubstituted $C_{1-20}$-alkyl, substituted $C_{1-20}$-alkyl, unsubstituted $C_{1-20}$-alkoxy, substituted $C_{1-20}$-alkoxy, unsubstituted $C_{5-20}$-aryl, substituted $C_{5-20}$-aryl;

$R_6$ is selected from the group consisting of unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, substituted $C_{4-20}$-heteroaryl, —NR'R''—COOR', —S(O)$_2$OH, —S(O)$_2$—R', —S(O)$_2$NR'R'' and —CONR'R'', wherein R' and R'' are independently selected from the group consisting of H, unsubstituted $C_{1-20}$-alkyl, substituted $C_{1-20}$-alkyl, unsubstituted $C_{5-20}$-aryl, substituted $C_{5-20}$-aryl, unsubstituted $C_{7-20}$-arylalkyl, substituted $C_{7-20}$-arylalkyl, or R' and R'' together with the atom to which they are attached form a substituted or unsubstituted $C_{2-20}$-heterocycloalkyl group;

$R_7$ is selected from the group consisting of —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, substituted $C_{4-20}$-heteroaryl, —NR'R''—COOR', —S(O)$_2$OH, —S(O)$_2$—R', —S(O)$_2$NR'R'' and —CONR'R'', wherein R' and R'' are independently selected from the group consisting of H, unsubstituted $C_{1-20}$-alkyl, substituted $C_{1-20}$-alkyl, unsubstituted $C_{5-20}$-aryl, substituted $C_{5-20}$-aryl, unsubstituted $C_{7-20}$-arylalkyl, substituted $C_{7-20}$-arylalkyl, or R' and R'' together with the atom to which they are attached form a substituted or unsubstituted $C_{2-20}$-heterocycloalkyl group;

b is an integer selected from 0, 1 or 2; and c is an integer selected from 0, 1, 2 or 3.

M is a transition metal selected from the group consisting of ruthenium, osmium or iron. In one embodiment, M is ruthenium. When M is ruthenium, M may be Ru(II). In another embodiment, M is osmium. When M is osmium, M may be Os(II). In another embodiment, M is iron.

X is an anionic ligand and may be a coordinating or non-coordinating. In one embodiment, X is a coordinating anionic ligand. In another embodiment, X is a non-coordinating anionic ligand. The anionic ligand may be selected from the group consisting of halide, hydride (—H) or $C_{1-10}$-alkoxide (—O—$C_{1-10}$-alkyl). When the anionic ligand is a halide, the halide may be selected from the group consisting of —Cl, —Br and —I, for example, X is —Cl. In another embodiment, the anionic ligand may be a hydride (—H). In yet another embodiment, the anionic ligand may be an alkoxide selected from the group consisting of —OMe, —OEt, —OPr (n- or i-), —OBu (n-, i- or t-).

$L^1$ is a phosphorus ligand and may be selected from those as described above.

$L^2$ is a CNN tridentate ligand of formula (2a) or (2b), each comprising a carbon-M bond, a pyridinyl group and an amino group. The ligands are tridentate as they each coordinate to the M atom via:

a) a carbon-M bond (at C-8). The carbon-M bond is a carbon-metal bond created by orthometallation during the synthesis of the [M X($L^1$)$_m$ ($L^2$)] complex of formula (3);

b) the nitrogen atom of the pyridinyl ring; and c) the nitrogen atom of the amino group.

In one embodiment, $L^2$ is a tridentate ligand of formula (2a). In another embodiment, $L^2$ is a tridentate ligand of formula (2b).

$R_1$, $R_2$, $R_3$, $R_4$, $R_5$, $R_6$, $R_7$ and b are as generally described above.

$R_7$ may be present or absent. When absent, c is 0 i.e. the aryl ring is unsubstituted. When $R_7$ is present, c may be 1, 2 or 3. When c is 2 or 3, each $R_7$ may be the same or different to each other. The or each $R_7$ are as generally described above. In one preferred embodiment, c is 0 i.e. $R_7$ is absent.

Preparation of the Complex of Formula (3)

The complex of formula (3) may be prepared by reacting a suitable transition metal complex, a ligand $L^1$, a compound of formula (1a) or (1 b) or salts thereof, and a base in an alcohol solvent, provided C-8 of the compound of formula (1a) or (1b) is —H.

The compound of formula (1a) or salts thereof, the compound of formula (1 b) or salts thereof and the ligand $L^1$ are as generally described above.

The ligand $L^1$ may be present in stoichiometric or greater quantities to the compound (1a) or (1 b), or salt thereof. When the free base of compound (1a) or (1 b) is reacted, stoichiometric or slight excess of $L^1$ may be suitable, for example, about 1:1.1 to 1:1.5 molar ratio of compound (1a) or (1 b) to $L^1$.

The transition metal complex may be selected from the group consisting of [ruthenium (arene) (halogen)$_2$]$_2$, [ruthenium (halogen) (P(unsubstituted or substituted aryl)$_3$)], [osmium (arene) (halogen)$_2$], [osmium (halogen)$_2$(P(unsubstituted or substituted aryl)$_3$)] and [osmium (N(unsubstituted or substituted alkyl)$_3$)$_4$ (halogen)$_2$].

The arene may be an unsubstituted or substituted benzene wherein the substituents are selected from chain $C_{1-6}$ alkyl, $C_{1-6}$ alkoxy, $C_{1-6}$ carboalkoxy, —OH or $NO_2$. In one embodiment, the arene may be selected from the group consisting of benzene, cymene, toluene, xylene, trimethylbenzene, hexamethylbenzene, ethylbenzene, t-butylbenzene, cumene (isopropylbenzene), anisole (methoxybenzene), methylanisole, chlorobenzene, dichlorobenzene, trichlorobenzene, bromobenzene, fluorobenzene, methylbenzoate and methyl methyl benzoate (e.g. methyl 2-methylbenzoate). In another embodiment, the arene is benzene, p-cymene or mesitylene (1,3,5-trimethylbenzene).

The halogen may be selected from the group consisting of chlorine, bromine and iodine, e.g. chlorine.

The P(unsubstituted or substituted aryl)$_3$ may be a P(substituted aryl)$_3$ or a P(unsubstituted aryl)$_3$. Examples of P(substituted aryl)$_3$ and P(unsubstituted aryl)$_3$ include but are not limited to $PPh_3$ or $P(Tol)_3$, where the tolyl group may be ortho-, para- or meta-substituted.

The N(unsubstituted or substituted alkyl)$_3$ may be a N(substituted alkyl)$_3$ or a N(unsubstituted alkyl)$_3$ (such as $NEt_3$).

In one embodiment, the [ruthenium (halogen) (P(unsubstituted or substituted aryl)$_3$)] may be $RuCl_2PPh_3$ or $RuCl_2(P(o-Tol)_3)$. In one embodiment, the [osmium (halogen)$_2$(P (unsubstituted or substituted aryl)$_3$)] may be $OsCl_2PPh_3$ or $OsCl_2(P(o-Tol)_3)$.

In one embodiment, the [ruthenium (arene) (halogen)$_2$]$_2$ may be [$RuCl_2$(p-cymene)]$_2$, [$RuCl_2$(benzene)]$_2$ or [$RuCl_2$(mesitylene)]$_2$. In one embodiment, the [osmium (arene) (halogen)$_2$] may be [$OsCl_2$(p-cymene)], [$OsCl_2$(benzene)] or [$OsCl_2$(mesitylene)]

In one embodiment, the [osmium (N(unsubstituted or substituted alkyl)$_3$)$_4$ (halogen)$_2$] may be [$(Et_3N)_4$ Os $Cl_2$].

In the presence of a suitable base and when a hydrogen atom is present at C-8 of the compounds (1a) and (1b), the compounds (1a) and (1b) orthometallate with the transition metal atom (e.g. Ru or Os) to form a transition metal complex comprising the CNN-tridentate ligands (2a) and (2b). $R_1$, $R_2$, $R_3$, $R_4$, $R_5$, $R_6$, $R_7$ and b are as generally described above and c may be 0, 1, 2 or 3 (but not 4).

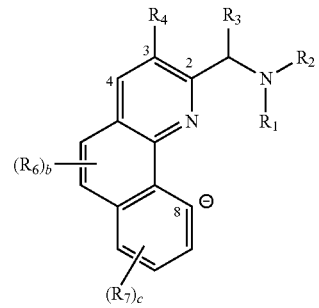

(2a)

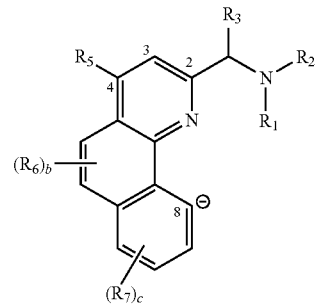

(2b)

The base may be any suitable base which is capable of removing the hydrogen at C-8 in the compounds (1a) or (1b). Examples of bases include trialkylamines (such as triethylamine), pyridine, dimethylpyridine (e.g. 2,6-, 2,3-, 3,5-, 2,5- or 3,4-dimethylpyridine), alkali metal hydroxides (such as sodium hydroxide or potassium hydroxide) or alkali metal alkoxides (such as sodium methoxide or potassium methoxide).

The base may be present in stoichiometric or greater quantities to the compound (1a) or (1b), or salt thereof. When the free base of compound (1a) or (1b) is reacted, stoichiometric or slight excess of base may be suitable, for example, about 1:1.1 to 1:1.5 molar ratio of compound (1a) or (1b) to base. When salts of compound (1a) or (1b) are utilised, however, excess base is generally required in order to form the free base of the compound (1a) or (1 b) from the salt of compound (1a) and (1b), and deprotonate the compound (1a) or (1b) at C-14 to form the ligand (2a) or (2b). In this respect, the molar ratio of the salts of compound (1a) or (1b) to base may be about 1:5 to about 1:20, such as about 1:7.5 to about 1:15, such as about 1:10.

Any suitable alcohol solvent may be utilised. Suitable alcohols have boiling points at atmospheric pressure (i.e. 1.0135×105 Pa) below 120° C., more preferably below 110° C. and even more preferably below 100° C. Preferably the alcohol is dry. The alcohol solvent may be selected from the group consisting of methanol, ethanol, isopropanol and mixtures thereof. In one embodiment, the alcohol solvent is iso-propanol (i.e. 2-propanol).

The concentration of the transition metal complex in the solvent may be about 0.001 mol/L to about 10.0 mol/L, such as about 0.01 to about 1.0 mol/L, for example, about 0.02 mol/L to about 0.5 mol/L.

In combining the transition metal complex, the ligand $L^1$, the ligand $L^2$ and base in the alcohol, the components may be mixed in any suitable order, although, in one embodiment, the transition metal complex and ligand $L^1$ are slurried or suspended in the alcohol solvent, followed by the addition of the ligand $L^2$ and the base. After the transition metal complex and the ligand $L^1$ are combined with the alcohol, the reaction mixture may be stirred and heated (e.g. at reflux) for a period of time (e.g. for up to 2-3 hours). The mixture may be stirred for a period e.g. preferably 1 minute to 3 hours, more preferably 2 minutes to 2 hours and most preferably 2.5 minutes to 1.5 hours. The ligand $L^2$ and the base may then be added to the reaction mixture and the reaction mixture stirred and heated (e.g. at reflux) for a further period of time (e.g. for up to 5-6 hours).

The reaction may be conducted under an inert atmosphere, such as nitrogen or argon.

The reaction mixture may be treated with an alkane (such as pentane, hexane or heptane) which causes the complex (3) to precipitate or crystallise. The solid complex (3) may be recovered directly by filtering, decanting or centrifuging. If desired a proportion of the alcohol/alkane solvent mixture may be evaporated prior to the recovery of the complex.

Alternatively, the solid complex (3) may be recovered simply by evaporating the alcohol/alkane solvent mixture.

Howsoever the complex is recovered, the separated complex is preferably dried. Drying may be performed using known methods, for example, at temperatures in the range of about 10-60° C. and such as about 20-40° C. under 0.1-30 mbar for 1 hour to 5 days. It may be desirable to store the complex under conditions which substantially excludes light.

The complexes prepared by the processes of the present invention are pure and may be used in catalytic applications as obtained or further dried. The methods are suited to large-scale manufacture and large-scale catalytic applications.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be described by the way of the following non-limiting Examples.

EXAMPLES

All reactions were carried out under argon or nitrogen atmosphere. Anhydrous THF, toluene, MeOH, 2-propanol and MEK were purchased from Aldrich and absolute EtOH was purchased from VWR. The bisphosphines dppp, dppb, dppf, dippf rac-BINAP and (R)-BINAP were purchased from Alfa Aesar. Xantphos and DPEPhos were purchased from Sigma Aldrich. AMPYRIM*HCl was purchased from Manchester Organics. NMR measurements were recorded on Bruker AC 200 and Bruker Advance 400 spectrometers and the chemical shifts, in ppm, are relative to TMS for $^1H$ and $^{13}C\{^1H\}$, and 85% $H_3PO_4$ for $^{31}P\{^1H\}$.

ABBREVIATIONS

AMPY 2-(aminomethyl)pyridine
AMPYRIM 2-(aminomethyl)pyrimidine
BINAP 2,2'-Bis(diphenylphosphino)-1,1'-binaphthyl
DCM dichloromethane
DMF dimethylformamide
dppp 1,3-bis(diphenylphosphino)propane
dppb 1,4-bis(diphenylphospino)butane
dppf 1,1'-bis(diphenylphosphino)ferrocene
dippf 1,1'-bis(diisopropylphosphino)ferrocene
dppm bis(diphenylphosphino)methane
dppe 1,2-bis(diphenylphosphino)ethane
Xantphos 4,5-bis(diphenylphosphino)-9,9-dimethylxanthene
DPEPhos (oxy-di2,1-phenylene)bis(diphenylphosphine)
en ethylenediamine
eq. equivalent
h hour
L Liter
MEK 2-butanone
mL milliliter
RT Room Temperature Synthesis of $Ru(OAc)_2(PPh_3)_2$(not According to the Invention)

$RuCl_2(PPh_3)_3$ may be converted to $Ru(OAc)_2(PPh_3)_2$ as described in R. W. Mitchell, A. Spencer, G. Wilkinson, J. Chem. Soc. Dalton Trans. (1973) 846.

Synthesis of $Ru(OAc)_2[(R)-BINAP]$. (not According to the Invention)

$Ru(OAc)_2(PPh_3)_2$ (200 mg, 0.268 mmol) and (R)-BINAP (167 mg, 0.268 mmol) are slurried in toluene (1.5 ml) and refluxed for 20 h. The solvent is removed under vacuum from the orange solution and pentane (5 ml) is added. The yellow suspension is stirred for 20 min at room temperature, then filtered, washed with pentane (3×5 ml) and dried under reduced pressure. Yield: 115 mg (51%). Spectroscopic data are consistent with those reported in J. Org. Chem. 1992, 57, 4053.

Example 1

Synthesis of Cis-[dppb $Ru(OAc)_2$ AMPY] (1)

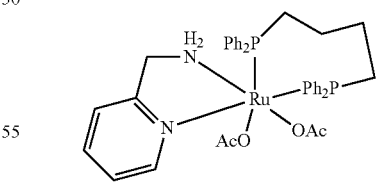

Into a stirred glass reactor equipped with an efficient reflux condenser is introduced 30 g of trans-[(dppb $RuCl_2$ AMPY], 32 g of anhydrous sodium acetate and 3 g of dppb. 500 mL of IPA is added and the stirred slurry is heated to reflux with an oil bath set at 107° C. After heating is continued for 3 days, it is switched off and the slurry is allowed to cool to RT. The slurry is suction filtered using a glass sinter filter until a wet cake of product is obtained. This cake is washed with 2×100 ml of water and the water washings are discarded. The filter cake is further washed with 3×100 mL of IPA. The orange-yellow product is dried at 10 mbar, 60° C. for 48 hours. After drying 30.1 g of cis-[dppb Ru(OAc)$_2$ AMPY] of >95% w/w is obtained. $^1$H NMR (300 MHz, CD$_3$OD): δ 8.26 (m, 1H, o-C$_5$H$_4$N), 7.89 (m, 2H), 7.76 (m, 2H), 7.70-7.46 (several m, 6H), 7.40-7.25 (several m, 6H), 7.20-7.02 (several m, 3H), 6.95 (m, 2H), 6.85 (m, 2H), 3.92, 3.47 (2 m, J=16.4 Hz, 2H, AMPY CH$_2$N), 3.0-2.8 (m, 2H, PCH$_2$), 2.4-1.8 and 1.7-1.4 (several m, 4H), 1.90 and 1.34 (2 s, 6H CH$_3$CO$_2$). $^{13}$C{$^1$H} NMR (100 MHz, CDCl$_3$): δ 182.9 (CH$_3$CO$_2$), 159.0, 150.8, 141-118 (m, aromatic carbons), 53.2, 31.7, 29.8, 27.7, 25.4, 26.3 (only underlined appear as singlets). $^{31}$P{$^1$H} NMR (162.0 MHz, CD$_3$OD): δ 58.2 (d, J=37.4 Hz), 45.9 (d, J=37.4 Hz).

Example 2

Synthesis of Trans-[dppb Ru(OAc)$_2$ AMPY] (2)

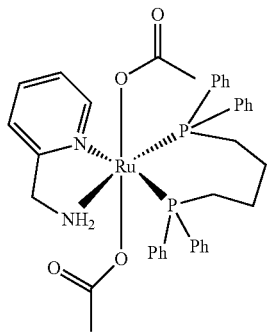

2

Ru(OAc)$_2$(PPh$_3$)$_2$(400 mg, 0.538 mmol) and dppb (230 mg, 0.539 mmol) is slurried in 3 ml of acetone. The slurry is stirred for 3 hours at RT and the acetone solution is separated from the solid by decantation. A $^{31}$P{$^1$H} NMR assay of the acetone solution shows full consumption of the dppb ligand and only traces of Ru(OAc)$_2$(PPh$_3$)$_2$(at δ 63.3 ppm). The main dissolved compound is PPh$_3$. AMPY (80 μl, 0.779 mmol) is added to the acetone solution. Then the solution of AMPY in the acetone solution is added to the solid and the slurry is stirred for 1 hr. The slurry is filtered and the yellow solid washed with 3×2 ml of hexane. After drying 310 mg (77%) of trans-[dppb Ru(OAc)$_2$ AMPY] (2) is obtained. $^1$H NMR (200.1 MHz, CD$_2$Cl$_2$): δ 8.95 (m, 1H, o-C$_5$H$_4$N), 7.83-7.08 (m, 22H, aromatic protons), 6.81 (pseudo t, J(H,H)=6.6 Hz, 1H, aromatic proton), 6.03 (m, 2H, NH$_2$), 4.06 (m, 2H, CH$_2$N), 2.78 (m, 2H, PCH$_2$), 2.25 (m, 2H, PCH$_2$), 1.94-1.64 (m, 4H, PCH$_2$CH$_2$CH$_2$), 1.53 (s, 6H CH$_3$CO$_2$). $^{13}$C{$^1$H} NMR (50.3 MHz, CD$_2$Cl$_2$): δ 181.0 (d, J(C,P)=1.5 Hz, CH$_3$CO$_2$), 167.5 (dd, J(C,P)=2.9, 1.4 Hz, CH$_3$CO$_2$) 154.9 (d, J(C,P)=3.7 Hz, NCH), 139.4-119.9 (m, aromatic carbons), 50.6 (dd, J(C,P)=3.8, 2.0 Hz, NCCH$_2$), 33.9 (dd, J(C,P)=27.1, 3.0 Hz, CH$_2$P), 27.7 (d, J(C,P)=25.3 Hz, CH$_2$P), 26.5 (m, CH$_2$CH$_2$P), 25.1 (m, CH$_3$CO$_2$), 19.9 (m, CH$_2$CH$_2$P). $^{31}$P{$^1$H} NMR (81.0 MHz, CD$_2$Cl$_2$): δ 44.6 (d, J=36.5 Hz), 36.5 (d, J=36.5 Hz).

Example 3

Synthesis of Trans-[dppb Ru(OAc)$_2$ AMPY] (2)

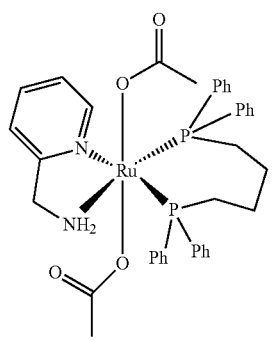

2

Ru(OAc)$_2$(PPh$_3$)$_2$(400 mg, 0.538 mmol) and dppb (230 mg, 0.539 mmol) are dissolved in dichloromethane (4 ml) and, after 1 h at room temperature under stirring, AMPY (80 μl, 0.779 mmol) is added. The light orange solution is stirred for 0.5-1 h at room temperature and concentrated to ca.1 ml. addition of pentane afforded a yellow precipitate, which is filtered, washed with pentane (3×8 ml) and dried under reduced pressure to yield 247 mg (61%).

Example 4

Isomerisation of Trans-[dppb Ru(OAc)$_2$ AMPY] (2)

In two experiments, 20 mg of the products from Examples 2 and 3 are dissolved in 2 ml of CD$_3$OD and a $^{31}$P{$^1$H} NMR spectrum run as soon as possible. In both cases, the $^{31}$P{$^1$H} NMR spectrum (162.0 MHz, CD$_3$OD) gave resonances δ 50.1 (d, J=36.5 Hz), 35.2 (d, J=36.5 Hz). Within 20 minutes after adding the CD$_3$OD, the spectrum contains resonances of the product of Example 1 i.e. cis-[dppb Ru(OAc)2 AMPY] (1) with $^{31}$P{$^1$H} NMR (162.0 MHz, CD$_3$OD): δ 58.2 (d, J=37.4 Hz), 45.9 (d, J=37.4 Hz). After 12 hours at room temperature, the same amount of trans (2) and cis (1) isomer are shown to be in solution. After 48 hours, the trans-(2) to cis-(1) isomerisation is complete.

This Example shows, that cis [dppb Ru(OAc)$_2$ AMPY] (2) can be prepared in two independent ways i.e. via Example 1 or via Examples 2 and 4.

In a separate experiment, 20 mg of the product from Example 3 is dissolved in d$^8$ toluene. The solution is heated for 18 hours to 100° C. The $^{31}$P{$^1$H} NMR spectrum (162.0 MHz, d$^8$ toluene) shows only little isomerisation has taken place.

Example 5

Synthesis of Trans, Cis-Ru(OAc)$_2$(PPh$_3$)$_2$(AMPY) (3)

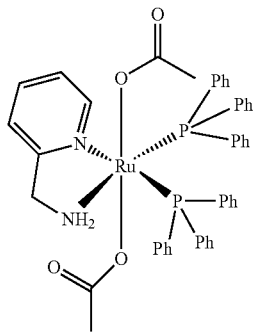

Ru(OAc)$_2$(PPh$_3$)$_2$(100 mg, 0.134 mmol) is slurried in 2 ml of d$^6$-acetone for 1 hour. Then AMPY (20 µl, 0.194 mmol) is added by syringe and the slurry is stirred for another hour. By filtration the acetone is separated and then analysed by $^{31}$P{$^1$H} NMR. The solvent contains little of cis-Ru(OAc)$_2$(PPh$_3$)$_2$(AMPY) (3) with $^{31}$P{$^1$H} NMR (162.0 MHz, d$^6$-acetone): δ 44.5 (d, J=31.1 Hz), 44.5 (d, J=31.1 Hz) and PPh$_3$. This assignment of (3) is confirmed by dissolving some of the isolated solid in d$^6$ acetone and running a $^{31}$P{$^1$H} NMR. $^1$H NMR (200.1 MHz, CD$_2$Cl$_2$): δ 8.44 (m, 1H, o-C$_5$H$_4$N), 7.57-6.88 (m, 32H, aromatic protons), 6.70 (m, 2H, NH$_2$), 6.53 (pseudo t, J(H,H)=6.4 Hz, 1H, aromatic proton), 4.18 (m, 2H, CH$_2$N), 1.67 (s, 6H CH$_3$CO$_2$). $^{13}$C{$^1$H} NMR (50.3 MHz, CD$_2$Cl$_2$): δ 180.9 (d, J(C,P)=1.6 Hz, CH$_3$CO$_2$), 166.5 (s, NCCH$_2$) 156.7 (d, J(C,P)=3.8 Hz, NCH), 137.2-119.3 (m, aromatic carbons), 51.6 (m, CH$_2$), 26.1 (s, CH$_3$CO$_2$). $^{31}$P{$^1$H} NMR (81.0 MHz, CD$_2$Cl$_2$): δ 44.6 (d, J=31.3 Hz), 39.4 (d, J=31.3 Hz). The same data are obtained when Ru(OAc)$_2$(PPh$_3$)$_2$(37 mg, 0.05 mmol) and AMPY (6 µl, 0.058 mmol) are weighed into an NMR-tube and dissolved in CD$_2$Cl$_2$ (0.45 ml). After 5 min. at room temperature quantitative formation of the expected complex occurs.

Example 6

Isomerisation of Trans, Cis-Ru(OAc)$_2$(PPh$_3$)$_2$ (AMPY) (3)

20 mg of the trans, cis-Ru(OAc)$_2$(PPh$_3$)$_2$(AMPY) (3) from Example 5 is dissolved in 2 ml of CD$_3$OD and a $^{31}$P{$^1$H} NMR spectrum is run after storing the NMR tube for 15 hours. A mixture of new isomers is obtained as follows: $^{31}$P{$^1$H} NMR (162.0 MHz, CD$_3$OD): δ 65.4 (d, J=28.4 Hz), 49.5 (d, J=28.4 Hz) (major) and as a minor isomer: δ 60.6 (d, J=26.3 Hz), 47.5 (d, J=26.3 Hz). A $^{31}$P{$^1$H} NMR spectrum, run 26 hours after the first shows that the amount of major isomer has increased compared to the minor isomer. The major isomer is cis-Ru(OAc)$_2$(PPh$_3$)$_2$ (AMPY).

In a comparative experiment, 20 mg of the product from example 5 is dissolved in d$^8$ toluene. The solution is heated for 18 hours to 100° C. The $^{31}$P{$^1$H} NMR spectrum (162.0 MHz, d$^8$ toluene) showed only little isomerisation but significant decomposition has taken place.

Example 7

Synthesis of Trans-Ru(OAc)$_2$(AMPY)(dppp) (4)

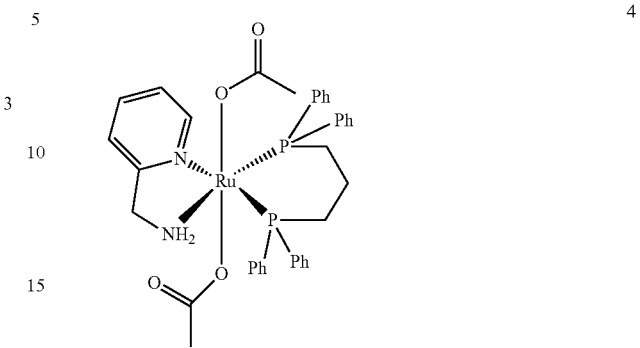

Ru(OAc)$_2$(PPh$_3$)$_2$(200 mg, 0.269 mmol) and dppp (112 mg, 0.272 mmol) is slurried in 2 ml of acetone. The slurry is stirred for 3 hours at RT and the acetone solution is separated from the solid by decantation. A $^{31}$P{$^1$H} NMR assay of the acetone solution shows full consumption of the dppp ligand and only traces of Ru(OAc)$_2$(PPh$_3$)$_2$(at δ 63.3 ppm). The main dissolved compound is PPh$_3$. AMPY (40 µl, 0.389 mmol) is added to the acetone solution. Then the solution of AMPY in the acetone solution is added to the solid and the slurry is stirred for 1 hr. The slurry is filtered and the solid washed with 3×2 ml of hexane. After drying 185 mg (93%) of trans-[dppp Ru(OAc)2 AMPY] (4) is obtained. $^1$H NMR (200.1 MHz, CD$_2$Cl$_2$): δ 8.42 (m, 1H, o-C$_5$H$_4$N), 7.78-6.96 (m, 22H, aromatic protons), 6.71 (pseudo t, J(H,H)=6.5 Hz, 1H, aromatic proton), 6.27 (m, 2H, NH$_2$), 4.12 (m, 2H, CH$_2$N), 2.61-1.77 (m, 6H, P(CH$_2$)$_3$P), 1.68 (s, 6H CH$_3$CO$_2$). $^{13}$C{$^1$H} NMR (50.3 MHz, CD$_2$Cl$_2$): δ 180.9 (d, J(C,P)=1.7 Hz, CH$_3$CO$_2$), 166.3 (dd, J(C,P)=2.7, 1.4 Hz, NCCH$_2$) 154.7 (dd, J(C,P)=3.9, 0.5 Hz, NCH), 138.6-119.7 (m, aromatic carbons), 50.5 (dd, J(C,P)= 3.6, 2.0 Hz, NCCH$_2$), 27.4 (m, CH$_2$P), 26.8 (m, CH$_2$P), 25.2 (s, CH$_3$CO$_2$), 19.5 (dd, J(C,P)=2.4, 0.5 Hz, CH$_2$CH$_2$P). $^{31}$P{$^1$H} NMR (81.0 MHz, CD$_2$Cl$_2$): δ 47.8 (d, J=49.1 Hz), 33.1 (d, J=49.1 Hz).

Analysis of the acetone mother liquor shows that little of the product is lost. $^{31}$P{$^1$H} NMR (162.0 MHz, acetone d$^6$): δ 47.4 (d, J=48.6 Hz), 32.6 (d, J=48.6 Hz).

Example 8

Synthesis of Trans-Ru(OAc)$_2$(AMPY)(dppp) (4)

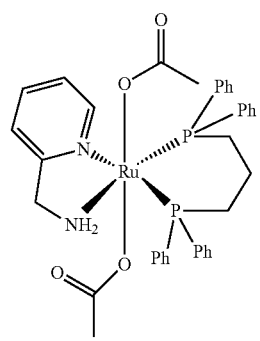

Ru(OAc)$_2$(PPh$_3$)$_2$(100 mg, 0.134 mmol) and dppp (56 mg, 0.136 mmol) are dissolved in dichloromethane (1.5 ml). After 1 h under stirring at room temperature, AMPY (20 μl, 0.194 mmol) is added. The light orange solution is stirred for 1 h at room temperature and the solvent removed under vacuum. Treatment of the residue with pentane gives a slurry which was stirred for 10 min. The obtained yellow precipitate is filtered, washed with pentane (4×3 ml) and dried under reduced pressure. Yield: 84 mg (85%). The product is identical to the one prepared in Example 7.

Example 9

Isomerisation of Trans-Ru(OAc)$_2$(AMPY)(dppp) (4)

20 mg of the product from Example 8 is dissolved in 2 ml of CD$_3$OD and a $^{31}$P{$^1$H} NMR spectrum is run after 32 hours. Two isomers are observed: a trace resonance for trans-Ru(OAc)$_2$(AMPY)(dppp) (4): $^{31}$P{$^1$H} NMR (162.0 MHz, CD$_3$OD): δ 49.3 (d, J=48.9 Hz), 31.1 (d, J=49.3 Hz) and a major resonance for the cis isomer: $^{31}$P{$^1$H} NMR (162.0 MHz, CD$_3$OD): δ 55.2 (d, J=48.4 Hz), 36.8 (d, J=48.4 Hz). The amount of cis-isomer is further increased 56 hours after it was dissolved.

Example 10

Synthesis of Trans-Ru(OAc)$_2$(AMPY)(dppf) (5)

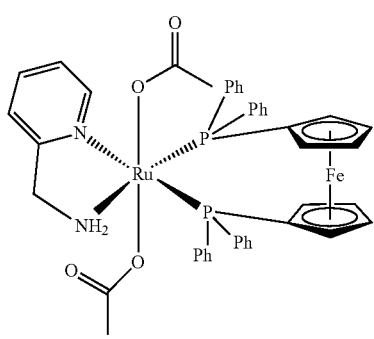

Ru(OAc)$_2$(PPh$_3$)$_2$(400 mg, 0.538 mmol) and dppf (298 mg, 0.539 mmol) is slurried in 3 ml of acetone. The slurry is stirred for 3 hours at RT and the acetone solution is separated from the solid by decantation. A $^{31}$P{$^1$H} NMR assay of the acetone solution shows full consumption of the dppf ligand and only traces of Ru(OAc)$_2$(PPh$_3$)$_2$(at δ 63.3 ppm). The main dissolved compound is PPh$_3$. AMPY (80 μl, 0.779 mmol) is added to the acetone solution. Then the solution of AMPY in the acetone solution is added to the solid and the slurry is stirred for 1 hr. The slurry is filtered and the yellow solid washed with 3×2 ml of hexane. After drying 405 mg (88%) of trans-[dppf Ru(OAc)$_2$ AMPY] (5) is obtained. $^1$H NMR (200.1 MHz, CD$_2$Cl$_2$): δ 8.62 (m, 1H, o-C$_5$H$_4$N), 8.01-6.92 (m, 22H, aromatic protons), 6.69 (pseudo t, J(H,H)=6.2 Hz, 1H, aromatic proton), 6.34 (m, 2H, NH$_2$), 4.68 (m, 2H, C$_5$H$_4$), 4.32 (m, 2H, C$_5$H$_4$), 4.15-3.88 (m, 4H C$_5$H$_4$+2H CH$_2$N), 1.55 (s, 6H CH$_3$CO$_2$). $^{13}$C{$^1$H} NMR (50.3 MHz, CD$_2$Cl$_2$): δ 181.2 (d, J(C,P)=1.3 Hz, CH$_3$CO), 167.7 (dd, J(C,P)=2.9, 1.6 Hz, NCCH$_2$) 154.6 (d, J(C,P)=3.2 Hz, NCH), 137.1-119.5 (m, aromatic carbons), 75.5 (pseudo t, J(C,P)=8.0 Hz, C$_5$H$_4$), 72.9 (d, J(C,P)=5.8 Hz, C$_5$H$_4$), 70.8 (d, J(C,P)=4.9 Hz, C$_5$H$_4$), 50.6 (m, NCCH$_2$), 25.5 (s, CH$_3$CO$_2$). $^{31}$P{$^1$H} NMR (81.0 MHz, CD$_2$Cl$_2$): δ 56.2 (d, J=37.8 Hz), 35.0 (d, J=37.8 Hz).

Example 11

Synthesis of Trans-Ru(OAc)$_2$(AMPY)(dppf) (5)

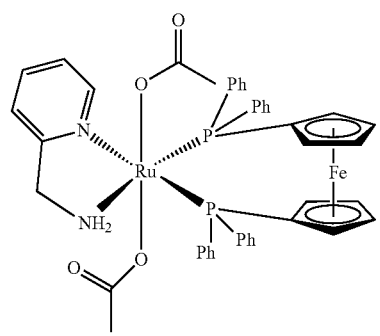

Ru(OAc)$_2$(PPh$_3$)$_2$(200 mg, 0.269 mmol) and dppf (149 mg, 0.269 mmol) are dissolved in dichloromethane (2 ml). After 1 h stirring at room temperature, AMPY (40 μl, 0.388 mmol) is added. The light orange solution is stirred for 1 h at room temperature and the solvent is removed under vacuum. Treatment of the residue with pentane gives a slurry which is stirred for 10 min. The obtained yellow precipitate is filtered, washed with pentane (3×5 ml) and dried under reduced pressure. Yield: 176 mg (74%). The product is identical to the one prepared in Example 10.

Example 12

Isomerisation of Trans-Ru(OAc)$_2$(AMPY)(dppf) (5)

20 mg of the product from Example 10 is dissolved in 2 ml of CD$_3$OD and a $^{31}$P{$^1$H} NMR spectrum is run after 4 hours. Cis-Ru(OAc)$_2$(AMPY)(dppf) is the only isomer observed. $^{31}$P{$^1$H} NMR (162.0 MHz, CD$_3$OD): δ 59.9 (d, J=35.4 Hz), 49.5 (d, J=35.4 Hz). $^1$H NMR (400 MHz, CD$_2$Cl$_2$): δ 8.03-7.0 (m, 24H, aromatic protons), 4.61-4.27 (m, 8H, C$_5$H$_4$), 3.91 and 3.60 (2 d, J=16.3 Hz, 2H, AMPY CH$_2$N), 1.9 and 1.5 (2 s, 6H, CH$_3$CO$_2$).

Example 13

Synthesis of Ru(OAc)$_2$(AMPY)[(R)-BINAP] (6)

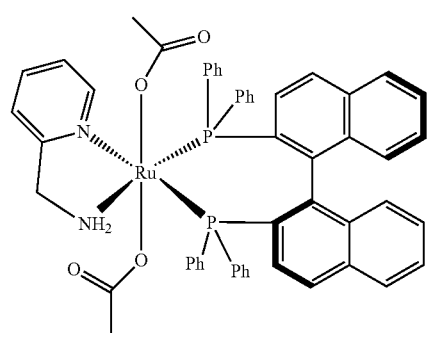

Ru(OAc)$_2$(PPh$_3$)$_2$ (100 mg, 0.134 mmol) and (R)-BINAP (83 mg, 0.134 mmol) are suspended in toluene (1.5 ml) and refluxed for 24 h. The orange solution was left cooling to room temperature and AMPY (20 µl, 0.194 mmol) is added. The light orange solution is stirred for 1 h at room temperature and the solvent removed under vacuum. Treatment of the residue with pentane gives a slurry which is stirred for 10 min. and the obtained yellow precipitate is filtered, washed with pentane (3×5 ml) and dried under reduced pressure. Yield: 150 mg (59%). The product Ru(OAc)$_2$(AMPY)[(R)-BINAP] (6) is characterised by $^{31}$P{$^1$H} NMR (81.0 MHz, CD$_2$Cl$_2$): δ 55.1 (d, J=36.7 Hz), 41.5 (d, J=36.7 Hz).

Example 14

Synthesis of Trans-Ru(OAc)$_2$(quinoline-8-NH$_2$)(dppb) (7)

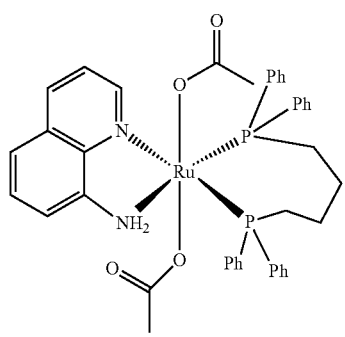

7

Ru(OAc)$_2$(PPh$_3$)$_2$ (100 mg, 0.134 mmol) and dppp (58 mg, 0.135 mmol) are dissolved in DCM (1.5 ml) and stirred for 1 h at room temperature. 8-Aminoquinoline (20 µl, 0.194 mmol) is added. The light orange solution is stirred for 1 h at room temperature and the solvent removed under vacuum. Treatment of the residue with pentane gives a slurry which is stirred for 10 min. and the obtained yellow precipitate is filtered, washed with pentane (3×5 ml) and dried under reduced pressure. Yield of trans-Ru(OAc)$_2$(quinoline-8-NH$_2$)(dppb) (7): 95 mg (90%). $^1$H NMR (200.1 MHz, CD$_2$Cl$_2$): δ 9.23 (m, 1H, 2-C$_9$H$_6$N), 8.24 (m, 2H, NH$_2$), 8.14 (d, 1H, J(H,H)=7.3 Hz, aromatic proton), 7.87-7.10 (m, 23H, aromatic protons), 7.02 (dd, 1H, J(H,H)=8.2, 5.0 Hz, aromatic protons), 2.80 (m, 2H, CH$_2$P), 2.26 (m, 2H, CH$_2$P), 2.04-1.52 (m, 4H, CH$_2$CH$_2$CH$_2$P), 1.37 (s, 6H, CH$_3$CO). $^{13}$C{$^1$H} NMR (50.3 MHz, CD$_2$Cl$_2$): δ 181.3 (m, CH$_3$CO$_2$), 156.2 (d, J(C,P)=3.9 Hz, NCH), 151-120 (m, aromatic carbons), 34.1 (d, J(C,P)=27.3 Hz, CH$_2$P), 27.8 (d, J(C,P)= 24.7 Hz, CH$_2$P), 26.9 (s, CH$_2$CH$_2$P), 25.0 (s, CH$_3$CO$_2$), 19.3 (s, CH$_2$CH$_2$P). $^{31}$P{$^1$H} NMR (81.0 MHz, CD$_2$Cl$_2$): δ 50.5 (d, J=36.7 Hz), 37.2 (d, J=36.7 Hz).

Example 15

Synthesis of Ru(OAc)(CNN)(PPh$_3$)$_2$ (8)

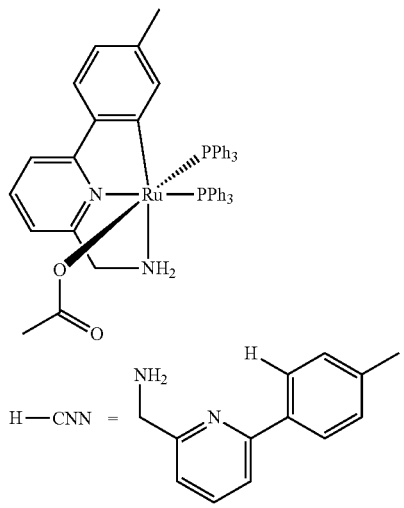

Ru(OAc)$_2$(PPh$_3$)$_2$ (78 mg, 0.105 mmol), ligand HCNN (as depicted above) (21 mg, 0.106 mmol) and NEt$_3$ (150 µl, 1.076 mmol) in 2-propanol (1.5 ml) are refluxed for 2 h. The deep orange solution is cooled to room temperature and the solvent removed under vacuum. Treatment of the residue with pentane at reflux for 20 min. gives a slurry which is filtered, washed with pentane (3 ml) and dried under reduced pressure. Yield of Ru(OAc)(CNN)(PPh$_3$)$_2$ (8): 79 mg (86%). $^{31}$P{$^1$H} NMR (81.0 MHz, CD$_2$Cl$_2$): δ 59.7 (d, J=33.6 Hz), 54.7 (d, J=33.6 Hz).

Example 16

Synthesis of Ru(OAc)(pH-AMBQ)dppb (9)

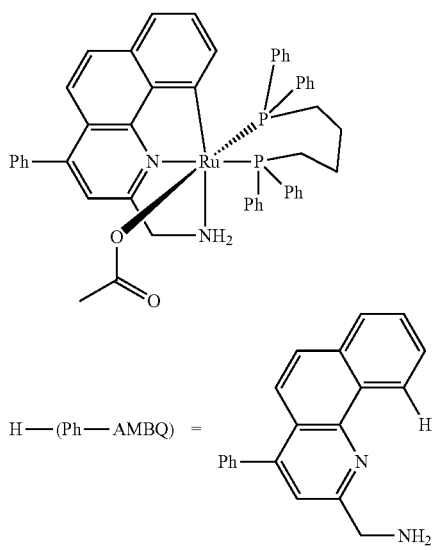

Ru(OAc)$_2$(PPh$_3$)$_2$ (198 mg, 0.266 mmol) and dppb (113.5 mg, 0.266 mmol) are slurried in toluene (1 ml). After 10 minutes of heating at reflux the initially orange reaction mixture turned into a yellow slurry. After 30 min, the reaction is allowed to cool to RT and pentane (7 ml) is added. The slurry is stirred for 20 min at room temperature, then filtered, washed with pentane (3×7 ml) and dried under reduced pressure. From the obtained 144 mg (84% yield) of isolated Ru(OAc)$_2$ dppb intermediate, 100 mg (0.155 mmol) are combined with ligand H—(Ph-AMBQ) (45.5 mg, 0.160 mmol) and NEt$_3$ (220 µl, 1.58 mmol) in 2-propanol (1 ml). The reaction mixture is refluxed for 3.5 h. The solvent is removed under reduced pressure and the residue slurried in pentane (5 ml) and stirred for 5 minutes. The slurry is filtered and the solid washed with 3 ml of pentane and dried. 80 mg of Ru(OAc)(Ph-AMBQ)dppb (9) (48% yield) are isolated as a yellow solid.

Ru(OAc)(Ph-AMBQ)dppb (9) may also be prepared in a one-pot procedure. For the one-pot procedure, Ru(OAc)$_2$ (PPh$_3$)$_2$ and dppb are refluxed in 2-propanol for 1 h, followed by addition of ligand H—(Ph-AMBQ) and NEt$_3$ and a further 3.5 hours of heating the mixture to reflux. Ru(OAc) (Ph-AMBQ)dppb (9) may be isolated as described above in an isolated yield of 32%. $^1$H NMR (200.1 MHz, CD$_2$Cl$_2$): δ 8.61 (m, 1H, NH$_2$), 8.22 (pseudo t, 2H, J(H,H)=7.5 Hz, aromatic protons), 7.91 (d, 1H, J(H,H)=7.1 Hz, aromatic proton), 7.80-7.15 (m, 23H, aromatic protons), 6.96 (s, 1H, benzo[h]quinoline-3-H), 6.54 (t, 1H, J(H,H)=7.4 Hz, aromatic proton), 6.22 (t, 2H, J(H,H)=6.8 Hz, aromatic protons), 5.54 (t, 2H, J(H,H)=8.3 Hz, aromatic protons), 4.45 (dd, 1H, J(H,H)=16.2, 5.0 Hz, NCH$_2$), 4.15-1.55 (m, 9H, CH$_2$ and 1 NH$_2$), 1.33 (s, 3H, CH$_3$CO). $^{31}$P{$^1$H} NMR (81.0 MHz, CD$_2$Cl$_2$): δ 59.8 (d, J=37.9 Hz), 44.9 (d, J=37.9 Hz).

Example 17

Synthesis of Isomers of [dppb Os(OAc)$_2$ AMPY] (10)

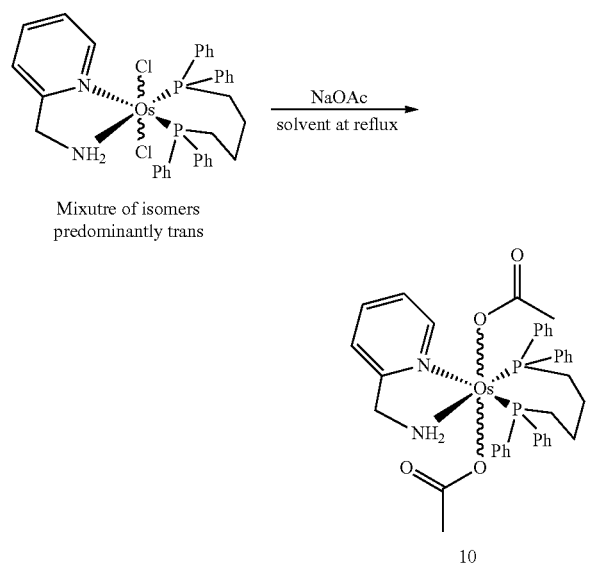

OsCl$_2$(AMPY)(dppb) mixture of isomers, predominantly trans (42 mg, 0.0527 mmol) and excess of sodium acetate are refluxed in degassed toluene or acetone (0.6 ml) for 16 h. The reaction mixture is filtered over a Celite pad and the solvent removed under vacuum to give a dark solid. With either solvent [dppb Os(OAc)$_2$ AMPY] isomers (10) are obtained as major component contaminated by remaining starting material and some cis-[dppb OsCl(OAc) AMPY].

From a reaction in toluene-d$_8$ and 5 molar equivalents of NaOAc added, isomers of [dppb Os(OAc)$_2$ AMPY] (10) are characterised: $^{31}$P{$^1$H} NMR (81.0 MHz, toluene-d$_8$): 6-11.0 (d, J=12.4 Hz, cis-10), −5.0 (d, J=12.4 Hz, cis-10); −11.6 (d, J=10.1 Hz, trans-10), −10.2 (d, J=10.1 Hz, trans-10). The mixed cis-[dppb OsCl(OAc) AMPY] is characterised as: $^{31}$P{$^1$H} NMR (81.0 MHz, toluene-d$_8$): −12.0 (d, J=13.5 Hz), −6.6 (d, J=13.5 Hz). About 10% of trans-OsCl$_2$ (AMPY)(dppb) remain: $^{31}$P{$^1$H} NMR (81.0 MHz, toluene-d$_8$): δ−15.7 (d, J=11.3 Hz), −12.6 (d, J=11.3 Hz).

Example 18

Synthesis of Ru(OAc)(CNN) dppb (11)

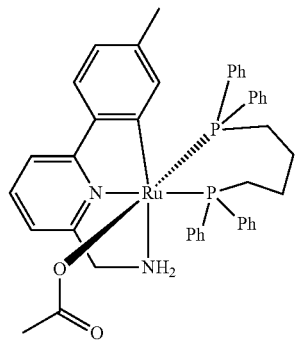

Ru(OAc)$_2$(PPh$_3$)$_2$(198 mg, 0.266 mmol) and dppb (113.5 mg, 0.266 mmol) are slurried in toluene (1 ml). After 10 minutes of heating at reflux, the initially orange reaction mixture turned into a yellow slurry. After 30 min, the reaction is allowed to cool to RT and pentane (7 ml) is added. The slurry is stirred for 20 min at room temperature, then filtered, washed with pentane (3×7 ml) and dried under reduced pressure. From the obtained 144 mg (84% yield) of isolated Ru(OAc)$_2$ dppb intermediate, 68 mg (0.105 mmol) are combined with ligand HCNN (21 mg, 0.106 mmol) and NEt$_3$ (150 µl, 1.076 mmol) in 2-propanol (1 ml). The reaction mixture is refluxed for 2 h. The solvent is removed under reduced pressure and the crude product is washed with water (1 ml) and dried under vacuum for 2-3 days. Yield: 70 mg (69% from Ru(OAc)$_2$(PPh$_3$)$_2$) of Ru(OAc)(CNN) dppb. The product is highly soluble in apolar solvents and has identical analytical data to those in Organometallics, 2009, 28, pp 4421.

Ru(OAc)(CNN) dppb (8) may also be prepared in a one-pot procedure. For the one-pot procedure Ru(OAc)$_2$ (PPh$_3$)$_2$ and dppb are refluxed in 2-propanol for 1 h, followed by addition of HCNN and NEt$_3$ and a further 2 hours of heating the mixture to reflux. Ru(OAc)(CNN) dppb (8) may be isolated as described above in an isolated yield of 45%.

Example 19

Trans-Ru(OAc)$_2$(en)(dppf) (12)

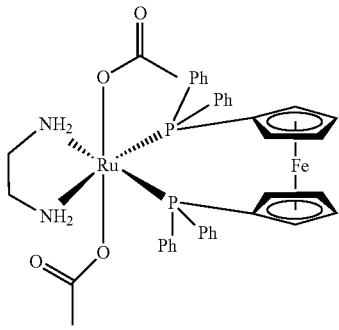

Ru(OAc)$_2$(PPh$_3$)$_2$(100 mg, 0.134 mmol) and dppf (75 mg, 0.135 mmol) are dissolved in dichloromethane (1.5 ml). After 1 h under stirring at room temperature, ethylenediamine (en) (13 μl, 0.195 mmol) is added. After 1-2 min. a yellow precipitate is formed and kept under stirring for 20 min. After addition of pentane (3 ml), the suspension is stirred for 0.5 h at room temperature, filtered, washed with pentane (3×5 ml) and dried under reduced pressure. Yield: 101 mg (91%). $^1$H NMR (200.1 MHz, CD$_2$Cl$_2$): δ 7.68-7.55 (m, 8H, aromatic protons), 7.43-7.25 (m, 12H, aromatic protons), 4.92 (m, 4H, C$_5$H$_4$), 4.46 (m, 4H, 2×NH$_2$), 4.24 (t, J(H,H)=1.8 Hz, 4H, C$_5$H$_4$), 2.64 (broad s, 4H, NCH$_2$CH$_2$N), 1.69 (s, 6H CH$_3$CO$_2$). $^{13}$C{$^1$H} NMR (50.3 MHz, CD$_2$Cl$_2$): δ 181.2 (t, J(C,P)=1.0 Hz, CH$_3$CO), 138.0 (pseudo t, J(C,P)=18.3 Hz, ipso-C$_6$H$_5$), 134.5 (t, J(C,P)=5.1 Hz, o-C$_6$H$_5$), 129.3 (t, J(C,P)=1.0 Hz, p-C$_6$H$_5$), 127.7 (t, J(C,P)=4.3 Hz, m-C$_6$H$_5$), 75.1 (t, J(C,P)=4.0 Hz, C$_5$H$_4$), 83.2 (pseudo t, J(C,P)=23.8 Hz, ipso-C$_5$H$_4$), 71.6 (d, J(C,P)=2.8 Hz, C$_5$H$_4$), 43.9 (m, NCH$_2$), 26.0 (s, CH$_3$CO$_2$). $^{31}$P{$^1$H} NMR (81.0 MHz, CD$_2$Cl$_2$): δ 48.2 (s).

Example 20

Synthesis of Trans-[dppm Ru(OAc)$_2$ AMPY] (13)

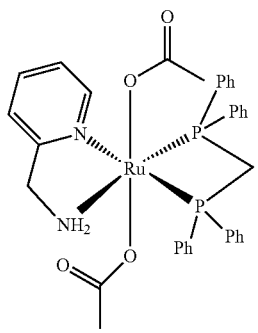

Ru(OAc)$_2$(PPh$_3$)$_2$(100 mg, 0.134 mmol) and dppm (51.5 mg, 0.134 mmol) are stirred in 1 mL of MEK at RT. After 3 h the $^{31}$P{$^1$H} NMR assay shows the presence of some remaining Ru(OAc)$_2$(PPh$_3$)$_2$. Dppm (7.2 mg, 0.02 mmol) was added and the mixture stirred at RT for further 4 h. AMPY (16 μL, 0.155 mmol) is then added and the mixture is stirred for 14 h at RT. The solvent is evaporated under reduced pressure and the obtained residue taken up with n-heptane (6 mL). The suspension is stirred for 10 min. and filtered, washed with n-heptane (2×2 mL), n-pentane (2×2 mL) and dried under reduced pressure, giving 146 mg of a mixture of 13/trans-Ru(OAc)$_2$(dppm)$_2$(16) (vide infra Example 23) in a 2/1 ratio. $^1$H NMR (200.1 MHz, CD$_2$Cl$_2$): δ 8.49 (m, 1H, o-C$_5$H$_4$N, 13), 7.78-6.86 (m, aromatic protons of 13 and 16), 5.79 (m, 4H, CH$_2$ of 16), 4.80 (pseudo t, 2H, J=10.8 Hz, PCH$_2$P of 13), 4.51 (m, 2H, NH$_2$), 1.28 (s, 6H, CH$_3$CO$_2$ of 13), 0.74 (s, 6H, CH$_3$CO$_2$ of 16). $^{31}$P{$^1$H} NMR (81.0 MHz, CD$_2$Cl$_2$): δ 19.4 (d, J=66.8 Hz, 13), 6.9 (d, J=66.8 Hz, 13), −6.8 (s, 16).

Complex 13 cannot be prepared from the chloride-containing [dppm Ru(Cl)$_2$ AMPY]. The synthesis therefore of complex 13 in a 2:1 ratio with trans-Ru(OAc)$_2$(dppm)$_2$(16) demonstrates the utility of the present invention.

Example 21

Synthesis of Cis-[dppm Ru(OAc)$_2$ AMPY] (14)

Ru(OAc)$_2$(PPh$_3$)$_2$(200 mg, 0.269 mmol) and dppm (103 mg, 0.269 mmol) are refluxed in 1 mL of toluene. After 1 h the $^{31}$P{$^1$H} NMR assay shows full consumption of Ru(OAc)$_2$(PPh$_3$)$_2$ and the formation of Ru(OAc)$_2$(PPh$_3$)(dppm). AMPY (31 μL, 0.300 mmol) is then added and the mixture is stirred at 95° C. for 12-14 h. The solvent is evaporated under reduced pressure and the obtained residue taken up with n-heptane (6 mL). The suspension is stirred for 10 min. and filtered, washed with n-heptane (2×2 mL), n-pentane (2×2 mL) and dried under reduced pressure. Yield: 145 mg (76%). Alternatively, the procedure can be replicated using MEK as the reaction solvent achieving similar results, although the use of toluene appears to give cleaner products in this instance. $^1$H NMR (200.1 MHz, CDCl$_3$): δ 9.74 (m, 1H, NH), 9.59 (m, 1H, o-C$_5$H$_4$N), 8.11-6.61 (m, 23H, aromatic protons), 5.84 (pseudo q, 1H, J=13.1 Hz, PCH$_2$P), 5.11 (m, 1H, PCH$_2$P), 3.58 (dd, 1H, J=5.0, 16.1 Hz, CH$_2$N), 2.00-0.99 (m, 2H, CH$_2$N+NH), 2.01 (s, 3H, CH$_3$CO$_2$), 1.57 (s, 3H, CH$_3$CO$_2$). $^{31}$P{$^1$H} NMR (81.0 MHz, CDCl$_3$): δ 23.4 (d, J=94.4 Hz), 7.9 (d, J=94.4 Hz).

Example 22

Synthesis of [dppe Ru(OAc)₂ AMPY] (15)

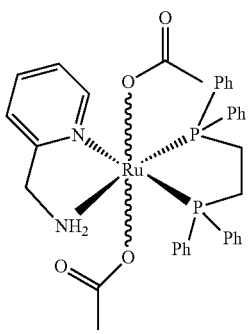

15

Ru(OAc)₂(PPh₃)₂ (200 mg, 0.269 mmol) and dppe (107 mg, 0.269 mmol) are refluxed in 1 mL of toluene. After 4 h the ³¹P{¹H} NMR assay shows full consumption of Ru(OAc)₂(PPh₃)₂ and the formation of Ru(OAc)₂(PPh₃)(dppe). AMPY (40 µL, 0.387 mmol) is then added and the mixture is stirred at RT for 36 h. The solution is evaporated under reduced pressure and the obtained residue taken up with n-heptane (8 mL). The suspension is stirred for 10 min. and filtered, washed with n-heptane (2×3 mL), n-pentane (2×2 mL) and dried under reduced pressure, affording 145 mg of a mixture of species, with two predominant compounds (ca. 75% of the mixture), identified as the cis and trans isomers (2/1 ratio) of the desired complexes. ³¹P{¹H} NMR (81.0 MHz, CDCl₃): δ 91.8 (d, J=17.0 Hz, cis-15), 86.4 (d, J=17.0 Hz, cis-15), 80.3 (d, J=21.7 Hz, trans-15), 63.9 (d, J=21.7 Hz, trans-15).

Example 23

Synthesis of Trans-[(dppm)₂Ru(OAc)₂] (16) (not According to the Invention)

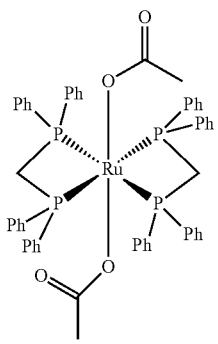

16

Ru(OAc)₂(PPh₃)₂ (50 mg, 0.067 mmol) and dppm (51.9 mg, 0.135 mmol) are stirred in 0.75 mL of toluene at 95° C. for 20 min. The solvent is evaporated under reduced pressure and the obtained residue taken up with n-heptane (4 mL). The suspension is stirred for 10 min. and then filtered, washed with n-heptane (2×1 mL), n-pentane (2×1 mL) and dried under reduced pressure. Yield: 45 mg (68%). ¹H NMR (200.1 MHz, CDCl₃): δ 7.41-7.03 (m, 40H, phenyl protons), 5.84 (m, 4H, PCH₂P), 0.80 (s, 6H, CH₃CO₂). ³¹P{¹H} NMR (81.0 MHz, CDCl₃): δ −5.9 (s).

Example 24

Synthesis of Trans-[(dppe)₂ Ru(OAc)₂] (17) (not According to the Invention)

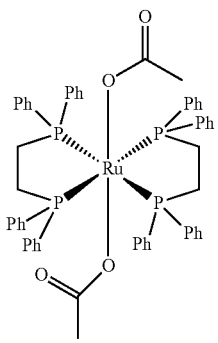

17

Ru(OAc)₂(PPh₃)₂ (50 mg, 0.067 mmol) and dppe (53.8 mg, 0.135 mmol) are stirred in 0.75 mL of toluene at 95° C. for 20 min. The solvent is evaporated under reduced pressure and the obtained residue taken up with n-heptane (4 mL). The suspension is stirred for 10 min. and then filtered, washed with n-heptane (2×1 mL), n-pentane (2×1 mL) and dried under reduced pressure. Yield: 49 mg (71%). ¹H NMR (200.1 MHz, CDCl₃): δ 7.56-6.88 (m, 40H, phenyl protons), 3.20 (m, 8H, PCH₂CH₂P), 0.80 (s, 6H, CH₃CO₂). ³¹P{¹H} NMR (81.0 MHz, CDCl₃): δ 44.8 (s).

Example 25

Synthesis of Trans, Cis-Ru(OAc)₂(PPh₃)₂(AMPY) (3)

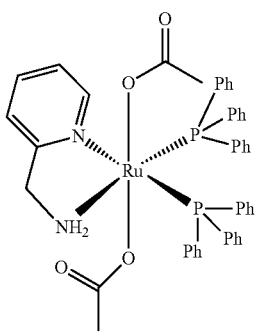

3

Ru(OAc)₂(PPh₃)₂ (1.00 g, 1.34 mmol) and AMPY (150 µL, 1.46 mmol) are stirred in MEK (8 ml) at RT for 45 min. n-Pentane (5 mL) is added and the yellow suspension filtered, washed with n-pentane (5 mL) and dried under reduced pressure. Yield: 1.14 g (>99%).

Example 26

Synthesis of Trans, Cis-Ru(OAc)$_2$(PPh$_3$)$_2$(EN) (18)

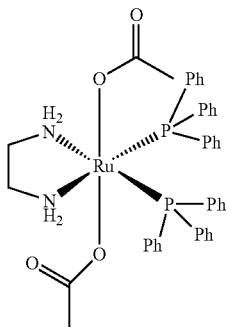

18

Ru(OAc)$_2$(PPh$_3$)$_2$ (1.00 g, 1.34 mmol) and EN (100 µL, 1.40 mmol) are stirred in MEK (12 ml) at RT for 45 min. n-Pentane (5 mL) is added to the yellow suspension, which is filtered, washed with n-pentane (5 mL) and dried under reduced pressure. Yield: 900 mg (83%).

Example 27

Synthesis of Trans-[dppb Ru(OAc)$_2$ AMPY] (2) Starting from (3)

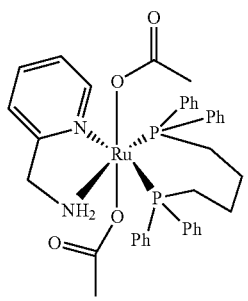

2 trans, cis-Ru(OAc)$_2$(PPh$_3$)$_2$(AMPY) 3 (100 mg, 0.117 mmol) and dppb (51.2 mg, 0.120 mmol) are stirred in MEK (1 ml) at 50° C. until $^{31}$P{$^1$H} NMR reveals the complete consumption of 3 (18-20 h). The solution is evaporated under reduced pressure and the obtained residue taken up with n-heptane (5 mL). The suspension is stirred for 10 min. and filtered, washed with n-heptane (2×3 mL), n-pentane (2×2 mL) and dried under reduced pressure. Yield: 62 mg (70%).

Example 28

Synthesis of Trans-[dppp Ru(OAc)$_2$ AMPY] (4) Starting from (3)

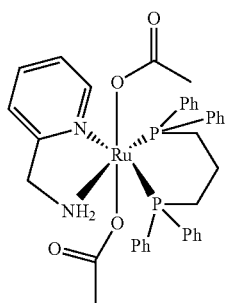

4 trans, cis-Ru(OAc)$_2$(PPh$_3$)$_2$(AMPY) 3 (100 mg, 0.117 mmol) and dppp (49.5 mg, 0.120 mmol) are stirred in MEK (1 ml) at 50° C. until $^{31}$P{$^1$H} NMR reveals the complete consumption of 3 (18-20 h). The solution is evaporated under reduced pressure and the obtained residue taken up with n-heptane (5 mL). The suspension is stirred for 10 min. and filtered, washed with n-heptane (2×3 mL), n-pentane (2×2 mL) and dried under reduced pressure. Yield: 53 mg (61%).

Example 29

Synthesis of Trans-[dppf Ru(OAc)$_2$ AMPY] (5) Starting from (3)

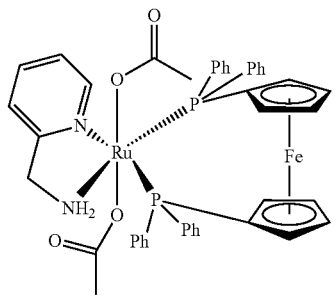

5 trans, cis-Ru(OAc)$_2$(PPh$_3$)$_2$(AMPY) 3 (100 mg, 0.117 mmol) and dppf (66.5 mg, 0.120 mmol) are stirred in MEK (1 ml) at 50° C. until $^{31}$P{$^1$H} NMR reveals the complete consumption of 3 (20-24 h). The solution is evaporated under reduced pressure and the obtained residue taken up with n-heptane (5 mL). The suspension is stirred for 10 min. and filtered, washed with n-heptane (2×3 mL), n-pentane (2×2 mL) and dried under reduced pressure. Yield: 75 mg (73%).

Example 30

Synthesis of [(R)-BINAP Ru(OAc)$_2$ AMPY] (6) Starting from (3)

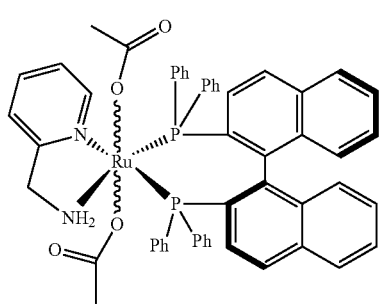

6 trans, cis-Ru(OAc)$_2$(PPh$_3$)$_2$(AMPY) 3 (100 mg, 0.117 mmol) and (R)-BINAP (80 mg, 0.128 mmol) are refluxed in toluene (1 ml). After 18 h a mixture of trans-6/Ru(OAc)$_2$[(R)-BINAP]/cis-6 in 4/2/1 ratio is obtained. $^{31}$P{$^1$H} NMR (81.0 MHz, CDCl$_3$): δ 65.1 (s, Ru(OAc)$_2$[(R)-BINAP]), 64.3 (d, J=35.6 Hz, cis-5), 55.0 (d, J=36.9 Hz, trans-5), 46.4 (d, J=35.6 Hz, cis-5), 42.6 (d, J=36.9 Hz, trans-5).

Example 31

Synthesis of [(R)-BINAP Ru(OAc)₂ EN] (19) Starting from (18)

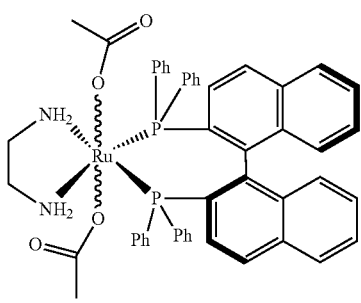

19 trans, cis-Ru(OAc)₂(PPh₃)₂(EN) 18 (100 mg, 0.124 mmol) and (R)-BINAP (79.1 mg, 0.127 mmol) are refluxed in toluene (1 ml). After 60 h a mixture of trans-19/3 in 1.2/1 ratio is obtained. $^{31}P\{^1H\}$ NMR (81.0 MHz, CDCl₃): δ 48.9 (s, trans-19), 45.5 (s, 18).

Example 32

Synthesis of [Xantphos Ru(OAc)₂ AMPY] (20)

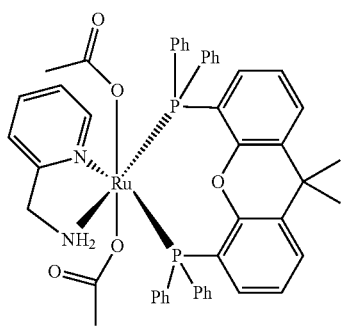

20

Ru(OAc)₂(PPh₃)₂(100 mg, 0.134 mmol) and Xantphos (78.7 mg, 0.136 mmol) are refluxed in 1 mL of MEK. After 1 h the $^{31}P\{^1H\}$ NMR assay shows full consumption of Ru(OAc)₂(PPh₃)₂. AMPY (20 μL, 0.194 mmol) is then added and the mixture is stirred at 50° C. for 2.5 h and refluxed for additional 5 h. The solution is evaporated under reduced pressure and the obtained residue taken up with n-heptane (8 mL). The suspension is stirred for 10 min. and filtered, washed with n-heptane (2×3 mL), n-pentane (2×4 mL) and dried under reduced pressure. Yield 95 mg (78%). $^{31}P\{^1H\}$ NMR (81.0 MHz, CDCl₃): δ 44.2 (broad m).

Example 33

Synthesis of Trans-[DPEPhos Ru(OAc)₂ AMPY] (21)

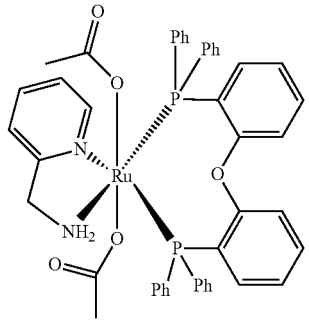

21

Ru(OAc)₂(PPh₃)₂(100 mg, 0.134 mmol) and DPEPhos (73.2 mg, 0.136 mmol) are refluxed in 1 mL of MEK. After 1 h the $^{31}P\{^1H\}$ NMR assay shows full consumption of Ru(OAc)₂(PPh₃)₂. AMPY (20 μL, 0.194 mmol) is then added and the mixture is stirred at 50° C. for. The solution is evaporated under reduced pressure and the obtained residue taken up with n-heptane (8 mL). The suspension is stirred for 10 min. and filtered, washed with n-heptane (2×3 mL), n-pentane (2×4 mL) and dried under reduced pressure. Yield 89 mg (77%). $^{31}P\{^1H\}$ NMR (81.0 MHz, CDCl₃): δ 47.3 (d, J=34.1 Hz), 38.6 (d, J=34.1 Hz).

Example 34

Synthesis of Trans, Cis-Ru(OAc)₂(PPh₃)₂(AMPY-RIM) (22)

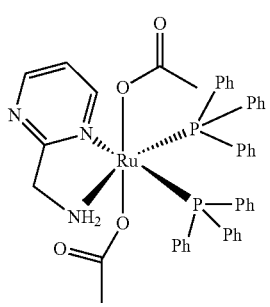

22

Ru(OAc)₂(PPh₃)₂(310 g, 0.418 mmol) and AMPYRIM* (50 μL, 0.521 mmol) are stirred in MEK (5 ml) at RT for 45 min. n-Pentane (3 mL) is added and the yellow suspension filtered, washed with n-pentane (3 mL) and dried under reduced pressure. Yield: 315 mg (88%). $^1H$ NMR (200.1 MHz, CD₂Cl₂): δ 8.49 (m, 1H, o-C₅H₄N—Ru), 8.36 (m, 1H, o-C₅H₄N), 7.46-6.88 (m, 30H, aromatic protons), 6.48 (pseudo t, J(H,H)=5.1 Hz, 1H, aromatic proton), 6.23 (m, 2H, NH₂), 4.31 (m, 2H, CH₂N), 1.71 (s, 6H CH₃ CO₂). $^{13}C\{^1H\}$ NMR (50.3 MHz, CD₂Cl₂): δ 180.9 (s, CH₃CO₂), 176.3 (dd, J(CP)=1.3, 3.2 Hz, NCCH₂), 162.6 (d, J(CP)=3.3 Hz, RuNCH), 155.1 (s, NCH), 136.3-117.6 (m, aromatic carbons), 51.5 (m, CH₂), 25.9 (s, CH₃

CO$_2$). $^{31}$P{$^1$H} NMR (81.0 MHz, CDCl$_3$): δ 43.6 (d, J=32.3 Hz), 39.7 (d, J=32.3 Hz). * [AMPYRIM free base is obtained upon treatment of AMPYRIM$^x$HCl with aqueous KOH until pH turns basic (litmus paper test) and subsequent extraction with DCM, filtration of the organic phase over Celite®, drying with MgSO$_4$ and further filtration. DCM is removed by slowly evaporation at atmospheric pressure.]

Example 35

Synthesis of Trans-[dppb Ru(OAc)$_2$ AMPYRIM] (23)

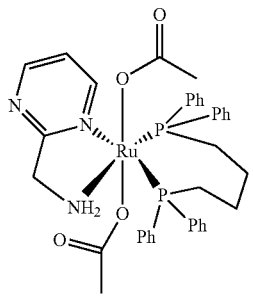

23 trans, cis-Ru(OAc)$_2$(PPh$_3$)$_2$(AMPYRIM) 22 (100 mg, 0.117 mmol) and dppb (51.2 mg, 0.120 mmol) are stirred in MEK (1 ml) at 50° C. until $^{31}$P{$^1$H} NMR reveals the complete consumption of 22 (16-18 h). The solution is evaporated under reduced pressure and the obtained residue taken up with n-heptane (5 mL). The suspension is stirred for 10 min. and filtered, washed with n-heptane (2×3 mL), n-pentane (2×2 mL) and dried under reduced pressure. Yield: 66 mg (75%). $^{31}$P{$^1$H} NMR (81.0 MHz, CDCl$_3$): δ 49.9 (d, J=37.7 Hz), 37.4 (d, J=37.7 Hz).

Example 36

Synthesis of Trans-[dppp Ru(OAc)$_2$ AMPYRIM] (24)

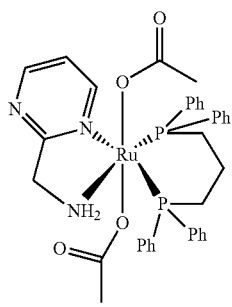

24 trans, cis-Ru(OAc)$_2$(PPh$_3$)$_2$(AMPYRIM) 22 (100 mg, 0.117 mmol) and dppp (49.5 mg, 0.120 mmol) are stirred in MEK (1 ml) at 50° C. until $^{31}$P{$^1$H} NMR reveals the complete consumption of 22 (16-18 h). The solution is evaporated under reduced pressure and the obtained residue taken up with n-heptane (5 mL). The suspension is stirred for 10 min. and filtered, washed with n-heptane (2×3 mL), n-pentane (2×2 mL) and dried under reduced pressure. Yield: 49 mg (56%). $^{31}$P{$^1$H} NMR (81.0 MHz, CDCl$_3$): δ 48.7 (d, J=50.3 Hz), 33.5 (d, J=50.3 Hz).

Example 37

Synthesis of Trans-[dppf Ru(OAc)$_2$ AMPYRIM] (25)

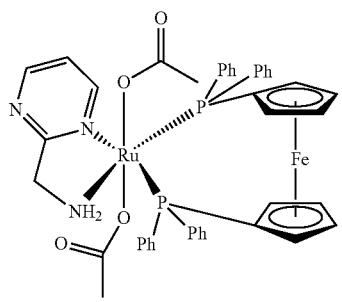

25 trans, cis-Ru(OAc)$_2$(PPh$_3$)$_2$(AMPYRIM) 22 (100 mg, 0.117 mmol) and dppf (66.5 mg, 0.120 mmol) are stirred in MEK (1 ml) at 50° C. until $^{31}$P{$^1$H} NMR reveals the complete consumption of 22 (36 h). The solution is evaporated under reduced pressure and the obtained residue taken up with n-heptane (5 mL). The suspension is stirred for 10 min. and filtered, washed with n-heptane (2×3 mL), n-pentane (2×2 mL) and dried under reduced pressure. Yield: 83 mg (80%). $^{31}$P{$^1$H} NMR (81.0 MHz, CDCl$_3$): δ 55.6 (d, J=38.6 Hz), 36.1 (d, J=38.6 Hz).

Example 38

One-Pot Synthesis of Trans, Cis-Ru(OAc)$_2$(PPh$_3$)$_2$(AMPY) (3)

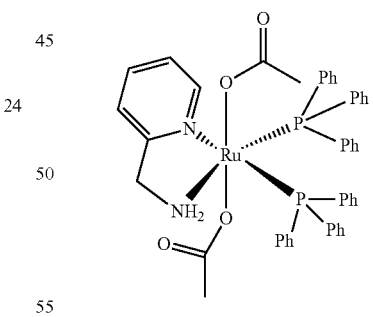

3

RuCl$_2$(PPh$_3$)$_3$ (450 mg, 0.469 mmol) and AcONa (354 mg, 4.32 mmol) are introduced into a 50 mL Schlenk and subjected to three vacuum-argon cycles and left under vacuum for 15 min. The reactor is filled with argon again and 5 mL of degassed acetone are added. The mixture is then refluxed for 2.5-3 h in an oil-bath at 70° C. A bright orange precipitate Ru(OAc)$_2$(PPh$_3$)$_2$ is observed. After the reaction has been cooled down to ca. 40° C., AMPY (52 μL, 0.500 mmol) is added and after 30 min. a bright yellow precipitate is formed. n-Heptane (8 mL) is then added, the solid filtered, washed with water (3×7 mL), 2-propanol (1 mL), n-pentane (3×5 mL) and dried under reduced pressure, attaining complex 3 as a bright yellow powder. Yield: 303 mg (75.8%).

Example 39 (not According to the Invention)

Synthesis of Trans, Cis-Ru(OPiv)$_2$(PPh$_3$)$_2$(37)

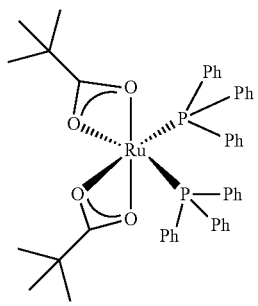

37

Compound 37 has been prepared following a slightly modified procedure of J. D. Gilbert, G. Wilkinson. J. Chem. Soc. (A) 1969, 1749: RuCl$_2$(PPh$_3$)$_3$ (1 g, 1.043 mmol) and sodium pivalate monohydrate (1.48 g, 10.43 mmol) are introduced into a 50 mL Schlenk and subjected to three vacuum-argon cycles and left under vacuum for 15 min. The reactor is filled with argon again and 20 mL of degassed t-butanol are added. The mixture is then refluxed for 2 h in an oil-bath at 70° C. A yellow precipitate is formed. After the reaction has been cooled down to RT, diethyl ether (10 mL) is added, the precipitate filtered, washed with water (3×10 mL), methanol (2×4 mL) and finally diethyl ether (3×5 mL) and dried under reduced pressure, attaining 37 as a pale orange powder. Yield: 650 mg (75.3%). $^1$H NMR (200.1 MHz, CDCl$_3$): δ 7.33-6.99 (m, 30H; phenyl protons), 0.78 (s, 18H; 2 (CH$_3$)$_3$CO). $^{13}$C{$^1$H} NMR (50.3 MHz, CDCl$_3$): δ 195.2 (m, (CH$_3$)$_3$CCO$_2$), 135.0-127.0 (m, aromatic carbons), 39.4 (s, (CH$_3$)$_3$CCO$_2$), 26.6 (s, (CH$_3$)$_3$CCO$_2$). $^{31}$P{$^1$H} NMR (81.0 MHz, CDCl$_3$): δ 64.0 (s, 2P).

Example 40

Synthesis of Trans, Cis-Ru(OPiv)$_2$(PPh$_3$)$_2$(AMPY) (38)

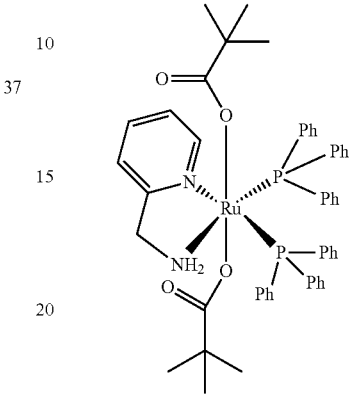

38

Ru(PivO)$_2$(PPh$_3$)$_2$ 37 (32.5 mg, 0.039 mmol) is dissolved in CDCl$_3$ and AMPY (4 μL, 0.039 mmol) is added. The colour changes immediately and after 5 min $^{31}$P-NMR spectrum show complete consumption of the starting material and formation trans, cis-Ru(PivO)$_2$(PPh$_3$)$_2$(AMPY) 38. $^1$H NMR (200.1 MHz, CDCl$_3$): δ 8.50 (m, 1H, o-C$_5$H$_4$N), 7.55-6.80 (m, 34H, 32 aromatic protons+2 NH$_2$), 6.54 (pseudo t, J(H,H)=6.4 Hz, 1H, aromatic proton), 4.03 (m, 2H, CH$_2$N), 0.85 (s, 18H, 2 (CH$_3$)$_3$CO). $^{13}$C{$^1$H} NMR (50.3 MHz, CDCl$_3$): δ 188.2 (d, J(C,P)=1.3 Hz, (CH$_3$)$_3$CCO$_2$), 166.5 (dd, NCCH$_2$, J(C,P)=2.7, 1.5 Hz), 156.5 (d, J(C,P)=3.8 Hz, NCH), 137.3-118.8 (m, aromatic carbons), 50.9 (m, CH$_2$), 40.1 (s, (CH$_3$)$_3$CCO$_2$), 26.1 (s, (CH$_3$)$_3$CCO$_2$). $^{31}$P{$^1$H} NMR (81.0 MHz, CDCl$_3$): δ 45.8 (d, J=31.2 Hz), 38.5 (d, J=31.2 Hz).

Example 41

Catalytic Activity in Transfer Hydrogenation of Ketones and Aldehydes (C=O Reduction)

TABLE 1

Transfer hydrogenation of carbonyl compounds in 2-propanol (0.1M) at reflux (82° C.) with complexes of the invention. Base added is 2 mol % i-PrONa (to carbonyl substrate)

| Entry | Ketone[a] | [Ru] complex | S/C | T (° C.) | Time (h) | Conv. (%)[b] |
|---|---|---|---|---|---|---|
| 1 | Acetophenone | 4 | 10000 | 82 | 1.5 | 70 |
|   |   |   |   |   | 4 | 95 |
| 2 | Acetophenone | 2 | 10000 | 82 | 4 | 47 |
|   |   |   |   |   | 19 | 87 |
| 3 | Acetophenone | 2 | 2000 | 82 | 10 min | 90 |
| 4 | Acetophenone | 5 | 10000 | 82 | 1.5 | 89 |
|   |   |   |   |   | 4 | 90 |
| 5 | Acetophenone | 6 | 2000 | 82 | 5 | 94 (30% ee) |
| 6 | Acetophenone | 7 | 2000 | 82 | 5 | 29 |
| 7 | Benzophenone | 5 | 10000 | 82 | 3 | 68 |
|   |   |   |   |   | 18 | 78 |
| 8 | Cyclohexanone | 5 | 5000 | 82 | 10 min | 98 |
| 9 | t-Butylphenylketone | 5 | 5000 | 82 | 3 | 62 |
|   |   |   |   |   | 18 | 98 |
| 10 | L-Menthone | 5 | 2000 | 82 | 0.5 | 77[c] |
|   |   |   |   |   | 3 | 92[c] |
|   |   |   |   |   | 18 | 98[c] |

TABLE 1-continued

Transfer hydrogenation of carbonyl compounds in 2-propanol (0.1M) at reflux (82° C.) with complexes of the invention. Base added is 2 mol % i-PrONa (to carbonyl substrate)

| Entry | Ketone[a] | [Ru] complex | S/C | T (° C.) | Time (h) | Conv. (%)[b] |
|---|---|---|---|---|---|---|
| 11[d] | 4-Bromobenzaldehyde | 1 | 800 | 82 | 24 | 30[e] |
| 12[d] | 4-Bromobenzaldehyde | 4 | 800 | 82 | 24 | 23[e] |

[a]Experimental procedure: The ketone substrate (1 mmol), 2-propanol and the specified amount of catalyst (taken from a 250 μM stock solution of catalyst) are combined in a Schlenk tube. The solution is purged with three vacuum-argon cycles and refluxed for 2 min. 200 μl (0.02 mmol) of a 0.1M NaOi-Pr solution in IPA is finally added to the refluxing mixture.
[b]The reaction is sampled by taking an aliquot of the reaction mixture (approximately 0.5 ml). This is diluted with MeOH (1.5 ml) and water (150 μl) and filtered over a short silica pad. The conversion is determined by GC analysis.
[c]All samples taken contain consistently a mixture of diastereomeric alcohols: (+)-neomenthol (63%), (+)-isomenthol (11%), (−)-menthol (14%); (+)-neoisomenthol (9%).
[d]Reaction performed without the presence of alkali-metal base.
[e]The conversion was determined by $^1$H-NMR.

As can been seen from the data in table 1, the complexes of the invention are highly active catalysts in transfer hydrogenation of ketones and aldehydes yielding alcohol products.

Base-free transfer hydrogenation (TH) of aldehydes with alcohols as hydrogen donors is not an easy process to accomplish. Entries 11 and 12 indicate that the present invention may be used to achieve base-free TH of carbonyl compounds in alcohols, such as 2-propanol.

Example 42

Catalytic Activity in the Hydrogenation of Carbonyl Compounds

TABLE 2

Hydrogenation of carbonyl compounds with complexes of the invention in the presence of t-BuOK as base (2 mol % to substrate in each case). Substrate concentration 2M in alcohol solvent.

| Entry | [Ru] | [S][a] | $H_2$ (atm) | Solvent | S/C | T (° C.) | Conv. (%)[b] | Alcohol (%)[b] | By-prds. (%)[b] |
|---|---|---|---|---|---|---|---|---|---|
| 1 | 5 | Acetophenone | 30 | EtOH | 10000 | 40 | 100 | 100 | 0 |
| 2 | 2 | Benzaldehyde | 20 | MeOH | 1000 | 50 | 56 | 55 | 1 |
| 3 | 1 | Benzaldehyde | 20 | MeOH | 1000 | 50 | 12 | 11 | 1 |
| 4 | 2 | Trans-cinnamaldehyde | 20 | MeOH | 1000 | 50 | >99 | 93 | 7 |

[a]Experimental procedure: The amount of complex (0.1-0.00125 mol %), 1 ml (10 mmol) of substrate, 4 ml of MeOH or EtOH and 0.2 ml (0.2 mmol) of a 1.0M solution potassium tert-butoxide in tert-butanol, are sequentially introduced into a 10 ml glass insert in an Biotage Endeavour unit. After assembling the unit, the reaction is stirred and purged with four cycles of filling with nitrogen (to 3 bar) and venting, while being heated to the reaction temperature. Then four cycles of purging with hydrogen (to reaction pressure) and venting are done. The reaction is started by pressurising to the reaction to reaction pressure with hydrogen and then left stirring at constant reaction pressure and temperature for 16 hours. Then the hydrogen pressure is released and the stirrer is stopped. The reaction is sampled as soon as RT is reached.
[b]The reaction is sampled by removing an aliquot of the reaction mixture (approximately 0.5 ml), followed by addition of MeOH (1.5 ml) and water (150 μl) and rapidly filtering over a short silica pad. The conversion is determined by GC analysis.

As can be seen from the data in table 2, the complexes of the invention are highly active catalysts in hydrogenation of ketones and aldehydes yielding alcohol products. The ketones and aldehydes used were of commercial grade and were not distilled prior to use. This Example, therefore, demonstrates the activity of the complexes of the invention in a more realistic context rather than under more artificial circumstances where the activity of the complexes can to a certain extent appear enhanced by ensuring the ketones and aldehydes are purified before use and are used immediately after purification.

Examples Relating to the Preparation of Ligands of Formula (4)

All reactions were carried out under argon or nitrogen atmosphere. Anhydrous THF, toluene, MeOH, 2-propanol were purchased from Aldrich and absolute EtOH was purchased from VWR. The bisphosphines dppp, dppb, dppf and rac-BINAP were purchased from Alfa Aesar (Johnson Matthey), whereas (S,R)-JOSIPHOS was purchased from STREM. $RuCl_2(PPh_3)_3$ and $[RuCl_2(p\text{-cymene})]_2$ used were commercial grade products from Johnson Matthey. NMR measurements were recorded on Bruker AC 200 and Bruker Advance 400 spectrometers and the chemical shifts, in ppm, are relative to TMS for $^1$H and $^{13}$C{$^1$H}, and 85% $H_3PO_4$ for $^{31}$P{$^1$H}. High-resolution mass spectra (HRMS) were acquired on a Bruker BioApex II 4.7e FTICR mass spectrometer, whereas the GC analysis was performed with a Varian GP-3380 gas chromatograph equipped with a MEGADEX-ETTBDMS-β chiral column.

ABBREVIATIONS

AMPY 2-(aminomethyl)pyridine
DCM dichloromethane
DMF dimethylformamide dppp 1,3-bis(diphenylphosphino)propane
dppb 1,4-bis(diphenylphospino)butane
dppf 1,1'-bis(diphenylphosphino)ferrocene
(S,R)-JOSIPHOS (S)-1-{(R)-2-[diphenylphosphine]ferrocenyl}ethyldicyclohexylphosphine
eq. equivalent
h hour
HY hydrogenation
L Liter
mL milliliter
RT Room Temperature
TH transfer hydrogenation Example 1

Synthesis of N-(naphthalen-1-yl)-3-Oxo-3-phenyl-propanamide (1)

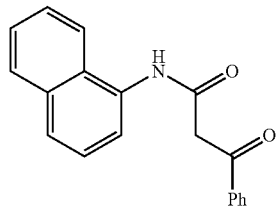 [SMILES: O=C(CC(=O)c1ccccc1)Nc1cccc2ccccc12]

The 1-naphthylamine reagent used might have contained a few ppm quantity of the highly carcinogenic 2-naphtylamine. While the 1-naphthylamine reagent had a quality allowing its use, 2-naphtylamine is banned from use in Europe and many other countries. An occupational health assessment required that in order to minimise exposure the N-(naphthalen-1-yl)-3-oxo-3-phenylpropanamide 1 should be assayed and characterised as a crude product and then converted on as described in Example 2.

1-Naphthylamine (1183 g, 8.26 mol) and xylene (isomer mixture, 10 L) was charged to a 20 L round bottom flask, equipped with a distillation setup that allowed distillation of the reaction side product ethanol as azeotrope with xylene. The reaction was heated at an oil bath temperature of 160° C. Ethyl benzoylacetate (1775 g, 9.23 mol) was added over 1.5 hours, resulting in a steady distillation of ethanol/xylene. After completion of the addition, the reaction temperature was kept at 160° C. (oil bath) for two hours and then allowed to cool to 120° C. At this temperature the reaction solvent was distilled by vacuum distillation. The resulting brown solid was cooled to room temperature and slurried in n-heptane (9 L).

The slurry was filtered, the solid product further washed with 1 L of heptane and dried under vacuum in a desiccator (over KOH) at 40° C. to afford the pale brown solid 1, 1929 g, 81% yield. The product may be used in the next step without further purification. $^1$H NMR (400 MHz, CDCl$_3$): δ 10.03 (br s, 1H, NH), 8.05 (d, 1H, J=7.6), 8.00 (d, 2H, J=7.8), 7.79 (d, 1H, J=7.8), 7.77 (d, 1H, J=8.3), 7.68-7.58 (m, 1H), 7.55-7.35 (m, 6H), 4.18 (s, 2H) (complex spectrum, only major resonances given). $^{13}$C{$^1$H} NMR (100.61 MHz, CDC$_3$): δ 197.31 (C C=O), 164.3 (C C=O amide), 136.11, 134.51, 134.10, 132.39, 129.05, 128.71, 128.63, 128.36, 128.71, 127.93, 126.51, 125.78, 125.47, 120.8, 119.72, 44.9 (complex spectrum, only major resonances given).

Example 2

Synthesis of 4-phenylbenzo[h]quinolin-2(1H)-one (2)

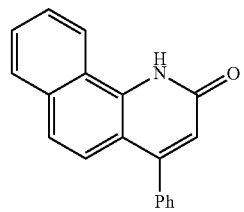 [SMILES: O=c1cc(-c2ccccc2)c2ccc3ccccc3c2[nH]1]

To crushed ice (1608 g) in a 20 L round bottom flask with efficient overhead stirring was added cautiously 4828 g of 98% sulphuric acid. At the end of the addition, the mixture had a temperature (internal) of 80° C. N-(naphthalen-1-yl)-3-oxo-3-phenylpropanamide (1, 1929 g, as produced in example 1) was added as solid in portions over 30 minutes. After the addition had completed, the mixture had a temperature (internal) of 49° C. The reaction was then carefully heated in an oil bath, set to 100° C. A very thick slurry of purple solid had formed after 5 hours at this temperature and the mixture was allowed to cool to room temperature. 3 L of cold water was added with external cooling by crushed ice and the mixture was stirred for three hours. The slurry was filtered and the solid purple product washed with 3 L of water and sucked dry as much as possible. The product was then transferred to a 10 L flask and stirred with 6 L of acetone for 30 minutes. The slurry was again filtered and the solid washed with 4×1 L of acetone. The pale brown purple solid was dried in a desiccator over KOH at 40° C. to afford the solid product 2 (1571 g, 87% yield, 70% in two steps from 1-naphtylamine used in Example 1). The product may be used in the next step without further purification. HRMS found: [M+H]$^+$ 272.1058; calcd for C$_{19}$H$_{14}$NO: 272.1070. $^1$H NMR (400 MHz, DMSO-d$^6$): δ 12.26 (s, br, NH) 8.94 (1H, d, J=7.9 Hz), 7.97 (1H, d, J=6.9 Hz), 7.72-7.62 (2H, m), 7.60-7.46 (6H, m), 7.40 (1H, d, J=8.8 Hz), 6.54 (1H, s). $^{13}$C{$^1$H} NMR (100.61 MHz, DMSO-d$^6$): δ 162.34, 152.95, 137.66, 134.06, 129.26, 129.20, 128.80, 128.66, 127.13, 123.46, 123.10, 122.65 (the solubility of the compound is so low that only the 12 non quaternary carbons are visible Example 3

Synthesis of 2-Bromo-4-phenylbenzo[h]quinoline (3)

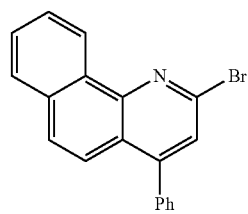 [SMILES: Brc1cc(-c2ccccc2)c2ccc3ccccc3c2n1]

The product obtained in example 2, 1571 g of 4-phenyl-benzo[h]quinolin-2(1H)-one (2, 5.79 mol) was dissolved in 7.8 L of toluene and azeotropically dried using Dean-Stark distillation. At room temperature 1660 g of POBr$_3$ was carefully added in portions. After the reaction mixture was heated overnight at 120° C. it was cooled to room temperature. This mixture was added to 10 L of water and aqueous concentrated NaOH was added until a pH=14 was measured in the water phase. At this stage the reaction mixture had to be filtered over Celite to remove a very fine, very insoluble impurity. The Celite pad was washed with several 1 L quantities of toluene. The organic filtrate was stripped to dryness and the residue recrystallized from isopropyl alcohol to afford the product 3 as a brown powder (1392 g, 72% yield). This batch was assayed for water content and 0.06% wt/wt residual water content was determined. HRMS found: [M+H]$^+$ 334.0221, calcd for $C_{19}H_{13}BrN$: 334.0226. $^1$H NMR (400 MHz, CDCl$_3$): δ 9.19 (1H, d, J=7.7 Hz), 7.79 (1H, d, J=7.5 Hz), 7.70-7.57 (4H, m), 7.51 (1H, s), 7.48-7.37 (5H, m). $^{13}$C{$^1$H} NMR (100.61 MHz, CDCl$_3$): δ 150.91, 147.61, 140.50, 137.05, 133.60, 130.70, 129.60, 129.55, 128.86, 128.81, 128.73, 128.03, 127.58, 127.32, 126.20, 125.24, 123.52, 122.64.

Example 4

Synthesis of 4-phenyl-Benzo[h]quinoline-2-Carbaldehyde (4)

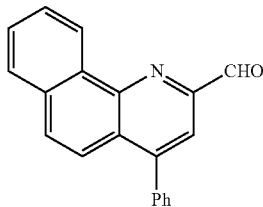 [SMILES: O=Cc1cc(-c2ccccc2)c2ccc3ccccc3c2n1]

33.1 g of 2-bromo-4-phenylbenzo[h]quinoline (3, 0.1 mol) was dissolved in dry THF (300 mL) in a 1 L three neck round bottom flask and the mixture was cooled to −75° C. (IPA/dry ice bath). 45 mL of 2.5M n-butyl lithium in hexanes (0.1125 mol, 1.125 eq) was added slowly so that the internal temperature never went above −70° C. After stirring the reaction for another one hour at −75° C., 11 g of anhydrous dimethylformamide (0.15 mol, 1.5 eq) was added in small drops so that the internal temperature never went above −65° C. The reaction was then allowed to reach room temperature overnight. The next day, 100 mL of water was added to quench the reaction, followed by 15 mL of glacial acetic acid. The organic layer was separated and washed with 50 ml of saturated sodium chloride solution. It was then dried over sodium sulphate. The filtrate after removal of the sodium sulphate was concentrated to dryness. The residue was treated with 75 mL of ethanol and the resulting slurry filtered to obtain the product 4, which is dried under vacuum. Yield 20.0 g (70.6%). HRMS found: [M+H]$^+$ 284.1073, calcd for $C_{20}H_{14}NO$: 284.1070. $^1$H NMR (400 MHz, CDCl$_3$): δ 10.41 (1H, s), 9.50 (1H, d, J=7.7 Hz), 8.12 (1H, s), 7.93 (1H, d, J=7.7 Hz), 7.89 (2H, s), 7.85-7.75 (7H, m). $^{13}$C{$^1$H} NMR (100 MHz, CDCl$_3$): δ 194.3, 150.5, 149.5, 147.0, 137.8, 133.5, 131.7, 130.5, 129.7, 129.0, 128.7, 128.2, 127.8, 127.0, 125.0, 124.0, 122.8, 118.9.

In a second reaction, 2-bromo-4-phenylbenzo[h]quinoline (21.56 g, 64.51 mmol) in less solvent (90 mL of dry THF) was reacted as above at −78° C. with 32.3 mL n-BuLi (2.5 M in hexane, 80.63 mmol, 1.25 eq.), then with dry DMF (6.29 mL, 80.63 mmol, 1.25 eq). After a workup similar to above, 19.35 g of impure product was obtained and used without further purification for the synthesis of 5.

Example 5

Synthesis of 2-Carbaldehyde-4-phenylbenzo[h]quinoline Oxime Hydrochloride (5)

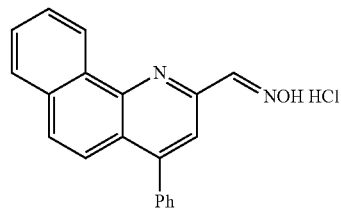

The crude aldehyde 4 from the second reaction above (19.35 g, 68.3 mmol) was slurried in absolute ethanol (240 mL) and heated at 40° C. Hydroxylamine hydrochloride (8.54 g, 122.3 mmol, 1.8 eq.) was added at once, affording a red solution which was stirred at 40° C. for 1.5 h. During this time the formed oxime started to precipitate as a bright yellow solid. The reaction mixture was cooled down to 0° C. for 1 h, affording an additional yellow precipitate. The solid was filtered, washed with EtOH (10 mL) and dried under reduced pressure to give the hydrochloride salt of the oxime as a bright yellow solid (5, 14 g, 41.82 mmol, 61%). HRMS found: [M+H]$^+$ 299.1166, calcd for $C_{20}H_{15}N_2O$: 299.1179. $^1$H NMR (400 MHz, methanol-d$_4$): δ 9.12 (1H, t, J=4.7 Hz), 8.63 (1H, s), 8.17 (1H, s), 7.99 (1H, t, J=4.6 Hz), 7.95 (1H, d, J=9.2 Hz), 7.82 (2H, t, J=4.6 Hz), 7.77 (1H, d, J=9.2 Hz), 7.57-7.50 (5H, m). $^{13}$C{$^1$H} NMR (100 MHz, methanol-d$_4$): δ 155.3, 147.5, 144.1, 140.25, 136.38, 134.5, 130.5, 130.2, 129.7, 129.5, 129.3, 128.8, 128.7, 128.3, 125.6, 125.45, 123.4, 122.2, 119.17.

When the 20 g (0.07 mol) of pure solid 4-phenylbenzoquinoline-2-carboxaldehyde (4) obtained in example 4 were slurried in 250 mL of ethanol followed by addition of 6.9 g (0.1 mol) of hydroxylamine hydrochloride in one lot, a quantitative yield of 20.93 g of 2-carbaldehyde-4-phenyl-benzo[h]quinoline oxime hydrochloride 5 was obtained. The ethanol slurry of the 4-phenylbenzoquinoline-2-carboxaldehyde and the hydroxylamine hydrochloride was heated to 50° C. for 2 hours. The slurry was filtered and the solid product washed with ethanol.

Example 5a

Synthesis of 4-phenyl-2-cyanobenzo[h]quinoline (5a)

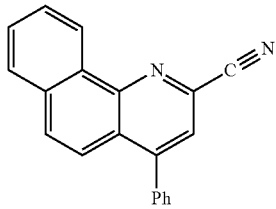 [SMILES: N#Cc1cc(-c2ccccc2)c2ccc3ccccc3c2n1]

Example 6

Synthesis of 4-phenyl-2-Aminomethyl-Benzo[h]quinoline Hydrochloride (HCNN$^{Ph}$.HCl) (6)

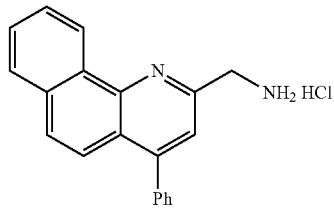

10 g (0.03 mol) of 4-phenyl-2-bromo-benzo[h]quinoline was combined with 3.2 g (0.036 mol) of copper(I) cyanide and 50 mL of commercial grade N-methylpyrrolidone. The reaction mixture was heated to 150° C. for 4 hours, at which point no starting material remained. The cooled reaction mixture was quenched by its addition to a mixture of 10 g iron(III) chloride hexahydrate, 1 L of water and a few drops of concentrated hydrochloric acid. The mixture was extracted with dichloromethane. The dichloromethane phase was stripped and the crude product slurried in water to give a solid which was isolated by filtration. The crude product was taken up in toluene. Fractional crystallisation gives initially a compound fraction that was identified and characterised as 4-phenyl-benzo[h] quinoline-2-carboxamide (5b). As second pure fraction 3.3 g (39%) of the title compound 4-phenyl-2-cyanobenzo[h]quinoline 5a was isolated.

4-phenyl-2-cyanobenzo[h] quinoline 5a: MS(ESI) m/z: 281 (MH+)$^1$H-NMR (DMSO-D6, 400 MHz) δ: 9.18 (1H, m), 8.18 (1H, s), 8.09 (2H, m, J=9.1), 7.86 (2H, m), 7.78 (1H, d, J=9.2), 7.64 (5H, m). $^{13}$C{$^1$H} NMR (DMSO-D6, 100 MHz) δ: 149.5, 146.7, 136.2, 133.3, 131.2, 131.1, 130.1, 129.9, 129.4, 129.0, 128.4, 128.3, 125.8, 125.7, 124.5, 122.2, 118.1 (shift overlap of two $^{13}$C resonances)

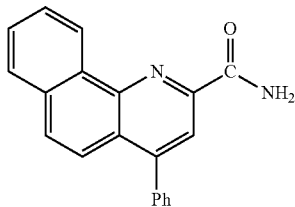 [SMILES: NC(=O)c1cc(-c2ccccc2)c2ccc3ccccc3c2n1]

4-phenylbenzo[h]quinoline-2-carboxamide 5b: MS(ESI) m/z: 299 (MH+). $^1$H-NMR (DMSO-D6, 400 MHz) δ: 9.68 (1H, m), 8.80 (1H, s), 8.19 (1H, s), 8.08 (1H, m), 8.03 (1H, d, J=9.2 Hz), 7.91 (1H, s), 7.84 (2H, m), 7.81 (1H, d, J=9.2 Hz), 7.63 (5H, m). $^{13}$C{$^1$H} NMR (DMSO-D6, 100 MHz) δ: 166.3, 149.2, 148.5, 145.2, 137.6, 133.3, 131.1, 129.7, 129.5, 129.2, 129.0, 128.9, 128.0, 127.7, 125.7, 125.1, 122.5, 120.0.

2-carbaldehyde-4-phenylbenzo[h]quinoline oxime hydrochloride (5, 6.0 g, 17.9 mmol) was placed in a 100 mL Parr autoclave followed by 10% Pd/C Type 338 (1.94 g of paste catalyst, Manufacturer Johnson Matthey). The autoclave was assembled, purged with nitrogen and depressurized. MeOH (60 mL) was added via the injection port. Stirring was started and autoclave was purged again with N$_2$ (5×2 bar) and H$_2$ (5×5 bar). The autoclave was pressurized with hydrogen to 5 bar and heated at 30° C. The gas uptake starts occurring after ca 45 min. Hydrogen was refilled to keep 5 bar and the reaction mixture was stirred until gas uptake was no longer apparent (ca. 90 min.). The autoclave was carefully depressurized and purged with N$_2$ (5×2 bar). Reaction mixture was filtered over a pad of celite and the pad was washed with MeOH (50 mL). The solvent was evaporated under reduced pressure to give the title compound as off-white solid (6, 5.5 g, 96% yield). HRMS found: [M+H]$^+$ 285.1387, calcd for C$_{20}$H$_{17}$N$_2$: 285.1386. $^1$H NMR (400 MHz, methanol-d$_4$): δ 9.52 (1H, d, J=8.0), 7.94 (1H, d, J=7.6), 7.86-7.70 (4H, m), 7.61-7.51 (6H, m), 4.5 (2H, s). $^{13}$C{$^1$H} NMR (100 MHz, methanol-d$_4$): δ 150.7, 149.9, 145.9, 137.8, 133.7, 131.0, 129.3, 128.5, 127.8, 127.5, 126.9, 124.8, 123.6, 122.2, 120.2, 43.1.

Example 7

Synthesis of N-(naphthalen-1-yl)-3-oxobutanamide (7)

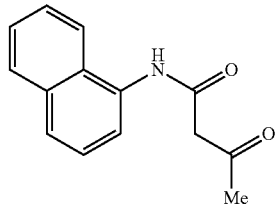 [SMILES: CC(=O)CC(=O)Nc1cccc2ccccc12]

The 1-naphthylamine reagent used might have contained a few ppm quantity of the highly carcinogenic 2-naphtylamine. While the 1-naphthylamine reagent had a quality allowing its use, 2-naphtylamine is banned from use in Europe and many other countries. An occupational health assessment required that in order to minimise exposure the N-(naphthalen-1-yl)-3-oxobutanamide 7 should be assayed and characterised as a crude product and then converted on as described in Example 8.

1-Naphthylamine (500 g, 3.49 mol) was placed in a 10 L round bottom flask and dissolved in THF (850 mL). Solid anhydrous sodium acetate (286.7 g, 3.6 mol) was charged next, followed by 2,2,6-trimethyl-4H-1,3-dioxin-4-one (700 g, 4.92 mol). The slurry was heated at reflux temperature for 26 hours. Then the reaction mixture was cooled to room temperature and 3 L dilute 2M aqueous HCl was added with vigorous stirring. The resulting slurry was stirred for 1 hour and then filtered. The pale purple solid was washed with water (2×150 mL) and dried in a desiccator over KOH at 40° C. 720 g of N-(naphthalen-1-yl)-3-oxobutanamide (7, 91% yield) were obtained. $^1$H NMR (400 MHz, CDCl$_3$): δ 9.97 (br s, 1H, NH), 7.98 (d, 1H, J=7.5), 7.94 (d, 1H, J=8.3), 7.78 (d, 1H, J=8.0), 7.59 (d, 1H, J=8.3), 7.48 (t, 1H, J=7.5), 7.42 (t, 1H, J=7.6), 7.37 (t, 1H, J=8.0), 3.64 (s, 2H), 2.28 (s, 3H). $^{13}$C{$^1$H} NMR (100.61 MHz, CDC$_3$): δ 206.22 (C C=O), 163.9 (C C=O amide), 134.07, 132.28, 128.70, 126.60, 126.47, 125.74, 125.51, 120.76, 119.79, 49.19, 31.43.

In a repeat synthesis 1-Naphthylamine (900 g, 6.29 mol) was dissolved in 1.5 L of THF in a 10 L round bottom flask with overhead stirrer. Solid anhydrous sodium acetate (516 g, 6.29 mol) was charged next, followed by 2,2,6-trimethyl-4H-1,3-dioxin-4-one (1260 g, 8.86 mol). In this repeat 952 g of N-(naphthalen-1-yl)-3-oxobutanamide (7, 67% yield) were obtained.

Example 8

Synthesis of 4-methylbenzo[h]quinolin-2(1H)-one (8)

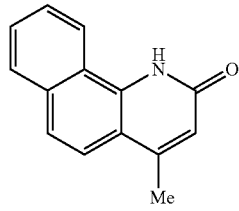

3000 g of 98% sulphuric acid were heated in a 10 L round bottom flask with efficient overhead stirring to an internal temperature of 65° C. 952 g of N-(naphthalen-1-yl)-3-oxobutanamide 7 was added in portions so that despite the very exothermic reaction the internal temperature did not exceed 90° C. The mixture was heated to 95° C. for 1 hour and then cooled to 50° C. This mixture was slowly added to 15 kg of crushed ice in another 20 L round bottom flask with efficient overhead stirring. The slurry was stirred for 1 hour and then filtered. The purple solid was washed with 3×1 L of water and sucked dry as much as possible. The product is then transferred to a 10 L flask and stirred with 4 L of ethanol for 30 minutes. The slurry is again filtered and the pale purple solid is dried in a desiccator over KOH at 40° C. to afford the solid product (8, 814 g, 93% yield). HRMS found: [M+H]$^+$ 210.0906, calcd for C$_{14}$H$_{10}$NO: 210.0913. $^1$H NMR (400 MHz, CDCl$_3$): δ 8.51 (1H, d, J=8.3 Hz), 7.85 (1H, d, J=8.0 Hz), 7.77-7.56 (4H, m), 6.68 (1H, s), 2.56 (3H, s). $^{13}$C{$^1$H} NMR (100.61 MHz, CDCl$_3$): δ 162.84, 150.70, 134.71, 134.05, 128.73, 128.18, 127.28, 123.4, 121.29, 121.89, 121.03, 119.90, 116.96, 19.94.

Example 9

Synthesis of 2-bromo-4-methylbenzo[h]quinoline (9)

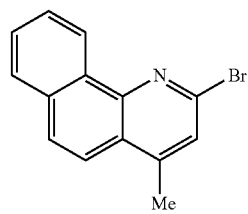

814 g of 4-methylbenzo[h]quinolin-2(1H)-one (8, 3.876 mol), obtained in Example 8 was dissolved in 4 L of toluene and azeotropically dried using Dean-Stark distillation. At room temperature 1115 g of POBr$_3$ was carefully added in portions. After the reaction mixture was heated overnight at 120° C. and 6.5 L of water were added, NaOH was added until a pH=14 was measured in the water phase. At this stage the reaction mixture had to be filtered over Celite to remove a very fine, very insoluble impurity. The Celite pad was washed with five 1 L quantities of toluene. The combined organic filtrate was dried and all toluene was removed by reduced pressure distillation. The residue was taken up in acetone (8.5 L), heated to reflux and the hot solution filtered through Celite. The acetone was partially distilled under reduced pressure until a very thick slurry was obtained. The slurry at room temperature was filtered to give the product 9 as a grey solid (584 g, 55% yield).

By repeating this reaction, another 621 g were obtained in higher yield of 75%. The 584 g and the 621 g were combined and dissolved in hot toluene, treated with activated charcoal and the charcoal was removed by filtration and the charcoal pad washed with further toluene. The combined toluene fractions were partially stripped giving a crop of 887 g of a pure cream solid 2-bromo-4-methylbenzo[h]quinoline 9. The water assay by Karl Fischer method gave 0.06% wt/wt residual water.

As further fractions 155 g, then 80 g of less pure material were obtained. Analysis on the pure product: HRMS found: [M+H]$^+$ 272.0059, calcd. for C$_{14}$H$_{11}$BrN: 272.0069. $^1$H NMR (400 MHz, CDCl$_3$): δ 9.0964 (1H, dd, J=2.0, 7.0 Hz), 7.75 (1H, dd, J=2.0, 7.0 Hz), 7.67 (s, 1H), 7.65 (s, 1H), 7.59 (1H, d, J=6.0 Hz), 7.65-7.56 (m, 1H), 7.31 (s, 1H), 2.51 (s, 3H). $^{13}$C{$^1$H} NMR (100 MHz, CDCl$_3$): δ 146.9, 146.5, 140.7, 133.5, 130.7, 128.5, 127.7, 127.6, 127.2, 126.6, 125.1, 124.6, 120.8, 18.7, Example 10

Synthesis of 4-methylbenzo[h]quinoline-2-carbaldehyde (10)

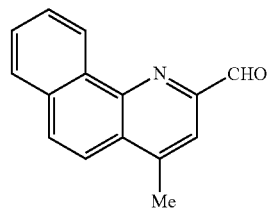 [SMILES: Cc1cc(C=O)nc2c1ccc1ccccc12]

54.4 g of 2-Bromo-4-methylbenzo[h]quinoline 9 (0.2 mol) was dissolved in 400 mL of THF in a 1 L three neck round bottom flask and the mixture was cooled to −75° C. (IPA/dry ice bath). 100 mL of 2.5 m n-butyl lithium in hexanes (0.25 mol, 1.25 eq) was added slowly so that the internal temperature never went above −70° C. The mixture was left to stir for 45 minutes at −75° C. Then 22 g of anhydrous dimethylformamide (0.30 mol, 1.5 eq) was added in small drops so that the internal temperature never went above −65° C. The reaction was then allowed to reach room temperature overnight. The next day, 350 mL of water was added to quench the reaction, followed by 40 mL of glacial acetic acid. A solid precipitated and was filtered off and washed with water and n-heptane to give a first crop. The organic layer of the filtrate was separated from the aqueous phase and the solvents were removed by distillation at reduced pressure. The residue was triturated with 150 mL of methanol to give a second crop that was filtered off and washed with methanol. The two crops were combined and dried under vacuum affording compound 10. Yield 29.4 g (68%). $^1$H NMR (400 MHz, CDCl$_3$): δ 10.35 (1H, s), 9.47 (1H, d, J=8.1 Hz), 8.04-7.93 (4H, m), 7.86-7.75 (3H, m), 2.89 (3H, s). $^{13}$C{$^1$H} NMR (100 MHz, CDCl$_3$): δ 194.5, 150.5, 146.1, 145.4, 133.4, 131.9, 130.3, 128.7, 128.4, 127.9, 127.7, 121.1, 119.3, 19.3.

Example 11

Synthesis of 4-methylbenzo[h]quinoline-2-carbaldehyde oxime hydrochloride (11)

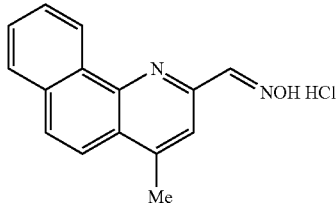

29 g of 4-methylbenzo[h]quinoline-2-carbaldehyde 10 (0.13 mol) from example 10 were slurried in 300 mL of ethanol followed by addition of 9.6 g (0.143 mol) of hydroxylamine hydrochloride in one lot. The ethanol slurry of the 4-phenylbenzoquinoline-2-carboxaldehyde and the hydroxylamine hydrochloride was heated to 50° C. for 90 minutes and the slurry then filtered and the solid product washed with cold ethanol. A 76% yield of 26.0 g of 2-carbaldehyde-4-methylbenzo[h]quinoline oxime hydrochloride 11 was obtained. HRMS found: [M+H]$^+$ 237.1018, calcd for $C_{15}H_{13}N_2O$: 237.1022. $^1$H NMR (400 MHz, methanol-d$_4$): δ 9.16-9.10 (1H, m), 8.75 (1H, s), 8.32 (1H, s), 8.20-8.10 (3H, m), 7.95-7.91 (2H, m), 3.05 (3H, s). $^{13}$C{$^1$H} NMR (100 MHz, methanol-d$_4$): δ 155.6, 146.6, 142.7, 137.4, 134.7, 130.79, 130.4, 129.0, 128.5, 127.2, 124.1, 123.03, 120.7, 119.7, 19.3

Example 11a

Synthesis of 4-Methyl-2-cyanobenzo[h]quinoline (11a)

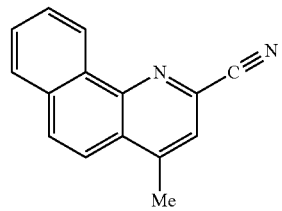

13.6 g (0.035 mol) of 4-methyl-2-bromo-benzo[h]quinoline (9) were combined with 5.6 g (0.062 mol) of copper(I) cyanide and 75 mL of commercial grade N-methylpyrrolidone. The reaction mixture was heated to 150° C. for 4 hours, at which point no starting material remained. The cooled reaction mixture was quenched by its addition to a mixture of 20 g iron(III) chloride hexahydrate, 150 mL of water and 2 mL of concentrated hydrochloric acid. A solid precipitated and was isolated by filtration. After washing with water and drying the solid was recrystallized from toluene to give 7.5 g of 4-methyl-2-cyanobenzo[h]quinoline (11a) contaminated with less than 20% w/w 4-methyl-benzo[h]quinoline-2-carboxamide (11b).

4-methyl-2-cyanobenzo[h]quinoline 11a: MS(ESI) m/z: 219 (MH$^+$). $^1$H-NMR (DMSO-D6, 400 MHz) δ : 9.08 (1H, m), 8.13-7.96 (4H, m), 7.82 (2H, m), 2.75 (3H, s). $^{13}$C{$^1$H} NMR (DMSO-D6, 100 MHz) δ: 147.3, 133.4, 130.6, 129.5, 128.3, 128.2, 126.9, 126.3, 124.4, 121.5, 118.2, 18.6 (shift overlap of four $^{13}$C resonances).

4-methylbenzo[h]quinoline-2-carboxamide 11 b has been identified as a separate peak in LCMS with MS(ESI) m/z: 237 (MH+). Mass difference+18 (water) as expected.

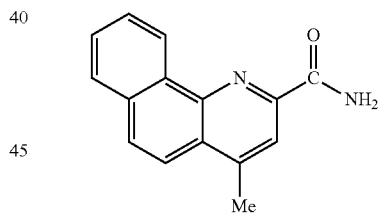

Example 12

Synthesis of 4-methyl-2-aminomethyl-benzo[h]quinoline hydrochloride (HCNN$^{Me}$.HCl) (12)

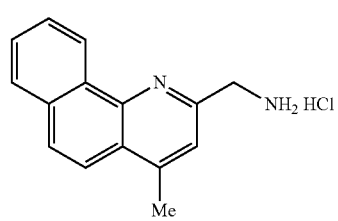

Compound 11 (100 mg, 0.36 mmol) was placed in an glass insert of an Biotage Endeavor pressure screening unit followed by 10% Pd/C Type 338 (15 mg of paste catalyst, Johnson Matthey product). The Biotage Endeavor was assembled, the vial purged with nitrogen and depressurized. MeOH (3 mL) was added via the injection port. The stirring was started and the autoclave was purged with $N_2$ (5× to 2 bar) and $H_2$ (5× to 5 bar). The system was pressurized with hydrogen to 5 bar and heated at 30° C. Gas uptake started after 45 minutes. The hydrogen pressure was kept at 5 bar and the reaction mixture was stirred until gas uptake was no longer apparent (ca. 90 min). The system was carefully depressurized and purged with $N_2$ (5× to 2 bar). The reaction mixture was filtered over a pad of celite and the pad was washed with MeOH (10 mL). The solvent was evaporated under reduced pressure to give 4-methyl-2-aminomethyl-benzo[h]quinoline hydrochloride 12 as an off-white solid (93 mg). HRMS found: $[M+H]^+$ 223.1230, calcd for $C_{15}H_{15}N_2$: 223.1230. $^1H$ NMR (400 MHz, methanol-$d_4$): δ 7.89 (1H, d, J=8.0 Hz), 6.41 (2H, d, J=8.7 Hz), 6.35 (1H, d, J=9.1 Hz), 6.25-6.14 (2H, m), 5.92 (1H, s), 2.97 (2H, s), 1.21 (3H, s). $^{13}C\{^1H\}$ NMR (100 MHz, methanol-$d_4$): δ 149.0, 144.5, 143.4, 132.2, 129.6, 126.5, 126.0, 125.9, 125.2, 123.6, 123.2, 119.3, 119.0, 41.4, 16.2.

Example 13

Synthesis of RuCl(CNN$^{Ph}$)(dppp) (13)

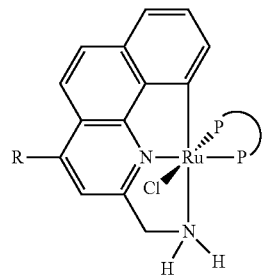

R = Ph; PP = dppp

RuCl$_2$(PPh$_3$)$_3$ (222 mg, 0.232 mmol) and dppp (101 mg, 0.244 mmol) were slurried in 2-propanol (4 mL) and the mixture was refluxed in a 25 mL round bottom flask for 1 h. Compound 6 (82 mg, 0.256 mmol) and NEt$_3$ (0.32 mL, 2.3 mmol) were added and the mixture was refluxed for 1 h. The suspension was cooled to room temperature and heptane (4 mL) was added. The orange precipitate was filtered, washed with MeOH (1 mL), heptane (3×1 mL) and dried under reduced pressure (13, 171 mg, 89% yield). HRMS found: $[M-Cl]^+$797.1787, calcd for $C_{47}H_{41}N_2P_2Ru$: 797.1783. $^1H$ NMR (200.1 MHz, CD$_2$Cl$_2$): δ 8.06 (m, 1H), 7.95-7.81 (m, 4H), 7.66-6.90 (m, 21H), 6.59 (t, J=7.1 Hz, 1H), 6.28 (t, J=6.8 Hz, 2H), 5.77 (t, J=8.2 Hz, 2H), 4.53 (d, J=14.4 Hz, NCH$_2$, 1H), 4.12 (m, NH$_2$, 1H), 3.91 (m, NCH$_2$, 1H), 2.98 (t, J=12.6 Hz, CH$_2$, 1H), 2.65 (t, J=12.4.1 Hz, CH$_2$, 1H), 2.37 (t, J=13.8 Hz, CH$_2$, 1H), 2.20 (m, NH$_2$, 1H), 1.72-1.58 (m, CH$_2$, 2H), 1.29 (m, CH$_2$, 1H). $^{13}C\{^1H\}$ NMR (50.3 MHz, CD$_2$Cl$_2$): δ 170.0 (dd, $^2$J(CP)=15.1, 9.5 Hz; CRu), 155.2, 152.2, 146.4, 146.1, 143.2, 142.4, 138.9, 138.6, 138.1, 137.7, 137.1, 135.9, 135.7, 134.3, 133.8, 133.6, 133.4, 131.6, 131.5, 130.0, 129.8, 129.2, 129.1, 128.9, 128.8, 128.6, 128.5, 128.2, 128.0, 127.6, 127.4, 127.2, 125.9, 125.7, 123.0, 120.5, 118.4, 117.1, 52.0 (d, J=2.0 Hz, CH$_2$N) 29.8, (d, J=26.4 Hz, CH$_2$P), 24.8, (d, J=35.6 Hz, CH$_2$P), 21.0 (s, CH$_2$P). $^{31}P\{^1H\}$ NMR (81.0 MHz, CD$_2$Cl$_2$): δ 54.7 (d, J=48.6 Hz), 35.7 (d, J=48.6 Hz).

Example 14

Synthesis of RuCl(CNN$^{Ph}$)(dppb) (14)

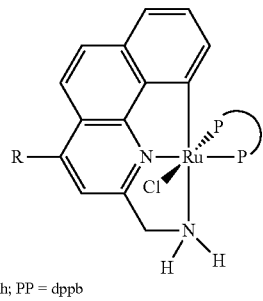

R = Ph; PP = dppb

RuCl$_2$(PPh$_3$)$_3$ (2.22 g, 2.32 mmol) and dppb (1.04 g, 2.44 mmol) were suspended in anhydrous 2-propanol (40 mL) and the mixture was refluxed in a 250 mL round bottom flask for 1.5 h. Compound 6 (820 mg, 2.56 mmol) and NEt$_3$ (3.2 mL, 23 mmol) were added and the mixture was refluxed for 1.5 h. The suspension was cooled to room temperature and the bright orange precipitate was filtered, washed with MeOH (10 mL), heptane (3×10 mL) and dried under reduced pressure (14, 1.68 g, 85% yield). HRMS found: $[M-Cl]^+$811.1943, calcd for $C_{48}H_{43}N_2P_2Ru$ 811.1940. $^1H$ NMR (200.1 MHz, CD$_2$Cl$_2$): δ 8.25 (pseudo t, J=7.6 Hz, 2H, aromatic protons), 8.04 (d, J=7.0 Hz, 1H, aromatic proton), 7.85 (pseudo t, J=8.0 Hz, 2H, aromatic protons), 7.65-7.31 (m, 20H, aromatic protons), 6.95 (s, 1H, aromatic proton), 6.56 (t, J=7.2 Hz, 1H, aromatic proton), 6.23 (pseudo t, J=7.4 Hz, 2H, aromatic protons), 5.54 (t, J=7.8 Hz, 2H, aromatic protons), 4.37 (dd, J=16.2, 5.2 Hz, 1H, NCH$_2$), 4.02 (m, 1H, NCH$_2$), 3.68 (m, 1H, NH$_2$), 2.96 (m, 2H, CH$_2$), 2.38-1.00 (m, 7H, CH$_2$ and NH$_2$). $^{13}C\{^1H\}$ NMR (50.3 MHz, CD$_2$Cl$_2$): δ 168.1, 166.0, 159.3, 159.1, 157.5, 150.0, 149.8, 144.8, 144.7, 143.3, 142.6, 142.2, 142.1, 141.8, 141.6, 141.4, 141.3, 140.8, 140.6, 139.1, 139.0, 133.9, 109.6, 43.9, 43.2, 40.1, 35.2. $^{31}P\{^1H\}$ NMR (81.0 MHz, CD$_2$Cl$_2$): δ 57.3 (d, J=38.1 Hz), 43.3 (d, J=38.1).

Example 15

Synthesis of RuCl(CNN$^{Ph}$)(dppf) (15)

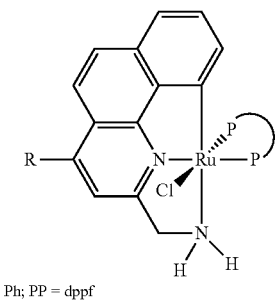

R = Ph; PP = dppf

RuCl$_2$(PPh$_3$)$_3$ (2.22 g, 2.32 mmol) and dppf (1.54 mg, 2.78 mmol) were suspended in 2-propanol (20 mL) and the mixture was refluxed in a 250 mL round bottom flask for 1.5 h. Compound 6 (820 mg, 2.55 mmol) and NEt$_3$ (3.2 mL, 23 mmol) were added and the mixture was refluxed for 5 h. The suspension was cooled to room temperature and heptane (40 mL) was added. The orange precipitate was filtered, washed with MeOH (10 mL), heptane (3×10 mL) and dried under reduced pressure (15, 2.03 g, 90% yield). HRMS found: [M-Cl]$^+$939.1301, calcd for C$_{54}$H$_{43}$FeN$_2$P$_2$Ru: 939.1289. $^1$H NMR (200.1 MHz, CD$_2$Cl$_2$): δ 8.65-8.5 (m, 1H), 8.13 (pseudo t, J=7.6 Hz, 2H), 7.85-7.0 (m, 22H), 6.64 (pseudo t, J=7.4 Hz, 1H), 6.31 (pseudo t, J=7.2 Hz, 2H), 6.08 (pseudo t, J=8.0 Hz, 2H), 4.85 (m, 1H), 4.5-4.1 (m, 5H), 3.9-3.68 (m, 3H), 3.2 (m, 1H), 2.24 (m, 1H). $^{13}$C{$^1$H} NMR (50.3 MHz, CD$_2$Cl$_2$): δ 176.3, 173.8, 167.9, 167.6, 167.3, 165.2, 164.6, 160.9, 160.2, 159.4, 159.1, 158.9, 155.3, 155.1, 154.9, 154.1, 153.3, 153.1, 151.6, 150.9, 150.7, 150.5, 150.2, 149.7, 149.5, 149.3, 149.1, 148.9, 147.9, 147.6, 147.4, 146.7, 146.6, 143.5, 141.4, 139.9, 138.4, 109.0, 108.2, 107.7, 106.7, 98.8, 98.5, 98.1, 96.8, 95.1, 94.6, 90.5, 90.4, 90.1, 53.1, 50.3, 44.0, 35.1. $^{31}$P{$^1$H} NMR (81.0 MHz, CD$_2$Cl$_2$): δ 62.0 (d, J=35.6 Hz), 45.3 (d, J=35.6 Hz).

Example 16

Synthesis of RuCl(CNN$^{Me}$)(dppp) (16)

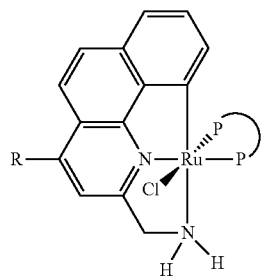

R = Me; PP = dppp

In a 100 mL Schlenk were introduced, under argon atmosphere, RuCl$_2$(PPh$_3$)$_3$ (445 mg, 0.46 mmol), dppp (199 mg, 0.48 mmol) and 2-propanol (10 mL). The reaction mixture was refluxed for 1 h, compound 12 (131 mg, 0.506 mmol) and triethylamine (0.64 mL, 4.6 mmol) were added and the reaction mixture was refluxed overnight. The reaction mixture was cooled to RT and the solid was filtered off. The precipitate was washed with MeOH (2 mL) and dried in vacuum (16, 278 mg, 78% yield). HRMS found: [M-Cl]$^+$ 735.1638, calcd for C$_{42}$H$_{39}$N$_2$P$_2$Ru: 735.1627. $^1$H NMR (400 MHz, CDCl$_3$): δ 8.47 (pseudo t, J=8.0 Hz, 2H), 8.37 (d, J=6.5 Hz, 1H), 8.11 (pseudo t, J=8.0 Hz, 2H), 8.0-6.9 (m, 15H), 6.48 (t, J=7.2 Hz, 1H), 6.42 (s, 1H, aromatic proton), 6.22 (t, J=6.9 Hz, 2H), 5.85 (t, J=8.1 Hz, 2H), 4.56 (m, 1H), 3.79 (m, 2H), 3.25 (m, 1H), 3.08 (m, 2H), 2.83 (m, 1H), 2.62 (m, 1H), 2.30 (m, 5H). $^{13}$C{$^1$H} NMR (100 MHz, C$_6$D$_6$): 142.9, 139.9, 139.4, 139.0, 136.2, 133.3, 132.1, 128.4, 127.1, 126.7, 125.2, 64.5, 28.5, 25.2, 18.7, 17.8. $^{31}$P{$^1$H} NMR (162 MHz, C$_6$D$_6$): δ 54.2 (d, J=47.7 Hz), 35.5 (d, J=47.7 Hz).

Example 17

Synthesis of RuCl(CNN$^{Me}$)(dppb) (17)

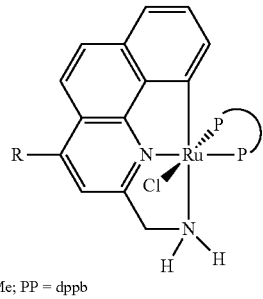

R = Me; PP = dppb

The preparation of 17 was carried out substantially as described for complex 16, but using dppb (237 mg, 0.56 mmol) in place of dppp (17, 300 mg, 83% yield). HRMS found: [M-Cl]$^+$749.1788, calcd for C$_{43}$H$_{41}$N$_2$P$_2$Ru: 749.1783. $^1$H NMR (400 MHz, CDCl$_3$): δ 8.71 (pseudo t, J=8.0 Hz, 2H), 8.45 (d, J=7.0 Hz), 8.23 (pseudo t, J=8.0 Hz, 2H), 7.85-7.36 (m, 8H), 7.25-7.16 (m, 7H), 6.39 (pseudo t, J=7.4 Hz, 1H), 6.28 (s, 1H, aromatic proton), 6.15 (pseudo t, J=7.5 Hz, 2H), 5.67 (t, J=7.8 Hz, 2H), 4.09 (m, 1H), 3.55-3.4 (m, 2H), 3.25-3.15 (m, 2H), 2.4-2.3 (m, 1H), 2.15 (s, 3H, Me), 2.10-1.70 (m, 6H). $^{13}$C{$^1$H} NMR (100 MHz, C$_6$D$_6$): 155.1, 153.7, 146.4, 154.3, 144.6, 141.7, 136.4, 136.3, 133.8, 133.6, 131.4, 131.3, 131.2, 130.6, 130.5, 129.6, 129.1, 125.8, 125.1, 125.0, 123.8, 118.6, 116.7, 51.6, 33.0, 29.7, 26.3, 21.4, 17.8. $^{31}$P{$^1$H} NMR (162 MHz, CDCl$_3$): δ 57.5 (d, J=38.5 Hz), 43.2 (d, J=38.5 Hz).

Example 18

Synthesis of RuCl(CNN$^{Me}$)(dppf) (18)

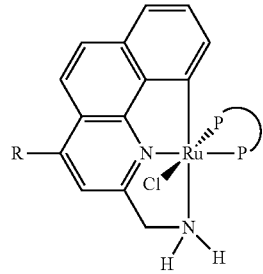

R = Me; PP = dppf

The preparation of 18 was carried out substantially as described for complex 16, but using dppf (311 mg, 0.56 mmol) in place of dppp (18, 184 mg, 44% yield). HRMS found: [M-Cl]$^+$877.1148, calcd for C$_{49}$H$_{41}$FeN$_2$P$_2$Ru: 877.1132. $^1$H NMR (400 MHz, CDCl$_3$): δ 9.11 (d, J=6.0 Hz, 1H), 9.0 (pseudo t, J=8.0 Hz, 2H), 8.79 (m, 1H), 8.0-7.71 (m, 5H), 7.4-7.07 (m, 10H), 6.45 (t, J=6.4 Hz, 1H), 6.27-6.17 (m, 4H), 5.8 (s, 1H, aromatic proton), 5.01 (m, 1H), 4.38-4.35 (m, 2H), 4.2 (m, 1H), 3.98 (m, 2H), 3.65 (m, 2H), 3.32 (m, 1H), 3.08 (m, 1H), 2.22 (s, 3H, Me), 1.92 (m, 1H). $^{13}$C{$^1$H} NMR (100 MHz, C$_6$D$_6$): 176.8, 155.4, 152.1, 147.2, 146.8, 144.1, 143.8, 141.6, 139.7, 139.4, 138.7, 138.6, 135.8, 135.4, 135.2, 133.9, 132.6, 126.6, 126.1, 125.3, 123.8, 119.0, 118.6, 117.5, 88.7, 88.3, 86.8, 86.3, 77.9, 77.2, 75.5, 73.9, 73.3, 69.2, 68.9, 68.6, 63.6, 50.9, 25.2, 17.9. $^{31}$P{$^1$H} NMR (162 MHz, C$_6$D$_6$): δ 61.4 (d, J=35.7 Hz), 45.1 (d, J=35.7 Hz).

Example 19

Synthesis of RuCl(CNN$^{Ph}$)(rac-BINAP) (19)

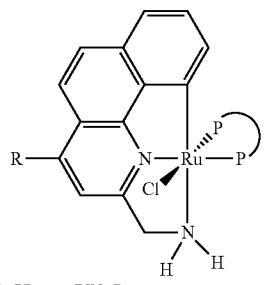

R = Ph; PP = rac-BINAP

[RuCl$_2$(p-cymene)]$_2$ (71 mg, 0.116 mmol) and rac-BINAP (152 mg, 0.244 mmol) were suspended in 2-propanol (2 mL) and the mixture was refluxed in a 25 mL round bottom flask for 2 h. Compound 6 (82 mg, 0.256 mmol) and NEt$_3$ (0.32 mL, 2.3 mmol) were added and the mixture was refluxed for 6 h. The mixture was cooled to room temperature and heptane (4 mL) was added. The precipitate was filtered, washed with MeOH (1 mL), diethyl ether (5×2 mL) and dried under reduced pressure, obtaining the complex as mixture of two stereoisomers in about 4/3 molar ratio (19, 150 g, 62% yield). HRMS found: [M-Cl]$^+$1007.2254, calcd for C$_{64}$H$_{47}$N$_2$P$_2$Ru: 1007.2258. $^1$H NMR (200.1 MHz, CD$_2$Cl$_2$): δ 8.59 (d, J=6.4 Hz), 8.40-8.13 (m), 8.02-6.22 (m, aromatic protons), 6.13-5.78 (m, aromatic protons), 5.36 (d, J=7.6 Hz), 4.74-3.35 (m, CH$_2$ and NH$_2$), 2.43-2.24 (m, CH$_2$), 1.73-1.40 (m, NH$_2$). $^{13}$C{$^1$H} NMR (50.3 MHz, CD$_2$Cl$_2$): δ 178.0 (dd, J=12.3, 9.1 Hz, CRu), 176.5 (dd, J=14.3, 9.2 Hz, CRu), 156.3, 154.6, 153.6, 153.2, 147.5-123.4 (m, aromatic carbon atoms), 120.5, 120.0, 119.3, 118.2, 117.4 (d, J=2.6 Hz), 115.9 (d, J=2.7 Hz), 52.8 (br s, NCH$_2$), 52.4 (br s, NCH$_2$). $^{31}$P{$^1$H} NMR (81.0 MHz, CD$_2$Cl$_2$): δ 60.6 (minor diastereoisomer, d, J=39.7 Hz), 52.4 (minor diastereoisomer, d, J=39.7 Hz), 52.1 (major diastereoisomer, d, J=34.8 Hz), 51.2 (major diastereoisomer, d, J=34.8 Hz).

Example 20

Synthesis of RuCl(CNN$^{Ph}$)[(S,R)-JOSIPHOS] (20)

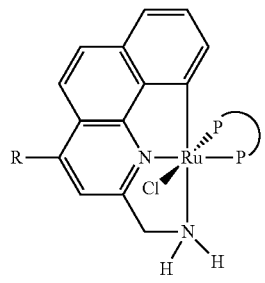

R = Ph; PP = (S,R)-JOSIPHOS

[RuCl$_2$(p-cymene)]$_2$ (71.0 mg, 0.116 mmol) and (S,R)-JOSIPHOS (165.5 mg, 0.278 mmol) were suspended in 2-propanol (4 mL) and the mixture was refluxed in a 25 mL round bottom flask for 1 h. Compound 6 (82 mg, 0.256 mmol) and NEt$_3$ (0.32 mL, 2.3 mmol) were added and the mixture was refluxed for 5 h. The solvent was removed and the solid was dried under reduced pressure The solid was dissolved in CH$_2$Cl$_2$ (1 mL), kept at −20° C. for 18 h, affording the precipitation of triethylammonium chloride which was eliminated by filtration. Addition of heptane (2 mL) to the filtrate gave an orange precipitate which was filtered, washed with heptane and dried under reduced pressure (20, 125 mg, 53% yield). HRMS found: [M-Cl]$^+$ 979.2543, calcd for C$_{56}$H$_{59}$FeN$_2$P$_2$Ru: 979.2546. $^1$H NMR (200.1 MHz, CD$_2$Cl$_2$): δ 8.38 (d, J=7 Hz, 1H), 8.21 (m, 2H), 7.82-7.13 (m, 20H), 4.76-4.35 (m, 5H), 4.22 (m, 1H), 3.79 (s, 5H), 1.98-1.7 (m, 3H), 1.45-0.95 (m, 22H). $^{13}$C{$^1$H} NMR (50.3 MHz, CD$_2$Cl$_2$): δ 157.3, 154.8, 147.7, 146.6, 146.0, 145.2, 144.7, 144.6, 140.1, 139.2, 138.7, 137.3, 133.4, 132.2, 130.1, 129.8, 129.2, 128.9, 128.6, 127.5, 127.1, 126.6, 120.3, 118.2, 117.2, 97.6 (dd, J=21.2 Hz, J=3.1 Hz; ipso-C$_5$H$_3$), 74.0 (s; C$_5$H$_3$), 72.5 (dd, J=37.2 Hz, J=5.0 Hz ipso-C$_5$H$_3$), 70.4 (s; C$_5$H$_5$), 69.8 (d, J=13.3 Hz; C$_5$H$_3$), 68.5 (m, C$_5$H$_3$), 52.2 (d, J=2.3 Hz; NCH$_2$), 40.0 (d, J=15.8 Hz; CH of Cy), 37.6 (d, J=17.6 Hz; CH of Cy), 31.5-26.2 (m; CH$_2$ of Cy), 29.1 (d, J=3.8 Hz; PCHCH$_3$), 15.5 ppm (d, J=6.9 Hz; PCHCH$_3$). $^{31}$P{$^1$H} NMR (81.0 MHz CD$_2$Cl$_2$): δ 66.5 (d, J=42.1 Hz), 41.3 (d, J=42.1 Hz).

Example 21

Synthesis of 1-napthyl-propionamide (21)

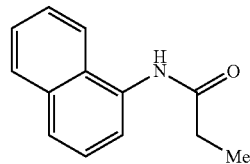 [SMILES: CCC(=O)Nc1cccc2ccccc12]

The 1-naphthylamine reagent used might have contained a few ppm quantity of the highly carcinogenic 2-naphtylamine. While the 1-naphthylamine reagent had a quality allowing its use, 2-naphtylamine is banned from use in Europe and many other countries. An occupational health assessment required that in order to minimise exposure the N-(naphthalen-1-yl)-propionamide 21 should be assayed and characterised as a crude product and then converted on as described in Example 22.

In a 500 mL round bottomed flask were introduced 1-naphthylamine (28.0 g; 156 mmol) and 200 mL of dry dichloromethane. The solution was cooled to 0° C. and triethylamine (24.0 mL, 172 mmol) was added. Propionyl chloride (15.88 g; 171.6 mmol; 14.8 mL) was slowly ((due to a very exothermic reaction) added. The reaction mixture was stirred at 0° C. and allowed to warm up slowly to room temperature. A formed precipitate was removed by filtration and the filtrate was extracted with 10% aqueous hydrochloric acid. The aqueous extract was further extracted twice with 100 mL of dichloromethane. The dichloromethane layers were combined and dried over magnesium sulfate. Dichloromethane was removed under reduced pressure, affording 21. Yield: 21.90 g; 109.9 mmol, 71%. $^1$H NMR (400 MHz, CDCl$_3$): δ 7.70 (4H, t, J=7.4 Hz), 7.56 (1H, d, J=7.9 Hz), 7.37 (2H, m, broad), 7.30 (1H, t, J=7.6 Hz), 2.36 (2H, d, J=7.0 Hz), 1.17 (3H, t, J=7.0 Hz). $^{13}$C{$^1$H} NMR (100.61 MHz, CDC$_3$): δ 172.95, 134.09, 128.62, 127.20, 126.14, 125.91, 125.82, 125.63, 121.39, 120.96, 30.43, 9.94 (possible overlap of two carbon resonances).

Example 22

Synthesis of 2-Chloro-3-methylbenzo[h]quinoline (22)

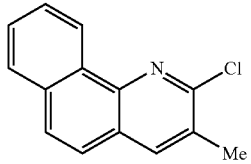 [SMILES: Cc1cc2ccc3ccccc3c2nc1Cl]

In a 100 mL two neck round bottom flask were introduced, under argon atmosphere, 1-naphthyl-propionamide (10.0 g, 50.2 mmol) and anhydrous dimethylformamide (3.89 mL, 1 eq). POCl$_3$ (20 mL; 4.2 eq) was added dropwise and the reaction mixture was heated to reflux releasing the formed HCl gas through a silicone oil filled bubbler. After heating overnight the reaction mixture was cooled to room temperature and then carefully hydrolysed in a mixture of crushed ice and water. After stirring for 2 hours, a precipitate had formed that was filtered off, washed with water and dried in vacuum. A yield of 8.01 g (35.18 mmol, 70%) of 22 was obtained. $^1$H NMR (400 MHz, CDCl$_3$): δ 9.19 (d, 1H, J=7.9 Hz), 7.93 (s, 1H), 7.88 (d, 1H, J=7.9 Hz) 7.78 (d, 1H, J=8.8 Hz), 7.71 (q, 2H, J=7.3 Hz), 7.58 (d, 1H, J=8.8 Hz) 2.55 (s, 3H). $^{13}$C{$^1$H} NMR (100.61 MHz, CDC$_3$): δ 150.67, 144.66, 138.02, 133.40, 130.64, 130.42, 128.24, 128.00, 127.74, 127.15, 125.59, 124.43, 124.20, 19.96.

The invention claimed is:

1. A process for preparing an [M(Y)$_2$(L$^1$)$_{m'}$(L$^2$)] complex, the process comprising the step of:
   (a) reacting an [M(Y)$_2$(L)$_2$] complex with L$^1$ and L$^2$ in a polar aprotic solvent; or
   (b) reacting an [M(X)$_2$(L)$_3$] complex, an alkali metal carboxylate salt, L$^1$ and L$^2$ in a polar aprotic solvent, an alcohol solvent or a mixture thereof; or
   (c) reacting an [M(Y)$_2$(L)$_2$(L$^2$)] complex with L$^1$ in a polar aprotic solvent,
   in each case forming the [M(Y)$_2$(L$^1$)$_{m'}$(L$^2$)] complex;
   wherein:
   M is ruthenium or osmium;
   X is a halide ligand;
   Y is a carboxylate ligand;
   L is a monodentate phosphorus ligand;
   L$^1$ is a monodentate phosphorus ligand that is different from L, or a bidentate phosphorus ligand;
   m' is 1 or 2, wherein:
     m' is 1, L$^1$ is a bidentate bis-phosphorus ligand;
     m' is 2, when each L$^1$ is a monodentate phosphorus ligand; and
   L$^2$ is a bidentate N,N ligand comprising two nitrogen-containing groups.

2. A process for preparing an [M(Y)$_2$(L)$_2$(L$^2$)] complex, the process comprising the step of:
   reacting an [M(Y)$_2$(L)$_2$] complex with L$^2$ in a polar aprotic solvent;
   wherein:
   M is ruthenium or osmium;
   Y is a carboxylate ligand;
   L is a monodentate phosphorus ligand; and
   L$^2$ is a bidentate N,N ligand comprising two nitrogen-containing groups.

3. The process according to claim 1, wherein M is ruthenium.

4. The process according to claim 1, wherein Y is —OC(O)R$_A$, wherein R$_A$ is —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl.

5. The process according to claim 1, wherein L is PR$_{11}$R$_{12}$R$_{13}$, wherein R$_{11}$, R$_{12}$ and R$_{13}$ are, independently, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{1-20}$-alkoxy, substituted C$_{1-20}$-alkoxy, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl.

6. The process according to claim 1, wherein the phosphorus atom of L$^1$ is covalently bound to 3 carbon atoms or to n heteroatoms and 3-n carbon atoms, where n=1, 2 or 3.

7. The process according to claim 6, wherein the heteroatom is N or O.

8. The process according to claim 6, wherein L$^1$ is an unsubstituted or substituted Binap ligand, PPhos ligand, PhanePhos ligand, QPhos ligand, Josiphos ligand, Bophoz ligand, or Skewphos ligand.

9. The process according to claim 6, wherein L$^1$ is PPh$_3$, dppf (1,1'-bis(diphenylphosphino)ferrocene), dppp (1,3-bis(diphenylphosphino)propane), dppb (1,4-bis(diphenylphosphino)butane), Dipfc (1,1'-bis(di-isopropylphosphino)ferrocene), or dCyPfc.

10. The process according to claim 1, wherein the bidentate N,N-ligand is of formulae (2), (3), (4), (5), (6), (7), (8), (9), or (10):

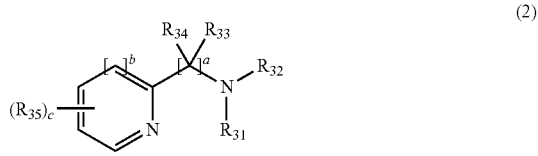

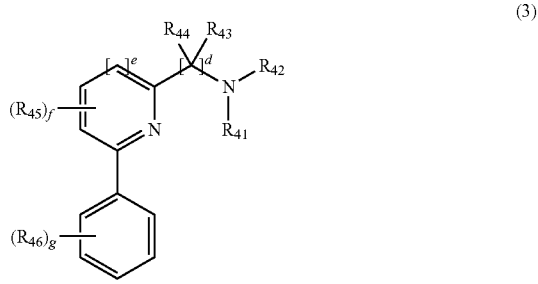

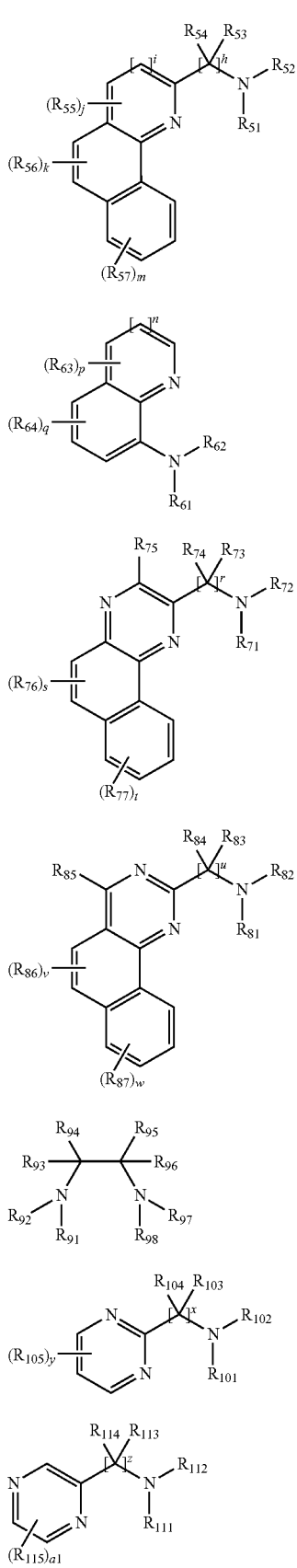

wherein:

$R_{31}$, $R_{32}$, $R_{41}$, $R_{42}$, $R_{51}$, $R_{52}$, $R_{61}$, $R_{62}$, $R_{71}$, $R_{72}$, $R_{81}$, $R_{82}$, $R_{91}$, $R_{92}$, $R_{97}$, $R_{98}$, $R_{101}$, $R_{102}$, $R_{111}$ and $R_{112}$ are, independently, —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, or substituted $C_{4-20}$-heteroaryl;

$R_{33}$, $R_{34}$, $R_{43}$, $R_{44}$, $R_{53}$, $R_{54}$, $R_{73}$, $R_{74}$, $R_{83}$, $R_{84}$, $R_{103}$, $R_{104}$, $R_{113}$ and $R_{114}$ are, independently, —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, or substituted $C_{4-20}$-heteroaryl;

$R_{35}$, $R_{45}$, $R_{46}$, $R_{55}$, $R_{56}$, $R_{57}$, $R_{63}$, $R_{64}$, $R_{76}$, $R_{77}$, $R_{86}$, $R_{87}$, $R_{105}$ and $R_{115}$ are, independently, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, or substituted $C_{4-20}$-heteroaryl;

$R_{75}$ and $R_{85}$ are, independently, —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{1-20}$-alkoxy, substituted $C_{1-20}$-alkoxy, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, or substituted $C_{4-20}$-heteroaryl;

$R_{93}$, $R_{94}$, $R_{95}$ and $R_{96}$ are, independently, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted-$C_{6-20}$-aryl, substituted-$C_{6-20}$-aryl, unsubstituted-$C_{6-20}$-aryloxy, or substituted-$C_{6-20}$-aryloxy; or $R_{93}$ and $R_{94}$ together with the carbon atom to which they are bound and/or $R_{95}$ and $R_{96}$ together with the carbon atom to which they are bound form an unsubstituted $C_{3-20}$-cycloalkyl or substituted $C_{3-20}$-cycloalkyl; or one of $R_{93}$ and $R_{94}$ and one of $R_{95}$ and $R_{96}$ together with the carbon atoms to which they are bound form an unsubstituted $C_{5-10}$-cycloalkyl or substituted $C_{5-10}$-cycloalkyl;

a, d, h, r, u, x and z are, independently, 1 or 2;

b, e, i and n are, independently, 0 or 1; wherein:
when b is 0, c is 0, 1, 2 or 3;
when b is 1, c is 0, 1, 2, 3 or 4;
when e is 0, f is 0, 1 or 2;
when e is 1, f is 0, 1, 2 or 3;
when i is 0, j is 0 or 1;
when i is 1, j is 0, 1 or 2;
when n is 0, p is 0, 1 or 2;
when n is 1, p is 0, 1, 2 or 3;

g is 0, 1, 2, 3, 4 or 5;

k, s, v are, independently, 0, 1 or 2;

m, t, w are, independently, 0, 1, 2, 3 or 4; and q, y and a1 are, independently, 0, 1, 2 or 3.

11. A $[M(Y)_2(L^1)_m(L^2)]$ complex prepared according to the process of claim 1, provided that:
(a) $L^2$ is not a bidentate N,N-ligand of formula (8):

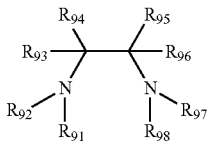

(8)

wherein:
R$_{91}$, R$_{92}$, R$_{97}$, and R$_{98}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl;

R$_{93}$, R$_{94}$, R$_{95}$ and R$_{96}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted-C$_{6-20}$-aryl, substituted-C$_{6-20}$-aryl, unsubstituted-C$_{6-20}$-aryloxy, or substituted-C$_{6-20}$-aryloxy; or R$_{93}$ and R$_{94}$ together with the carbon atom to which they are bound and/or R$_{95}$ and R$_{96}$ together with the carbon atom to which they are bound form an unsubstituted C$_{3-20}$-cycloalkyl or substituted C$_{3-20}$-cycloalkyl; or one of R$_{93}$ and R$_{94}$ and one of R$_{95}$ and R$_{96}$ together with the carbon atoms to which they are bound form an unsubstituted C$_{5-10}$-cycloalkyl or substituted C$_{5-10}$-cycloalkyl; or (b) Y is not RCOO— wherein R is a branched or cyclic C$_2$-C$_{12}$ hydrocarbon group in the α and or β position; or (c) $L^2$ is not 2-aminomethylpyridine when $(L^1)_{m'}$ is diphenylphosphinoethane.

12. A complex according to claim 11, that is a cis-$[M(Y)_2(L^1)_m(L^2)]$ complex.

13. A method of catalysing a reaction, the method comprising the step of reacting a substrate comprising a carbon-oxygen double bond in the presence of $[M(Y)_2(L^1)_m(L^2)]$ of claim 11.

14. The method according to claim 13, wherein the $[M(Y)_2(L^1)_m(L^2)]$ complex is a cis-$[M(Y)_2(L^1)_m(L^2)]$ complex.

15. The method of claim 13, which is a reduction.

16. The method of claim 15, where the reduction comprises reacting the substrate with hydrogen, deuterium or tritium.

17. A method of catalysing a reaction, the method comprising the step of reacting a substrate comprising a carbon-oxygen double bond in the presence of a compound of formula $[M(Y)_2(L^1)_m(L^2)]$,
wherein
M is ruthenium or osmium;
Y is a carboxylate ligand;
$L^1$ is a monodentate phosphorus ligand or a bidentate phosphorus ligand;

m' is 1 or 2, wherein:
m' is 1, when $L^1$ is a bidentate bis-phosphorus ligand;
m' is 2, when $L^1$ is a monodentate phosphorus ligand; and $L^2$ is a bidentate N,N ligand comprising two nitrogen-containing groups, and further where the reaction is a reduction comprising a transfer hydrogenation, provided that in the compound $[M(Y)_2(L^1)_m(L^2)]$:
(a) $L^2$ is not a bidentate N,N-ligand of formula (8):

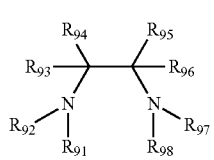

(8)

wherein:
R$_{91}$, R$_{92}$, R$_{97}$, and R$_{98}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted C$_{5-20}$-aryl, substituted C$_{5-20}$-aryl, unsubstituted C$_{1-20}$-heteroalkyl, substituted C$_{1-20}$-heteroalkyl, unsubstituted C$_{2-20}$-heterocycloalkyl, substituted C$_{2-20}$-heterocycloalkyl, unsubstituted C$_{4-20}$-heteroaryl, or substituted C$_{4-20}$-heteroaryl;

R$_{93}$, R$_{94}$, R$_{95}$ and R$_{96}$ are, independently, —H, unsubstituted C$_{1-20}$-alkyl, substituted C$_{1-20}$-alkyl, unsubstituted C$_{3-20}$-cycloalkyl, substituted C$_{3-20}$-cycloalkyl, unsubstituted-C$_{6-20}$-aryl, substituted-C$_{6-20}$-aryl, unsubstituted-C$_{6-20}$-aryloxy, or substituted-C$_{6-20}$-aryloxy; or R$_{93}$ and R$_{94}$ together with the carbon atom to which they are bound and/or R$_{95}$ and R$_{96}$ together with the carbon atom to which they are bound form an unsubstituted C$_{3-20}$-cycloalkyl or substituted C$_{3-20}$-cycloalkyl; or one of R$_{93}$ and R$_{94}$ and one of R$_{95}$ and R$_{96}$ together with the carbon atoms to which they are bound form an unsubstituted C$_{5-10}$-cycloalkyl or substituted C$_{5-10}$-cycloalkyl; or (b) Y is not RCOO— wherein R is a branched or cyclic C$_2$-C$_{12}$ hydrocarbon group in the α and or β position.

18. A method of catalysing a reaction, the method comprising the step of performing the reaction in the presence of a compound of formula $[M(Y)_2(L^1)_m(L^2)]$, wherein
M is ruthenium or osmium;
Y is a carboxylate ligand;
L is a monodentate phosphorus ligand;
$L^1$ is a monodentate phosphorus ligand that is different from L, or a bidentate phosphorus ligand;
m' is 1 or 2, wherein:
when m' is 1, $L^1$ is a bidentate bis-phosphorus ligand;
when m' is 2, each $L^1$ is a monodentate phosphorus ligand; and
$L^2$ is a bidentate N,N ligand comprising two nitrogen-containing groups, and further,
where the reaction is an alcohol racemization, alcohol dehydrogenation, or carbon-carbon coupling, provided that in the compound $[M(Y)_2(L^1)_m(L^2)]$:

(a) $L^2$ is not a bidentate N,N-ligand of formula (8):

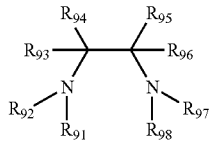

(8)

wherein:

$R_{91}$, $R_{92}$, $R_{97}$, and $R_{98}$ are, independently, —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, or substituted $C_{4-20}$-heteroaryl;

$R_{93}$, $R_{94}$, $R_{95}$ and $R_{96}$ are, independently, —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted-$C_{6-20}$-aryl, substituted-$C_{6-20}$-aryl, unsubstituted-$C_{6-20}$-aryloxy, or substituted-$C_{6-20}$-aryloxy; or $R_{93}$ and $R_{94}$ together with the carbon atom to which they are bound and/or $R_{95}$ and $R_{96}$ together with the carbon atom to which they are bound form an unsubstituted $C_{3-20}$-cycloalkyl or substituted $C_{3-20}$-cycloalkyl; or one of $R_{93}$ and $R_{94}$ and one of $R_{95}$ and $R_{96}$ together with the carbon atoms to which they are bound form an unsubstituted $C_{5-10}$-cycloalkyl or substituted $C_{5-10}$-cycloalkyl; or (b) Y is not RCOO— wherein R is a branched or cyclic $C_2$-$C_{12}$ hydrocarbon group in the α and or β position.

19. A [M (Y)$_2$(L)$_2$(L$^2$)] complex prepared according to the process of claim 2, provided that:

(a) $L^2$ is not a bidentate N,N-ligand of formula (8):

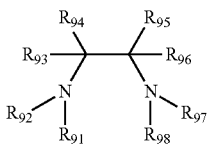

(8)

wherein:

$R_{91}$, $R_{92}$, $R_{97}$, and $R_{98}$ are, independently, —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted $C_{5-20}$-aryl, substituted $C_{5-20}$-aryl, unsubstituted $C_{1-20}$-heteroalkyl, substituted $C_{1-20}$-heteroalkyl, unsubstituted $C_{2-20}$-heterocycloalkyl, substituted $C_{2-20}$-heterocycloalkyl, unsubstituted $C_{4-20}$-heteroaryl, or substituted $C_{4-20}$-heteroaryl;

$R_{93}$, $R_{94}$, $R_{95}$ and $R_{96}$ are, independently, —H, unsubstituted $C_{1-20}$-alkyl, substituted $C_{1-20}$-alkyl, unsubstituted $C_{3-20}$-cycloalkyl, substituted $C_{3-20}$-cycloalkyl, unsubstituted-$C_{6-20}$-aryl, substituted-$C_{6-20}$-aryl, unsubstituted-$C_{6-20}$-aryloxy, or substituted-$C_{6-20}$-aryloxy; or $R_{93}$ and $R_{94}$ together with the carbon atom to which they are bound and/or $R_{95}$ and $R_{96}$ together with the carbon atom to which they are bound form an unsubstituted $C_{3-20}$-cycloalkyl or substituted $C_{3-20}$-cycloalkyl; or one of $R_{93}$ and $R_{94}$ and one of $R_{95}$ and $R_{96}$ together with the carbon atoms to which they are bound form an unsubstituted $C_{5-10}$-cycloalkyl or substituted $C_{5-10}$-cycloalkyl; or (b) the carboxylate ligand Y is not RCOO— wherein R is a $C_2$-$C_{12}$ hydrocarbon group branched or cyclic in the α and or β position.

20. The method of claim 15, where the reduction is a transfer hydrogenation.

* * * * *